US008309071B2

(12) United States Patent
Lindemann et al.

(10) Patent No.: US 8,309,071 B2
(45) Date of Patent: Nov. 13, 2012

(54) FOAMY VIRAL ENVELOPE GENES

(75) Inventors: Dirk Lindemann, Dresden (DE); Kristin Stirnnagel, Dresden (DE); Daniel Lueftenegger, Erlangen (DE)

(73) Assignee: Vectoria Forschungsforderungs Verein E.V., Wuerzburg (DE)

( * ) Notice: Subject to any disclaimer, the term of this patent is extended or adjusted under 35 U.S.C. 154(b) by 859 days.

(21) Appl. No.: 12/147,947

(22) Filed: Jun. 27, 2008

(65) Prior Publication Data

US 2009/0325870 A1 Dec. 31, 2009

(51) Int. Cl.
*A61K 48/00* (2006.01)

(52) U.S. Cl. .......................... 424/93.1; 424/93.2; 435/5

(58) Field of Classification Search ........................ None
See application file for complete search history.

(56) References Cited

U.S. PATENT DOCUMENTS 5,929,222 A 7/1999 Lindemann et al.
6,111,087 A 8/2000 Rethwilm et al.

FOREIGN PATENT DOCUMENTS

DE 698 29 174 T2 1/2006
EP 0 977 881 B1 3/2005
WO WO 98/40507 9/1998

OTHER PUBLICATIONS

Baker et al., Protein Structure Predication and Structural Genomics, Science (2001) vol. 294, No. 5540, pp. 93-96.*

Attwood, T. The Babel of Bioinformatics, Science (2000) vol. 290, No. 5491, pp. 471-473.*

Schmidt et al. Long Terminal Repeat U3 Length Polymorphism of Human Foamy Virus. Virology, 230, p. 167-178, 1997.*

Duda et al. Characterization of the Prototype Foamy Virus Envelope Glycoprotein Receptor-Binding Domain. J. Virology, 2006, vol. 80, No. 16, p. 8158-8167.*

Anderson, W.F., et al. "The ADA Human Gene Therapy Clinical Protocol", Human Gene Therapy 1(3),pp. 331-362, (1990).

Bieniasz, P.D., et al. "Cell Cycle Dependence of Foamy Retrovirus Infection", Journal of Virology, vol. 69, No. 11, pp. 7295-7299, (Nov. 1995).

Check, E., "Gene Therapy Put on Hold as Third Child Develops Cancer", Nature, vol. 433, p. 561, (Feb. 2005).

Nienhuis, A.W., et al. "Development of Gene Therapy for Hemoglobin Disorders", Annals N.Y. Academy of Sciences, pp. 101-111, (2003).

Li, X., et al., "Transduction of CD34$^+$Cells by a Vesicular Stomach Virus Protein G (VSV-G) Pseudotyped HIV-1 Vector,", Journal of Human Virology, vol. 1, No. 5, pp. 346-352, (1998).

Li, Z., et al., "Murine Leukemia Induced by Retroviral Gene Marking," Science, vol. 296, p. 497, (Apr. 2002).

Lindemann, D., et al., "Efficient Pseudotyping of Murine Leukemia Virus Particles with Chimeric Human Foamy Virus Envelope Proteins," Journal of Virology, pp. 4815-4820, (Jun. 1997).

Lindemann, D., et al., "A Particle-Associated Glycoprotein Signal Peptide Essential for Virus Maturation and Infectivity," Journal of Virology, vol. 75, No. 13, pp. 5762-5771, (Jul. 2001).

Russell, D.W., et al., "Foamy Virus Vectors", Journal of Virology, vol. 70, No. 1, pp. 217-222, (Jan. 1996).

Stanke, N., et al., "Ubiquitination of the Prototype Foamy Virus Envelope Glycoprotein Leader Peptide Regulates Subviral Particle Release," Jnl. of Virology, vol. 79, No. 24, pp. 15074-15083, (Dec. 2005).

Schmidt, M., et al., "Replicating Foamy Virus-Based Vectors Directing High Level Expression of Foreign Games," Virology 210, pp. 168-178, (1995).

Weiss, R.A., "Foamy Viruses Bubble On," Nature 380, p. 201, (1996).

Wilk, T., "The Intact Retroviral Env Glycoprotein of Human Foamy Virus is a Trimer," Journal of Virology, vol. 74, No. 6, pp. 2885-2887, (Mar. 2000).

PhD, Thesis of Wurm, M. "Transduction of hematopoietic stem cells from new world monkeys with foamy viruses," University of Duesseldorf, pp. 1-4, 2007.

PhD. Thesis of Stange A. "Determinants and mechanisms of the foamy viral particle realease", University of Dresden, pp. 1-5, 2008.

PhD Thesis of Luftenegger, D., "The influence of posttranslational modifications on the function of prototype foamy virus envelope proteins", University of Dresden, pp. 1-5, 2008.

PhD Thesis of Stirnnagel, K., "Intracellular distribution and interaction of prototype foamy virus structural proteins", University of Dresden, pp. 1-4, 2007.

* cited by examiner

*Primary Examiner* — Stacy B Chen
*Assistant Examiner* — Michelle S Horning
(74) *Attorney, Agent, or Firm* — Viksnins Harris & Padys PLLP

(57) ABSTRACT

The present invention concerns the technical field of nucleic acids and expression-optimized nucleic acids. The present invention concerns especially nucleic acids comprising a mutated foamy viral envelope gene encoding a foamy viral envelope polypeptide, which comprises a leader peptide (LP), a surface unit (SU) and a transmembrane domain (TM). The present invention also relates to modified polypeptides encoded by these nucleic acids. Furthermore, the present invention regards a method for preparing pseudotyped vector particles as well as a method for treating a genetic disorder comprising administering a nucleic acid or a polypeptide encoded by that nucleic acid.

16 Claims, 25 Drawing Sheets

| Vector System | Envelope env | relative infectivity | | absolute infectivity | |
|---|---|---|---|---|---|
| | | Mean | StdDev | Mean | StdDev |
| HIV-1 | VSV-G | 100.00% | 0.0% | 5.5E+05 | 2.4E+05 |
| | PFVwt, EM002 | 0.28% | 0.2% | 1.8E+03 | 2.3E+03 |
| | PFVwt ER, EM225 | 0.47% | 0.2% | 2.7E+03 | 1.7E+03 |
| | PFVwt ER+, EM226 | 0.57% | 0.1% | 3.2E+03 | 1.4E+03 |
| | PFV Ubi, EM140 | 325.24% | 127.0% | 1.9E+06 | 1.4E+06 |
| | PFV Ubi ER, EM167 | 905.25% | 468.2% | 5.2E+06 | 3.0E+06 |
| | PFV Ubi ER+, EM168 | 901.03% | 520.6% | 5.2E+06 | 3.1E+06 |
| | SFV-1wt, SM00 | 0.84% | 0.2% | 4.4E+03 | 1.5E+03 |
| | SFV-1 Ubi, SM04 | 369.34% | 119.9% | 2.1E+06 | 1.2E+06 |
| | SFV-1 Ubi ER, SM05 | 1067.78% | 451.8% | 6.4E+06 | 4.1E+06 |
| | SFV-1 Ubi ER+, SM06 | 1484.81% | 237.1% | 8.3E+06 | 3.8E+06 |
| MLV | VSV-G | 100.00% | 0.0% | 6.6E+04 | 2.8E+04 |
| | PFVwt, EM002 | 5.44% | 7.2% | 3.3E+03 | 4.0E+03 |
| | PFVwt ER, EM225 | 8.35% | 4.0% | 5.1E+03 | 1.9E+03 |
| | PFVwt ER+, EM226 | 7.82% | 3.1% | 5.0E+03 | 2.3E+03 |
| | PFV Ubi, EM140 | 2475.69% | 1618.3% | 1.6E+06 | 1.6E+06 |
| | PFV Ubi ER, EM167 | 2752.80% | 1506.1% | 1.8E+06 | 1.1E+06 |
| | PFV Ubi ER+, EM168 | 2861.47% | 1487.2% | 1.9E+06 | 1.4E+06 |
| | SFV-1wt, SM00 | 86.08% | 51.4% | 5.0E+04 | 2.2E+04 |
| | SFV-1 Ubi, SM04 | 629.41% | 219.2% | 4.0E+05 | 1.7E+05 |
| | SFV-1 Ubi ER, SM05 | 1359.27% | 791.6% | 8.4E+05 | 4.1E+05 |
| | SFV-1 Ubi ER+, SM06 | 3411.55% | 1880.0% | 2.4E+06 | 1.6E+06 |
| PFV | VSV-G | 0.01% | 0.0% | 7.8E+01 | 3.6E+00 |
| | PFVwt, EM002 | 100.00% | 0.0% | 7.8E+05 | 3.5E+05 |
| | PFVwt ER, EM225 | 34.07% | 9.6% | 2.9E+05 | 1.6E+05 |
| | PFVwt ER+, EM226 | 48.45% | 13.2% | 3.5E+05 | 1.3E+05 |
| | PFV Ubi, EM140 | 87.76% | 18.1% | 6.7E+05 | 3.2E+05 |
| | PFV Ubi ER, EM167 | 69.58% | 8.6% | 5.3E+05 | 2.3E+05 |
| | PFV Ubi ER+, EM168 | 78.37% | 24.4% | 6.6E+05 | 3.7E+05 |
| | SFV-1wt, SM00 | 166.16% | 116.2% | 1.3E+06 | 1.2E+06 |
| | SFV-1 Ubi, SM04 | 34.31% | 10.4% | 2.5E+05 | 1.0E+05 |
| | SFV-1 Ubi ER, SM05 | 45.33% | 18.5% | 3.4E+05 | 2.0E+05 |
| | SFV-1 Ubi ER+, SM06 | 56.65% | 19.2% | 4.0E+05 | 1.5E+05 |
| | uninfected | 0.02% | 0.0% | 7.8E+01 | 3.6E+00 |

Fig. 6

| Vector System | Envelope env | relative infectivity | | absolute infectivity | |
|---|---|---|---|---|---|
| | | Mean | StdDev | Mean | StdDev |
| HIV-1 | VSV-G | 100,00% | 7,4% | 8,2E+05 | 6,1E+04 |
| | EM002 | 8,47% | 4,0% | 6,9E+04 | 3,3E+04 |
| | EM140 | 982,21% | 124,1% | 8,1E+06 | 1,0E+06 |
| | EM167 | 1295,86% | 226,9% | 1,1E+07 | 1,9E+06 |
| | EM168 | 2483,57% | | 2,0E+07 | |
| | PE01 | 11101,25% | | 9,1E+07 | |
| | PE02 | 11416,80% | | 9,4E+07 | |
| | PE03 | 14132,97% | | 1,2E+08 | |
| MLV | VSV-G | 100,00% | 12,8% | 2,0E+04 | 2,5E+03 |
| | EM002 | 20,94% | 10,9% | 4,1E+03 | 2,2E+03 |
| | EM140 | 1013,49% | 1157,2% | 2,0E+05 | 2,3E+05 |
| | EM167 | 1633,18% | 1054,1% | 3,2E+05 | 2,1E+05 |
| | EM168 | 1690,35% | 1078,1% | 3,3E+05 | 2,1E+05 |
| | PE01 | 49512,26% | 11465,7% | 9,8E+06 | 2,3E+06 |
| | PE02 | 9407,12% | 8549,7% | 1,9E+06 | 1,7E+06 |
| | PE03 | 10464,81% | 10706,9% | 2,1E+06 | 2,1E+06 |
| | uninfected | 0,02% | 0,0% | 1,4E+02 | 0,0E+00 |

Fig. 8

| Vector System | Envelope env | relative Infectivity | | absolute infectivity | |
|---|---|---|---|---|---|
| | | Mean | StdDev | Mean | StdDev |
| HIV-1 | VSV-G | 100,00% | 3,3% | 1,9E+06 | 6,4E+04 |
| | EM002 | 0,16% | 0,1% | 3,0E+03 | 1,9E+03 |
| | EM140 | 910,40% | | 1,8E+07 | |
| | EM042 | 4,14% | 2,3% | 8,0E+04 | 4,5E+04 |
| | EM228 | 53,53% | 11,7% | 1,0E+06 | 2,3E+05 |
| | EM043 | 2,24% | 1,0% | 4,3E+04 | 1,9E+04 |
| | EM170 | 5,59% | 2,6% | 1,1E+05 | 5,1E+04 |
| | EM070 | 4,67% | 2,5% | 9,0E+04 | 4,8E+04 |
| | EM171 | 9,05% | 4,1% | 1,7E+05 | 7,9E+04 |
| MLV | VSV-G | 100,00% | 32,8% | 8,3E+04 | 2,7E+04 |
| | EM002 | 2,64% | 1,7% | 2,2E+03 | 1,4E+03 |
| | EM140 | 7794,59% | 518,2% | 6,5E+06 | 4,3E+05 |
| | EM042 | 6,69% | 3,3% | 5,6E+03 | 2,7E+03 |
| | EM228 | 573,83% | 76,3% | 4,8E+05 | 6,4E+04 |
| | EM043 | 546,16% | 125,5% | 4,6E+05 | 1,0E+05 |
| | EM170 | 1468,81% | 185,9% | 1,2E+06 | 1,6E+05 |
| | EM070 | 786,23% | 110,6% | 6,6E+05 | 9,2E+04 |
| | EM171 | 2211,23% | 250,0% | 1,8E+06 | 2,1E+05 |
| | uninfected | 0,01% | 0,0% | 1,4E+02 | 0,0E+00 |

Fig. 11

| Vector System | Envelope env | relative infectivity | | absolute infectivity | |
|---|---|---|---|---|---|
| | | Mean | StdDev | Mean | StdDev |
| HIV-1 | VSV-G | 100,00% | 9,3% | 1,9E+05 | 1,8E+04 |
| | EM140 | 1328,09% | | 2,5E+06 | |
| | EM002 | 0,22% | 0,1% | 4,1E+02 | 1,0E+02 |
| | EM236 | 813,61% | 262,4% | 1,5E+06 | 5,0E+05 |
| | EM238 | 110,39% | 46,4% | 2,1E+05 | 8,8E+04 |
| MLV | VSV-G | 100,00% | 6,3% | 5,1E+04 | 3,2E+03 |
| | EM140 | 10328,33% | | 5,3E+06 | |
| | EM002 | 2,80% | 2,0% | 1,4E+03 | 1,0E+03 |
| | EM236 | 359,02% | 161,0% | 1,8E+05 | 8,2E+04 |
| | EM238 | 607,39% | 88,1% | 3,1E+05 | 4,5E+04 |
| | uninfected | 0,08% | 0,0% | 1,4E+02 | 0,0E+00 |

Fig. 14

FOAMY VIRAL ENVELOPE GENES

FIELD OF THE INVENTION

The present invention concerns the technical field of nucleic acids and expression-optimized nucleic acids. The present invention especially concerns nucleic acids comprising a mutated foamy viral envelope gene encoding a foamy viral envelope polypeptide, which comprises a leader peptide (LP), a surface unit (SU) and a transmembrane domain (TM). The present invention also relates to modified polypeptides encoded by these nucleic acids. Furthermore, the present invention regards a method for preparing pseudotyped vector particles as well as a method for treating a genetic disorder comprising administering a nucleic acid or a polypeptide encoded by that nucleic acid.

BACKGROUND OF THE INVENTION

Gene therapy is used to insert genes into a patient's cells or tissues to treat hereditary diseases, whereby a defective mutant allele can be replaced by a functional one. Though the technology is still in its beginning and has been used with little success, it is promising for the future.

In 1990, the first approved gene therapy was performed at the U.S. National Institutes of Health on a four-year old girl. She was born with a rare genetic disease, called severe combined immunodeficiency (SCID). Children with this illness usually develop overwhelming infections and rarely survive to adulthood. In this first gene therapy, white blood cells were removed, cultivated and the missing gene was inserted into these cells. The genetically modified blood cells were reinfused into the patient's bloodstream (Anderson et al., 1990). Laboratory tests have shown that the therapy strengthened the immune system, but this procedure is not a cure. The genetically treated white blood cells only are functional for a few months, after which the procedure must be repeated.

The biology of human gene therapy is very complex, and there are many techniques that still need to be developed before gene therapy can be used appropriately. Scientists took the step of trying to introduce genes directly into human cells, focusing on diseases caused by single-gene defects, such as cystic fibrosis, hemophilia, muscular dystrophy and sickle cell anemia (Nienhuis et al., 2003). However, this has been much harder than modifying simple bacteria, primarily because of the problems involved in carrying large sections of DNA and delivering them to the correct site on the comparatively large human genome. To deliver a therapeutic gene to a patient's target cells, a carrier of genetic material, e.g. a vector must be used. The most common types of vectors are viruses that have been genetically altered to loose e.g. their pathogenity. Retroviruses are suitable carriers, because they invert the genetic flow of information by reverse transcriptase-mediated conversion of their RNA genome into DNA and physically insert their genes into the host's genome by the enzyme integrase.

However, numerous problems exist that impede gene therapy using viral vectors, such as undesired side effects. For example, it has to be ensured that the virus will infect the correct cellular target and that the inserted gene does not disrupt any vital genes in the human genome. If the transduced gene is inserted into genes regulating cell division uncontrolled cell growth, i.e. cancer can occur by activation of oncogenes (Li et al., 2002; Check, 2005). Gene therapy trials to treat SCID were halted or restricted in the USA, when leukemia was reported in three of eleven patients treated in the French Therapy X-linked SCID gene therapy trial.

Viruses have natural host cell populations that they infect most efficiently, wherein retroviruses have limited natural host cell ranges. Attachment to and entry into a susceptible cell is mediated by the envelope polypeptide on the surface of a virus. Therefore, entry into potential host cells requires a favorable interaction between a protein on the surface of the virus and a protein on the surface of the host cell. For the purposes of gene therapy, one might either want to shift, limit or expand the range of cells susceptible to transduction by a gene therapy vector. To this end, many vectors have been developed in which the endogenous viral envelope proteins have been replaced by either envelope proteins from other viruses or by chimeric proteins. Viruses in which the envelope proteins have been replaced are referred to as pseudotyped viruses. For example, a popular retroviral vector for use in gene therapy trials has been the lentiviral simian immunodeficiency virus (Li et al., 1998) as well as the human immunodeficiency virus both coated with an envelope protein from a vesicular stomatitis virus.

The foamy virus subgroup of retroviruses has attracted scientific interest, because of their unique replication strategy and their potential use as gene transfer vectors (Weiss, 1996). It has been proposed that foamy viruses may be ideal tools for the development of a gene delivery system, due to specific properties of this virus group, such as the benign course of natural foamy viral infections, their very broad host cell range, and an extended packaging limit, due to the size of the foamy virus genome (Russel and Miller, 1996; Schmidt and Rethwilm, 1995; U.S. Pat. No. 5,929,222; U.S. Pat. No. 6,111,087). However, limited availability of improved foamy virus envelope genes has so far not allowed developing methods for preparing pseudotyped viral vectors that efficiently transfer genes into a wide variety of cell types.

Therefore, there is a demand for new nucleic acids, polypeptides and methods that improve efficiency of preparing pseudotyped vector particles and improve efficiency of transduction.

The solution to this problem is achieved by the embodiments of the present invention characterized by the claims, and described further below.

SUMMARY OF THE INVENTION

It is an object of the present invention to provide a nucleic acid comprising a foamy viral envelope gene encoding a foamy viral envelope polypeptide, which comprises leader peptide (LP), surface unit (SU) and transmembrane domain (TM), the foamy viral envelope gene comprises at least one mutation, which leads on expression of the mutated foamy viral envelope gene to a modified envelope polypeptide, which comprises at least one inactivated ubiquitination site, wherein the at least one inactivated ubiquitination site is located at the TM of the modified envelope polypeptide.

Furthermore, the invention provides a polypeptide encoded by the nucleic acid comprising a foamy viral envelope gene, which comprises at least one mutation, which leads on expression of the mutated foamy viral envelope gene to a modified envelope polypeptide, which comprises at least one inactivated ubiquitination site, wherein the at least one inactivated ubiquitination site is located at the TM of the modified envelope polypeptide.

In addition, the present invention is directed to a nucleic acid comprising a foamy viral envelope gene, which comprises a sequence selected from the group consisting of SEQ ID NO: 13 (EM236), SEQ ID NO: 14 (EM238) and SEQ ID NO: 15 (EM261).

The present invention is also directed to a polypeptide encoded by the nucleic acid comprising a foamy viral envelope gene, which comprises a sequence selected from the group consisting of SEQ ID NO: 13 (EM236), of SEQ ID NO: 14 (EM238) and SEQ ID NO: 15 (EM261).

Moreover, the invention relates to a nucleic acid comprising a foamy viral envelope gene encoding a foamy viral envelope polypeptide, which comprises LP, SU and TM, the foamy viral envelope gene comprises at least one mutation, which leads on expression of the mutated foamy viral envelope gene to a modified envelope polypeptide, which comprises at least one inactivated ubiquitination site at the LP, wherein the modified envelope polypeptide further comprises at least one deletion at the N terminus.

Furthermore, the invention relates to a polypeptide encoded by the nucleic acid comprising a foamy viral envelope gene encoding a foamy viral envelope polypeptide, which comprises LP, SU and a transmembrane domain, the foamy viral envelope gene comprises at least one mutation, which leads on expression of the mutated foamy viral envelope gene to a modified envelope polypeptide, which comprises at least one inactivated ubiquitination site at the LP, wherein the modified envelope polypeptide further comprises at least one deletion at the N terminus.

In addition, the present invention concerns an expression-optimized nucleic acid comprising a foamy viral envelope gene encoding a foamy viral envelope polypeptide, the foamy viral envelope gene comprises at least one mutation, which leads on expression of the mutated foamy viral envelope gene to a modified envelope polypeptide, which comprises at least one inactivated ubiquitination site, the modified envelope polypeptide pseudotypes a viral vector for infecting at least one host cell, wherein infectivity of the pseudotyped viral vector is increased by expression-optimization up to about 50-fold compared to an non-optimized nucleic acid encoding the same modified envelope polypeptide.

In addition, the present invention is directed to a method for preparing at least one pseudotyped vector particle comprising the steps of:

a) providing at least one cell;
b) adding to the cell a non-foamy viral vector and a nucleic acid, which comprises a foamy viral envelope gene encoding a foamy viral envelope polypeptide, the foamy viral envelope gene comprises at least one mutation, which leads on expression of the mutated foamy viral envelope gene to a modified envelope polypeptide, which comprises at least one inactivated ubiquitination site; and
c) harvesting at least one pseudotyped vector particle produced by the cell.

The present invention also relates to a method for treating a genetic disorder comprising administering to a subject a nucleic acid comprising a foamy viral envelope gene comprising at least one mutation, wherein the mutation leads on expression of the mutated foamy viral envelope gene to a modified envelope polypeptide, which comprises at least one inactivated ubiquitination site.

Furthermore, the invention relates to a method for treating a genetic disorder comprising administering to a subject a polypeptide encoded by a foamy viral envelope gene comprising at least one mutation, wherein the mutation leads on expression of the mutated foamy viral envelope gene to a modified envelope polypeptide, which comprises at least one inactivated ubiquitination site.

BRIEF DESCRIPTION OF THE FIGURES

In FIGS. 5 and 6 absolute and relative infectivities of vectors including wt env and modified env compared to vectors including vesicular stomatitis virus G protein (VSV-G) are shown. Env was used to pseudotype prototype foamy virus (PFV), murine leukemia virus (MLV) and human deficiency virus 1 (HIV-1). Relative infectivities are normalized to VSV-G for MLV and HIV-1 and to PVF env wt for PFV vectors, and absolute infectivities are indicated as focus-forming units per ml (ffu/ml) by means of enhanced green fluorescent protein (EGFP).

In FIGS. 7 and 8 absolute and relative infectivities of vectors including wt env, modified env and expression-optimized env compared to vectors including VSV-G are shown.

In FIGS. 10 and 11 absolute and relative infectivities of vectors including wt env, modified env comprising deletions compared to vectors including VSV-G are shown.

In FIGS. 13 and 14 absolute and relative infectivities of vectors including wt env, modified env and modified env comprising fluorescent proteins compared to vectors including VSV-G are shown.

In FIG. 20 the gene transfer rate is indicated by GFP positive cells measured by fluorescent activated cell sorting (FACS), and in FIG. 21 the gene transfer rate is indicated by GFP positive colonies measured by a progenitor assay.

DETAILED DESCRIPTION OF THE INVENTION

It is an object of the present invention to provide a nucleic acid comprising a foamy viral envelope gene encoding a foamy viral envelope polypeptide, which comprises leader peptide (LP), surface unit (SU) and a transmembrane domain (TM), the foamy viral envelope gene comprises at least one mutation, which leads on expression of the mutated foamy viral envelope gene to a modified envelope polypeptide, which comprises at least one inactivated ubiquitination site, wherein the at least one inactivated ubiquitination site is located at the transmembrane domain of the modified envelope polypeptide.

The term "nucleic acid" as used herein refers to a macromolecule composed of monomeric nucleotides, wherein nucleic acids include amongst others deoxynucleic acids (DNA); ribonucleic acids (RNA); artificial nucleic acids, like peptide nucleic acid (PNA) and glycolic nucleic acid (GNA); single stranded nucleic acids and double stranded nucleic acids.

Figure 1:
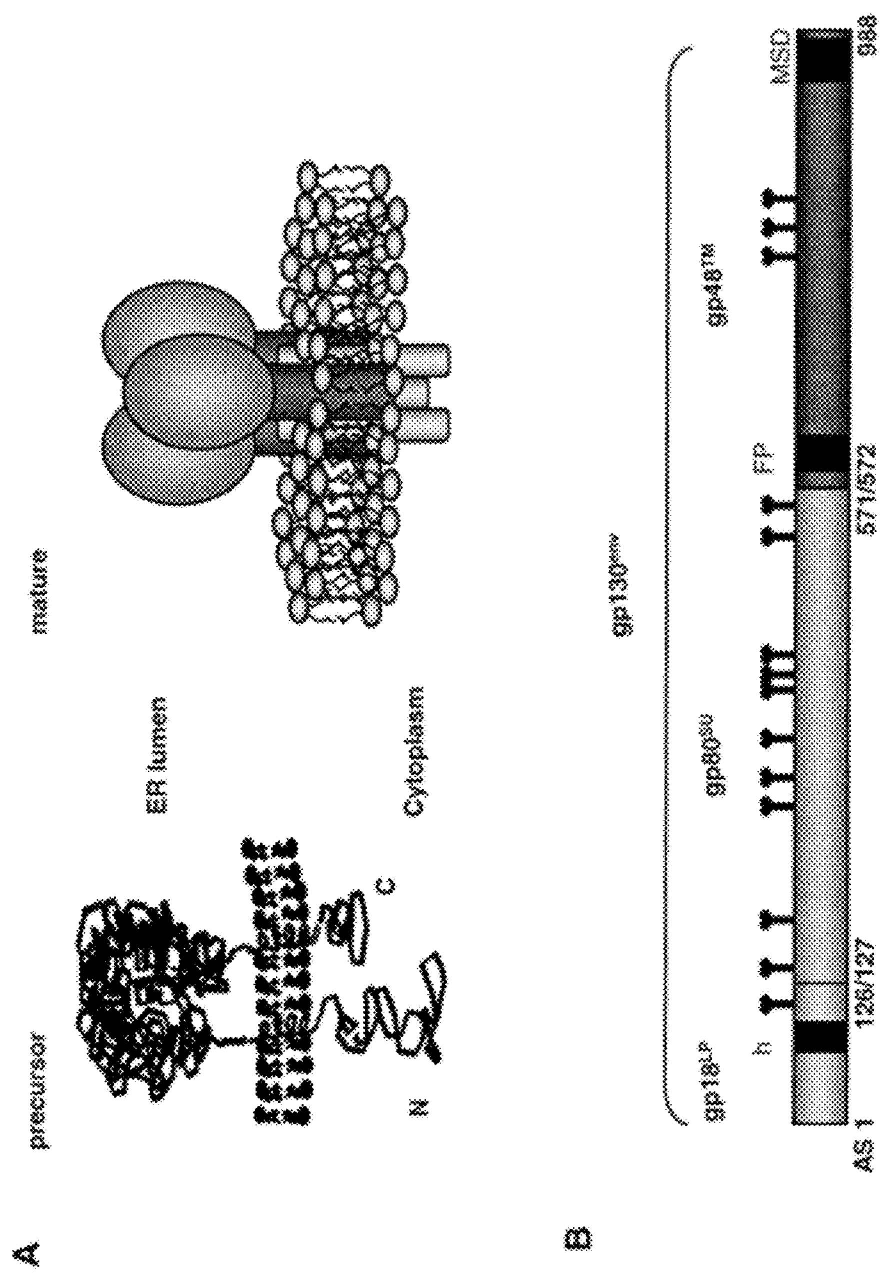
FIG. 1A shows the putative membrane topology of a precursor and a mature foamy viral envelope polypeptide (env) inserted into the cell membrane.
FIG. 1B shows the domain organization of a foamy viral env including LP (glycoprotein (gp) 18), SU (gp80) and TM (gp48) according to the prior art.

The term "envelope gene" as used herein refers to a foamy viral sequence encoding an envelope polypeptide (env), which is a glycoprotein that forms prominent surface spikes within the viral envelope. Env is a trimeric complex with a highly unusual biosynthesis among retroviral glycoproteins. It is translated as a full length precursor protein into the rough endoplasmatic reticulum (ER) and initially has a type II protein conformation with both its N and C termini located intracytoplasmatically (FIG. 1A). During its transport to the cell surface it is postranslationally processed by cellular proteases into three subunits. Env is responsible for the foamy viral host tropism and is also found on the surface of transduced cells. Binding of env to a specific receptor on the host cell's membrane leads to a conformational change of env and finally to a fusion of viral envelope and cell membrane. In contrast to other retroviral envelope proteins, foamy viral env is essential for budding, it carries an ER-retrieval signal for retention in the ER, and its LP is not processed by a signal peptide complex, but by a furin or furin like protease. A foamy viral env is an envelope polypeptide from a foamy virus or an envelope polypeptide derived from an envelope polypeptide from a foamy virus. FIG. 1A shows the putative membrane topology of the precursor and the mature env inserted into the cell membrane. FIG. 1B shows the domain organization of PFV env with LP, SU and TM from amino acid position 1 (AS 1) to 988.

The term "leader peptide" (LP) as used herein refers to a foamy viral N terminal signal sequence that comprises two polar domains and an intermediate hydrophobic domain. In contrast to other retroviral signal sequences, LP is essential for morphogenesis, infectivity and release of vector particles, wherefore coexpressed env and gag interact specifically with each other via a so-called budding region in LP.

The term "surface unit" (SU) as used herein refers to a domain of env that is located at an exposed position at a cell surface. The SU comprises the major immunogenic epitope responsible for receptor specific binding of a foamy viral vector particle to a host cell. Typically, the SU shows a globular structure that is linked to the extracellular domain of the TM.

The term "transmembrane domain" (TM) as used herein refers to a domain of env that completely or partly spans a biological membrane to anchor the peptide within the membrane and to retain the peptide within the cell. The TM comprises among others a fusion peptide (FP) and a membrane spanning domain (MSD) that are both essential for the fusion of viral and host membranes. MSD also plays a role in the release of vector particles.

The term "mutation" as used herein refers to a change or an amendment of a particular nucleotide sequence of a nucleic acid. The mutation includes small-scale mutations, like point mutations, single nucleotide exchanges, insertions, deletions as well as large scale mutations, like amplifications, deletions of larger regions, translocations and inversions. Included are also loss- and gain-of-function mutations, antimorphic, lethal and conditional mutations.

The term "ubiquitination" as used herein refers to a post-translational covalent linking of a polypeptide to ubiquitin by a lysine-dependent or lysine-independent process. Ubiquitin can be linked as a monomer, as oligomeric chains or cross-linked oligomers. The process of ubiquitination can comprise an activation of ubiquitin, its transfer to the binding site, and its linking to the polypeptide. The ubiquitination site is the location of the polypeptide, where ubiquitin can be linked to, like a lysine residue. The term "ubiquitination site" also comprises locations, where ubiquitin can potentially be coupled to, but physiologically no ubiquitination occurs, e.g. the ubiquitination sites in TM env (Stanke et al., 2005). If the ubiquitination site of a polypeptide is inactivated, it is no longer possible to couple ubiquitin to this polypeptide. This can be due to a failure in the mechanism of the ubiquitination or preferably the lack of a binding site or a specific binding site. The function of ubiquitination is manifold. It can be a signal for polypeptide degradation, preservation or a label for polypeptide endocytosis. Viruses like the Kaposi sarcoma associated herpes virus can use the ubiquitination system of a cell for their own benefits as degradation signal for immune relevant factors e.g. an interferon regulation factor.

The term "polypeptide" as used herein refers to a polymer that comprises multiple amino acids linked by peptide bonds regardless of length and conformation. Therefore, the term "polypeptide" includes chains of several amino acids, oligomers, polymers as well as proteins. Non-amino acid units, like steroids or carbohydrates, linked to the polypeptide can also be included.

Viral vectors transduce limited amounts of host cells. Attachment to and entry into a susceptible cell are mediated by the polypeptide envelope on the surface of a virus. Foamy viral envelopes comprise env inserted into their membrane. This env binds to a host's cell-surface receptor that is unknown up to now - possibly an ubiquitary receptor as heparin sulfate—wherein the vector particle is localized upon the surface of the potential host. For the purposes of gene transfer, it is desirable to expand the amount of transduced cells and to increase infectivity of vector particles. The present invention provides a new nucleic acid comprising a mutated foamy viral envelope gene encoding a modified env, in which at least one inactivated ubiquitination site is located at the transmembrane domain of the modified envelope polypeptide.

In Stanke et al. (2005) the role of certain modified env in glycoprotein function and foamy viral replication is investigated. The modified env of this publication show inactivated ubiquitination sites within the LP. In contrast to Stanke et al.

(2005), the modified env according to the invention shows inactivated ubiquitination sites in the TM of the polypeptides. Stanke et al. (2005) describe that no ubiquitination of other PFV env domains than LP is observed. In particular, for TM containing at least four additional lysine residues, i.e. potential ubiquitination sites in its C terminal cytoplasmic tail no ubiquitination can be shown. LP and TM are different domains of env that are located at antipodal ends of the precursor polypep-tide. The LP has a type II conformation, whereas the TM subunit has a type I conformation and associates with the SU on the luminal side. For a foamy viral budding process the contact of LP containing an essential, conserved WXXW sequence motif with the N terminus of the foamy viral gag protein is an essential interaction (Wilk et al., 2001; Lindemann at al., 2001). Most probably due to the crucial interaction between capsid and foamy viral env LP, this cleavage product is particle associated. In contrast to LP, TM is responsible for fusion with the host's membrane, anchoring within the viral membrane as well as retrieval and retention in the ER. Therefore, these findings demonstrate the functional uniqueness of LP.

In spite of Stanke et al. (2005) describe no ubiquitination of other PFV env domains than LP during budding, the inventors were surprisingly able to considerably improve infectivity of viral vectors enveloped or pseudotyped by foamy viral env according to the invention, wherein at least one ubiquitination site of env is inactivated at TM.

Figure 5:
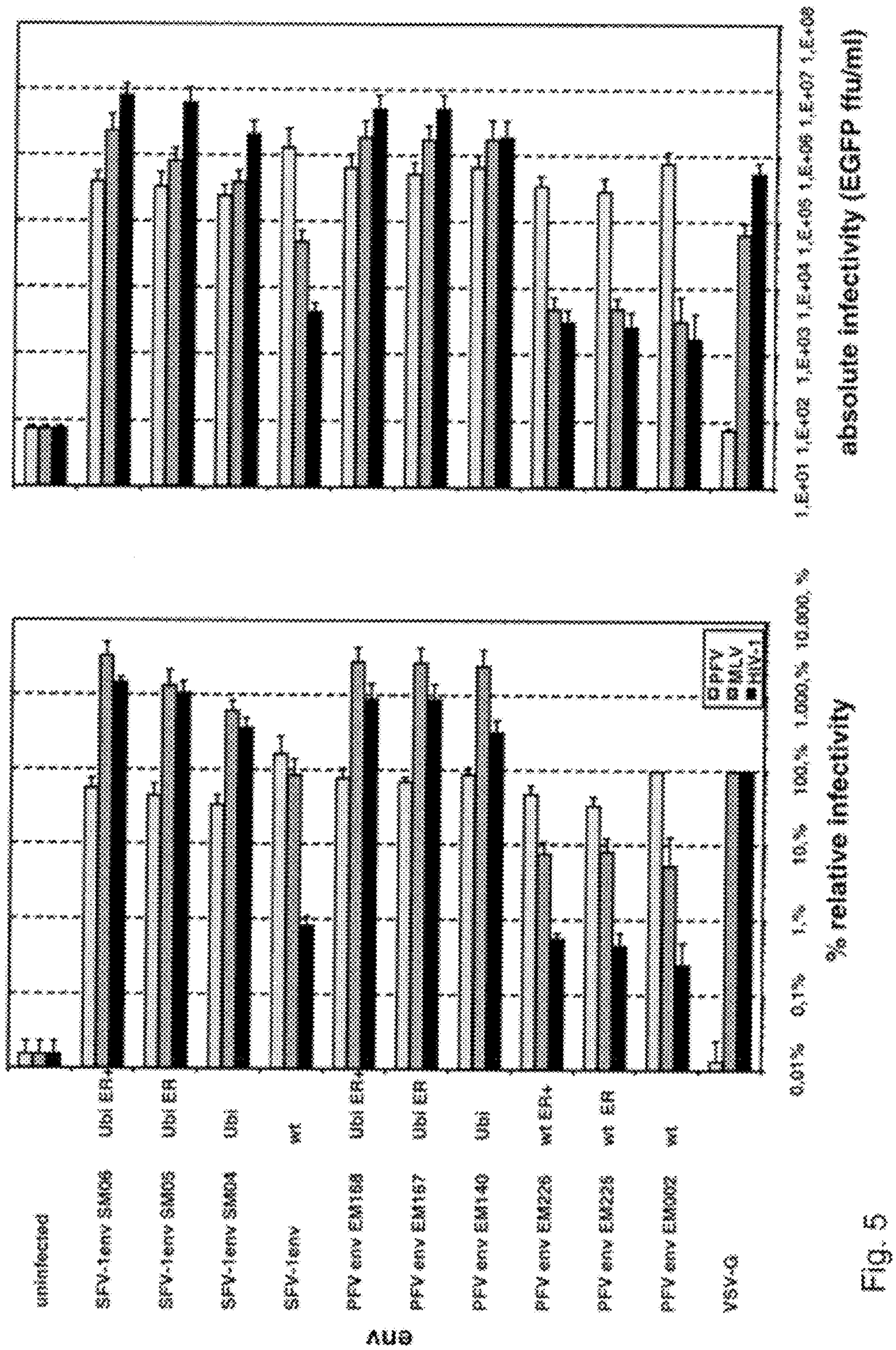

The modified env according to the invention, which comprises at least one inactivated ubiquitination site located at the TM of the modified envelope polypeptide were used to pseudotype different types of vectors that were applied to eukaryotic cells. The measured infectivities of these vectors pseudotyped by modified env were increased due to the inactivated ubiquitination site located at the TM of the modified env. As can be seen in FIGS. 5 and 6 the infectivities of vectors including env comprising at least one inactivated ubiquitination site located at the TM, like env EM225 and env EM226, compared to wt env were increased about 2-times. The infectivities of vectors comprising env with at least one inactivated ubiquitination site located at TM and an inactivated ubiquitination site located at the LP, like env EM167, EM168, SM05 and SM06, compared to env comprising at least one inactivated ubiquitination site located at LP, like env EM140 and env SM04, were increased up to 5-times. Therefore, the efficiency of viral transduction and gene transfer is raised by the modified env according to the invention.

In a preferred embodiment of the invention the mutation of the foamy viral envelope gene, which leads on expression of the mutated foamy viral envelope gene to a modified envelope polypeptide, which comprises at least one inactivated ubiquitination site located at the transmembrane domain of the modified envelope polypeptide, leads on expression of the foamy viral envelope gene to a lysine exchange in the envelope polypeptide.

In a further preferred embodiment of the invention lysine is exchanged against an amino acid selected from the group consisting of alanine, histidine, glycine and arginine. Arginine and histidine are positively charged amino acids like lysine. Glycine and alanine posses uncharged side chains.

The exchange of the amino acid lysine against another amino acid removes the lysine binding site of ubiquitin, whereby the ubiquitination site is inactivated, i.e. the env cannot be ubiquitinated at these exchanged amino acid sites. On the level of the env gene all possible base triplets encoding lysine can be exchanged with all possible base triplets encoding arginine, glycine, histidine and alanine.

In another preferred embodiment of the invention the mutation of the foamy viral envelope gene, which leads on expression of the mutated foamy viral envelope gene to a modified envelope polypeptide, which comprises at least one inactivated ubiquitination site located at the transmembrane domain of the modified envelope polypeptide, leads on expression of the foamy viral envelope gene to a modification of the envelope polypeptide at an amino acid position selected from the amino acid positions 952 to 988, and amino acid position 1 is the first amino acid of the N terminus of the envelope polypeptide.

Figure 25:
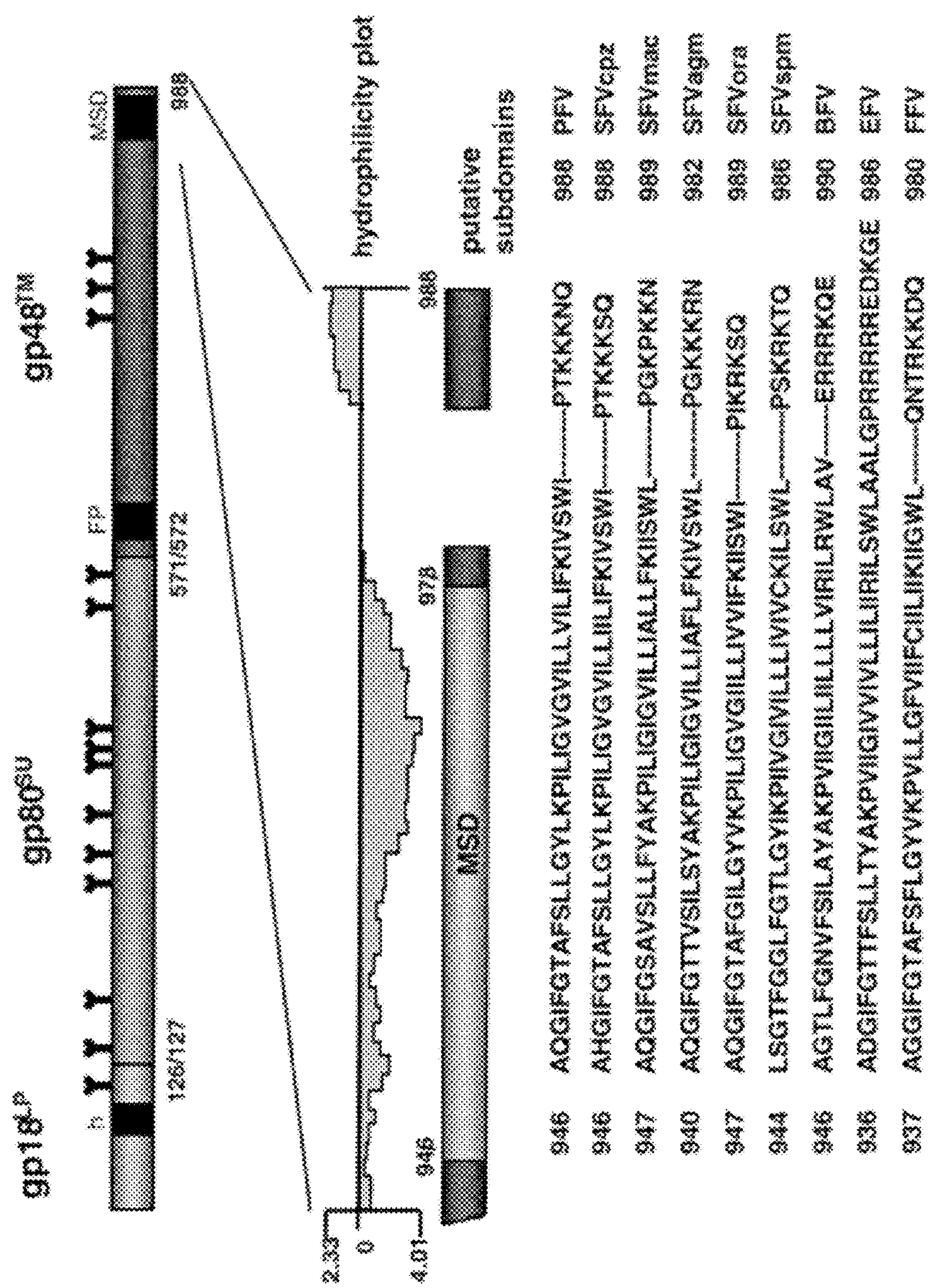
FIG. 25 gives an overview of the domain organization of foamy viral env and an expanded view of different N terminal TM sequences of env derived from foamy viruses infecting different hosts, like cats, cattle, horses etc. Homologue lysine residues of env are indicated by K.

The counting of the amino acids begins with amino acid position 1 at the N terminus of the polypeptide and ends with the highest amino acid position, e.g. in FIG. 1B with position 988, at the C terminus of the polypeptide. In the most preferred embodiment of the invention the mutation leads on expression of the foamy viral envelope gene to a modification of the envelope polypeptide at an amino acid position including 951, 952, 955, 959, 960, 961, 962, 968, 969, 972, 976 to 982 and 984 to 988. In another preferred embodiment of the invention the mutation leads on expression of the foamy viral env gene to a modification of the envelope polypeptide at lysine residues in TM of PFV env, human foamy viral env, bovine foamy viral env, equine foamy viral env, feline foamy viral env, SFV chimpanzee env, SFV macaque env, SFV African green monkey env, SFV orangutan env, SFV spider monkey env or homologues, i.e. functional equivalent ubiquitination sites in TM of other foamy viral env, e.g. derived from other species (FIG. 25).

In another preferred embodiment of the invention the mutated foamy viral envelope gene, which leads on expression to a modified envelope polypeptide, which comprises at least one inactivated ubiquitination site located at TM of the modified envelope polypeptide, comprises at least one second mutation, which is located at the LP of the modified envelope polypeptide.

In a further preferred embodiment the second mutation leads on expression of the foamy viral envelope gene to a modification of the envelope polypeptide at an amino acid position selected from the amino acid positions 14 to 55, and amino acid position 1 is the first amino acid of the N terminus of the envelope polypeptide. In the most preferred embodiment of the invention the second mutation leads on expression of the foamy viral envelope gene to a modification of the envelope polypeptide at an amino acid position selected from the group consisting of amino acid positions 14, 15, 18, 34, 53 and 55.

In another preferred embodiment of the invention the mutated foamy viral envelope gene, which leads on expression to a modified envelope polypeptide, which comprises at least one inactivated ubiquitination site located at TM of the modified envelope polypeptide, comprises a sequence selected from the group consisting of SEQ ID NO: 1 (EM167), SEQ ID NO: 2 (EM168), SEQ ID NO: 3 (EM225), SEQ ID NO: 4 (EM226), SEQ ID NO: 5 (SM05), SEQ ID NO: 6 (SM06), SEQ ID NO: 8 (PE02), SEQ ID NO: 9 (PE03), SEQ ID NO: 11 (SE02) and SEQ ID NO: 12 (SE03).

The mutated foamy viral envelope genes, which comprise a sequence selected from the group consisting of SEQ ID NO: 1 (EM167), SEQ ID NO: 2 (EM168), SEQ ID NO: 3 (EM225), SEQ ID NO: 4 (EM226), SEQ ID NO: 5 (SM05), SEQ ID NO: 6 (SM06), SEQ ID NO: 8 (PE02), SEQ ID NO: 9 (PE03), SEQ ID NO: 11 (SE02) and SEQ ID NO: 12 (SE03), encode the corresponding modified polypeptide selected from the group consisting of env EM167, env EM168, env EM225, env EM226, env SM05, env SM06, env PE02, env PE03, env SE02 and env SE03.

Figure 2:
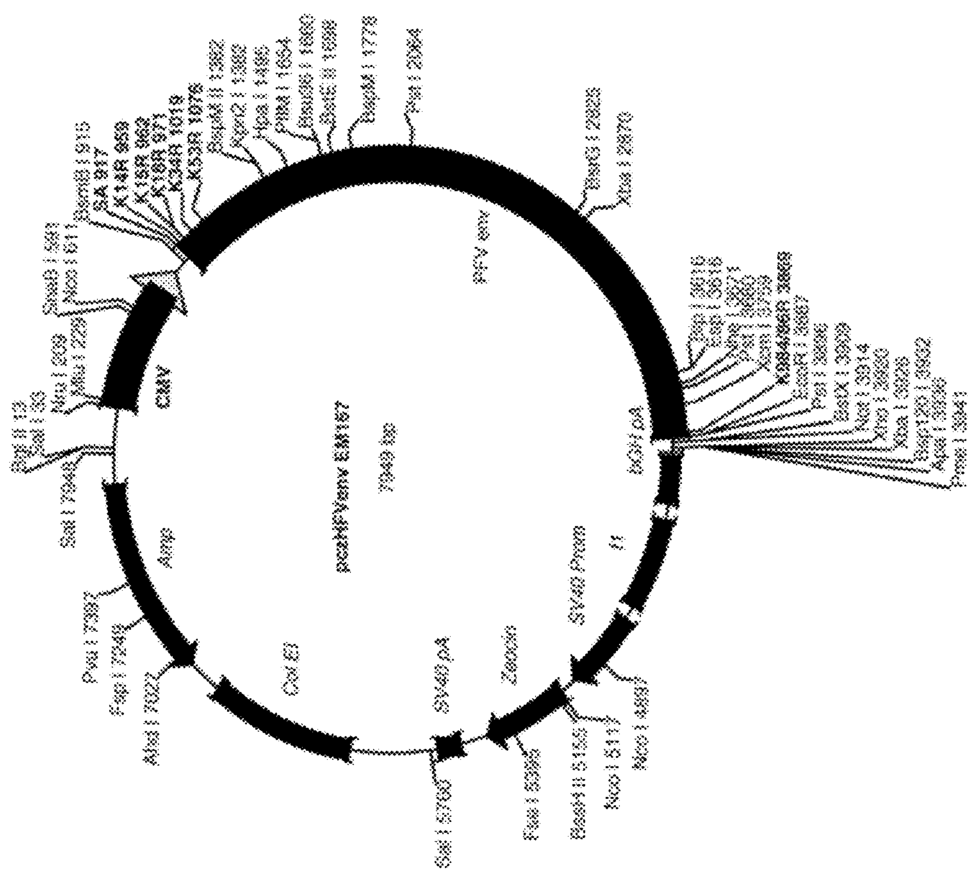
FIG. 2 displays a pcz human foamy viral vector (HFV) with a coding domain of env EM167.
Figure 3:
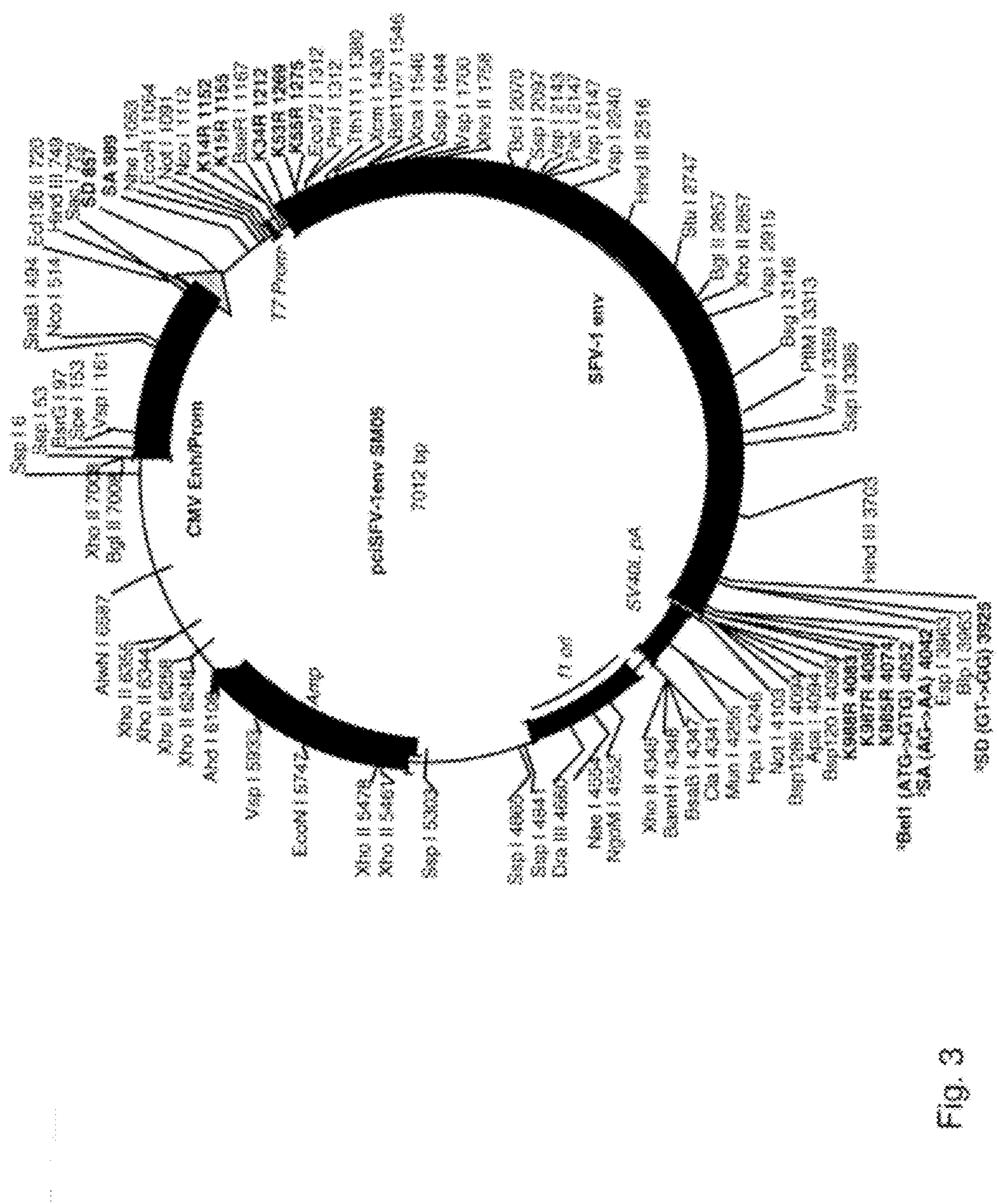
FIG. 3 displays a pci simian foamy viral (SFV) 1 vector with a coding domain of env SM05.
Figure 4:
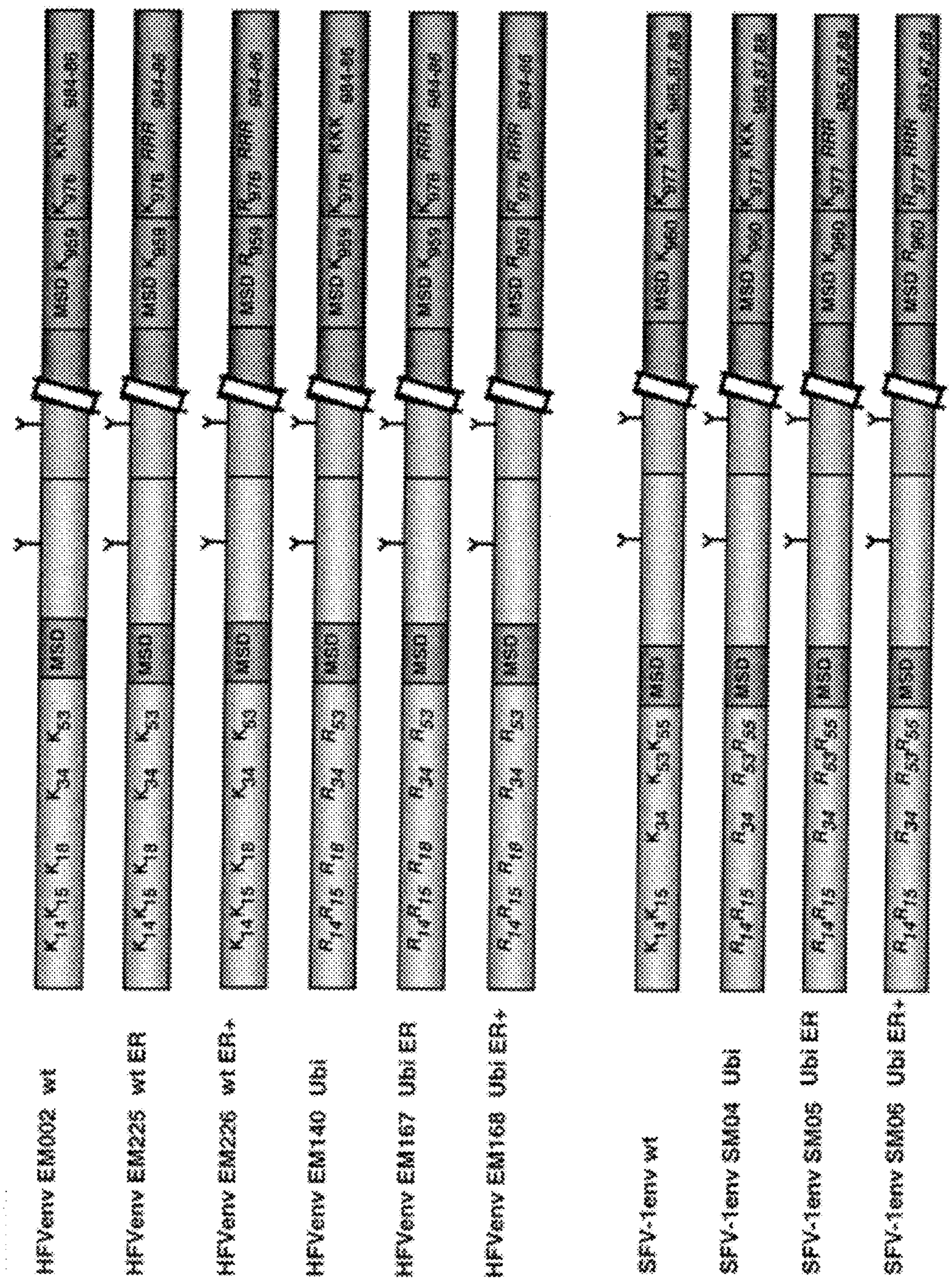
FIG. 4 shows wild type (wt) env and a selection of its different modifications. The encoding env genes were cloned in pczHFV or pciSFV-1 vectors as indicated. Amino acids resulting from a mutation are indicated as R instead of K. The open rectangle is a replacement character for sequences that are not displayed. Y indicates glycosylation.

The modified env of this preferred embodiment as well as the corresponding wt env are shown in FIG. 2 encoded by mutated HFV env genes and SFV-1 env genes. In env EM225, env EM226, env EM167, env EM168, and also in env PE02 and env PE03 the mutations cause modifications in TM of the expressed env at amino acid positions 984 to 986, also called ER modifications, and/or at amino acid positions 959 and 976, also called ER+ modifications. In env SM05, env SM06 and also in env SE02, env SE03, the mutations cause modifications in TM of the expressed env at amino acid positions 985, 987 and 988, also called ER modifications, and/or at amino acid positions 960 and 977, also called ER+ modifications.

HFV env EM167, env EM168, env PE02 and env PE03 possess additional modifications in LP at amino acid positions 14, 15, 18, 34 and 53 similar as in env EM140, and SFV-1 env SM05, env SM06, env SE02 and env SE03 possess additional modifications in LP at amino acid positions 14, 15, 34, 53 and 55 similar as in env SM04. Modifications in LP are also called Ubi modifications. Env EM002 is the human wt polypeptide, and env wt is the simian wt polypeptide.

The present invention is also directed to a polypeptide encoded by the nucleic acid comprising a foamy viral envelope gene encoding a foamy viral envelope polypeptide, which comprises a leader peptide, a surface unit and a transmembrane domain, the foamy viral envelope gene comprises at least one mutation, which leads on expression of the mutated foamy viral envelope gene to a modified envelope polypeptide, which comprises at least one inactivated ubiquitination site, wherein the at least one inactivated ubiquitination site is located at the transmembrane domain of the modified envelope polypeptide. The polypeptide can be expressed in an expression system or can be synthesized artificially.

The present invention further relates to a nucleic acid comprising a foamy viral envelope gene, which comprises a sequence selected from the group consisting of SEQ ID NO: 13 (EM236), SEQ ID NO: 14 (EM238) and SEQ ID NO: 15 (EM261).

These fusion genes comprising a sequence selected from the group consisting of SEQ ID NO: 13 (EM236), of SEQ ID NO: 14 (EM238) and SEQ ID NO: 15 (EM261) encode corresponding env polypeptides env EM236, env EM238 and env EM261, respectively.

The present invention relates also to a polypeptide encoded by a nucleic acid comprising a foamy viral envelope gene, which comprises a sequence selected from the group consisting of SEQ ID NO: 13 (EM236), SEQ ID NO: 14 (EM238) and SEQ ID NO: 15 (EM261).

Figure 12:
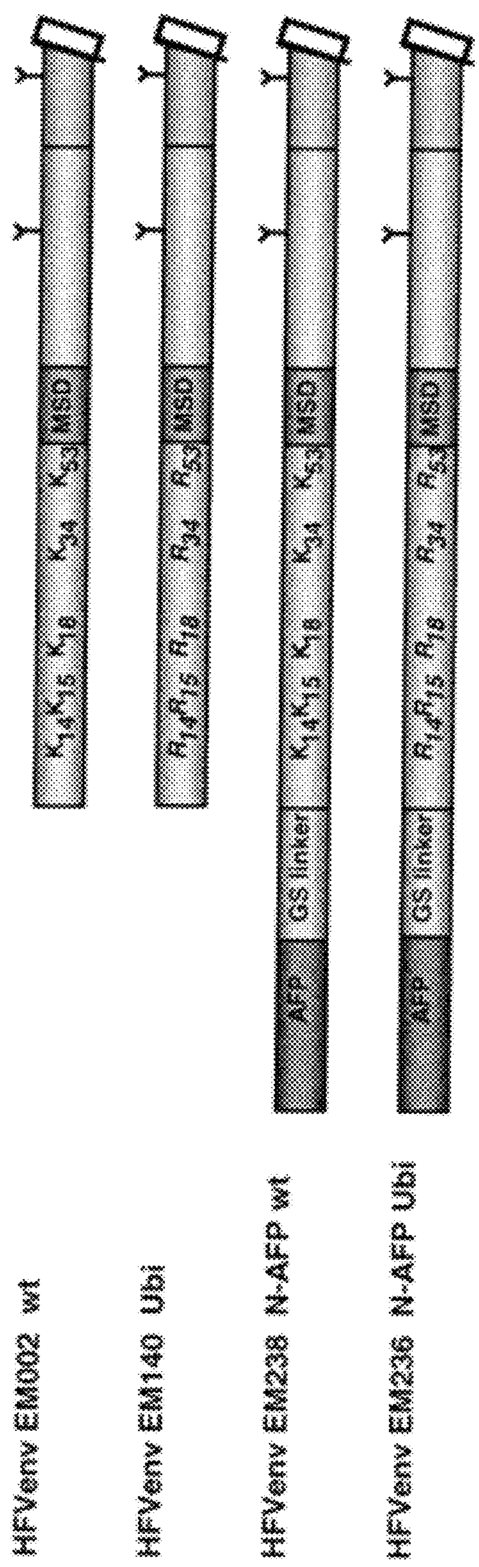
FIG. 12 shows a wt env gene and a selection of its different modified env comprising glycine-serine linked fluorescent proteins.
Figure 13:
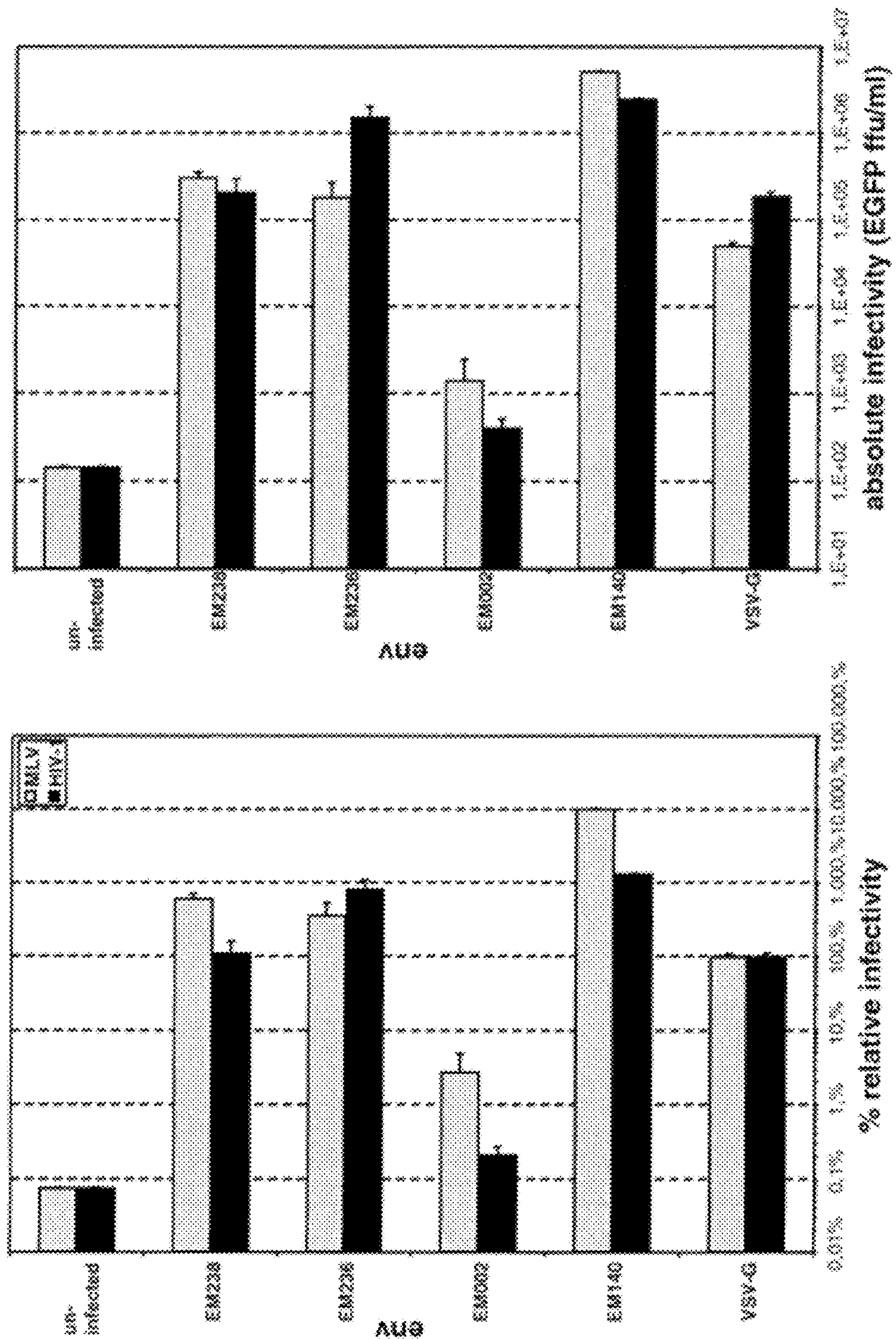
Figure 15:
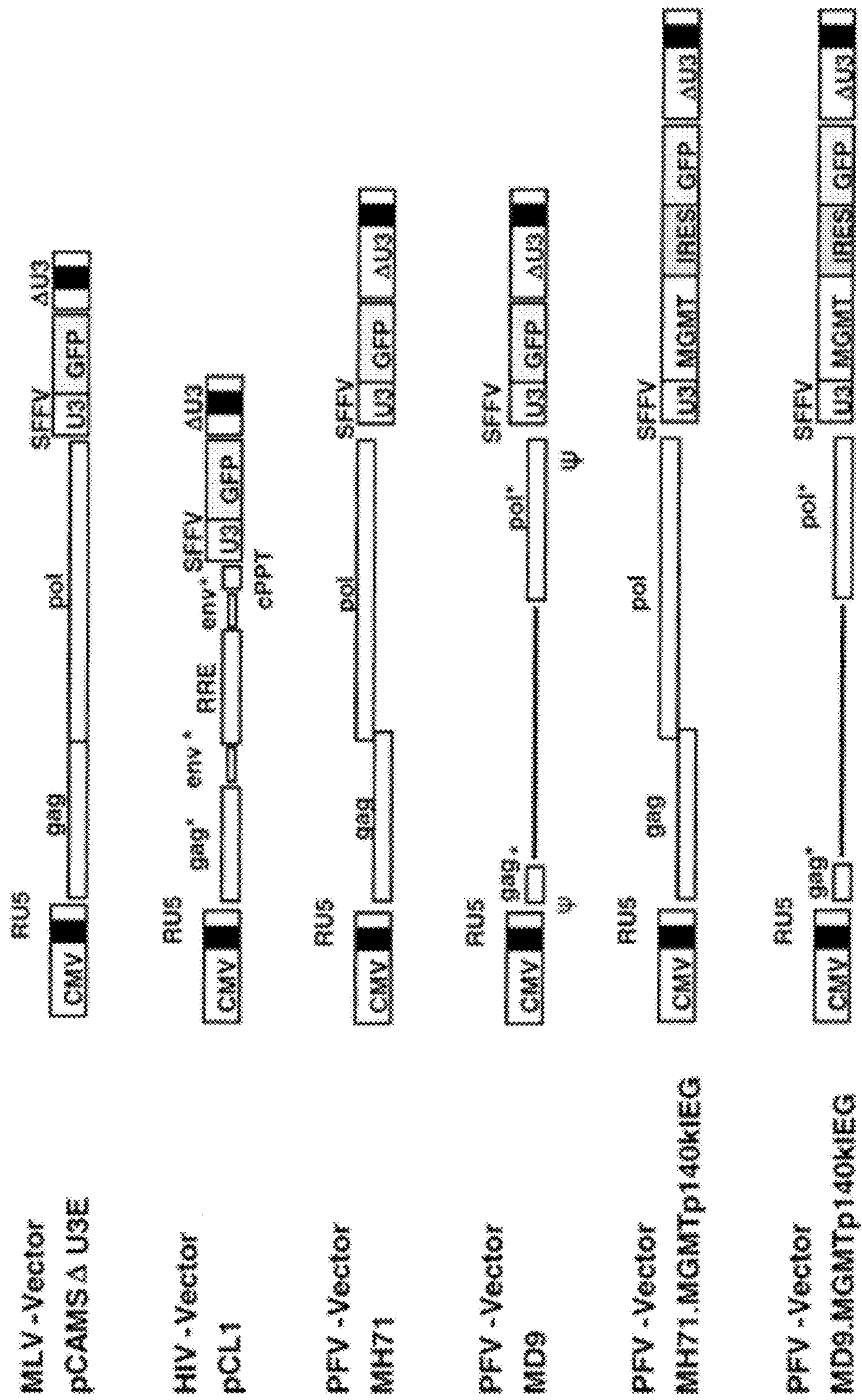
FIG. 15 exemplifies a selection of vectors used among others in the invention for preparing pseudotyped vector particles.
Figure 16:
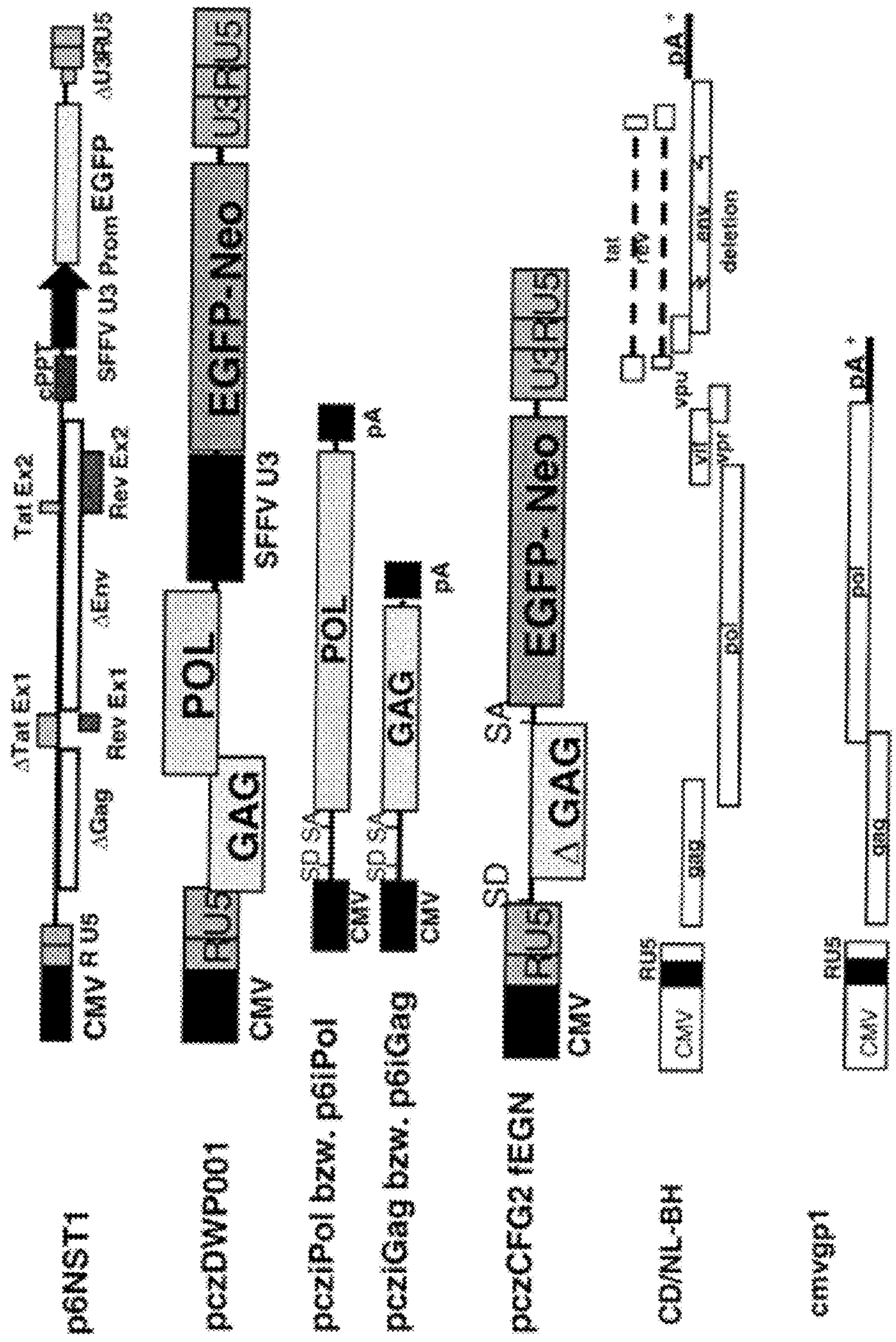
FIG. 16 exemplifies a selection of expression constructs used in the invention for preparing pseudotyped vector particles.

An overview of the polypeptides env EM236 and env EM238 is given in FIG. 12. The polypeptides env EM236 and env EM238 are fusion polypeptides comprising an N terminal fluorescent mCherry coupled to the env EM140 and env EM002, respectively, via a glycine-serine linker. The polypeptide env EM261 is a fusion polypeptide comprising an N terminal enhanced yellow fluorescent protein coupled to the env EM002 also via a glycineserine linker. The glycine-serine linker has the favorable effect of a spacer, so that the fluorescent polypeptide and the env convolute independently. This is necessary for env to fulfill its physiological function. Infectivities of vector particles pseudotyped by fluorescent env EM236 or env EM238 demonstrated by FIGS. 13, 14 are up to about 8-times higher compared to the same vector particles pseudotyped by VSV-G. Therefore, vector particles pseudotyped by fluorescent env according to the invention very efficiently transfer nucleic acids into host cells. The fluorescent env can be expressed in an expression system or synthesized artificially.

By means of env EM236, env EM238 or env EM261 vector particles, transduced cells and the fluorescent polypeptides themselves, e.g. expressed within the host cell, can be visualized and tracked in a system, like an organism, a cell culture or a single cell by an imaging technique, like fluorescent microscopy.

The present invention also concerns a nucleic acid comprising a foamy viral envelope gene encoding a foamy viral envelope polypeptide, which comprises a leader peptide, a surface unit and a transmembrane domain, the foamy viral envelope gene comprises at least one mutation, which leads on expression of the mutated foamy viral envelope gene to a modified envelope polypeptide, which comprises at least one inactivated ubiquitination site at the leader peptide, wherein the modified envelope polypeptide further comprises at least one deletion at the N terminus.

The term “deletion” as used herein refers to a loss of a part of a polypeptide. Any number of amino acids can be deleted, from a single amino acid up to an entire piece of a polypeptide, e.g. a subunit or domain.

Figure 10:
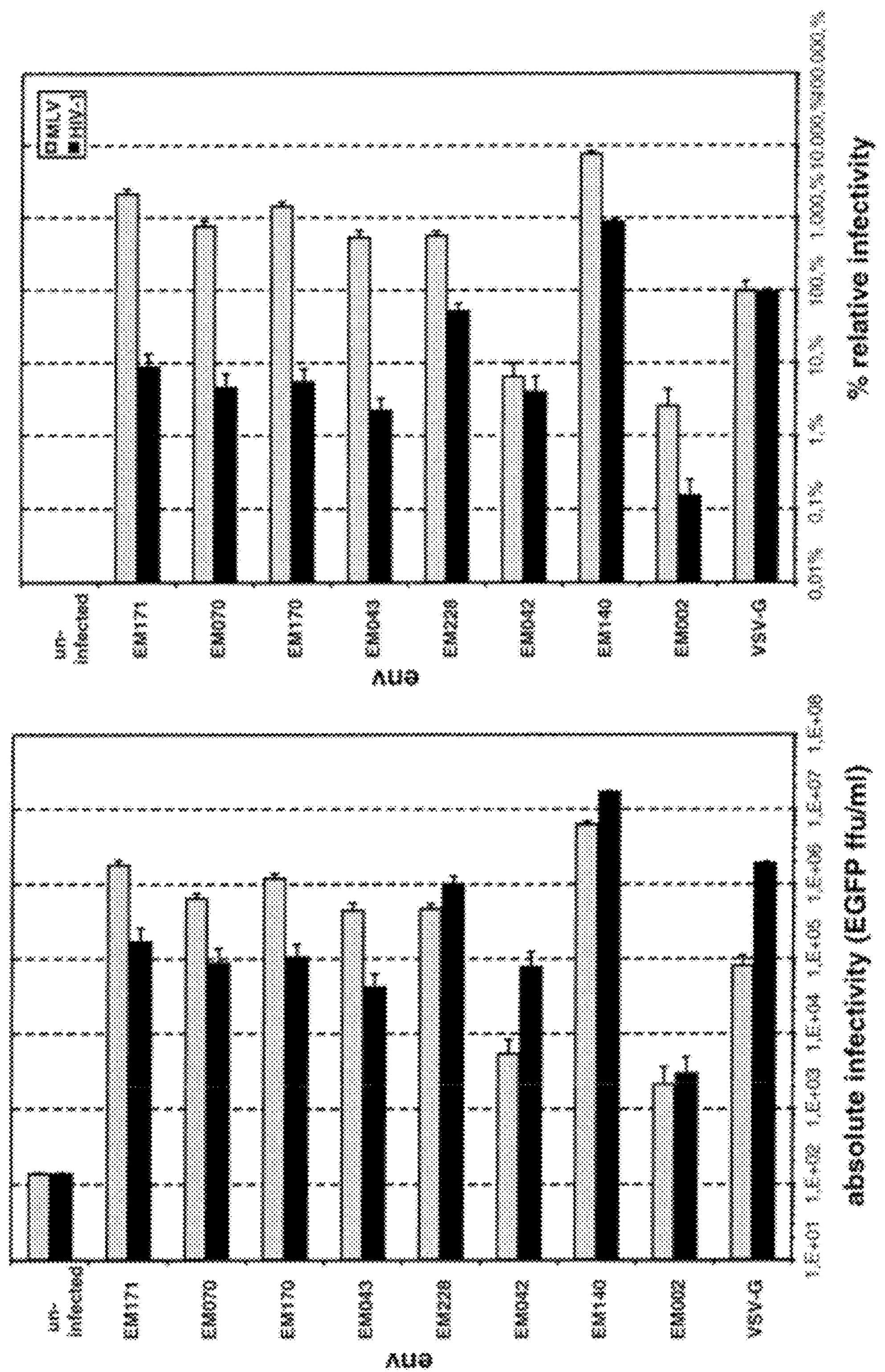

The modified env according to the invention, which comprises the deletion were used to pseudotype different types of vectors that were applied to eukaryotic cells. The measured infectivities of these vectors pseudotyped by env comprising the deletion are increased significantly due to the deletion. As can be seen in FIGS. 10 and 11 the infectivities of env EM170, env EM171 and env EM228 compared to the corresponding full length env EM043, env EM070 and env EM042 increased about 3-times, up to about 3-times and up to about 84-times, respectively. Therefore, the efficiency of viral transduction and gene transfer is raised by the env comprising the deletion according to the invention.

In a preferred embodiment of the invention the deletion of the modified envelope polypeptide comprises 5 to 25 amino acids. Hence, the preferred modified envelope polypeptide is 5 to 25 amino acids shorter than a full length wt env.

In another preferred embodiment of the invention the foamy viral envelope gene comprises at least one mutation, which leads on expression of the mutated foamy viral envelope gene to a modified envelope polypeptide, which comprises at least one inactivated ubiquitination site at the leader peptide, wherein the modified envelope polypeptide further comprises at least one deletion at the N terminus and wherein the mutation leads on expression of the foamy viral envelope gene to a lysine exchange in the envelope polypeptide.

In a further preferred embodiment of the invention lysine is exchanged against an amino acid selected from the group consisting of alanine, histidine, glycine and arginine.

In a further preferred embodiment of the invention the foamy viral envelope gene comprises at least one mutation, which leads on expression of the mutated foamy viral envelope gene to a modified envelope polypeptide, which comprises at least one inactivated ubiquitination site at the leader peptide, wherein the modified envelope polypeptide further comprises at least one deletion at the N terminus and wherein the mutation leads on expression to a modification of the envelope polypeptide at an amino acid position selected from the amino acid positions 14 to 55, amino acid position 1 is the first amino acid of the N terminus of the envelope polypeptide. In the most preferred embodiment of the invention the mutation leads on expression of the foamy viral envelope gene to a modification of the envelope polypeptide at an amino acid position selected from the group consisting of amino acid positions 14, 15, 18, 34, 53 and 55.

In yet another preferred embodiment of the invention the nucleic acid comprising a foamy viral envelope gene, which comprises at least one mutation, which leads on expression of the mutated foamy viral envelope gene to a modified envelope polypeptide, which comprises at least one inactivated ubiquitination site at the leader peptide, wherein the modified envelope polypeptide further comprises at least one deletion at the N terminus, comprises a sequence selected from the group consisting of SEQ ID NO: 16 (EM170), SEQ ID NO: 17 (EM171) and SEQ ID NO: 18 (EM228).

Figure 9:
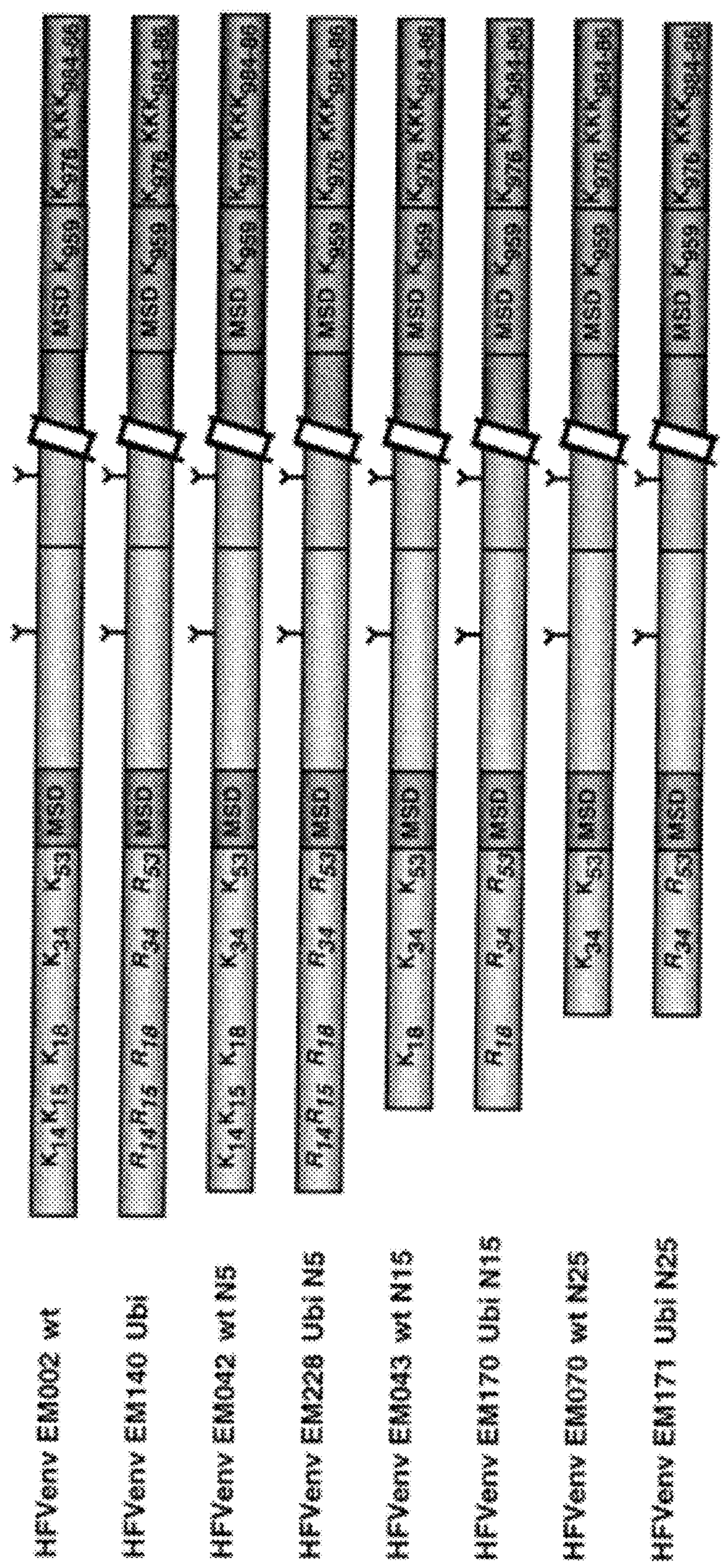
FIG. 9 shows a wt env gene and a selection of its different modified env comprising deletions.

The env genes comprising a sequence selected from the group consisting of SEQ ID NO: 16 (EM170), SEQ ID NO: 17 (EM171) and SEQ ID NO: 18 (EM228) encode corresponding polypeptides env EM170, env EM171 and env EM228, respectively. Env EM170, env EM171 and env EM228 as well as their corresponding wt and/or full length polypeptides env EM002, env EM140, env EM042, env EM043, env EM070 are displayed in FIG. 9.

The present invention relates also to a polypeptide encoded by the nucleic acid comprising a foamy viral envelope gene encoding a foamy viral envelope polypeptide, which comprises a leader peptide, a surface unit and a transmembrane domain, the foamy viral envelope gene comprises at least one mutation, which leads on expression of the mutated foamy viral envelope gene to a modified envelope polypeptide, which comprises at least one inactivated ubiquitination site at the leader peptide, wherein the modified envelope polypeptide further comprises at least one deletion at the N terminus. The modified env comprising a deletion can be expressed in an expression system or can be synthesized artificially.

The present invention is also directed to an expression-optimized nucleic acid comprising a foamy viral envelope gene encoding a foamy viral envelope polypeptide, the foamy viral envelope gene comprises at least one mutation, which leads on expression of the mutated foamy viral envelope gene to a modified envelope polypeptide, which comprises at least one inactivated ubiquitination site, the modified envelope polypeptide pseudotypes a viral vector for infecting at least one host cell, wherein infectivity of the pseudotyped viral vector is increased by expression-optimization up to about 50-fold compared to a non-optimized nucleic acid encoding the same modified envelope polypeptide.

The term "expression-optimized" as used herein refers to an alteration of genetic code, codons in the gene or coding regions of nucleic acids, so that the genetic code and the codons are more suitable for the expression system of the host organism, e.g. primates, with-out altering the amino acids encoded by the nucleic acid. The term "expression-optimized" includes among others codon-optimization, i.e. a gene's frequency of codon usage is designed to mimic the frequency of preferred codon usage of the host cell. The term also includes avoiding internal TATA-boxes, chi-sites and ribosomal entry sites; AT-rich or GC-rich sequence stretches; ARE, INS, CRS sequence elements; repeat sequences and RNA secondary structures; splice donor and acceptor sites, branch points.

The term "vector" as used herein refers to a vehicle for transferring genetic material into a cell, wherein plasmids, viral vectors, cloning vectors, expression vectors, transcription vectors, artificial particles and artificial chromosomes are included. The vector comprises double or single stranded nucleic acids as DNA or RNA and includes at least a transgene, a backbone and optionally a promoter and a marker. Preferably the vector comprises a sequence comprising a sequence encoding a promoter of a green fluorescent protein, a green fluorescent protein itself, a promoter of preferably a cytomegalie virus, a gag gene, a pol gene and a sequence comprising long terminal repeats, which comprises preferably a deletion. The preferred vector includes amongst others PFV, MLV, HIV-1, bovine foamy viral vector (BFV), equine foamy viral vector (EFV), feline foamy viral vector (FFV), SFV chimpanzee (cpz), SFV macaque (mac), SFV African green monkey (agm), SFV orangutan (ora), SFV spider monkey (spm), SFVpcz, e.g. pczHFV, pczHSRV2 and pczDL; pci, e.g. pciSFV; pMH, e.g. pMH71, pMH118, pMH120; pMD, e.g. pMD9, pMD11; pCL1; pCAMSdeltaU3E and a nucleic acid comprising an MGMT gene with a point mutation p140k.

The term "infectivity" as used herein refers to an entry of a vector into a host cell. Thereby, a nucleic acid is introduced into the host cell, and the host's and particle's membranes can fuse. The term "infectivity" also includes penetration, transduction, transfection and transformation. Infectivity can be enhanced by certain procedures or reagents e.g. to penetrate the cell membrane or to promote fusion or penetration. The transferred genetic material can be expressed or inserted, and genetic recombination can occur. Infectivity is measured e.g. by FACS analysis or progenitor assays indicated as relative infectivity normalized to VSV-G or absolute infectivity quoted as EGFP ffu/ml. Infection can be achieved by different methods, like by means of calcium phosphate, polyethyleneimine (PEI) or nonliposomale lipid agents, like PolyFect® (Qiagene) and Fugene® HD (Roche Diagnostics, Basel, Switzerland).

Genes foreign to a species are not expressed with optimal efficiency in hosts cells, since the codons in the foreign genes do not reflect the typical codon usage of the host organism. Therefore, to improve expression levels of env, their env codon was optimized by a specific exchange of certain codons. Hereafter is an exemplary selection of codons that were exchanged by optimized codons according to the invention.

TABLE 1

| original codons | optimized codons |
|---|---|
| gca, gcg | gcc |
| gaa, gta | gag |
| aga, agg | cgg |
| agg | cgg |
| att | atc |
| aca, act | acc |
| aat | aac |
| gta | gtg |
| ata | atc |
| agt | agc |
| cat | cac |
| ctt, ctc | ctg |
| caa | cag |
| cgc | cgg |
| caa | cct, ccc |
| tta, ttg | ctg |

Figure 7:
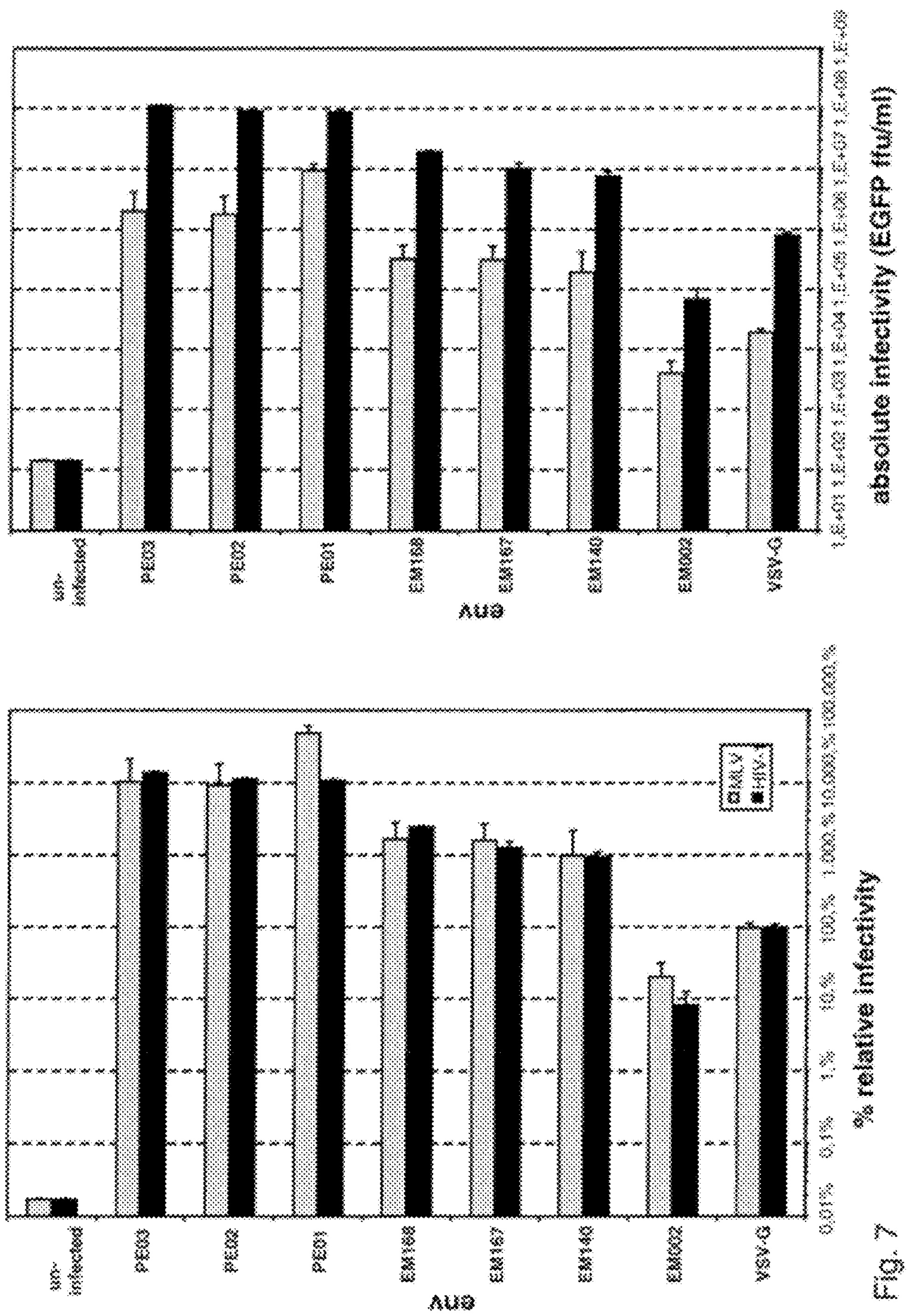

The listed codons were not completely exchanged, i.e. at specific locations of the nucleic acid the non-optimized codons were exchanged and at other specific locations the codons remained unchanged. Therefore, a very specific selection of codons was exchanged at very specific locations of the nucleic acid to get an optimized expression of env and consequently an improved infectivity and transduction. For example gaa and agg codons were exchanged at specific locations of PE01, SE01 and SE03 and remained at certain locations unchanged. Thereby, codon usage was adapted to the bias of Homo sapiens resulting in a high codon adaptation index value of 0.98. Infectivity and transduction of viral vectors comprising codon-optimized nucleic acids according to the invention were improved up to about 50-fold compared to the original non-optimized nucleic acids (FIGS. 7 and 8).

In addition to the codon-optimization the expression-optimization of env includes skipping of negatively cis-acting motifs as splice sites and poly(A) signals, and the low GC content of wt env was increased to prolong mRNA lifetime. Internal TATA-boxes, chi-sites, RNA secondary structure and ribosomal entry sites were avoided.

In a preferred embodiment the expression-optimized nucleic acid according to the invention comprises a foamy viral envelope gene selected from the group consisting of SEQ ID NO: 7 (PE01), SEQ ID NO: 8 (PE02), SEQ ID NO: 9 (PE03), SEQ ID NO: 10 (SE01), SEQ ID NO: 11 (SE02) and SEQ ID NO: 12 (SE03). PE01, PE02 and PE03 are expression-optimized sequences derived from EM140, EM167 and EM168, respectively. SE01, SE02 and SE03 are expression-optimized sequences derived from SM04, SM05 and SM06, respectively. Infectivities and transductions for viral vectors comprising PE01, PE02 or PE03 are improved up to about 50-fold, 10-fold and 6-fold compared to the original non-optimized nucleic acids EM140, EM167 and EM168, respectively.

The present invention is objected to a method for preparing at least one pseudotyped vector particle comprising the steps of:

a) providing at least one cell;
b) adding to the cell a non-foamy viral vector and a nucleic acid, which comprises a foamy viral envelope gene encoding a foamy viral envelope polypeptide, the foamy viral envelope gene comprises at least one mutation, which leads on expression of the mutated foamy viral envelope gene to a modified envelope polypeptide, which comprises at least one inactivated ubiquitination site; and
c) harvesting at least one pseudotyped vector particle produced by the cell.

The term "pseudotyping" and "pseudotyped" as used herein refers to a process or status, when a viral envelope polypeptide that is endogenous to the vector particle is replaced by a foreign polypeptide. The foreign polypeptide is derived from a virus that differs from the pseudotyped virus at least like two viruses from different species. The foreign polypeptide can also be a chimeric polypeptide.

Figure 20:
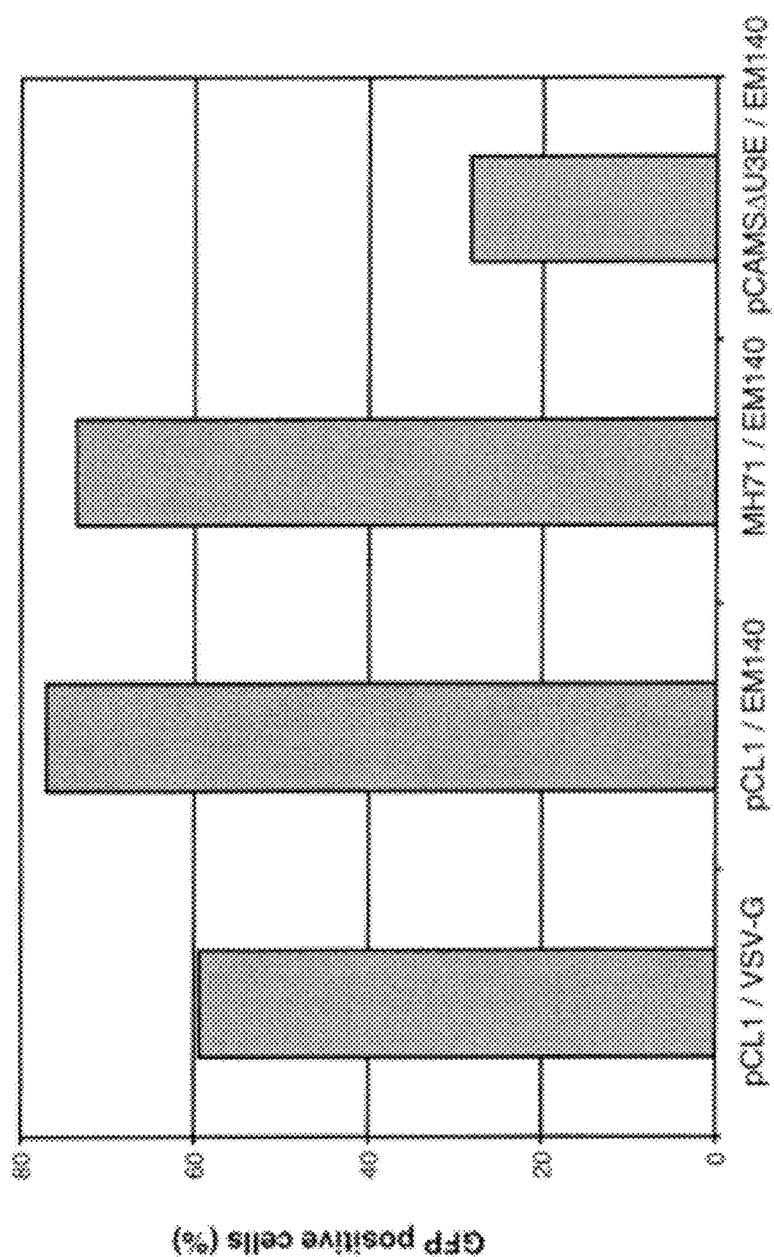
FIGS. 20 and 21 show rates of gene transfer in human CD34+ cells after transduction with viral vectors comprising env EM140 or VSV-G.
Figure 21:
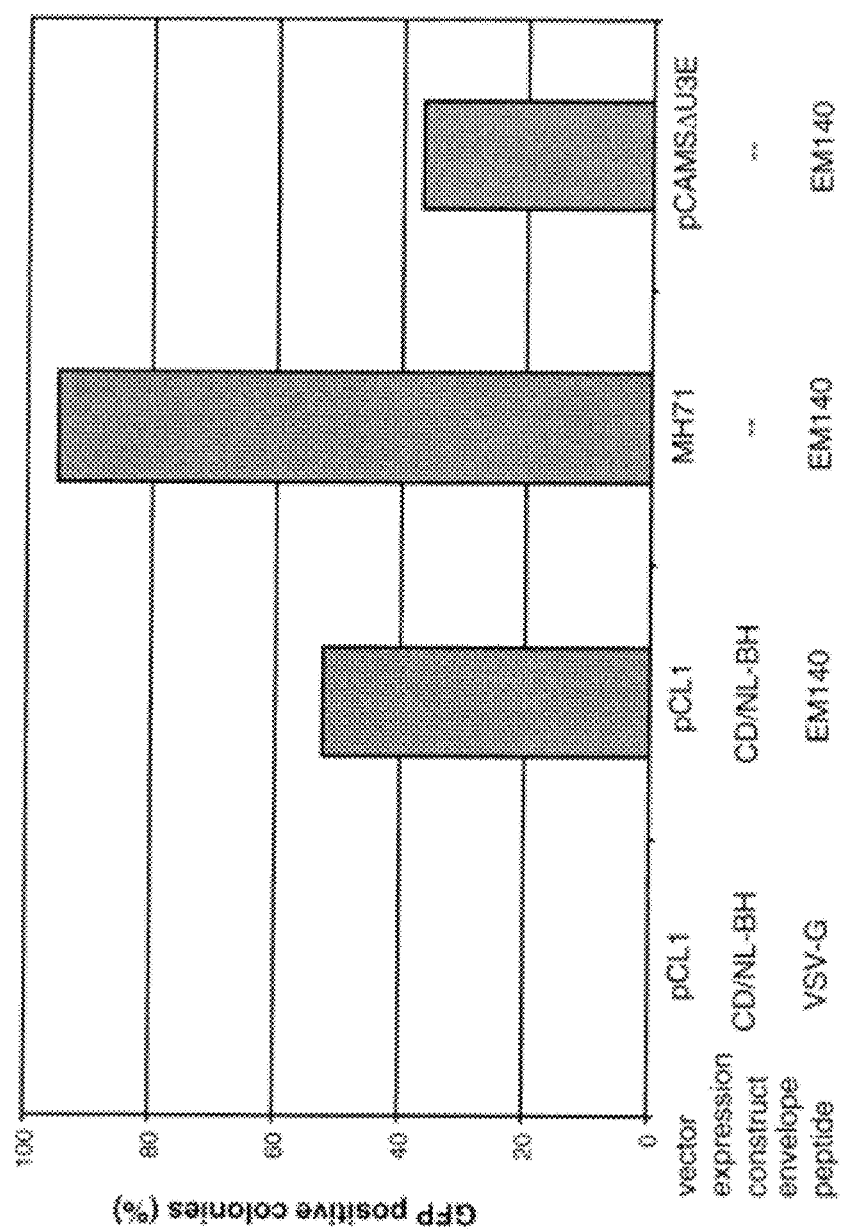
Figure 23:
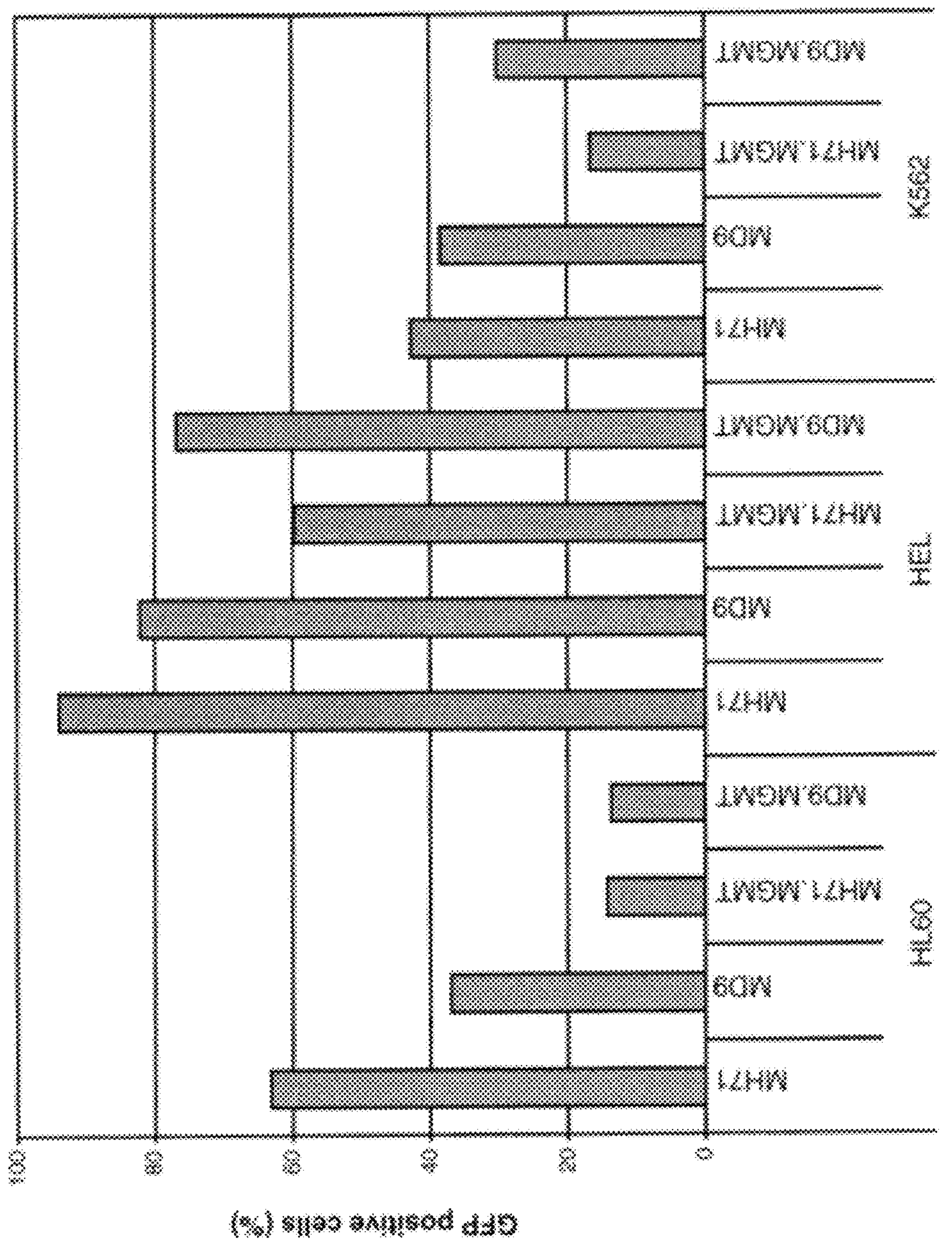
FIG. 23 displays the transduction efficiency of various foamy viral vectors enveloped by env EM140 depending on the type of target cell line used.

The term "cell" as used herein comprises in vivo systems, like single cells or multicellular organisms; ex vivo systems, like explants and slice cultures; and in vitro system, like cell culture systems. In a preferred embodiment of the invention the cell comprises a mammalian, like mice, rats, guinea pigs, pigs, marmosets and primates; HEK cells, like a HEK293T cell; fibrosarcoma cells, like HT1080; and hematopoietic cells, like CD34+ cells, HEL, HL60 and K562. As can be seen in FIGS. 20, 21 and 23 hematopoietic cells, especially CD34+ cells, HEL, HL60 and K562 are very efficiently infected.

The term "vector particle" as used herein refers to a vehicle of genetic information that is packed by substances including among others membranes, envelope polypeptides, capsid polypeptides and other glycoproteins. Optionally enzymes, like polymerases can also be packed within a vector particle. The term "vector particle" includes also viral particles and viral subparticles. The vector particle can be functional or non-functional.

The term "adding" as used herein refers to any kind of bringing a vector into contact with a cell. The term "adding" includes among others mixing, blending, shaking, over-laying, applying, administering, putting together, loading, multiple loadings, incubating, culturing and pipetting.

The term "harvesting" as used herein refers to any kind of collecting and processing of viral vectors from an intracellular and/or extracellular space, e.g. a supernatant of a cell culture. The term "harvesting" includes among others lysis of cells as well as sedimentation, centrifugation, filtration, concentration, extraction, purification and induction of vector particles.

For preparing pseudotyped vector particles the polypeptide synthesis system of the host cell was used. The viral vector comprised endogenous nucleic acids, e.g. gag and pol, and foreign nucleic acids encoding envelope polypeptides, like env, for pseudotyping. The cell took up the added viral vector, optionally integrated it into its genome, transcribed it and translated the transcribed RNA into viral polypeptides. Subsequently, the polypeptides were processed, and the vector particles including nucleic acids were assembled and released.

Figure 17:
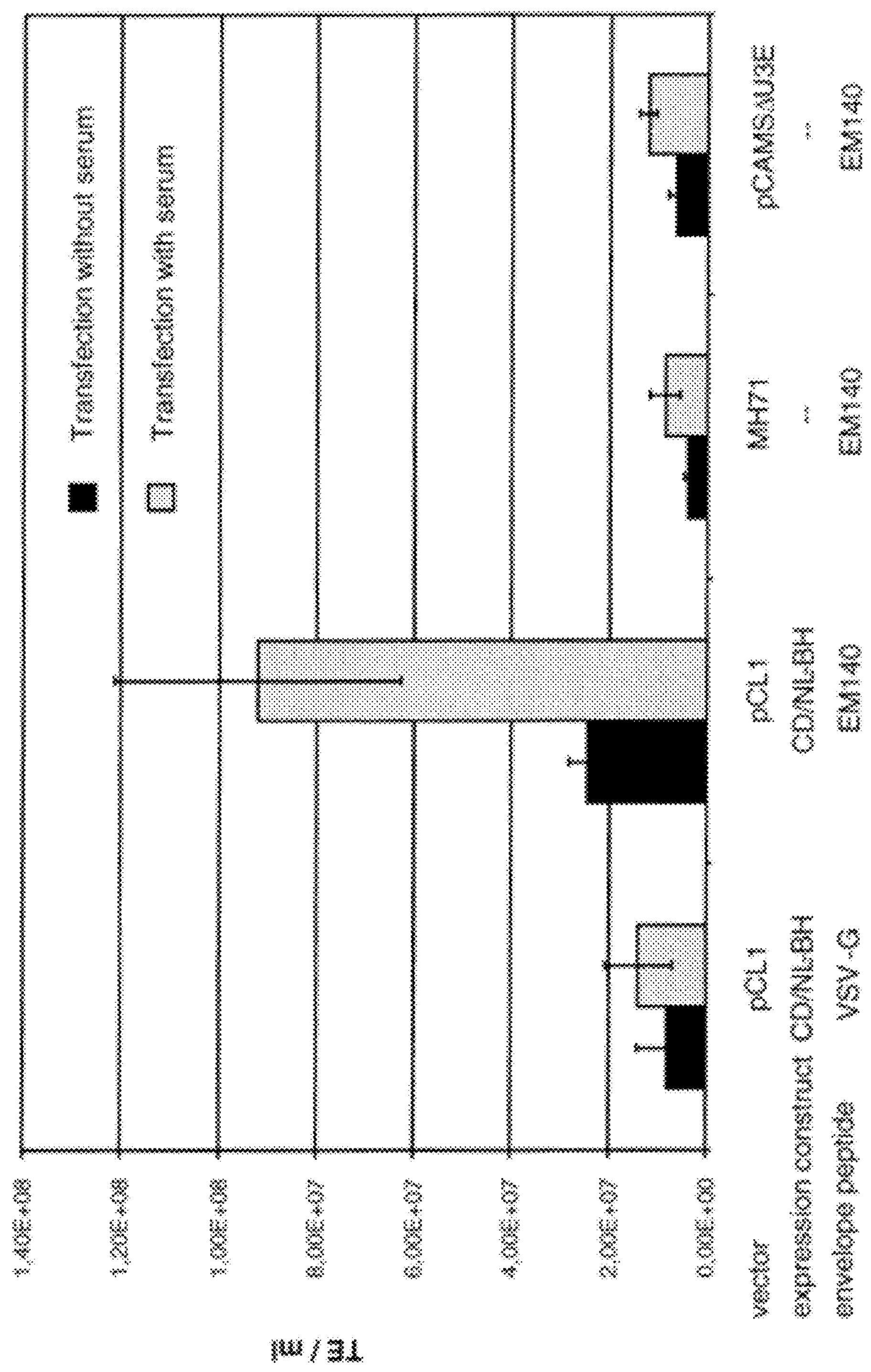
FIG. 17 compares titers of vector particles as transfection results with and without serum application.
Figure 18:
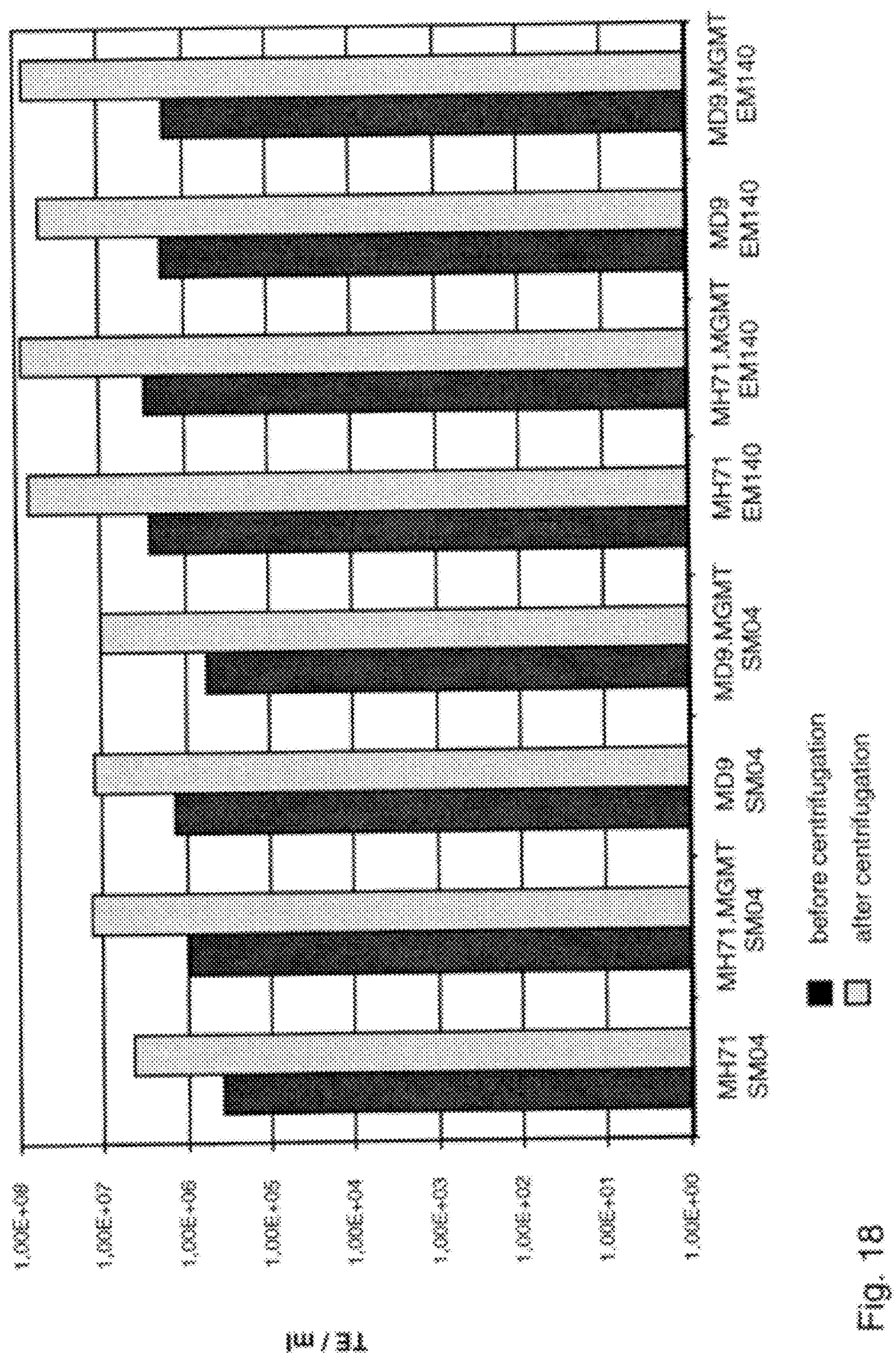
FIG. 18 displays titers of enveloped vector particles carrying a therapeutically useful gene, MGMT, before and after concentrating by centrifugation using foamy viral env EM140 and SM04.
Figure 19:
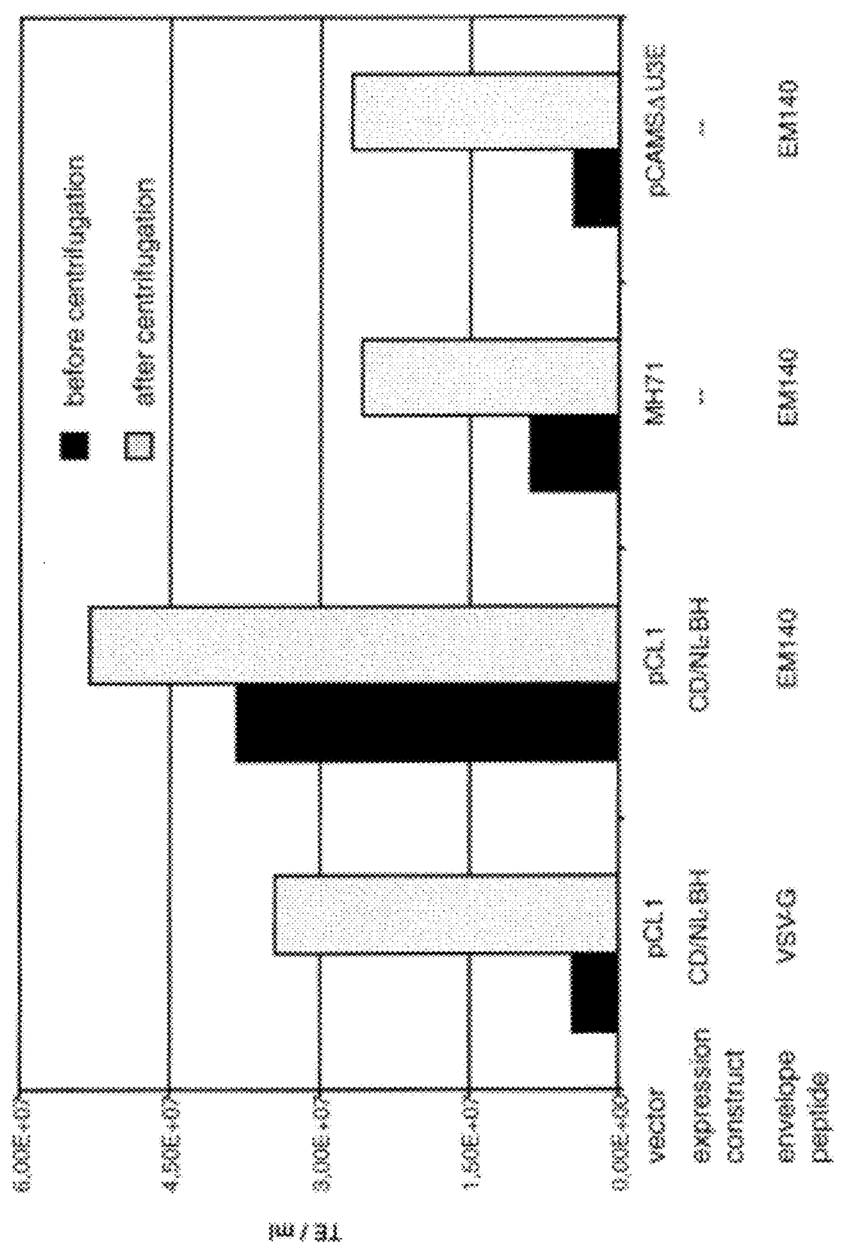
FIG. 19 displays titers of vector particles enveloped and pseudotyped by env EM140 compared to VSV-G before and after concentrating by centrifugation.

Vectors pseudotyped by the modified env according to the invention are highly efficient in gene transfer. Yield, ability to be concentrated, infectivity and stability are greatly increased by pseudotyping with the modified env according to the invention. FIGS. 17 to 19 show the result of a preparation of pseudotyped vector particles according to the invention with different expression constructs, like CD/NL-BH or pcziGag/pcziPol. Viral titers are indicated as transfection units (TE) per ml calculated by the following formula:

$$TE/\text{ml} = \frac{\text{number of cells at the time of infection}}{100\%} \times \text{number of } GFPpositive \text{ cells} \times \text{dilution factor}$$

The gained vector particles were concentrated by centrifugation, whereby a concentration up to 20-fold was achieved using e.g. env EM140. The yield of vector particles pseudotyped by env EM140 was about 8-times higher before and about 1.4-times higher after centrifugation compared to VSV-G in case the same lentiviral vector and expression construct were used. Therefore, the preparation of pseudotyped vector particles according to the invention results in a higher yield and a more effective concentration of pseudotyped vector particles.

Figure 22:
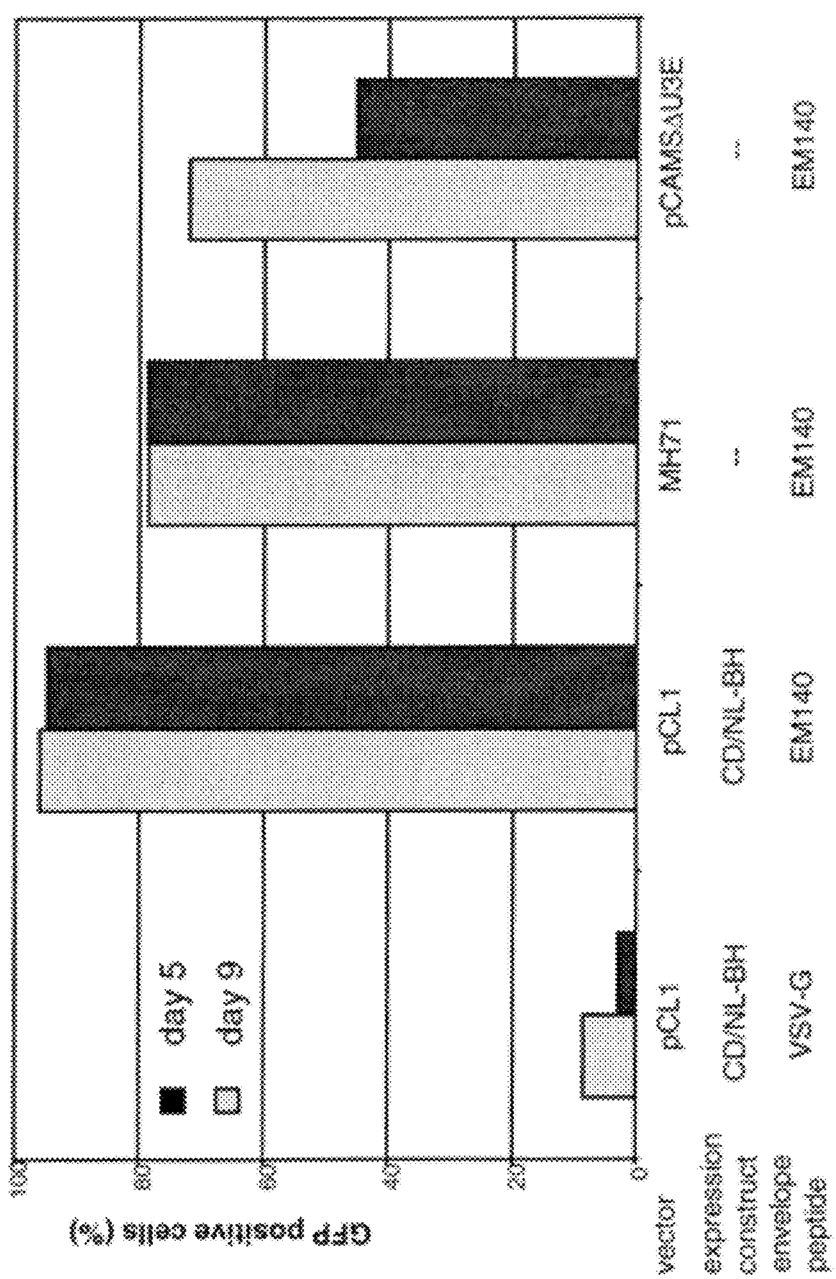
FIG. 22 depicts the efficiency of transduction in marmoset CD34+ cells with VSV-G and env EM140 5 and 9 days after transduction measured by FACS.

The stability of gene transfer or the stability of expression of transferred genes attained by pseudotyped vectors prepared according to the invention is demonstrated in FIG. 22. If vector particles pseudotyped by env EM140 were used the stability decreased to a significant lower degree within four further days of cell culture compared to VSV-G provided that the same vector and expression construct were employed. In the case a prototype foamy viral vector was used instead of a lentiviral vector the expression of transferred genes even increase slightly.

In a preferred embodiment of the invention the method for preparing at least one pseudotyped vector particle comprises further the step of d) adding the harvested pseudotyped vector particle to at least one second cell, wherein efficiency of infecting the second cell by the vector particle pseudotyped by the modified envelope polypeptide is increased compared to a vector particle pseudotyped by a wild-type envelope polypeptide.

The increased infectivity of pseudotyped viral vectors prepared according to the invention is demonstrated in FIGS. 20 and 21 measured by FACS and progenitor assay, respectively. If a foamy viral envelope polypeptide is used to pseudotype a lentiviral vector the number of GFP positive cells is increased about almost 20% compared to the same lentiviral vector pseudotyped by VSV-G, and it is slightly increased compared to a prototype foamy viral vector enveloped by a foamy viral envelope polypeptide (FIG. 20). Clonal cells that were infected by a lentiviral vector pseudotyped by VSV-G were not detected. In contrast to that, more than about 50% GFP positive colonies were counted after an infection by a lentiviral vector pseudotyped by a foamy viral envelope polypeptide, e.g. env EM140. Thereby, the broad foamy viral host spectrum can be used in combination with non-foamy viral vectors.

Figure 24:
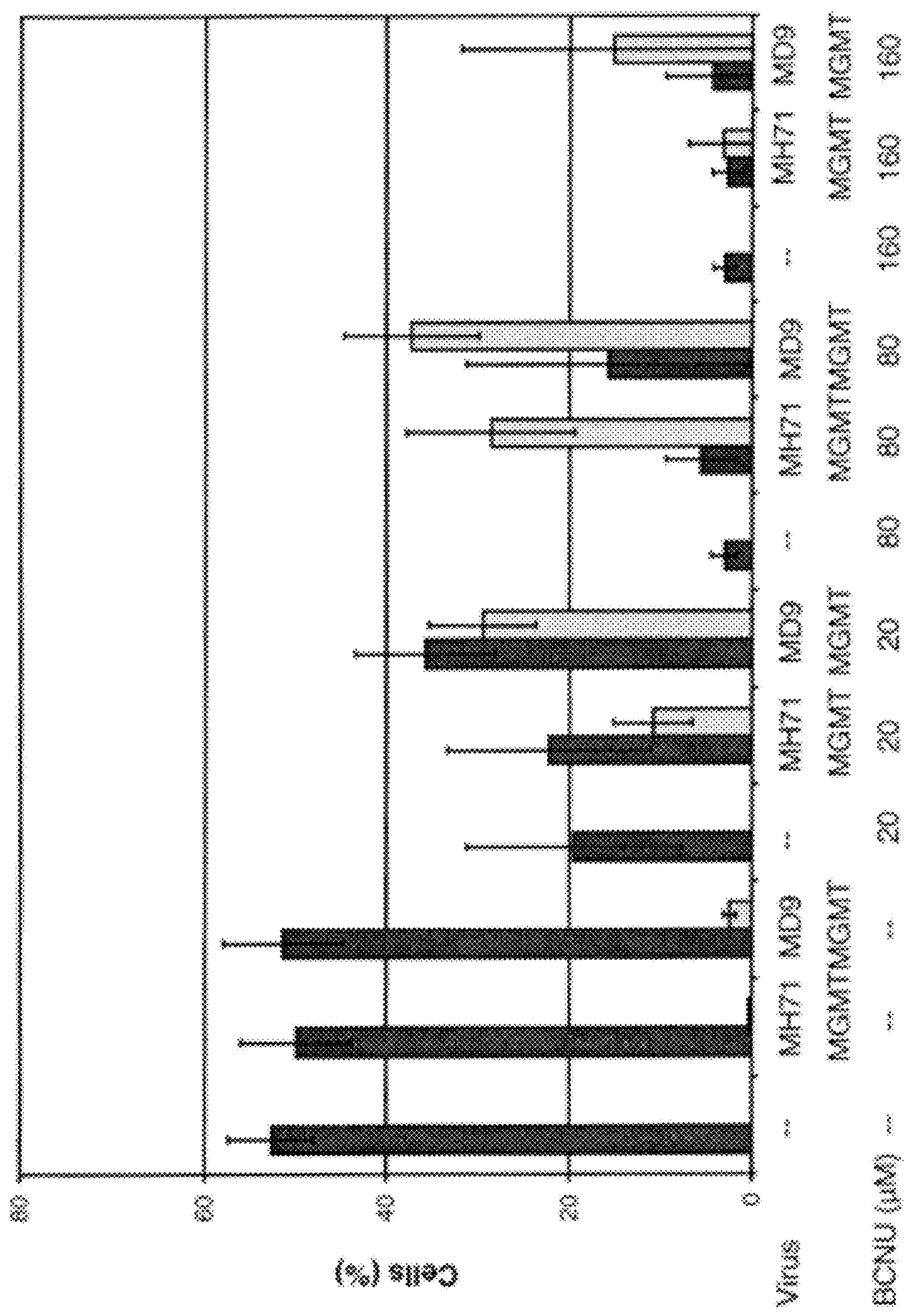
FIG. 24 demonstrates the effect of the transferred MGMTp140k gene in K562 cells after treatment with 1,3-bis-(2-chloroethyl)-1-nitrosourea (BCNU).

The pseudotyped vector particle is added to the second cell, whereby it transfers genetic material into the second cell, like MGMTP140K for therapeutic purposes (FIGS. 18 and 24). The step of adding the pseudotyped viral particle to a second cell includes transduction, transfection or infection.

In another preferred embodiment of the invention the foamy viral envelope polypeptide is labeled by a marker.

The term "marker" as used herein refers to a molecular label that can be a peptide or a non-peptide label linked to a molecule to be tracked. The marker can be detectable by e.g. calorimetric, fluorescent, spectroscopic or radioactive signals as well as by a secondary detection system, like streptavidine/biotin, whereby the signals can be also amplified.

In another preferred embodiment of the invention the marker is a fluorescent protein.

The fluorescent protein includes preferably among others green fluorescent proteins, like EGFP, blue fluorescent proteins, like EBFP, red fluorescent proteins, like, DsRed and mCherry, yellow fluorescent proteins, like EYFP, cyan fluorescent proteins, like ECFP, and orange fluorescent proteins, like mOrange.

In a further preferred embodiment of the invention the foamy viral envelope polypeptide is tracked by an imaging technique.

The imaging technique includes among others confocal microscopy, multi photon microscopy, fluorescent microscopy, tomography methods, e.g. fluorescence enhanced optical tomography, macroscopy, spectroscopy, positron emission tomography, molecular imaging, fluorescence resonance energy transfer based methods and FACS. The labeled foamy viral envelope polypeptide itself as well as a vector particle enveloped by the labeled polypeptide or a cell expressing the labeled polypeptide can be tracked.

In a further preferred embodiment of the invention the method for preparing at least one pseudotyped vector particle further comprises the step of: e) adding serum to the cell.

As shown in FIG. 17 adding serum to the cell and/or to the viral vector increases the viral titer significantly, whereby the preparation of vector particles according to the invention gets more efficient. In a preferred embodiment 10% to 20% serum, more preferably 10%, 15% or 20% serum are added.

In another preferred embodiment of the invention at least one growth factor, e.g. a cytokine, like SCT, TPO, CSF, G-CSF, TPO, IL6 and FH3-L, is added to the cell, or growth factors are added together with serum.

In a further preferred embodiment of the invention the cell is provided in coated cell culture dishes, preferably coated by CH296, BSA or TCD.

In another preferred embodiment of the invention the method for preparing the pseudotyped vector particle is a high throughput method.

In an also preferred embodiment the nucleic acid added to the cell comprises a foamy viral envelope gene comprising at least one mutation, wherein the mutation leads on expression of the foamy viral envelope gene to a lysine exchange in the envelope polypeptide.

In a further preferred embodiment of the invention lysine is exchanged against an amino acid selected from the group consisting of alanine, histidine, glycine and arginine.

In a particularly preferred embodiment the nucleic acid added to the cell comprises a foamy viral envelope gene comprising at least one mutation, wherein the mutated foamy viral envelope gene is selected from the group consisting of EM135 to EM139, SEQ ID NO: 1 to 20 and SEQ ID NO: 21.

In a likewise preferred embodiment of the invention the viral vector added to the cell is derived from the family of retroviridae.

The term "retroviridae" as used herein refers to a family of retroviruses comprising two subfamilies, orthoretrovirinae and spumaretrovirinae as well as currently unknown or unclassified retroviruses. Retroviruses possess an envelope and are distinguished from other viruses by an RNA genome. Therefore, they replicate by a DNA intermediate, wherein a reverse transcriptase performs a reverse transcription from RNA to DNA. The resulting DNA can be integrated into the host's genome by integrase, and the virus then replicates as part of the host cell's DNA. The genome of a retrovirus comprises two long terminal repeats and three genes, namely gag, pol and env.

In another preferred embodiment of the invention the retroviridae is selected from the group consisting of lentiviruses, alpha retroviruses, beta retroviruses, gamma retroviruses, delta retroviruses, epsilon retroviruses and spumaretrovirinae.

The term "lentiviruses" as used herein refers to a genus of the subfamily orthoretrovirinae. Up to now five lentiviral serogroups are known, reflecting the vertebrate hosts, with which they are associated, like primates, cats and horses. The primate lentiviruses, e.g. HIV1, HIV2 and SIV are distinguished by the use of CD4 as receptor. Some lentiviral groups have cross-reactive gag antigens, like the feline lentivirus FIV.

The terms "alpha retrovirus", "beta retrovirus", "gamma retrovirus" and "delta retrovirus", "epsilon retrovirus" as used herein refers to further genera of the subfamily orthoretrovirinae. The alpha retrovirus is predominantly an avian virus causing tumors, like sarcomas and anemia, but it also affects rats. Representative examples of alpha retroviruses are Rous sarcoma virus, avian leucosis virus and avian myeloblastosis virus. The beta retrovirus, like a mouse mammary tumor virus, the gamma retrovirus, like a murine leukemia virus or a feline sarcoma virus, the delta retrovirus, like a human T-lymphotropic virus, often cause tumors, like leukemia and sarcoma. Undiscovered retroviral species and genera are also included in this listing.

The term "spumaretrovirinae" as used herein refers to a subfamily of retroviridae comprising the genus of the foamy viruses. In natural host it causes persisting infections despite a high titer of antibodies and without a pathological phenotype. In contrast to its apathogenity in vivo, the foamy virus shows a strong cytopathogenity in vitro generating cellular syncytia. The foamy viral genome exists as two identical versions with a large amount of double-stranded full-length DNA. Foamy viruses are complex exogenous viruses with a specific morphology having prominent surface spikes assembled by trimeric subunits of env, namely SU, TM and LP. In addition to gag, pol and env genes, foamy viruses possess further accessory regulatory genes, like tas and bel, and an addition internal promoter for the expression of these genes. In contrast to the orthoretrovirinae foamy viral pol expression is independent from gag, so that no gag/pol fusion protein is formed, but a pol mRNA separated by splicing. Unlike in other retroviruses, the foamy viral gag antigen lacks a processing in the common three subunits. Instead of this, only one peptide is cleaved at the C terminus. The budding of foamy viruses is rather unusual. Normally, the envelope membrane is acquired by budding through the ER. However, e.g. in an equine foamy virus budding occurs from the cytoplasmic membrane.

In an also preferred embodiment of the invention the viral vector and the mutated foamy viral envelope gene are located on a single construct.

The term "construct" as used herein refers to any kind of vehicle that can carry nucleic acids. The term "construct" includes plasmids, vectors, artificial chromosomes and artificial particles. The viral vector and the mutated foamy viral envelope gene can follow each other on the construct or can be located at separate places of the construct.

In an additional preferred embodiment of the invention at least one expression construct is added comprising at least one gene selected from the group consisting of a gag gene, a pol gene and an envelope gene.

The term "expression construct" as used herein refers to an expression vector that encodes auxiliary peptides, like a retroviral group-specific antigen and/or a retroviral polymerase. These auxiliary peptides are essential or supporting for viral morphogenesis, release, infectivity or other replicative functions. In a preferred embodiment the expression construct includes among others pzc vectors, like pczDWP001, pcziGag, pcziPol and pczCFG2fEGN; p6 vectors, like p6NST 1, p6iPol and p6iGag; CD/NL-BH and cmvgp 1.

The term "gag" as used herein refers to a retroviral group-specific antigen, which encodes the internal structural proteins of the capsid. During maturation non-foamy viral gag is processed in its subunits comprising a matrix, a capsid and a nucleocapsid.

The term "pol" as used herein refers to enzymatic components of retroviruses, like reverse transcriptase, integrase and protease.

The invention is also directed to a method for treating a genetic disorder comprising administering to a subject a nucleic acid comprising a foamy viral envelope gene comprising at least one mutation, wherein the mutation leads on expression of the mutated foamy viral envelope gene to a modified envelope polypeptide, which comprises at least one inactivated ubiquitination site.

The term "treating" as used herein also comprises curing, preventing and attenuating a disorder or a disease. The term "treating" according to the invention also includes genetic engineering, genetic manipulation and gene therapy. By the method according to the invention a faulty gene is replaced by a functional gene or in the case of an absent gene a functional or additional gene is provided. The added gene can express a therapeutic polypeptide or provide a favorable property, like a chemotherapeutic resistance by MGMTP140K (FIG. 24). This is achieved by administering to a subject a nucleic acid comprising a mutated foamy viral envelope gene according to the invention. Therefore, the body can make the correct e.g. enzyme, regulator or protein also encoded by the administered nucleic acid, and consequently the root cause of a disease can be eliminated. Gene therapy includes the insertion of a normal gene into a non-specific location within the genome to replace a non-functional gene. An abnormal gene could also be swapped for a normal gene by homologous recombination or an abnormal gene could be repaired by selective reverse mutation, which returns the gene to its normal function. In addition, the regulation of a particular gene could be altered, i.e. the degree to which a gene is turned on or off.

The term "genetic disorder" as used herein refers to hereditable and acquired disorders of genetic or epigenetic origin, like hemophilia, Lesch-Nyhan syndrome, retinoblastoma, phenylketonuria and metabolic diseases in which a defective gene causes e.g. an enzyme to be either absent or ineffective in catalyzing a particular metabolic reaction effectively. Genetic disorders include single-gene disorders, caused by a defect in a single gene, like Huntington's disease, cystic fibrosis, and sickle cell anemia; multifactorial disorders, caused by a combination of genes like Alzheimer's, certain heart diseases and cancer; chromosomal disorders, such as Down syndrome; and mitochondrial disorders, caused by a defect in a mitochondrial gene. Genetic disorders also include immunological disorders, like coeliac disease, diabetes mellitus type 1, systemic lupus erythematosus, Sjögren's syndrome, Churg-Strauss Syndrome, multiple sclerosis, Hashimoto's thyroiditis, Graves' disease, idiopathic thrombocytopenic purpura, and rheumatoid arthritis; cancer, like liver cancer, gastric cancer or carcinoma of the uterus; and other disorders induced by dysregulation of genes.

The term "genetic disorder" also includes among others acquired diseases and virally induced diseases, e.g. diseases of viral origin, like human papillomavirus, hepatitis B and hepatitis C virus, Epstein-Barr virus, human T-lymphotropic virus; cancer; metabolic diseases and AIDS. The method of this invention for preventing or treating a genetic disorder includes also the introduction of an env gene into a cell, wherein the cell becomes resistant to superinfection by other retroviruses with the same receptor specificity, a phenomenon base on receptor interference.

The term "administering" as used herein refers to any kind of applying a gene or a gene comprising a substance to a subject. The term "administering" includes local administration, e.g. by surgery, a plaster, tincture, lotion, cream, ointment, solution or gel; and systemic administration, e.g. by injection, infusion, tablets, pills, capsules, dragées, admixing with food or drinking. The place or mode of injection is not restricted, but includes e.g. intramuscular, intraperitoneal, intravenous, and subcutaneous. Application of pharmaceutical retard forms is also included. The administration can be targeted to germ cells as well as to somatic cells.

In a preferred embodiment of the invention the administered nucleic acid comprises a foamy viral envelope gene comprising at least one mutation, wherein the mutation leads on expression of the foamy viral envelope gene to a lysine exchange in the envelope polypeptide.

In a further preferred embodiment of the invention lysine is exchanged against an amino acid selected from the group consisting of alanine, histidine, glycine and arginine.

In a further preferred embodiment of the invention the administered nucleic acid comprises a foamy viral envelope gene comprising at least one mutation, wherein the mutated foamy viral envelope gene is selected from the group consisting of EM135 to EM139, SEQ ID NO: 1 to 20 and SEQ ID NO: 21.

The invention relates in addition to a method for treating a genetic disorder comprising administering to a subject a polypeptide encoded by a foamy viral envelope gene comprising at least one mutation, wherein the mutation leads on expression of the mutated foamy viral envelope gene to a modified envelope polypeptide, which comprises at least one inactivated ubiquitination site.

The polypeptide comprising a modified env can be used as a carrier to deliver polypeptides and other substances, like drugs, enzymes, lipids and steroids, with a therapeutic effect to the target cell or organism. The administered polypeptide according to the invention can e.g. deliver enclosed DOPA to the brain cells of a Parkinson patient or an enclosed chemotherapeutical agent to the erythrocytes of a malaria patient, whereas the broad host range and the apathogenity of the env is of favor.

Methods

1. Cell Culture Techniques 1.1 Eukaryotic Cell Lines

Eukaryotic cell were incubated in cell culture dishes at 37° C. in a humidified atmosphere with 5% $CO_2$. Adherent cells were passaged 2 to 3 times per week depending on the proliferation rate. Thereto, cells without medium were washed with calcium/magnesium free phosphate buffered saline (PBS) and incubated in trypsin/EDTA PBS. The detached cells were resuspended in medium, and ⅕ of the cells were transferred to new culture dishes. For the passage of hematopoietic cells, they were uniformly distributed in medium, and a major part of the supernatant was discarded. The volume of the discarded medium was replaced by fresh medium.

1.2 Obtaining Primary Cells

Blood samples from human umbilical cords were diluted in a solution of 22 g/l sodium citrate, 28 g/l glucose and 8 g/l citric acid (50 to 70 ml blood in a total volume of 60 to 90 ml). The blood was diluted 1:1 with PBS, and subsequently a density gradient centrifugation was performed (400 g, 25 min, RT). The obtained erythrocytes were lysed with ammonium chloride solution and washed twice with PBS. From this cell mixture CD34+ cells were selected by magnetic cell separation. The obtained CD34+ cells can be used immediately or cryo-conserved.

For isolating mononuclear cells, the extracted bone marrow of marmosets was applied to a cell strainer, and subsequently a density gradient centrifugation was performed. The isolated cells were labeled by a biotinylated CD34+ antibody and by microbeads coupled to streptavidine. Thereafter, the labeled cells were separated by a magnetic cell sorter, and the purity of the isolated cells was determined by FACS.

2. Cloning of pczHFVenv EM167 and EM168

PczHFVenv EM140 was linearised by EcoRI/NheI, and a PCR fragment PCR-0 digested with the same enzyme was inserted. The resulting construct pczHFVenv EM167 was used as vector for preparing pczHFVenv EM168. The overlapping PCR fragment PCR1/2 prepared as indicated in table 1 below was digested by EcoRI/NheI and ligated with pczHFVenv EM167/EcoRI/NheI.

TABLE 2

| Vector | Template | Primers | PCR product |
|---|---|---|---|
| pczHFVenv EM167 | EM140 | 826 + 2271 | PCR-0 |
| pczHFVenv EM168 | EM167 | 2272 + 406 | PCR-1 |
| | EM167 | 826 + 2273 | PCR-2 |
| | PCR-1 + PCR-2 | 826 + 406 | overlap PCR1/2 |

2. Preparation of Vector Particles 2.1 Transfection by PEI

For a production of transient vector particles all nucleic acids were introduced into cells by co-transfection. Thereto, adherent cells were cultured on cell culture dishes, overlaid with a 0.1% gelatine solution and incubated for 30 min to 3 days. On the first day of transfection the gelatine solution was removed, and HEK cells were seeded in a concentration of about 6×106 HEK cells per 10 ml medium (DMEM). On the second day DMEM was re-placed by a transfection medium containing 5 to 15 μg/ml PEI, 5 to 15 μg/ml DNA, DMEM and optionally 10% -20% fetal calf serum (FCS). On the third day the cells with serum were washed with DMEM.

About 10 mM to 20 mM sodium butyrate dissolved in PBS can be added to the medium of serum treated and non-treated cells. It was replaced after 6 hours by DMEM. On the fourth day at the earliest of 19 hours the supernatant containing vector particles was harvested and filtrated to remove cells and fragments thereof. The vector particles were either used immediately or stored at −80° C. or −20° C. after detecting the viral titer.

2.2 Transfection by Calcium Phosphate

2×106 cells per 5 ml medium, preferably DMEM, were incubated over night. On the following day ⅕ of the medium was removed, and a solution containing 423 μl distillated water, 62 μl of 2 M $CaCl_2$, 500 μl 2× HBS and 15 μg DNA obtained by plasmid preparation was added (ratio solution/medium 1:5) to the cells. The DNA was applied to the cells as a precipitate of calcium phosphate/DNA.

2× HBS comprises:

50 mM HEPES 10 mM KCl 12 mM dextrose×$H_2O$ (glucose monophosphate)

280 mM NaCl 1.5 mM $Na_2HPO4$×2 $H_2O$

After 7 hours of further incubation the medium was changed, and one day after transfection the cells were treated by sodium butyrate as described above (see 2.1).

2.3 Transfection by Polyfect 1.6×106 cells per 5 ml medium, preferably DMEM, were incubated over night. On the following day the medium was replaced by pre-heated medium (4 ml per well). 6 μg DNA and 30 μl polyfect were mixed in 114 μl medium, incubated for 15 min at RT, and subsequently 1 ml medium was added before the mixture was dropped to the cells. The cells were incubated overnight and subsequently treated by sodium butyrate as described above (see 2.1).

3. Preparation of Vector Particles 3.1 Preparation from Supernatants

Supernatants from a cell culture containing vector particles were purified from debris by a short period of centrifugation (about 5 min at 1,200 rpm) and subsequently sterile filtrated. Obtained vector particles were pooled and centrifuged at 4° C. for 2-3 hours (at about 25.000 rpm) by means of a dense gradient with 20% sucrose. Subsequently, the supernatant was drawn off, and invisible viral sediment was resuspended in fresh medium. Before transduction the viral titer was functionally detected.

3.2 Preparation of Intracellular Viral Vectors

Cells were broken by freezing and thawing, and viral vectors were released. Thereto, washed transfected cells were placed on dry ice or kept at about −80° C. until the medium was completely frozen. Subsequently, they were thawed at temperatures between RT and 37° C. Cell debris can be removed by filtration.

4. Transduction of Hematopoietic and Fibrosarcoma Cells

Untreated multiple well plates were coated with a recombinant fibronectin fragment (e.g. CH296). After washing dishes the centrifuged viral sediment was diluted in 3 ml medium, distributed to 6 wells and incubated. After half an hour 100.000 cells of lines HT1080, K562, HL60 and HEL contained in 50 to 100 μl medium were pipetted to the vector particles and incubated. About 16 hours later fresh medium was added to the cells, and after further two days the cells were transferred to a flask to continue cell culturing. A minor part of the cells was analyzed by FACS in a solution of PBS with 1% FCS and 1 μg propidium iodide to evaluate transfection efficiency by detecting the ratio of GFP positive cells to GFP negative cells.

5. Transduction of Human CD34+ Cells

The transduction of human CD34+ cells was performed on multiple well plates coated with a recombinant fibronectin fragment. The fibronectin was preloaded once or twice with fresh or thawed vector, and 15,000 to 20,000 human CD34+ cells per well were pipetted to the vector particles. In addition, cytokines SCT, TPO and G-CSF were added at a concentration of 100 ng/ml. Soonest 16 hours after transduction, cells were transferred to fresh medium and cultivated as described above.

6. Transduction of Marmoset CD34+ Cells

Transduction of marmoset cells was performed on multiple well plates coated with a recombinant fibronectin fragment. Thawed or fresh vector particles were centrifuged, diluted in 1 ml medium and then put to the coated wells. After half an hour CD34+ cells of marmosets were added and incubated with cytokines CSF, TPO, IL6 and FH3-L at a concentration of 100 ng/ml. The concentration of applied cells ranged from 10,000 to 60,000 cells per well. Soonest 16 hours after transduction, marmoset cells were transferred to fresh medium and cultivated as described above.

7. Progenitor Assay

To detect clonal cells by a progenitor assay CD34+ cells were seeded at low concentrations (e.g. 200 to 500 cells per ml) on a viscous medium containing cytokines on the day after transduction. Differentiated cells die during culture within a short period. Therefore, colonies generated by clonal cells were counted after 14 days of incubation under a fluorescence microscope, and the ratio of GFP positive and GFP negative cells was detected.

8. FACS Analysis

A GFP gene was used as reporter gene. To count transfected cells expressed GFP was detected by its excitation by a laser beam. Thereto, cells were incubated with trypsin-EDTA for 5 to 10 min. The trypsin treatment was stopped by medium, and the cell suspension was centrifuged and immediately measured via FACS.

Alternative β-galactosidase staining was performed, and lacZ was used as a reporter gene 9. Tracking Experiments To detect vector particles coupled to a labeled env gene confocal laser scanning microscopy was used. Filter systems and laser types were chosen to detect GFP (absorption: 498 nm, emission: 516 nm) and dsRed (absorption: 556 nm, emission: 583 nm) or mCherry (absorption: 587, emission: 610) within a sample in vitro or in vivo.

For in vitro tracking experiments cells e.g. HT1080 were grown on coated cover slips. After transfection they were washed with PBS and optionally fixed by paraformaldehyde (3%) at RT for 15 to 30 min or observed in vivo. After three more washing steps with PBS/glycine fixed or unfixed cells were observed by a confocal laser scanning microscope.

For in vivo tracking experiments with low resolution a macroscopic fluorescent system (Leica MacroFluo™) is used for a non invasive observation of labeled env in large samples, like behaving mice. For a higher resolution multi-photon microscopy is used to detect labeled env in vivo or ex vivo, e.g. in anesthetized animals or in tissue slices.

Results

1. Preparation of Vector Particles

FIGS. 17-19 show the results of pseudotyping foamy viral and orthoretroviral vectors with mutated env according to the invention derived from a foamy virus. Enveloping lentiviral, foamy viral and gamma retroviral vectors comprising env EM140 resulted in an increased viral titer compared to VSV-G. The gained vector particles were concentrated by centrifugation, whereby a concentration up to 20-fold was achieved using env EM140. The yield of vector particles pseudotyped by env EM140 was about 8-times higher before and about 1.4-times higher after centrifugation compared to VSV-G in case the same lentiviral vector pCL1 and expression construct CD/NL-BH were used. The yield of env EM140 pseudotyping pCL1/CD/NL-BH was about $3.8\times10^7$ TE/ml and was concentrated 2-fold. VSV-G pseudotyping pCL1 achieved only a yield of about $0.5\times10^7$ TE/ml, and env EM 140 enveloping pCL1 produced only $0.8\times10^7$ TE/ml before centrifugation. Env EM140 pseudotyping pCAMΔU3E provided the highest concentration of 5.5-fold by centrifugation. Therefore, the preparation of env EM140 pseudotyped vector particles resulted in a higher yield and a more effective concentration of pseudotyped vector particles.

To further improve transfection efficiency serum was added to the transfection mixture. As shown in FIG. 17, in all cases yield of vector particles was increased by the serum. This serum increase was more than 6-fold for env EM140 pseudotyping pCL1, but only 2.5 for VSV-G pseudotyping pCL1. Therefore, the addition of serum increased the vector particle titer. This effect was enhanced by env EM140.

2. Gene Transfer to CD34+ Cells

The portions of GFP positive cells reflecting gene transfer rate into CD34+ cells is shown in FIGS. 20 and 21 for human CD34+ cells and in FIG. 22 for marmoset CD34+ cells. PCL1 and MH71 enveloped by EM140 had the highest gene transfer rate with about 77% and about 74% GFP positive human cells, respectively, measured by FACS. For comparison a lentiviral vector was pseudotyped by VSV-G, which showed a gene transfer rate that was almost 20% lower compared to env EM140/pCL1.

If the same experiments were performed by a progenitor assay clonal cells comprising transferred genes were evaluated, wherein clonal cells are the more important cell type for gene therapy. Pseudotyping pCL1 by env EM140 achieved more than 50-fold increase of gene transfer compared to VSV-G showing no GFP positive clonal cells. Therefore, the transduction efficiency was clearly increased by enveloping foamy viral and orthoretroviral vectors with env EM140.

FIG. 22 shows the gene transfer rate in marmoset CD34+ cells sorted by FACS on day 5 and day 9 after transduction. Compared to pCL1 pseudotyped by VSV-G the number of GFP positive cells was almost 10-fold higher for pCL1 pseudotyped by env EM140. From day 5 to day 9 after transduction the portion of GFP positive cells slightly increased (about 1%) for MH71 enveloped by env EM140, and it decreased only about 2% for pCL1/env EM140. However, the number of cells labeled by pCL1/VSV-G decreased clearly of about 60% within four days. Therefore, the transduction stability was also improved by env EM140 for marmoset CD34+ cells.

3. Transduction of Hematopoietic Cell Lines

Cells of lines HL60, HEL and K562 were transduced with the vectors MH71, MH71.MGMT, MD9 and MD9.MGMT using EM140. For the vectors containing MD9 the expression construct pcziGag and pcziPol were added. The centrifuged viral sediment was resuspended in 3 ml medium with a titer of 1.7 x 106 TE/ml (MH71.MGMT), 1.4×107 TE/ml (MD9.MGMT), 1.8×107 TE/ml (MD9) and 2.5×107 TE/ml (MH71).

FIG. 23 shows that the portion of GFP positive cells depends on the used cell line, wherein HEL cells display the most efficient transduction. With HL60 cells the portion of GFP positive cells remained constant during a long period of time, e.g. 8 weeks. Therefore, HL60 and HEL cells are preferred for transduction.

4. MGMTp140k and Resistance Against BCNU

In addition, the resistance of transduced cells comprising the transgene MGMTp140k against BCNU was tested. FIG. 24 shows the percentage of GFP positive cells of different cell lines that survive a treatment with 0, 20, 80 and 160 μM of the cytostatic drug BCNU. The amount of GFP positive cells based on the total amount of surviving cells is increased by the transgene MGMTp140k, which provides resistance against BCNU. Therefore, it was shown that genes like MGMTp140k can be successfully transduced.

5. Infectivity of Pseudotyped Vector Particles 5.1 Env EM167, EM168, EM225, EM226, SM05 and SM04

The modified env according to the invention, which comprises at least one inactivated ubiquitination site located at TM of the modified envelope polypeptide were used to pseudotype different types of viruses. The absolute infectivities and relative infectivities of these env pseudotyped viruses applied to eukaryotic cells were measured. The relative infectivity was normalized to the same viruses pseudotyped by VSV-G. As a result, there was a clear increase of infectivity due to the at least one inactivated ubiquitination site located at TM of the modified envelope polypeptide. As can be seen in FIGS. 5 and 6 the infectivities rose about 2-times by env EM225 and env EM226 compared to env EM002 for pseudotyped HIV-1 vectors and MLV vectors. Env EM167 and env EM168 enhanced infectivities about 3-times compared to env EM140 for pseudotyped HIV-1 vectors. The infectivities were increased about 3-times and 4-times by env SM05 and env SM06, respectively, compared to env SM04 for pseudotyped HIV-1 vectors, and about 2- times and 5-times, respectively, for pseudotyped MLV vectors. Therefore, the efficiency of viral transduction and gene transfer was raised by the modified env EM167, EM168, EM225, EM226, SM05 and SM06.

5.2 Env PE01, PE02 and PE03

Relative and absolute infectivities of viral vectors enveloped or pseudotyped by the modified env encoded by codon optimized env genes according to the invention were highly improved (FIGS. 7, 8). Using PE01 infectivity rose about 11-times for pseudotyped HIV-1 vectors and 49-times for pseudotyped MLV vectors compared to env EM140. The infectivities were increased about 9-times by PE02 for pseudotyped HIV-1 vectors and 6-times for pseudotyped MLV vectors compared to env EM167. PE03 enhanced infectivity 6-times for pseudotyped MLV and HIV-1 vectors compared to env EM168. Therefore, the efficiency of viral transduction and gene transfer was raised by expression-optimized env genes PE01-PE03.

5.3 Env EM228, env EM170 and env EM171

Relative and absolute infectivities of viral vectors enveloped or pseudotyped by the modified env comprising deletions according to the invention were also highly improved (FIGS. 10, 11). Using env EM228 infectivity rose about 13-times for pseudotyped HIV-1 vectors and 82-times for pseudotyped MLV vectors compared to env EM042. The infectivities were increased about 3-times by env EM170 for pseudotyped HIV-1 vectors and MLV vectors compared to env EM043. Env EM171 enhanced infectivity 6-times for pseudotyped MLV and HIV-1 vectors compared to env EM070. Therefore, the efficiency of viral transduction and gene transfer was raised by modified env EM228, EM170, EM171.

6. Tracking env

Cells transfected with vector particles comprising env EM238, env EM236 or env EM261 show fluorescent signals in the cytoplasm (predominantly around the nucleus) and in the cell membrane. Vector particles enveloped or pseudotyped by env EM238, env EM236 or env EM261 can be also detected as small fluorescent dots with a size of about 100 nm.

7. Sequence Listing

| SEQ ID NO: | Internal reference: |
|---|---|
| 1 | EM167 |
| 2 | EM168 |
| 3 | EM225 |
| 4 | EM226 |
| 5 | SM05 |
| 6 | SM06 |
| 7 | PE01 |
| 8 | PE02 |
| 9 | PE03 |
| 10 | SE01 |
| 11 | SE02 |
| 12 | SE03 |
| 1 | EM236 |
| 3 | EM238 |
| 14 | EM261 |
| 15 | EM170 |
| 16 | EM171 |
| 17 | EM228 |
| 18 | SM04 |
| 19 | EM134 |
| 20 | EM140 |
| 21 | pczHFV EM167 |
| 22 | pczHFV EM168 |
| 23 | pczHFV EM225 |
| 24 | pciSFV-1 SM05 |
| 25 | pciSFV-1 SM06 |
| 26 | pczHFV EM236 |
| 27 | pczHFV EM238 |
| 28 | pczHFV EM261 |
| 29 | pczHFV EM170 |
| 30 | pczHFV EM171 |
| 31 | pczHFV EM228 |
| 32 | pciSFV-1 SM04 |
| 33 | pczHFV EM140 |
| 34 | pczHFV EM002 |
| 35 | pczHFV EM134 |
| 36 | pczHFV EM043 |
| 37 | pczHFV EM070 |

References:

Anderson et al., Hum. Gene. Ther. 1(3), pp. 331-62, 1990
Check, Nature 433, p. 561, 2005
Nienhuis et al., Ann. N. Y. Acad. Sci. 996, pp.101-11, 2003
Li et al., J. Hum. Virol. 1(5), pp. 346-52, 1998
Li et al., Science 296, p. 497, 2002
Lindemann et al., J. Virol. 75, pp. 5762-5771, 2001
Russel and Miller, J. Virol. 70, pp. 217-222, 1996
Stanke et al., J. Virol. 79, pp. 15074-15083, 2005
Schmidt and Rethwilm, Virology 210, pp. 167-178, 1995
Weiss, Nature 380, p. 201, 1996
Wilk et al., J. Virol. 74, pp. 2885-2887, 2001
U.S. Pat. No. 6,111,087
U.S. Pat. No. 5,929,222

What is claimed is:

1. A nucleic acid comprising a foamy viral envelope gene encoding a modified foamy viral envelope polypeptide comprising a leader peptide (LP), a surface unit (SU) and a transmembrane domain (TM), wherein the polypeptide has an N terminus, wherein the nucleic acid is expression-optimized, wherein the nucleic acid encodes a modified foamy viral envelope gene comprising at least one mutation in a nucleic acid sequence encoding the LP, wherein the mutation results in inactivation of at least one ubiquitination site in the modified envelope polypeptide, and, wherein the foamy viral envelope gene comprises a sequence selected from the group consisting of SEQ ID NO: 7 (PE01), SEQ ID NO: 8 (PE02), SEQ ID NO: 9 (PE03), SEQ ID NO: 10 (SE01), SEQ ID NO: 11 (SE02) and SEQ ID NO: 12 (SE03).

2. A nucleic acid comprising a foamy viral envelope gene encoding a modified foamy viral envelope polypeptide comprising a leader peptide (LP), a surface unit (SU) and a transmembrane domain (TM), wherein the polypeptide has an N terminus, wherein the nucleic acid is expression-optimized, wherein the nucleic acid encodes a modified foamy viral envelope gene comprising at least one mutation in a nucleic acid sequence encoding the LP, wherein the mutation results in inactivation of at least one ubiquitination site in the modified envelope polypeptide, wherein the modified envelope polypeptide pseudotypes a viral vector for infecting at least one host cell, wherein infectivity of the pseudotyped viral vector is increased by expression-optimization up to about 50-fold compared to a non-optimized nucleic acid encoding the same modified envelope polypeptide, and, wherein the foamy viral envelope gene comprises a sequence selected from the group consisting of SEQ ID NO: 7 (PE01), SEQ ID NO: 8 (PE02), SEQ ID NO: 9 (PE03), SEQ ID NO: 10 (SE01), SEQ ID NO: 11 (SE02) and SEQ ID NO: 12 (SE03).

3. The nucleic acid of claim 1, wherein the mutation substitutes a lysine in the LP with a different amino acid.

4. The nucleic acid of claim 3, wherein the lysine is substituted with an amino acid selected from the group consisting of alanine, histidine, glycine and arginine.

5. The nucleic acid of claim 1, wherein the nucleic acid sequence encoding the LP encodes a mutation at an amino acid position selected from the amino acid positions 14 to 55, wherein amino acid position 1 is the first amino acid of the N terminus of the envelope polypeptide.

6. The nucleic acid of claim 1, wherein the foamy viral envelope gene comprises at least one second mutation in a nucleic acid encoding the TM, wherein the mutation results in inactivation of at least one ubiquitination site in the modified envelope polypeptide.

7. The nucleic acid of claim 6, wherein the nucleic acid sequence encoding the TM encodes a second mutation at an amino acid position selected from the amino acid positions 952 to 988, wherein amino acid position 1 is the first amino acid of the N terminus of the envelope polypeptide.

8. The nucleic acid of claim 1, further comprising at least one deletion in the nucleic acid encoding the N terminus of the foamy viral envelope polypeptide.

9. The nucleic acid of claim 8, wherein the deletion results in deletion of 5 to 25 amino acids of the modified envelope polypeptide.

10. The nucleic acid of claim 8, wherein the mutation leads on expression of the foamy viral envelope gene to a lysine exchange in the envelope polypeptide.

11. The nucleic acid of claim 10, wherein lysine is exchanged against an amino acid selected from the group consisting of alanine, histidine, glycine and arginine.

12. The nucleic acid of claim 8, wherein the mutation leads on expression to a modification of the envelope polypeptide at an amino acid position selected from the amino acid positions 14 to 55, and amino acid position 1 is the first amino acid of the N terminus of the envelope polypeptide.

13. The nucleic acid of claim 8 comprising a sequence selected from the group consisting of SEQ ID NO: 16 (EM170), SEQ ID NO: 17 (EM171) and SEQ ID NO: 18 (EM228).

14. The nucleic acid of claim 6, wherein the mutation substitutes a lysine in the TM with a different amino acid.

15. The nucleic acid of claim 14, wherein the lysine is substituted with an amino acid selected from the group consisting of alanine, histidine, glycine and arginine.

16. The nucleic acid of claim 6, wherein the nucleic acid sequence encodes a mutation at an amino acid position selected from the amino acid positions 952 to 988, wherein amino acid position 1 is the first amino acid of the N terminus of the envelope polypeptide.

* * * * *

SEQUENCE LISTING

```
<160> NUMBER OF SEQ ID NOS: 39

<210> SEQ ID NO 1
<211> LENGTH: 2967
<212> TYPE: DNA
<213> ORGANISM: Artificial Sequence
```

<220> FEATURE:
<223> OTHER INFORMATION: Foamy Viral Envelope Gene EM167

<400> SEQUENCE: 1

```
atggcaccac caatgacact gcaacaatgg atcatttgga gaagaatgaa tagagcgcat     60

gaggcacttc aaaatacaac aactgtgact gaacagcagc gcgaacaaat tatactggac    120

attcaaaatg aagaagtaca accaactagg agagatcgct ttagatatct gctttatact    180

tgttgtgcta ctagctcaag agtattggcc tggatgtttt tagtttgtat attgttaatc    240

attgttttgg tttcatgctt tgtgactata tccagaatac aatggaataa ggatattcag    300

gtattaggac ctgtaataga ctggaatgtt actcaaagag ctgtttatca acccttacag    360

actagaagga ttgcacgttc ccttagaatg cagcatcctg ttccaaaata tgtggaggta    420

aatatgacta gtattccaca aggtgtatac tatgaacccc atccggaacc catagtggtg    480

aaggagaggg tcctgggtct ttctcaaatt ctgatgatta attcagaaaa cattgctaat    540

aatgctaatt tgacacaaga agtaaagaag ttgttaactg aaatggttaa tgaagaaatg    600

caaagtttgt cagatgtaat gattgacttt gaaattcctt taggagaccc tcgtgatcaa    660

gaacaatata tacatagaaa atgctatcaa gaatttgcaa attgttattt agtaaaatat    720

aaagaaccca aaccgtggcc taaggagggc cttatagctg atcaatgccc attaccaggt    780

taccatgctg gattaaccta taatagacag tctatttggg attactatat taaagtggag    840

agtattagac ctgcaaattg gacaacaaag agtaaatatg gacaagctag actaggaagt    900

ttttatattc ctagcagtct gagacaaatc aatgttagtc atgtactatt ctgtagtgat    960

caattatatt ctaaatggta taatatagaa aataccatag aacaaaacga gcggtttctg   1020

cttaataaac taaataacct tacatctgga acctcagtat tgaagaaaag agctcttccg   1080

aaggattgga gttctcaagg taaaaatgct ctgtttagag aaatcaatgt gttagatatc   1140

tgcagtaaac ctgaatctgt aatactattg aatacttcat actattcctt ctctttatgg   1200

gaaggagatt gtaattttac taaagatatg atttctcagt tggttccaga atgtgatgga   1260

ttttataaca attctaagtg gatgcatatg catccatatg cttgtagatt ctggagaagt   1320

aagaatgaaa aagaagaaac taaatgtaga gatggggaaa ctaagagatg tctgtattat   1380

cctttatggg acagtcccga atctacatat gattttggtt atttagcata ccaaaagaat   1440

tttccttccc ctatctgtat agaacaacag aaaattagag atcaagatta tgaagtttat   1500

tctttgtatc aagaatgcaa aatagcttct aaagcatatg gaattgatac agttttattc   1560

tctctaaaga attttcttaa ttatacagga actcctgtaa atgaaatgcc taatgcaaga   1620

gcttttgtag gcctaataga tcccaagttt cctccttcct atcccaatgt tactagggaa   1680

cattatactt cctgtaataa taggaaaaga agaagtgttg ataataacta tgctaagtta   1740

aggtctatgg ggtatgcact tacaggagca gtgcaaacct tatctcaaat atcagatatt   1800

aatgatgaaa acttacagca aggaatatat ttattaaggg atcatgtaat aaccttaatg   1860

gaagctacat tgcatgatat atctgttatg gaaggaatgt ttgctgtaca acatttgcat   1920

acacatttga atcatttgaa gacaatgctt ctagaaagaa gaatagactg gacctatatg   1980

tctagtactt ggctacaaca acaattacag aaatctgatg atgagatgaa agtaataaag   2040

agaattgcta gaagtttggt atattatgtt aaacaaaccc atagttctcc cacagctaca   2100

gcctgggaga ttggattata ttatgaattg gttataccta aacatattta cttgaataat   2160

tggaatgttg tcaatatagg tcacttagtt aaatcagctg gacaattgac tcatgtaact   2220

atagctcatc cttatgaaat aatcaataag gaatgtgtag agactatata tctgcatctt   2280
```

```
gaagactgca caagacaaga ttatgtcata tgtgatgtgg taaagatagt gcagccttgt   2340

ggcaatagct cagacacgag tgattgtcct gtctgggctg aagctgtaaa agaaccattt   2400

gtgcaagtca atcctctgaa aaacggaagt tatctggttt tggcaagttc cacagactgt   2460

cagatcccac catatgttcc tagcatcgtg actgttaatg aaacaacgtc atgctttgga   2520

ctggacttta aaaggccact ggttgcggaa gaaagattga gctttgagcc acgactgcca   2580

aatctacaac taagattacc acatttggtt ggaattattg caaaaatcaa agggataaaa   2640

atagaagtca catcctctgg agaaagtata aaagagcaga ttgaaagagc aaaagctgag   2700

ctccttcgac tggacattca cgagggagat actcctgcct ggatacaaca gctagctgca   2760

gcaacaaagg acgtctggcc agcagcagct tctgctctac aaggaattgg gaacttttta   2820

tctgggactg cccaaggaat atttggaact gcctttagtc tcttgggata cttaaagcct   2880

atcctaatag gagtaggggt cattctcttg gttattctta tatttaaaat tgtatcctgg   2940

attcctacga gaaggaggaa tcagtag                                       2967
```

<210> SEQ ID NO 2
<211> LENGTH: 2967
<212> TYPE: DNA
<213> ORGANISM: Artificial Sequence
<220> FEATURE:
<223> OTHER INFORMATION: Foamy Viral Envelope Gene EM168

<400> SEQUENCE: 2

```
atggcaccac caatgacact gcaacaatgg atcatttgga gaagaatgaa tagagcgcat     60

gaggcacttc aaaatacaac aactgtgact gaacagcagc gcgaacaaat tatactggac    120

attcaaaatg aagaagtaca accaactagg agagatcgct ttagatatct gctttatact    180

tgttgtgcta ctagctcaag agtattggcc tggatgtttt tagtttgtat attgttaatc    240

attgttttgg tttcatgctt tgtgactata tccagaatac aatggaataa ggatattcag    300

gtattaggac ctgtaataga ctggaatgtt actcaaagag ctgtttatca acccttacag    360

actagaagga ttgcacgttc ccttagaatg cagcatcctg ttccaaaata tgtggaggta    420

aatatgacta gtattccaca aggtgtatac tatgaacccc atccggaacc catagtggtg    480

aaggagaggg tcctgggtct ttctcaaatt ctgatgatta attcagaaaa cattgctaat    540

aatgctaatt tgacacaaga agtaaagaag ttgttaactg aaatggttaa tgaagaaatg    600

caaagtttgt cagatgtaat gattgacttt gaaattcctt taggagaccc tcgtgatcaa    660

gaacaatata tacatagaaa atgctatcaa gaatttgcaa attgttattt agtaaaatat    720

aaagaaccca aaccgtggcc taaggagggc cttatagctg atcaatgccc attaccaggt    780

taccatgctg gattaaccta taatagacag tctatttggg attactatat taaagtggag    840

agtattagac ctgcaaattg gacaacaaag agtaaatatg gacaagctag actaggaagt    900

ttttatattc ctagcagtct gagacaaatc aatgttagtc atgtactatt ctgtagtgat    960

caattatatt ctaaatggta taatatagaa aataccatag aacaaaacga gcggtttctg   1020

cttaataaac taaataacct tacatctgga acctcagtat tgaagaaaag agctcttccg   1080

aaggattgga gttctcaagg taaaaatgct ctgtttagag aaatcaatgt gttagatatc   1140

tgcagtaaac ctgaatctgt aatactattg aatacttcat actattcctt ctctttatgg   1200

gaaggagatt gtaattttac taaagatatg atttctcagt tggttccaga atgtgatgga   1260

ttttataaca attctaagtg gatgcatatg catccatatg cttgtagatt ctggagaagt   1320

aagaatgaaa aagaagaaac taaatgtaga gatggggaaa ctaagagatg tctgtattat   1380
```

```
cctttatggg acagtcccga atctacatat gattttggtt atttagcata ccaaaagaat   1440

tttccttccc ctatctgtat agaacaacag aaaattagag atcaagatta tgaagtttat   1500

tctttgtatc aagaatgcaa aatagcttct aaagcatatg gaattgatac agttttattc   1560

tctctaaaga attttcttaa ttatacagga actcctgtaa atgaaatgcc taatgcaaga   1620

gcttttgtag gcctaataga tcccaagttt cctccttcct atcccaatgt tactagggaa   1680

cattatactt cctgtaataa taggaaaaga agaagtgttg ataataacta tgctaagtta   1740

aggtctatgg ggtatgcact tacaggagca gtgcaaacct tatctcaaat atcagatatt   1800

aatgatgaaa acttacagca aggaatatat ttattaaggg atcatgtaat aaccttaatg   1860

gaagctacat tgcatgatat atctgttatg gaaggaatgt ttgctgtaca acatttgcat   1920

acacatttga atcatttgaa gacaatgctt ctagaaagaa gaatagactg gacctatatg   1980

tctagtactt ggctacaaca acaattacag aaatctgatg atgagatgaa agtaataaag   2040

agaattgcta gaagtttggt atattatgtt aaacaaaccc atagttctcc cacagctaca   2100

gcctgggaga ttggattata ttatgaattg gttataccta aacatattta cttgaataat   2160

tggaatgttg tcaatatagg tcacttagtt aaatcagctg gacaattgac tcatgtaact   2220

atagctcatc cttatgaaat aatcaataag gaatgtgtag agactatata tctgcatctt   2280

gaagactgca caagacaaga ttatgtcata tgtgatgtgg taaagatagt gcagccttgt   2340

ggcaatagct cagacacgag tgattgtcct gtctgggctg aagctgtaaa agaaccattt   2400

gtgcaagtca atcctctgaa aaacggaagt tatctggttt tggcaagttc cacagactgt   2460

cagatcccac catatgttcc tagcatcgtg actgttaatg aaacaacgtc atgctttgga   2520

ctggacttta aaaggccact ggttgcggaa gaaagattga gctttgagcc acgactgcca   2580

aatctacaac taagattacc acatttggtt ggaattattg caaaaatcaa agggataaaa   2640

atagaagtca catcctctgg agaaagtata aaagagcaga ttgaaagagc aaaagctgag   2700

ctccttcgac tggacattca cgagggagat actcctgcct ggatacaaca gctagctgca   2760

gcaacaaagg acgtctggcc agcagcagct tctgctctac aaggaattgg gaacttttta   2820

tctgggactg cccaaggaat atttggaact gcctttagtc tcttgggata cttaaggcct   2880

atcctaatag gagtaggggt cattctcttg gttattctta tatttagaat tgtatcctgg   2940

attcctacga gaaggaggaa tcagtag                                       2967
```

<210> SEQ ID NO 3
<211> LENGTH: 2967
<212> TYPE: DNA
<213> ORGANISM: Artificial Sequence
<220> FEATURE:
<223> OTHER INFORMATION: Foamy Viral Envelope Gene EM225

<400> SEQUENCE: 3

```
atggcaccac caatgacact gcaacaatgg atcatttgga aaaaaatgaa taaagcgcat     60

gaggcacttc aaaatacaac aactgtgact gaacagcaga aggaacaaat tatactggac    120

attcaaaatg aagaagtaca accaactagg agagataaat ttagatatct gctttatact    180

tgttgtgcta ctagctcaag agtattggcc tggatgtttt tagtttgtat attgttaatc    240

attgttttgg tttcatgctt tgtgactata tccagaatac aatggaataa ggatattcag    300

gtattaggac ctgtaataga ctggaatgtt actcaaagag ctgtttatca acccttacag    360

actagaagga ttgcacgttc ccttagaatg cagcatcctg ttccaaaata tgtggaggta    420

aatatgacta gtattccaca aggtgtgtac tatgaacccc atccggaacc catagtggtg    480
```

```
aaggagaggg tcctaggtct ttctcaaatt ctgatgatta attcagaaaa cattgctaat    540

aatgctaatt tgacacaaga agtaaagaag ttgttaactg aaatggttaa tgaagaaatg    600

caaagtttgt cagatgtaat gattgacttt gaaattcctt taggagaccc tcgtgatcaa    660

gaacaatata tacatagaaa atgctatcaa gaatttgcaa attgttattt agtaaaatat    720

aaagaaccca aaccgtggcc taaggagggc cttatagctg atcaatgccc attaccaggt    780

taccatgctg gattaaccta taatagacag tctatttggg attactatat taaagtggag    840

agtattagac ctgcaaattg gacaacaaag agtaaatatg gacaagctag actaggaagt    900

ttttatattc ctagcagtct gagacaaatc aatgttagtc atgtactatt ctgtagtgat    960

caattatatt ctaaatggta taatatagaa aataccatag aacaaaacga gcggtttctg   1020

cttaataaac taaataacct tacatctgga acctcagtat tgaagaaaag agctcttccg   1080

aaggattgga gttctcaagg taaaaatgct ctgtttagag aaatcaatgt gttagatatc   1140

tgcagtaaac ctgaatctgt aatactattg aatacttcat actattcctt ctctttatgg   1200

gaaggagatt gtaattttac taaagatatg atttctcagt tggttccaga atgtgatgga   1260

ttttataaca attctaagtg gatgcatatg catccatatg cttgtagatt ctggagaagt   1320

aagaatgaaa aagaagaaac taaatgtaga gatggggaaa ctaagagatg tctgtattat   1380

cctttatggg acagtcccga atctacatat gattttggtt atttagcata ccaaaagaat   1440

tttccttccc ctatctgtat agaacaacag aaaattagag atcaagatta tgaagtttat   1500

tctttgtatc aagaatgcaa aatagcttct aaagcatatg gaattgatac agttttattc   1560

tctctaaaga attttcttaa ttatacagga actcctgtaa atgaaatgcc taatgcaaga   1620

gcttttgtag gcctaataga tcccaagttt cctccttcct atcccaatgt tactagggaa   1680

cattatactt cctgtaataa taggaaaaga agaagtgttg ataataacta tgctaagtta   1740

aggtctatgg ggtatgcact tacaggagca gtgcaaacct tatctcaaat atcagatatt   1800

aatgatgaaa acttacagca aggaatatat ttattaaggg atcatgtaat aaccttaatg   1860

gaagctacat tgcatgatat atctgttatg gaaggaatgt ttgctgtaca acatttgcat   1920

acacatttga atcatttgaa gacaatgctt ctagaaagaa gaatagactg gacctatatg   1980

tctagtactt ggctacaaca acaattacag aaatctgatg atgagatgaa agtaataaag   2040

agaattgcta gaagtttggt atattatgtt aaacaaaccc atagttctcc cacagctaca   2100

gcctgggaga ttggattata ttatgaattg gttataccta aacatattta cttgaataat   2160

tggaatgttg tcaatatagg tcacttagtt aaatcagctg gacaattgac tcatgtaact   2220

atagctcatc cttatgaaat aatcaataag gaatgtgtag agactatata tctgcatctt   2280

gaagactgca caagacaaga ttatgtcata tgtgatgtgg taaagatagt gcagccttgt   2340

ggcaatagct cagacacgag tgattgtcct gtctgggctg aagctgtaaa agaaccattt   2400

gtgcaagtca atcctctgaa aaacggaagt tatctggttt tggcaagttc cacagactgt   2460

cagatcccac catatgttcc tagcatcgtg actgttaatg aaacaacgtc atgctttgga   2520

ctggacttta aaaggccact ggttgcggaa gaaagattga gctttgagcc acgactgcca   2580

aatctacaac taagattacc acatttggtt ggaattattg caaaaatcaa agggataaaa   2640

atagaagtca catcctctgg agaaagtata aaagagcaga ttgaaagagc aaaagctgag   2700

ctccttcgac tggacattca cgagggagat actcctgcct ggatacaaca gctagctgca   2760

gcaacaaagg acgtctggcc agcagcagct tctgctctac aaggaattgg gaacttttta   2820

tctgggactg cccaaggaat atttggaact gcctttagtc tcttgggata cttaaagcct   2880
```

```
atcctaatag gagtaggggt cattctcttg gttattctta tatttaaaat tgtatcctgg   2940

attcctacga gaaggaggaa tcagtag                                       2967
```

<210> SEQ ID NO 4
<211> LENGTH: 2967
<212> TYPE: DNA
<213> ORGANISM: Artificial Sequence
<220> FEATURE:
<223> OTHER INFORMATION: Foamy Viral Envelope Gene EM226

<400> SEQUENCE: 4

```
atggcaccac caatgacact gcaacaatgg atcatttgga aaaaaatgaa taaagcgcat     60

gaggcacttc aaaatacaac aactgtgact gaacagcaga aggaacaaat tatactggac    120

attcaaaatg aagaagtaca accaactagg agagataaat ttagatatct gctttatact    180

tgttgtgcta ctagctcaag agtattggcc tggatgtttt tagtttgtat attgttaatc    240

attgttttgg tttcatgctt tgtgactata tccagaatac aatggaataa ggatattcag    300

gtattaggac ctgtaataga ctggaatgtt actcaaagag ctgtttatca acccttacag    360

actagaagga ttgcacgttc ccttagaatg cagcatcctg ttccaaaata tgtggaggta    420

aatatgacta gtattccaca aggtgtatac tatgaacccc atccggaacc catagtggtg    480

aaggagaggg tcctgggtct ttctcaaatt ctgatgatta attcagaaaa cattgctaat    540

aatgctaatt tgacacaaga agtaaagaag ttgttaactg aaatggttaa tgaagaaatg    600

caaagtttgt cagatgtaat gattgacttt gaaattcctt taggagaccc tcgtgatcaa    660

gaacaatata tacatagaaa atgctatcaa gaatttgcaa attgttattt agtaaaatat    720

aaagaaccca aaccgtggcc taaggagggc cttatagctg atcaatgccc attaccaggt    780

taccatgctg gattaaccta taatagacag tctatttggg attactatat taaagtggag    840

agtattagac ctgcaaattg gacaacaaag agtaaatatg gacaagctag actaggaagt    900

ttttatattc ctagcagtct gagacaaatc aatgttagtc atgtactatt ctgtagtgat    960

caattatatt ctaaatggta taatatagaa aataccatag aacaaaacga gcggtttctg   1020

cttaataaac taaataacct tacatctgga acctcagtat tgaagaaaag agctcttccg   1080

aaggattgga gttctcaagg taaaaatgct ctgtttagag aaatcaatgt gttagatatc   1140

tgcagtaaac ctgaatctgt aatactattg aatacttcat actattcctt ctctttatgg   1200

gaaggagatt gtaattttac taaagatatg atttctcagt tggttccaga atgtgatgga   1260

ttttataaca attctaagtg gatgcatatg catccatatg cttgtagatt ctggagaagt   1320

aagaatgaaa aagaagaaac taaatgtaga gatggggaaa ctaagagatg tctgtattat   1380

cctttatggg acagtcccga atctacatat gattttggtt atttagcata ccaaaagaat   1440

tttccttccc ctatctgtat agaacaacag aaaattagag atcaagatta tgaagtttat   1500

tctttgtatc aagaatgcaa aatagcttct aaagcatatg gaattgatac agttttattc   1560

tctctaaaga attttcttaa ttatacagga actcctgtaa atgaaatgcc taatgcaaga   1620

gcttttgtag gcctaataga tcccaagttt cctccttcct atcccaatgt tactagggaa   1680

cattatactt cctgtaataa taggaaaaga agaagtgttg ataataacta tgctaagtta   1740

aggtctatgg ggtatgcact tacaggagca gtgcaaacct tatctcaaat atcagatatt   1800

aatgatgaaa acttacagca aggaatatat ttattaaggg atcatgtaat aaccttaatg   1860

gaagctacat tgcatgatat atctgttatg gaaggaatgt ttgctgtaca acatttgcat   1920

acacatttga atcatttgaa gacaatgctt ctagaaagaa gaatagactg gacctatatg   1980
```

```
tctagtactt ggctacaaca acaattacag aaatctgatg atgagatgaa agtaataaag   2040

agaattgcta gaagtttggt atattatgtt aaacaaaccc atagttctcc cacagctaca   2100

gcctgggaga ttggattata ttatgaattg gttataccta aacatattta cttgaataat   2160

tggaatgttg tcaatatagg tcacttagtt aaatcagctg gacaattgac tcatgtaact   2220

atagctcatc cttatgaaat aatcaataag gaatgtgtag agactatata tctgcatctt   2280

gaagactgca caagacaaga ttatgtcata tgtgatgtgg taaagatagt gcagccttgt   2340

ggcaatagct cagacacgag tgattgtcct gtctgggctg aagctgtaaa agaaccattt   2400

gtgcaagtca atcctctgaa aaacggaagt tatctggttt tggcaagttc cacagactgt   2460

cagatcccac catatgttcc tagcatcgtg actgttaatg aaacaacgtc atgctttgga   2520

ctggacttta aaaggccact ggttgcggaa gaaagattga gctttgagcc acgactgcca   2580

aatctacaac taagattacc acatttggtt ggaattattg caaaaatcaa agggataaaa   2640

atagaagtca catcctctgg agaaagtata aaagagcaga ttgaaagagc aaaagctgag   2700

ctccttcgac tggacattca cgagggagat actcctgcct ggatacaaca gctagctgca   2760

gcaacaaagg acgtctggcc agcagcagct tctgctctac aaggaattgg gaacttttta   2820

tctgggactg cccaaggaat atttggaact gcctttagtc tcttgggata cttaaggcct   2880

atcctaatag gagtaggggt cattctcttg gttattctta tatttagaat tgtatcctgg   2940

attcctacga gaaggaggaa tcagtag                                       2967
```

<210> SEQ ID NO 5
<211> LENGTH: 2970
<212> TYPE: DNA
<213> ORGANISM: Artificial Sequence
<220> FEATURE:
<223> OTHER INFORMATION: Foamy Viral Envelope Gene SM05

<400> SEQUENCE: 5

```
atggcacctc caatgactct ggaacaatgg ctcttatgga ggaggatgag tcaagcacat     60

caagcacttg aaaatgtaac caccttgact gaggaacaga ggcaacaagt tataatagac    120

attcagcatg aagatgttgt tcctactagg atggacagat tgagatatct ggcctattca    180

tgctgcgcta ctagcacacg tgtattgtgc tggatagtgt tagtttgcgt cttgctatta    240

gttgtattta tatcctgctt tgtgacaatg tccaggatac aatggaataa ggatattgct    300

gtttttggtc cagtcattga ctggaatgtt agccaacaag ctgtgattca acaaataaga    360

gctaaaagat tagcaagatc aattagggtg gaacatgcta ctgagacata tgtagaggtc    420

aatatgacca gtatacctca aggggtgtta tatgtgcctc atccagaacc aataattctc    480

aaggagagga ttcttggttt atctcaggtc atgatgataa actctgaaaa tattgctaat    540

actgctaacc ttactcaaga aactaaggta ctgttagcag acatgattaa tgaagagatg    600

aatgatttag ctaatcaaat gatagatttt gaaatcccat taggagatcc cagagatcaa    660

aaacaatacc agcatcaaaa atgttttcaa gaatttgcac attgttattt agtaaaatat    720

aaaactacta aaggatggcc tagttctact gttatagcag atcaatgccc tttgcctggt    780

aaccatccta cagtacaata tgcacatcaa aatatatggg attattatgt ccccttttgaa    840

caaattcggc cagaaggatg gaactcaaaa agttattatg aagatgctag aataggaggg    900

ttttatatac caaaatggtt acgaaataat tcctataccc atgtcttatt ttgttctgat    960

caaatttatg gaaaatggta taatattgat ctcacagccc aggagaggga aaatttatta   1020

gtccgaaaat taattaattt agctaaagga aattcatcac aattaaaaga tagagctatg   1080
```

```
ccagctgaat gggataaaca aggaaaagct gatctattta gacaaattaa tactttagat   1140

gtttgtaata gaccagaaat ggtatttttg ttaaattcct catattatga attttcccta   1200

tgggaaggag attgtggttt taccagacag aatgttacac aggctaattc cttatgtaaa   1260

gatttctata ataactcaaa atggcaaaaa ttacatccat attcgtgtag attttggaga   1320

tataaacaag agaaagaaga aactaaatgt agtaatggtg aaaagaaaaa atgtctttat   1380

tacccacaat gggatactcc tgaagcttta tatgactttg ggttcctagc atatttaaat   1440

tcttttcctt ctccaatctg tataaaaaat cagactataa gggaacctga gtataaaatc   1500

tcttctttat acctagaatg catgaatgct tcagacagac atggtataga tagtgcttta   1560

ttagctttga agacattttt aaactttact ggtcagtctg taaacgaaat gccattagct   1620

agagcctttg taggccttac tgaccctaaa tttccaccaa catatcccaa cattacaagg   1680

gaatcttctg gttgtaataa taacaaaaga aaaaggagaa gtgttaataa ttatgaaaga   1740

cttagatcta tgggatatgc tttaactgga gctgttcaaa ctttatctca aatatctgat   1800

attaatgatg agaggctgca acacggagta tatttactcc gggatcatgt ggtaaccctg   1860

atggaagctg cccttcatga tgtttcgatt atggaaggaa tgttagcaat tcaacatgtg   1920

catactcatc tcaatcatct caagaccatg cttttgatga gaaagattga ttggacattc   1980

atcagaagtg actggattca acagcaatta cagaagacag atgatgaaat gaaattgata   2040

cgaagaactg cacgaagtct agtctactat gtcacacaaa cctccagttc tcctacagct   2100

acttcctggg agattggaat atattatgaa atagtaattc ctaaacatat atatttaaat   2160

aattggcaag taatcaatgt aggtcattta ttggagtcag ctggtcatct gactcatgta   2220

aaggttaagc atccttatga aataattaat aaggaatgta gtgacactca atatttacat   2280

cttgaggaat gcattagaga ggattatgtg atttgtgaca tagtacaaat agttcaacca   2340

tgtggaaatg caacagaatt gagtgattgt ccagtaacag cattaaaggt gaagactcca   2400

tatattcaag tgtctcccct gaagaatgga agttatttag ttttatctag tactaaggat   2460

tgttctatac ctgcatatgt acctagtgtg gtcacagtca atgaaacagt taagtgcttt   2520

ggagtagagt ttcacaaacc actttatgct gaaacaaaaa ccagctatga accacaagtt   2580

ccgcatttga agcttcgttt accccacttg actgggatta ttgccagctt gcaatcactg   2640

gaaatagaag ttacttctac acaagagaat ataaaagacc agatcgaaag ggccaaagca   2700

cagcttctcc ggctggacat tcacgaagga gactttcctg actggctgaa acaagtcgcc   2760

tctgcaacca gggacgtttg gcctgctgca gcttccttta tacaaggagt agggaacttc   2820

ttatctaata ctgcccaggg gatattcggc tcagcggtaa gcctcctatc ctatgcaaaa   2880

cctattttga taggaatagg agttatactg cttattgccc ttctttttaa aataatatcg   2940

tggcttcctg ggaggcccag gaggaattga                                    2970
```

<210> SEQ ID NO 6
<211> LENGTH: 2970
<212> TYPE: DNA
<213> ORGANISM: Artificial Sequence
<220> FEATURE:
<223> OTHER INFORMATION: Foamy Viral Envelope Gene SM06

<400> SEQUENCE: 6

```
atggcacctc caatgactct ggaacaatgg ctcttatgga ggaggatgag tcaagcacat     60

caagcacttg aaaatgtaac caccttgact gaggaacaga ggcaacaagt tataatagac    120

attcagcatg aagatgttgt tcctactagg atggacagat tgagatatct ggcctattca    180
```

```
tgctgcgcta ctagcacacg tgtattgtgc tggatagtgt tagtttgcgt cttgctatta    240
gttgtattta tatcctgctt tgtgacaatg tccaggatac aatggaataa ggatattgct    300
gtttttggtc cagtcattga ctggaatgtt agccaacaag ctgtgattca acaaataaga    360
gctaaaagat tagcaagatc aattagggtg gaacatgcta ctgagacata tgtagaggtc    420
aatatgacca gtatacctca aggggtgtta tatgtgcctc atccagaacc aataattctc    480
aaggagagga ttcttggttt atctcaggtc atgatgataa actctgaaaa tattgctaat    540
actgctaacc ttactcaaga aactaaggta ctgttagcag acatgattaa tgaagagatg    600
aatgatttag ctaatcaaat gatagatttt gaaatcccat taggagatcc cagagatcaa    660
aaacaatacc agcatcaaaa atgttttcaa gaatttgcac attgttattt agtaaaatat    720
aaaactacta aaggatggcc tagttctact gttatagcag atcaatgccc tttgcctggt    780
aaccatccta cagtacaata tgcacatcaa aatatatggg attattatgt ccccttttgaa    840
caaattcggc cagaaggatg gaactcaaaa agttattatg aagatgctag aataggaggg    900
ttttatatac caaaatggtt acgaaataat tcctataccc atgtcttatt ttgttctgat    960
caaatttatg gaaaatggta taatattgat ctcacagccc aggagaggga aaatttatta   1020
gtccgaaaat taattaattt agctaaagga aattcatcac aattaaaaga tagagctatg   1080
ccagctgaat gggataaaca aggaaaagct gatctattta gacaaattaa tactttagat   1140
gtttgtaata gaccagaaat ggtatttttg ttaaattcct catattatga attttcccta   1200
tgggaaggag attgtggttt taccagacag aatgttacac aggctaattc cttatgtaaa   1260
gatttctata ataactcaaa atggcaaaaa ttacatccat attcgtgtag attttggaga   1320
tataaacaag agaaagaaga aactaaatgt agtaatggtg aaaagaaaaa atgtctttat   1380
tacccacaat gggatactcc tgaagcttta tatgactttg ggttcctagc atatttaaat   1440
tcttttcctt ctccaatctg tataaaaaat cagactataa gggaacctga gtataaaatc   1500
tcttctttat acctagaatg catgaatgct tcagacagac atggtataga tagtgcttta   1560
ttagctttga agacattttt aaactttact ggtcagtctg taaacgaaat gccattagct   1620
agagcctttg taggccttac tgaccctaaa tttccaccaa catatcccaa cattacaagg   1680
gaatcttctg gttgtaataa taacaaaaga aaaaggagaa gtgttaataa ttatgaaaga   1740
cttagatcta tgggatatgc tttaactgga gctgttcaaa ctttatctca aatatctgat   1800
attaatgatg agaggctgca acacggagta tatttactcc gggatcatgt ggtaaccctg   1860
atggaagctg cccttcatga tgtttcgatt atggaaggaa tgttagcaat tcaacatgtg   1920
catactcatc tcaatcatct caagaccatg cttttgatga gaaagattga ttggacattc   1980
atcagaagtg actggattca acagcaatta cagaagacag atgatgaaat gaaattgata   2040
cgaagaactg cacgaagtct agtctactat gtcacacaaa cctccagttc tcctacagct   2100
acttcctggg agattggaat atattatgaa atagtaattc ctaaacatat atatttaaat   2160
aattggcaag taatcaatgt aggtcattta ttggagtcag ctggtcatct gactcatgta   2220
aaggttaagc atccttatga aataattaat aaggaatgta gtgacactca atatttacat   2280
cttgaggaat gcattagaga ggattatgtg atttgtgaca tagtacaaat agttcaacca   2340
tgtggaaatg caacagaatt gagtgattgt ccagtaacag cattaaaggt gaagactcca   2400
tatattcaag tgtctcccct gaagaatgga agttatttag ttttatctag tactaaggat   2460
tgttctatac ctgcatatgt acctagtgtg gtcacagtca atgaaacagt taagtgcttt   2520
ggagtagagt ttcacaaacc actttatgct gaaacaaaaa ccagctatga accacaagtt   2580
```

```
ccgcatttga agcttcgttt accccacttg actgggatta ttgccagctt gcaatcactg   2640

gaaatagaag ttacttctac acaagagaat ataaaagacc agatcgaaag ggccaaagca   2700

cagcttctcc ggctggacat tcacgaagga gactttcctg actggctgaa acaagtcgcc   2760

tctgcaacca gggacgtttg gcctgctgca gcttccttta tacaaggagt agggaacttc   2820

ttatctaata ctgcccaggg gatattcggc tcagcggtaa gcctcctatt ctatgcaaga   2880

cctattttga taggaatagg agttatactg cttattgccc ttctttttag aataatatcg   2940

tggcttcctg ggaggcccag gaggaattga                                    2970
```

```
<210> SEQ ID NO 7
<211> LENGTH: 2967
<212> TYPE: DNA
<213> ORGANISM: Artificial Sequence
<220> FEATURE:
<223> OTHER INFORMATION: Foamy Viral Envelope Gene PE01

<400> SEQUENCE: 7

atggcccctc ccatgaccct gcagcagtgg atcatctggc ggcggatgaa ccgggcccac     60

gaggccctgc agaacaccac caccgtgacc gagcagcagc gggagcagat catcctggac    120

atccagaacg aggaagtgca gcccaccagg cgggaccggt tcagatacct gctgtacacc    180

tgctgcgcca cctccagccg ggtgctggcc tggatgttcc tggtgtgcat cctgctgatc    240

atcgtgctgg tgtcctgctt cgtgaccatc agccggatcc agtggaacaa ggacatccag    300

gtgctgggcc ccgtgatcga ctggaacgtg acccagcggg ccgtgtacca gcccctgcag    360

acccggcgga tcgcccggtc cctgcggatg cagcaccccg tgcccaagta cgtggaggtg    420

aacatgacca gcatccccca gggcgtgtac tacgagcccc accccgagcc catcgtggtg    480

aaagaaagag tgctgggcct gagccagatc ctgatgatca acagcgagaa catcgccaac    540

aacgccaacc tgacccagga agtgaagaaa ctgctgaccg agatggtgaa cgaagagatg    600

cagagcctga gcgacgtgat gatcgacttc gagatccccc tgggcgaccc cagggaccag    660

gaacagtaca tccaccggaa gtgctaccag gaatttgcca actgctacct ggtgaagtac    720

aaagagccca agccctggcc caaagagggc ctgatcgccg accagtgccc cctgcccggc    780

tatcacgccg gcctgaccta caaccggcag agcatctggg actactacat caaggtggag    840

agcatcaggc ccgccaactg gaccaccaag agcaagtacg gccaggcccg gctgggcagc    900

ttctacatcc ccagcagcct gcggcagatc aacgtgagcc acgtgctgtt ctgcagcgac    960

cagctgtaca gcaagtggta caacatcgag aacaccatcg agcagaacga gcggttcctg   1020

ctgaacaagc tgaataacct gaccagcggc accagcgtgc tgaagaagag agccctgccc   1080

aaggactggt ccagccaggg caagaacgcc ctgttccggg agatcaatgt gctggacatc   1140

tgcagcaagc ccgagagcgt gatcctgctg aataccagct actacagctt cagcctgtgg   1200

gagggcgact gcaacttcac caaggacatg atcagccagc tggtgcccga gtgcgacggc   1260

ttctacaaca actccaagtg gatgcacatg cacccctacg cctgccggtt ctggcggagc   1320

aagaacgaga aagaggaaac caagtgccgg gacggcgaga ccaagcggtg cctgtactac   1380

cccctgtggg acagccctga gagcacctac gacttcggct acctggccta ccagaagaac   1440

ttccccagcc ccatctgcat cgaacagcag aagatccggg accaggacta cgaggtgtac   1500

agcctgtacc aggaatgcaa gatcgccagc aaggcctacg gcatcgacac cgtgctgttc   1560

agcctgaaga atttcctgaa ctacaccggc acccccgtga acgagatgcc caacgccagg   1620

gccttcgtgg gcctgattga ccccaagttc ccccccagct accccaacgt gacccgggag   1680
```

```
cactacacca gctgcaacaa ccggaagcgg cggagcgtgg acaacaacta cgccaagctg   1740

cggagcatgg gctacgctct gacaggcgcc gtgcagaccc tgtcccagat cagcgacatc   1800

aacgacgaga acctgcagca gggcatctac ctgctgcggg accacgtgat caccctgatg   1860

gaagccaccc tgcacgacat cagcgtgatg gaaggcatgt tcgccgtgca gcacctgcac   1920

acccacctga atcacctgaa aaccatgctg ctggaacggc gcatcgactg gacctacatg   1980

agcagcacct ggctgcagca gcagctgcag aaaagcgacg acgagatgaa ggtgatcaag   2040

cggatcgcca gatctctggt gtactacgtg aagcagaccc acagcagccc caccgccacc   2100

gcctgggaga tcggcctgta ctatgagctg gtgatcccca agcacatcta cctgaacaac   2160

tggaatgtgg tgaacatcgg ccacctggtg aaaagcgccg gacagctgac ccacgtgacc   2220

atcgcccacc cctacgagat catcaacaaa gaatgcgtgg agaccatcta tctgcacctg   2280

gaagattgca cccggcagga ctacgtgatc tgcgacgtgg tgaagatcgt gcagccctgc   2340

ggcaacagca gcgacaccag cgactgcccc gtgtgggccg aggccgtgaa agaacccttc   2400

gtgcaggtga acccccctgaa gaacggctcc tacctggtgc tggccagcag caccgactgc   2460

cagatccccc cctacgtgcc cagcatcgtg accgtgaatg agaccacctc ctgcttcggc   2520

ctggacttca agcggcccct ggtggccgag gaaagactga gcttcgagcc ccggctgccc   2580

aacctgcagc tgaggctgcc ccacctggtg ggcatcatcg ccaagatcaa gggcatcaag   2640

atcgaggtga ccagcagcgg cgagagcatc aaagaacaga tcgagcgggc caaggccgag   2700

ctgctgcggc tggatatcca cgagggcgac acacccgcct ggatccagca gctggccgcc   2760

gccaccaagg acgtgtggcc cgctgcagcc agcgccctgc agggcatcgg caactttctg   2820

agcggcaccg cccagggcat cttcggcacc gccttctccc tgctgggcta cctgaagccc   2880

atcctgatcg gcgtgggcgt gattctgctg gtgattctga tcttcaagat cgtgagctgg   2940

atccccacca agaaaaagaa ccagtga                                        2967
```

<210> SEQ ID NO 8
<211> LENGTH: 2967
<212> TYPE: DNA
<213> ORGANISM: Artificial Sequence
<220> FEATURE:
<223> OTHER INFORMATION: Foamy Viral Envelope Gene PE02

<400> SEQUENCE: 8

```
atggcccctc ccatgaccct gcagcagtgg atcatctggc ggcggatgaa ccgggcccac     60

gaggccctgc agaacaccac caccgtgacc gagcagcagc gggagcagat catcctggac    120

atccagaacg aggaagtgca gcccaccagg cgggaccggt tcagatacct gctgtacacc    180

tgctgcgcca cctccagccg ggtgctggcc tggatgttcc tggtgtgcat cctgctgatc    240

atcgtgctgg tgtcctgctt cgtgaccatc agccggatcc agtggaacaa ggacatccag    300

gtgctgggcc ccgtgatcga ctggaacgtg acccagcggg ccgtgtacca gcccctgcag    360

acccggcgga tcgcccggtc cctgcggatg cagcaccccg tgcccaagta cgtggaggtg    420

aacatgacca gcatccccca gggcgtgtac tacgagcccc accccgagcc catcgtggtg    480

aaagaaagag tgctgggcct gagccagatc ctgatgatca acagcgagaa catcgccaac    540

aacgccaacc tgacccagga agtgaagaaa ctgctgaccg agatggtgaa cgaagagatg    600

cagagcctga gcgacgtgat gatcgacttc gagatccccc tgggcgaccc cagggaccag    660

gaacagtaca tccaccggaa gtgctaccag gaatttgcca actgctacct ggtgaagtac    720

aaagagccca agccctggcc caaagagggc ctgatcgccg accagtgccc cctgcccggc    780
```

```
tatcacgccg gcctgaccta caaccggcag agcatctggg actactacat caaggtggag    840

agcatcaggc ccgccaactg gaccaccaag agcaagtacg gccaggcccg gctgggcagc    900

ttctacatcc ccagcagcct gcggcagatc aacgtgagcc acgtgctgtt ctgcagcgac    960

cagctgtaca gcaagtggta caacatcgag aacaccatcg agcagaacga gcggttcctg   1020

ctgaacaagc tgaataacct gaccagcggc accagcgtgc tgaagaagag agccctgccc   1080

aaggactggt ccagccaggg caagaacgcc ctgttccggg agatcaatgt gctggacatc   1140

tgcagcaagc ccgagagcgt gatcctgctg aataccagct actacagctt cagcctgtgg   1200

gagggcgact gcaacttcac caaggacatg atcagccagc tggtgcccga gtgcgacggc   1260

ttctacaaca actccaagtg gatgcacatg cacccctacg cctgccggtt ctggcggagc   1320

aagaacgaga aagaggaaac caagtgccgg gacggcgaga ccaagcggtg cctgtactac   1380

cccctgtggg acagccctga gagcacctac gacttcggct acctggccta ccagaagaac   1440

ttccccagcc ccatctgcat cgaacagcag aagatccggg accaggacta cgaggtgtac   1500

agcctgtacc aggaatgcaa gatcgccagc aaggcctacg gcatcgacac cgtgctgttc   1560

agcctgaaga atttcctgaa ctacaccggc accccccgtga acgagatgcc caacgccagg   1620

gccttcgtgg gcctgattga ccccaagttc ccccccagct accccaacgt gacccgggag   1680

cactacacca gctgcaacaa ccggaagcgg cggagcgtgg acaacaacta cgccaagctg   1740

cggagcatgg gctacgctct gacaggcgcc gtgcagaccc tgtcccagat cagcgacatc   1800

aacgacgaga acctgcagca gggcatctac ctgctgcggg accacgtgat caccctgatg   1860

gaagccaccc tgcacgacat cagcgtgatg gaaggcatgt tcgccgtgca gcacctgcac   1920

acccacctga atcacctgaa aaccatgctg ctggaacggc gcatcgactg gacctacatg   1980

agcagcacct ggctgcagca gcagctgcag aaaagcgacg acgagatgaa ggtgatcaag   2040

cggatcgcca gatctctggt gtactacgtg aagcagaccc acagcagccc caccgccacc   2100

gcctgggaga tcggcctgta ctatgagctg gtgatcccca agcacatcta cctgaacaac   2160

tggaatgtgg tgaacatcgg ccacctggtg aaaagcgccg gacagctgac ccacgtgacc   2220

atcgcccacc cctacgagat catcaacaaa gaatgcgtgg agaccatcta tctgcacctg   2280

gaagattgca cccggcagga ctacgtgatc tgcgacgtgg tgaagatcgt gcagccctgc   2340

ggcaacagca gcgacaccag cgactgcccc gtgtgggccg aggccgtgaa agaacccttc   2400

gtgcaggtga acccccctgaa gaacggctcc tacctggtgc tggccagcag caccgactgc   2460

cagatccccc cctacgtgcc cagcatcgtg accgtgaatg agaccacctc ctgcttcggc   2520

ctggacttca agcggcccct ggtggccgag gaaagactga gcttcgagcc ccggctgccc   2580

aacctgcagc tgaggctgcc ccacctggtg ggcatcatcg ccaagatcaa gggcatcaag   2640

atcgaggtga ccagcagcgg cgagagcatc aaagaacaga tcgagcgggc caaggccgag   2700

ctgctgcggc tggatatcca cgagggcgac acacccgcct ggatccagca gctggccgcc   2760

gccaccaagg acgtgtggcc cgctgcagcc agcgccctgc agggcatcgg caactttctg   2820

agcggcaccg cccagggcat cttcggcacc gccttctccc tgctgggcta cctgaagccc   2880

atcctgatcg gcgtgggcgt gattctgctg gtgattctga tcttcaagat cgtgagctgg   2940

atccccaccc ggagacggaa ccagtga                                       2967
```

<210> SEQ ID NO 9
<211> LENGTH: 2967
<212> TYPE: DNA
<213> ORGANISM: Artificial Sequence
<220> FEATURE:
<223> OTHER INFORMATION: Foamy Viral Envelope Gene PE03

<400> SEQUENCE: 9

```
atggcccctc ccatgaccct gcagcagtgg atcatctggc ggcggatgaa ccgggcccac     60
gaggccctgc agaacaccac caccgtgacc gagcagcagc gggagcagat catcctggac    120
atccagaacg aggaagtgca gcccaccagg cgggaccggt tcagatacct gctgtacacc    180
tgctgcgcca cctccagccg ggtgctggcc tggatgttcc tggtgtgcat cctgctgatc    240
atcgtgctgg tgtcctgctt cgtgaccatc agccggatcc agtggaacaa ggacatccag    300
gtgctgggcc ccgtgatcga ctggaacgtg acccagcggg ccgtgtacca gcccctgcag    360
acccggcgga tcgcccggtc cctgcggatg cagcaccccg tgcccaagta cgtggaggtg    420
aacatgacca gcatccccca gggcgtgtac tacgagcccc accccgagcc catcgtggtg    480
aaagaaagag tgctgggcct gagccagatc ctgatgatca acagcgagaa catcgccaac    540
aacgccaacc tgacccagga agtgaagaaa ctgctgaccg agatggtgaa cgaagagatg    600
cagagcctga gcgacgtgat gatcgacttc gagatccccc tgggcgaccc cagggaccag    660
gaacagtaca tccaccggaa gtgctaccag gaatttgcca actgctacct ggtgaagtac    720
aaagagccca agccctggcc caaagagggc ctgatcgccg accagtgccc cctgcccggc    780
tatcacgccg gcctgaccta caaccggcag agcatctggg actactacat caaggtggag    840
agcatcaggc ccgccaactg gaccaccaag agcaagtacg gccaggcccg gctgggcagc    900
ttctacatcc ccagcagcct gcggcagatc aacgtgagcc acgtgctgtt ctgcagcgac    960
cagctgtaca gcaagtggta caacatcgag aacaccatcg agcagaacga gcggttcctg   1020
ctgaacaagc tgaataacct gaccagcggc accagcgtgc tgaagaagag agccctgccc   1080
aaggactggt ccagccaggg caagaacgcc ctgttccggg agatcaatgt gctggacatc   1140
tgcagcaagc ccgagagcgt gatcctgctg aataccagct actacagctt cagcctgtgg   1200
gagggcgact gcaacttcac caaggacatg atcagccagc tggtgcccga gtgcgacggc   1260
ttctacaaca actccaagtg gatgcacatg cacccctacg cctgccggtt ctggcggagc   1320
aagaacgaga aagaggaaac caagtgccgg gacggcgaga ccaagcggtg cctgtactac   1380
cccctgtggg acagccctga gagcacctac gacttcggct acctggccta ccagaagaac   1440
ttccccagcc ccatctgcat cgaacagcag aagatccggg accaggacta cgaggtgtac   1500
agcctgtacc aggaatgcaa gatcgccagc aaggcctacg gcatcgacac cgtgctgttc   1560
agcctgaaga atttcctgaa ctacaccggc acccccgtga acgagatgcc caacgccagg   1620
gccttcgtgg gcctgattga ccccaagttc ccccccagct accccaacgt gacccgggag   1680
cactacacca gctgcaacaa ccggaagcgg cggagcgtgg acaacaacta cgccaagctg   1740
cggagcatgg gctacgctct gacaggcgcc gtgcagaccc tgtcccagat cagcgacatc   1800
aacgacgaga acctgcagca gggcatctac ctgctgcggg accacgtgat caccctgatg   1860
gaagccaccc tgcacgacat cagcgtgatg gaaggcatgt tcgccgtgca gcacctgcac   1920
acccacctga atcacctgaa aaccatgctg ctggaacggc gcatcgactg gacctacatg   1980
agcagcacct ggctgcagca gcagctgcag aaaagcgacg acgagatgaa ggtgatcaag   2040
cggatcgcca gatctctggt gtactacgtg aagcagaccc acagcagccc caccgccacc   2100
gcctgggaga tcggcctgta ctatgagctg gtgatcccca agcacatcta cctgaacaac   2160
tggaatgtgg tgaacatcgg ccacctggtg aaaagcgccg gacagctgac ccacgtgacc   2220
atcgcccacc cctacgagat catcaacaaa gaatgcgtgg agaccatcta tctgcacctg   2280
```

```
gaagattgca cccggcagga ctacgtgatc tgcgacgtgg tgaagatcgt gcagccctgc   2340

ggcaacagca gcgacaccag cgactgcccc gtgtgggccg aggccgtgaa agaacccttc   2400

gtgcaggtga accccctgaa gaacggctcc tacctggtgc tggccagcag caccgactgc   2460

cagatccccc cctacgtgcc cagcatcgtg accgtgaatg agaccacctc ctgcttcggc   2520

ctggacttca agcggcccct ggtggccgag gaaagactga gcttcgagcc ccggctgccc   2580

aacctgcagc tgaggctgcc ccacctggtg ggcatcatcg ccaagatcaa gggcatcaag   2640

atcgaggtga ccagcagcgg cgagagcatc aaagaacaga tcgagcgggc caaggccgag   2700

ctgctgcggc tggatatcca cgagggcgac acacccgcct ggatccagca gctggccgcc   2760

gccaccaagg acgtgtggcc cgctgcagcc agcgccctgc agggcatcgg caactttctg   2820

agcggcaccg cccagggcat cttcggcacc gccttctccc tgctgggcta cctgcggccc   2880

atcctgatcg gcgtgggcgt gattctgctg gtgattctga tcttccggat cgtgagctgg   2940

atccccaccc ggagacggaa ccagtga                                       2967
```

<210> SEQ ID NO 10
<211> LENGTH: 2970
<212> TYPE: DNA
<213> ORGANISM: Artificial Sequence
<220> FEATURE:
<223> OTHER INFORMATION: Foamy Viral Envelope Gene SE01

<400> SEQUENCE: 10

```
atggcccctc ccatgaccct ggaacagtgg ctgctgtggc ggcggatgag ccaggcccac     60

caggccctgg aaaacgtgac caccctgacc gaggaacagc ggcagcaggt gatcatcgac    120

atccagcacg aggacgtggt gcccacccgg atggaccggc tgcggtacct ggcctacagc    180

tgctgcgcca cctccacccg ggtgctgtgc tggatcgtgc tggtgtgcgt gctgctgctg    240

gtggtgttca tcagctgctt cgtgaccatg agccggatcc agtggaacaa ggacatcgcc    300

gtgttcggcc ccgtgatcga ctggaacgtg agccagcagg ccgtgatcca gcagatccgg    360

gccaagcggc tggccagatc catccgggtc gagcacgcca ccgagaccta cgtggaggtg    420

aacatgacca gcatccccca gggcgtgctg tacgtgcccc accccgagcc catcatcctg    480

aaagaacggg tgctgggcct gagccaggtg atcatgatca acagcgagaa catcgccaac    540

accgccaacc tgacccagga aaccaaggtc ctgctggccg acatgatcaa cgaggaaatg    600

aacgacctgg ccaaccagat gatcgacttc gagatccccc tgggcgaccc cagggaccag    660

aagcagtacc agcaccagaa gtgcttccag gaatttgccc actgctacct ggtgaagtac    720

aagaccacca agggctggcc tagcagcacc gtgatcgccg accagtgccc cctgcccggc    780

aaccacccca ccgtgcagta cgcccaccag aacatctggg actactacgt gcccttcgag    840

cagatcaggc ccgagggctg gaacagcaag agctactacg aggacgcccg gatcggcggc    900

ttctacatcc ccaagtggct gcggaacaac agctacaccc acgtgctgtt ctgcagcgac    960

cagatctacg gcaagtggta caacatcgac ctgaccgccc aggaacggga gaacctgctg   1020

gtgcagaagc tgatcaacct ggccaagggc aacagcagcc agctgaagga cagagccatg   1080

cccgccgagt gggacaagca gggcaaggcc gacctgttcc ggcagatcaa caccctggac   1140

gtgtgcaacc ggcccgagat ggtgttcctg ctgaacagct cctactacga gttcagcctg   1200

tgggagggcg actgcggctt cacccggcag aacgtgaccc aggccaacag cctgtgcaag   1260

gacttctaca acaacagcaa gtggcagaag ctgcaccctt acagctgccg gttctggcgg   1320

tacaagcagg aaaaagaaga gaccaagtgc agcaacggcg agaagaagaa gtgcctgtac   1380
```

```
taccccccagt gggacacccc tgaggccctg tacgacttcg gcttcctggc ctacctgaac   1440

agcttcccca gccccatctg catcaagaac cagaccatcc gggagcccga gtacgagatc   1500

agcagcctgt acctggaatg catgaacgcc agcgaccggc acggcatcga cagcgccctg   1560

ctggccctga aaaccttcct gaacttcacc ggccagagcg tgaacgagat gcccctggcc   1620

agggccttcg tgggcctgac cgaccccaag ttccccccca cctaccccaa catcacccgg   1680

gagagcagcg gctgcaacaa caacaagcgg aagcggcgga gcgtgaacaa ctacgagcgg   1740

ctgcggagca tgggctacgc tctgacaggc gccgtgcaga ccctgagcca gatcagcgac   1800

atcaacgacg agaggctgca gcacggcgtg tacctgctgc gggaccacgt ggtgaccctg   1860

atggaagccg ccctgcacga cgtgagcatc atggaaggca tgctggccat tcagcacgtg   1920

cacacccacc tgaatcacct gaaaaccatg ctgctgatga ggaagatcga ttggaccttc   1980

atcagaagcg actggatcca gcagcagctg cagaaaaccg acgacgagat gaagctgatc   2040

cggcggaccg cccggtccct ggtgtactac gtgacacaga ccagcagctc ccccaccgcc   2100

acaagctggg agatcggcat ctactacgag atcgtgatcc ccaagcacat ctacctgaat   2160

aactggcagg tgatcaacgt gggccacctg ctggaaagcg ccggacacct gacccacgtg   2220

aaggtgaaac acccctacga gatcatcaac aaagagtgca gcgacaccca gtacctgcac   2280

ctggaagagt gcatccggga ggactacgtg atctgcgaca tcgtgcagat tgtgcagccc   2340

tgcggcaatg ccaccgagct gtccgactgc cccgtgaccg ccctgaaagt gaaaaccccc   2400

tacatccagg tgtccccccct gaagaacggc tcctacctgg tgctgtccag caccaaggac   2460

tgcagcatcc ccgcctacgt gcccagcgtg gtgaccgtga atgagaccgt gaagtgcttc   2520

ggcgtggagt tccacaagcc cctgtacgcc gagaccaaga ccagctacga gccccaggtg   2580

ccacacctga agctgcggct gccccacctg accggcatca tcgccagcct gcagagcctg   2640

gaaatcgagg tgaccagcac ccaggaaaac atcaaggacc agatcgagcg ggccaaggcc   2700

cagctgctga ggctggacat ccacgagggc gacttccccg actggctgaa gcaggtggcc   2760

agcgccacca gggacgtgtg gcctgccgcc gccagcttca tccagggcgt gggcaacttc   2820

ctgagcaaca ccgcccaggg catcttcggc agcgccgtga gcctgctgtc ctacgccaag   2880

cccatcctga tcggcatcgg cgtgattctg ctgatcgccc tgctgttcaa gatcatcagc   2940

tggctgcctg gcaagcccaa gaagaactga                                   2970
```

<210> SEQ ID NO 11
<211> LENGTH: 2970
<212> TYPE: DNA
<213> ORGANISM: Artificial Sequence
<220> FEATURE:
<223> OTHER INFORMATION: Foamy Viral Envelope Gene SE02

<400> SEQUENCE: 11

```
atggcccctc ccatgaccct ggaacagtgg ctgctgtggc ggcggatgag ccaggcccac     60

caggccctgg aaaacgtgac caccctgacc gaggaacagc ggcagcaggt gatcatcgac    120

atccagcacg aggacgtggt gcccacccgg atggaccggc tgcggtacct ggcctacagc    180

tgctgcgcca cctccacccg ggtgctgtgc tggatcgtgc tggtgtgcgt gctgctgctg    240

gtggtgttca tcagctgctt cgtgaccatg agccggatcc agtggaacaa ggacatcgcc    300

gtgttcggcc ccgtgatcga ctggaacgtg agccagcagg ccgtgatcca gcagatccgg    360

gccaagcggc tggccagatc catccgggtc gagcacgcca ccgagaccta cgtggaggtg    420

aacatgacca gcatccccca gggcgtgctg tacgtgcccc accccgagcc catcatcctg    480
```

```
aaagaacggg tgctgggcct gagccaggtg atcatgatca acagcgagaa catcgccaac    540
accgccaacc tgacccagga aaccaaggtc ctgctggccg acatgatcaa cgaggaaatg    600
aacgacctgg ccaaccagat gatcgacttc gagatccccc tgggcgaccc cagggaccag    660
aagcagtacc agcaccagaa gtgcttccag gaatttgccc actgctacct ggtgaagtac    720
aagaccacca agggctggcc tagcagcacc gtgatcgccg accagtgccc cctgcccggc    780
aaccacccca ccgtgcagta cgcccaccag aacatctggg actactacgt gcccttcgag    840
cagatcaggc ccgagggctg gaacagcaag agctactacg aggacgcccg gatcggcggc    900
ttctacatcc ccaagtggct gcggaacaac agctacaccc acgtgctgtt ctgcagcgac    960
cagatctacg gcaagtggta caacatcgac ctgaccgccc aggaacggga gaacctgctg   1020
gtgcagaagc tgatcaacct ggccaagggc aacagcagcc agctgaagga cagagccatg   1080
cccgccgagt gggacaagca gggcaaggcc gacctgttcc ggcagatcaa caccctggac   1140
gtgtgcaacc ggcccgagat ggtgttcctg ctgaacagct cctactacga gttcagcctg   1200
tgggagggcg actgcggctt cacccggcag aacgtgaccc aggccaacag cctgtgcaag   1260
gacttctaca acaacagcaa gtggcagaag ctgcaccctt acagctgccg gttctggcgg   1320
tacaagcagg aaaaagaaga gaccaagtgc agcaacggcg agaagaagaa gtgcctgtac   1380
tacccccagt gggacacccc tgaggccctg tacgacttcg gcttcctggc ctacctgaac   1440
agcttcccca gccccatctg catcaagaac cagaccatcc gggagcccga gtacgagatc   1500
agcagcctgt acctggaatg catgaacgcc agcgaccggc acggcatcga cagcgccctg   1560
ctggccctga aaaccttcct gaacttcacc ggccagagcg tgaacgagat gcccctggcc   1620
agggccttcg tgggcctgac cgaccccaag ttccccccca cctaccccaa catcacccgg   1680
gagagcagcg gctgcaacaa caacaagcgg aagcggcgga gcgtgaacaa ctacgagcgg   1740
ctgcggagca tgggctacgc tctgacaggc gccgtgcaga ccctgagcca gatcagcgac   1800
atcaacgacg agaggctgca gcacggcgtg tacctgctgc gggaccacgt ggtgaccctg   1860
atggaagccg ccctgcacga cgtgagcatc atggaaggca tgctggccat tcagcacgtg   1920
cacacccacc tgaatcacct gaaaaccatg ctgctgatga ggaagatcga ttggaccttc   1980
atcagaagcg actggatcca gcagcagctg cagaaaaccg acgacgagat gaagctgatc   2040
cggcggaccg cccggtccct ggtgtactac gtgacacaga ccagcagctc ccccaccgcc   2100
acaagctggg agatcggcat ctactacgag atcgtgatcc ccaagcacat ctacctgaat   2160
aactggcagg tgatcaacgt gggccacctg ctggaaagcg ccggacacct gacccacgtg   2220
aaggtgaaac accccctacga gatcatcaac aaagagtgca gcgacaccca gtacctgcac   2280
ctggaagagt gcatccggga ggactacgtg atctgcgaca tcgtgcagat tgtgcagccc   2340
tgcggcaatg ccaccgagct gtccgactgc cccgtgaccg ccctgaaagt gaaaaccccc   2400
tacatccagg tgtcccccct gaagaacggc tcctacctgg tgctgtccag caccaaggac   2460
tgcagcatcc ccgcctacgt gcccagcgtg gtgaccgtga atgagaccgt gaagtgcttc   2520
ggcgtggagt tccacaagcc cctgtacgcc gagaccaaga ccagctacga gccccaggtg   2580
ccacacctga agctgcggct gccccacctg accggcatca tcgccagcct gcagagcctg   2640
gaaatcgagg tgaccagcac ccaggaaaac atcaaggacc agatcgagcg ggccaaggcc   2700
cagctgctga ggctggacat ccacgagggc gacttccccg actggctgaa gcaggtggcc   2760
agcgccacca gggacgtgtg gcctgccgcc gccagcttca tccagggcgt gggcaacttc   2820
ctgagcaaca ccgcccaggg catcttcggc agcgccgtga gcctgctgtc ctacgccaag   2880
```

```
cccatcctga tcggcatcgg cgtgattctg ctgatcgccc tgctgttcaa gatcatcagc   2940

tggctgcctg gccggccccg gcggaactga                                     2970


<210> SEQ ID NO 12
<211> LENGTH: 2970
<212> TYPE: DNA
<213> ORGANISM: Artificial Sequence
<220> FEATURE:
<223> OTHER INFORMATION: Foamy Viral Envelope Gene SE03

<400> SEQUENCE: 12

atggcccctc ccatgaccct ggaacagtgg ctgctgtggc ggcggatgag ccaggcccac     60

caggccctgg aaaacgtgac caccctgacc gaggaacagc ggcagcaggt gatcatcgac    120

atccagcacg aggacgtggt gcccacccgg atggaccggc tgcggtacct ggcctacagc    180

tgctgcgcca cctccacccg ggtgctgtgc tggatcgtgc tggtgtgcgt gctgctgctg    240

gtggtgttca tcagctgctt cgtgaccatg agccggatcc agtggaacaa ggacatcgcc    300

gtgttcggcc ccgtgatcga ctggaacgtg agccagcagg ccgtgatcca gcagatccgg    360

gccaagcggc tggccagatc catccgggtc gagcacgcca ccgagaccta cgtggaggtg    420

aacatgacca gcatccccca gggcgtgctg tacgtgcccc accccgagcc catcatcctg    480

aaagaacggg tgctgggcct gagccaggtg atcatgatca acagcgagaa catcgccaac    540

accgccaacc tgacccagga aaccaaggtc ctgctggccg acatgatcaa cgaggaaatg    600

aacgacctgg ccaaccagat gatcgacttc gagatccccc tgggcgaccc cagggaccag    660

aagcagtacc agcaccagaa gtgcttccag gaatttgccc actgctacct ggtgaagtac    720

aagaccacca agggctggcc tagcagcacc gtgatcgccg accagtgccc cctgcccggc    780

aaccacccca ccgtgcagta cgcccaccag aacatctggg actactacgt gcccttcgag    840

cagatcaggc ccgagggctg gaacagcaag agctactacg aggacgcccg gatcggcggc    900

ttctacatcc ccaagtggct gcggaacaac agctacaccc acgtgctgtt ctgcagcgac    960

cagatctacg gcaagtggta caacatcgac ctgaccgccc aggaacggga gaacctgctg   1020

gtgcagaagc tgatcaacct ggccaagggc aacagcagcc agctgaagga cagagccatg   1080

cccgccgagt gggacaagca gggcaaggcc gacctgttcc ggcagatcaa caccctggac   1140

gtgtgcaacc ggcccgagat ggtgttcctg ctgaacagct cctactacga gttcagcctg   1200

tgggagggcg actgcggctt cacccggcag aacgtgaccc aggccaacag cctgtgcaag   1260

gacttctaca acaacagcaa gtggcagaag ctgcaccctt acagctgccg gttctggcgg   1320

tacaagcagg aaaaagaaga gaccaagtgc agcaacggcg agaagaagaa gtgcctgtac   1380

tacccccagt gggacacccc tgaggccctg tacgacttcg gcttcctggc ctacctgaac   1440

agcttcccca gccccatctg catcaagaac cagaccatcc gggagcccga gtacgagatc   1500

agcagcctgt acctggaatg catgaacgcc agcgaccggc acggcatcga cagcgccctg   1560

ctggccctga aaaccttcct gaacttcacc ggccagagcg tgaacgagat gcccctggcc   1620

agggccttcg tgggcctgac cgaccccaag ttccccccca cctaccccaa catcacccgg   1680

gagagcagcg gctgcaacaa caacaagcgg aagcggcgga gcgtgaacaa ctacgagcgg   1740

ctgcggagca tgggctacgc tctgacaggc gccgtgcaga ccctgagcca gatcagcgac   1800

atcaacgacg agaggctgca gcacggcgtg tacctgctgc gggaccacgt ggtgaccctg   1860

atggaagccg ccctgcacga cgtgagcatc atggaaggca tgctggccat tcagcacgtg   1920

cacacccacc tgaatcacct gaaaaccatg ctgctgatga ggaagatcga ttggaccttc   1980
```

atcagaagcg actggatcca gcagcagctg cagaaaaccg acgacgagat gaagctgatc 2040
cggcggaccg cccggtccct ggtgtactac gtgacacaga ccagcagctc ccccaccgcc 2100
acaagctggg agatcggcat ctactacgag atcgtgatcc ccaagcacat ctacctgaat 2160
aactggcagg tgatcaacgt gggccacctg ctggaaagcg ccggacacct gacccacgtg 2220
aaggtgaaac accccctacga gatcatcaac aaagagtgca gcgacaccca gtacctgcac 2280
ctggaagagt gcatccggga ggactacgtg atctgcgaca tcgtgcagat tgtgcagccc 2340
tgcggcaatg ccaccgagct gtccgactgc cccgtgaccg ccctgaaagt gaaaaccccc 2400
tacatccagg tgtccccccct gaagaacggc tcctacctgg tgctgtccag caccaaggac 2460
tgcagcatcc ccgcctacgt gcccagcgtg gtgaccgtga atgagaccgt gaagtgcttc 2520
ggcgtggagt tccacaagcc cctgtacgcc gagaccaaga ccagctacga gccccaggtg 2580
ccacacctga agctgcggct gccccacctg accggcatca tcgccagcct gcagagcctg 2640
gaaatcgagg tgaccagcac ccaggaaaac atcaaggacc agatcgagcg ggccaaggcc 2700
cagctgctga ggctggacat ccacgagggc gacttccccg actggctgaa gcaggtggcc 2760
agcgccacca gggacgtgtg gcctgccgcc gccagcttca tccagggcgt gggcaacttc 2820
ctgagcaaca ccgcccaggg catcttcggc agcgccgtga gcctgctgtc ctacgcccgg 2880
cccatcctga tcggcatcgg cgtgattctg ctgatcgccc tgctgttccg gatcatcagc 2940
tggctgcctg gccggccccg gcggaactga 2970

<210> SEQ ID NO 13
<211> LENGTH: 3729
<212> TYPE: DNA
<213> ORGANISM: Artificial Sequence
<220> FEATURE:
<223> OTHER INFORMATION: Foamy Viral Envelope Gene EM236

<400> SEQUENCE: 13
atgggatccc acgtgagcaa gggcgaggag gataacatgg ccatcatcaa ggagttcatg 60
cgcttcaagg tgcacatgga gggctccgtg aacggccacg agttcgagat cgagggcgag 120
ggcgagggcc gcccctacga gggcacccag accgccaagc tgaaggtgac caagggtggc 180
cccctgccct tcgcctggga catcctgtcc cctcagttca tgtacggctc caaggcctac 240
gtgaagcacc ccgccgacat ccccgactac ttgaagctgt ccttccccga gggcttcaag 300
tgggagcgcg tgatgaactt cgaggacggc ggcgtggtga ccgtgaccca ggactcctcc 360
ctgcaggacg gcgagttcat ctacaaggtg aagctgcgcg gcaccaactt cccctccgac 420
ggccccgtaa tgcagaagaa gaccatgggc tgggaggcct cctccgagcg gatgtacccc 480
gaggacggcg ccctgaaggg cgagatcaag cagaggctga agctgaagga cggcggccac 540
tacgacgctg aggtcaagac cacctacaag gccaagaagc ccgtgcagct gcccggcgcc 600
tacaacgtca acatcaagtt ggacatcacc tcccacaacg aggactacac catcgtggaa 660
cagtacgaac gcgccgaggg ccgccactcc accggcggca tggacgagct gtacaagaga 720
tctggcggcg gcagcggcgg gggcgggagc ggcggcgggg gatccgcacc accaatgaca 780
ctgcaacaat ggatcatttg gagaagaatg aatagagcgc atgaggcact tcaaaataca 840
acaactgtga ctgaacagca gcgcgaacaa attatactgg acattcaaaa tgaagaagta 900
caaccaacta ggagagatcg ctttagatat ctgctttata cttgttgtgc tactagctca 960
agagtattgg cctggatgtt tttagtttgt atattgttaa tcattgtttt ggtttcatgc 1020
tttgtgacta tatccagaat acaatggaat aaggatattc aggtattagg acctgtaata 1080

```
gactggaatg ttactcaaag agctgtttat caacccttac agactagaag gattgcacgt   1140
tcccttagaa tgcagcatcc tgttccaaaa tatgtggagg taaatatgac tagtattcca   1200
caaggtgtat actatgaacc ccatccggaa cccatagtgg tgaaggagag ggtcctgggt   1260
ctttctcaaa ttctgatgat taattcagaa aacattgcta ataatgctaa tttgacacaa   1320
gaagtaaaga agttgttaac tgaaatggtt aatgaagaaa tgcaaagttt gtcagatgta   1380
atgattgact ttgaaattcc tttaggagac cctcgtgatc aagaacaata tatacataga   1440
aaatgctatc aagaatttgc aaattgttat ttagtaaaat ataaagaacc caaaccgtgg   1500
cctaaggagg gccttatagc tgatcaatgc ccattaccag gttaccatgc tggattaacc   1560
tataatagac agtctatttg ggattactat attaaagtgg agagtattag acctgcaaat   1620
tggacaacaa agagtaaata tggacaagct agactaggaa gtttttatat tcctagcagt   1680
ctgagacaaa tcaatgttag tcatgtacta ttctgtagtg atcaattata ttctaaatgg   1740
tataatatag aaaataccat agaacaaaac gagcggtttc tgcttaataa actaaataac   1800
cttacatctg gaacctcagt attgaagaaa agagctcttc cgaaggattg gagttctcaa   1860
ggtaaaaatg ctctgtttag agaaatcaat gtgttagata tctgcagtaa acctgaatct   1920
gtaatactat tgaatacttc atactattcc ttctctttat gggaaggaga ttgtaatttt   1980
actaaagata tgatttctca gttggttcca gaatgtgatg gattttataa caattctaag   2040
tggatgcata tgcatccata tgcttgtaga ttctggagaa gtaagaatga aaaagaagaa   2100
actaaatgta gagatgggga aactaagaga tgtctgtatt atcctttatg ggacagtccc   2160
gaatctacat atgattttgg ttatttagca taccaaaaga atttccttc ccctatctgt   2220
atagaacaac agaaaattag agatcaagat tatgaagttt attctttgta tcaagaatgc   2280
aaaatagctt ctaaagcata tggaattgat acagttttat tctctctaaa gaattttctt   2340
aattatacag gaactcctgt aaatgaaatg cctaatgcaa gagcttttgt aggcctaata   2400
gatcccaagt ttcctccttc ctatcccaat gttactaggg aacattatac ttcctgtaat   2460
aataggaaaa gaagaagtgt tgataataac tatgctaagt taaggtctat ggggtatgca   2520
cttacaggag cagtgcaaac cttatctcaa atatcagata ttaatgatga aaacttacag   2580
caaggaatat atttattaag ggatcatgta ataaccttaa tggaagctac attgcatgat   2640
atatctgtta tggaaggaat gtttgctgta caacatttgc atacacattt gaatcatttg   2700
aagacaatgc ttctagaaag aagaatagac tggacctata tgtctagtac ttggctacaa   2760
caacaattac agaaatctga tgatgagatg aaagtaataa agagaattgc tagaagtttg   2820
gtatattatg ttaaacaaac ccatagttct cccacagcta cagcctggga gattggatta   2880
tattatgaat tggttatacc taaacatatt tacttgaata attggaatgt tgtcaatata   2940
ggtcacttag ttaaatcagc tggacaattg actcatgtaa ctatagctca tccttatgaa   3000
ataatcaata aggaatgtgt agagactata tatctgcatc ttgaagactg cacaagacaa   3060
gattatgtca tatgtgatgt ggtaaagata gtgcagcctt gtggcaatag ctcagacacg   3120
agtgattgtc ctgtctgggc tgaagctgta aaagaaccat ttgtgcaagt caatcctctg   3180
aaaaacggaa gttatctggt tttggcaagt tccacagact gtcagatccc accatatgtt   3240
cctagcatcg tgactgttaa tgaaacaacg tcatgctttg gactggactt taaaaggcca   3300
ctggttgcgg aagaaagatt gagctttgag ccacgactgc caaatctaca actaagatta   3360
ccacatttgg ttggaattat tgcaaaaatc aaagggataa aaatagaagt cacatcctct   3420
ggagaaagta taaaagagca gattgaaaga gcaaaagctg agctccttcg actggacatt   3480
```

```
cacgagggag atactcctgc ctggatacaa cagctagctg cagcaacaaa ggacgtctgg   3540

ccagcagcag cttctgctct acaaggaatt gggaactttt tatctgggac tgcccaagga   3600

atatttggaa ctgcctttag tctcttggga tacttaaagc ctatcctaat aggagtaggg   3660

gtcattctct tggttattct tatatttaaa attgtatcct ggattcctac gaaaaagaag   3720

aatcagtag                                                           3729
```

<210> SEQ ID NO 14
<211> LENGTH: 3729
<212> TYPE: DNA
<213> ORGANISM: Artificial Sequence
<220> FEATURE:
<223> OTHER INFORMATION: Foamy Viral Envelope Gene EM261

<400> SEQUENCE: 14

```
atgaccggtc acgtgagcaa gggcgaggag gataacatgg ccatcatcaa ggagttcatg     60

cgcttcaagg tgcacatgga gggctccgtg aacggccacg agttcgagat cgagggcgag    120

ggcgagggcc gcccctacga gggcacccag accgccaagc tgaaggtgac caagggtggc    180

cccctgccct tcgcctggga catcctgtcc cctcagttca tgtacggctc caaggcctac    240

gtgaagcacc ccgccgacat ccccgactac ttgaagctgt ccttccccga gggcttcaag    300

tgggagcgcg tgatgaactt cgaggacggc ggcgtggtga ccgtgaccca ggactcctcc    360

ctgcaggacg gcgagttcat ctacaaggtg aagctgcgcg gcaccaactt cccctccgac    420

ggccccgtaa tgcagaagaa gaccatgggc tgggaggcct cctccgagcg gatgtacccc    480

gaggacggcg ccctgaaggg cgagatcaag cagaggctga agctgaagga cggcggccac    540

tacgacgctg aggtcaagac cacctacaag gccaagaagc ccgtgcagct gcccggcgcc    600

tacaacgtca acatcaagtt ggacatcacc tcccacaacg aggactacac catcgtggaa    660

cagtacgaac gcgccgaggg ccgccactcc accggcggca tggacgagct gtacaagaga    720

tctggcggcg gcagcggcgg gggcgggagc ggcggcgggg gatccgcacc accaatgaca    780

ctgcaacaat ggatcatttg gaaaaaaatg aataaagcgc atgaggcact tcaaaataca    840

acaactgtga ctgaacagca gaaggaacaa attatactgg acattcaaaa tgaagaagta    900

caaccaacta ggagagataa atttagatat ctgctttata cttgttgtgc tactagctca    960

agagtattgg cctggatgtt tttagtttgt atattgttaa tcattgtttt ggtttcatgc   1020

tttgtgacta tatccagaat acaatggaat aaggatattc aggtattagg acctgtaata   1080

gactggaatg ttactcaaag agctgtttat caaccccttac agactagaag gattgcacgt   1140

tcccttagaa tgcagcatcc tgttccaaaa tatgtggagg taaatatgac tagtattcca   1200

caaggtgtat actatgaacc ccatccggaa cccatagtgg tgaaggagag ggtcctgggt   1260

ctttctcaaa ttctgatgat taattcagaa aacattgcta ataatgctaa tttgacacaa   1320

gaagtaaaga agttgttaac tgaaatggtt aatgaagaaa tgcaaagttt gtcagatgta   1380

atgattgact ttgaaattcc tttaggagac cctcgtgatc aagaacaata tatacataga   1440

aaatgctatc aagaatttgc aaattgttat ttagtaaaat ataaagaacc caaaccgtgg   1500

cctaaggagg gccttatagc tgatcaatgc ccattaccag gttaccatgc tggattaacc   1560

tataatagac agtctatttg ggattactat attaaagtgg agagtattag acctgcaaat   1620

tggacaacaa agagtaaata tggacaagct agactaggaa gtttttatat tcctagcagt   1680

ctgagacaaa tcaatgttag tcatgtacta ttctgtagtg atcaattata ttctaaatgg   1740

tataatatag aaaataccat agaacaaaac gagcggtttc tgcttaataa actaaataac   1800
```

```
cttacatctg gaacctcagt attgaagaaa agagctcttc cgaaggattg gagttctcaa   1860

ggtaaaaatg ctctgtttag agaaatcaat gtgttagata tctgcagtaa acctgaatct   1920

gtaatactat tgaatacttc atactattcc ttctctttat gggaaggaga ttgtaatttt   1980

actaaagata tgatttctca gttggttcca gaatgtgatg gattttataa caattctaag   2040

tggatgcata tgcatccata tgcttgtaga ttctggagaa gtaagaatga aaaagaagaa   2100

actaaatgta gagatgggga aactaagaga tgtctgtatt atcctttatg ggacagtccc   2160

gaatctacat atgattttgg ttatttagca taccaaaaga attttccttc ccctatctgt   2220

atagaacaac agaaaattag agatcaagat tatgaagttt attctttgta tcaagaatgc   2280

aaaatagctt ctaaagcata tggaattgat acagttttat tctctctaaa gaattttctt   2340

aattatacag gaactcctgt aaatgaaatg cctaatgcaa gagcttttgt aggcctaata   2400

gatcccaagt ttcctccttc ctatcccaat gttactaggg aacattatac ttcctgtaat   2460

aataggaaaa gaagaagtgt tgataataac tatgctaagt taaggtctat ggggtatgca   2520

cttacaggag cagtgcaaac cttatctcaa atatcagata ttaatgatga aaacttacag   2580

caaggaatat atttattaag ggatcatgta ataaccttaa tggaagctac attgcatgat   2640

atatctgtta tggaaggaat gtttgctgta caacatttgc atacacattt gaatcatttg   2700

aagacaatgc ttctagaaag aagaatagac tggacctata tgtctagtac ttggctacaa   2760

caacaattac agaaatctga tgatgagatg aaagtaataa agagaattgc tagaagtttg   2820

gtatattatg ttaaacaaac ccatagttct cccacagcta cagcctggga gattggatta   2880

tattatgaat tggttatacc taaacatatt tacttgaata attggaatgt tgtcaatata   2940

ggtcacttag ttaaatcagc tggacaattg actcatgtaa ctatagctca tccttatgaa   3000

ataatcaata aggaatgtgt agagactata tatctgcatc ttgaagactg cacaagacaa   3060

gattatgtca tatgtgatgt ggtaaagata gtgcagcctt gtggcaatag ctcagacacg   3120

agtgattgtc ctgtctgggc tgaagctgta aaagaaccat ttgtgcaagt caatcctctg   3180

aaaaacggaa gttatctggt tttggcaagt tccacagact gtcagatccc accatatgtt   3240

cctagcatcg tgactgttaa tgaaacaacg tcatgctttg gactggactt taaaaggcca   3300

ctggttgcgg aagaaagatt gagctttgag ccacgactgc caaatctaca actaagatta   3360

ccacatttgg ttggaattat tgcaaaaatc aaagggataa aaatagaagt cacatcctct   3420

ggagaaagta taaaagagca gattgaaaga gcaaaagctg agctccttcg actggacatt   3480

cacgagggag atactcctgc ctggatacaa cagctagctg cagcaacaaa ggacgtctgg   3540

ccagcagcag cttctgctct acaaggaatt gggaactttt tatctgggac tgcccaagga   3600

atatttggaa ctgcctttag tctcttggga tacttaaagc ctatcctaat aggagtaggg   3660

gtcattctct tggttattct tatatttaaa attgtatcct ggattcctac gaaaaagaag   3720

aatcagtag                                                           3729
```

<210> SEQ ID NO 15
<211> LENGTH: 3741
<212> TYPE: DNA
<213> ORGANISM: Artificial Sequence
<220> FEATURE:
<223> OTHER INFORMATION: Foamy Viral Envelope Gene EM170

<400> SEQUENCE: 15

```
atggccagat ctgtgagcaa gggcgaggag ctgttcaccg ggtggtgcc catcctggtc     60

gagctggacg gcgacgtaaa cggccacaag ttcagcgtgt ccggcgaggg cgagggcgat    120
```

```
gccacctacg gcaagctgac cctgaagttc atctgcacca ccggcaagct gcccgtgccc    180
tggcccaccc tcgtgaccac cttcggctac ggcctgcagt gcttcgcccg ctaccccgac    240
cacatgaagc agcacgactt cttcaagtcc gccatgcccg aaggctacgt ccaggagcgc    300
accatcttct tcaaggacga cggcaactac aagacccgcg ccgaggtgaa gttcgagggc    360
gacaccctgg tgaaccgcat cgagctgaag ggcatcgact tcaaggagga cggcaacatc    420
ctggggcaca agctggagta caactacaac agccacaacg tctatatcat ggccgacaag    480
cagaagaacg gcatcaaggt gaacttcaag atccgccaca acatcgagga cggcagcgtg    540
cagctcgccg accactacca gcagaacacc cccatcggcg acggccccgt gctgctgccc    600
gacaaccact acctgagcta ccagtccgcc ctgagcaaag accccaacga gaagcgcgat    660
cacatggtcc tgctggagtt cgtgaccgcc gccgggatca ctctcggcat ggacgagctg    720
tacaagacct tcgaaggcgg cggcagcggc gggggcggga gcggcggcgg gggatccgca    780
ccaccaatga cactgcaaca atggatcatt tggaaaaaaa tgaataaagc gcatgaggca    840
cttcaaaata caacaactgt gactgaacag cagaaggaac aaattatact ggacattcaa    900
aatgaagaag tacaaccaac taggagagat aaatttagat atctgcttta tacttgttgt    960
gctactagct caagagtatt ggcctggatg tttttagttt gtatattgtt aatcattgtt   1020
ttggtttcat gctttgtgac tatatccaga atacaatgga ataaggatat tcaggtatta   1080
ggacctgtaa tagactggaa tgttactcaa agagctgttt atcaaccctt acagactaga   1140
aggattgcac gttcccttag aatgcagcat cctgttccaa aatatgtgga ggtaaatatg   1200
actagtattc cacaaggtgt atactatgaa ccccatccgg aacccatagt ggtgaaggag   1260
agggtcctgg gtctttctca aattctgatg attaattcag aaaacattgc taataatgct   1320
aatttgacac aagaagtaaa gaagttgtta actgaaatgg ttaatgaaga aatgcaaagt   1380
ttgtcagatg taatgattga ctttgaaatt cctttaggag accctcgtga tcaagaacaa   1440
tatatacata gaaaatgcta tcaagaattt gcaaattgtt atttagtaaa atataaagaa   1500
cccaaaccgt ggcctaagga gggccttata gctgatcaat gcccattacc aggttaccat   1560
gctggattaa cctataatag acagtctatt tgggattact atattaaagt ggagagtatt   1620
agacctgcaa attggacaac aaagagtaaa tatggacaag ctagactagg aagtttttat   1680
attcctagca gtctgagaca aatcaatgtt agtcatgtac tattctgtag tgatcaatta   1740
tattctaaat ggtataatat agaaaatacc atagaacaaa acgagcggtt tctgcttaat   1800
aaactaaata accttacatc tggaacctca gtattgaaga aaagagctct tccgaaggat   1860
tggagttctc aaggtaaaaa tgctctgttt agagaaatca atgtgttaga tatctgcagt   1920
aaacctgaat ctgtaatact attgaatact tcatactatt ccttctcttt atgggaagga   1980
gattgtaatt ttactaaaga tatgatttct cagttggttc cagaatgtga tggattttat   2040
aacaattcta agtggatgca tatgcatcca tatgcttgta gattctggag aagtaagaat   2100
gaaaaagaag aaactaaatg tagagatggg gaaactaaga gatgtctgta ttatccttta   2160
tgggacagtc ccgaatctac atatgatttt ggttatttag cataccaaaa gaattttcct   2220
tcccctatct gtatagaaca acagaaaatt agagatcaag attatgaagt ttattctttg   2280
tatcaagaat gcaaaatagc ttctaaagca tatggaattg atacagtttt attctctcta   2340
aagaattttc ttaattatac aggaactcct gtaaatgaaa tgcctaatgc aagagctttt   2400
gtaggcctaa tagatcccaa gtttcctcct tcctatccca atgttactag ggaacattat   2460
acttcctgta ataataggaa aagaagaagt gttgataata actatgctaa gttaaggtct   2520
```

```
atggggtatg cacttacagg agcagtgcaa accttatctc aaatatcaga tattaatgat   2580

gaaaacttac agcaaggaat atatttatta agggatcatg taataacctt aatggaagct   2640

acattgcatg atatatctgt tatggaagga atgtttgctg tacaacattt gcatacacat   2700

ttgaatcatt tgaagacaat gcttctagaa agaagaatag actggaccta tatgtctagt   2760

acttggctac aacaacaatt acagaaatct gatgatgaga tgaaagtaat aaagagaatt   2820

gctagaagtt tggtatatta tgttaaacaa acccatagtt ctcccacagc tacagcctgg   2880

gagattggat tatattatga attggttata cctaaacata tttacttgaa taattggaat   2940

gttgtcaata taggtcactt agttaaatca gctggacaat tgactcatgt aactatagct   3000

catccttatg aaataatcaa taaggaatgt gtagagacta tatatctgca tcttgaagac   3060

tgcacaagac aagattatgt catatgtgat gtggtaaaga tagtgcagcc ttgtggcaat   3120

agctcagaca cgagtgattg tcctgtctgg gctgaagctg taaaagaacc atttgtgcaa   3180

gtcaatcctc tgaaaaacgg aagttatctg gttttggcaa gttccacaga ctgtcagatc   3240

ccaccatatg ttcctagcat cgtgactgtt aatgaaacaa cgtcatgctt tggactggac   3300

tttaaaaggc cactggttgc ggaagaaaga ttgagcttgg agccacgact gccaaatcta   3360

caactaagat taccacattt ggttggaatt attgcaaaaa tcaaagggat aaaaatagaa   3420

gtcacatcct ctggagaaag tataaaagag cagattgaaa gagcaaaagc tgagctcctt   3480

cgactggaca ttcacgaggg agatactcct gcctggatac aacagctagc tgcagcaaca   3540

aaggacgtct ggccagcagc agcttctgct ctacaaggaa ttgggaactt tttatctggg   3600

actgcccaag gaatatttgg aactgccttt agtctcttgg gatacttaaa gcctatccta   3660

ataggagtag gggtcattct cttggttatt cttatattta aaattgtatc ctggattcct   3720

acgaaaaaga agaatcagta g                                             3741
```

```
<210> SEQ ID NO 16
<211> LENGTH: 2922
<212> TYPE: DNA
<213> ORGANISM: Artificial Sequence
<220> FEATURE:
<223> OTHER INFORMATION: Foamy Viral Envelope Gene EM171

<400> SEQUENCE: 16
```

```
atgaatagag cgcatgaggc acttcaaaat acaacaactg tgactgaaca gcagcgcgaa     60

caaattatac tggacattca aaatgaagaa gtacaaccaa ctaggagaga tcgctttaga    120

tatctgcttt atacttgttg tgctactagc tcaagagtat tggcctggat ctttttagtt    180

tgtatattgt taatcattgt tttggtttca tgctttgtga ctatatccag aatacaatgg    240

aataaggata ttcaggtatt aggacctgta atagactgga atgttactca aagagctgtt    300

tatcaaccct tacagactag aaggattgca cgttccctta gaatgcagca tcctgttcca    360

aaatatgtgg aggtaaatat gactagtatt ccacaaggtg tatactatga accccatccg    420

gaacccatag tggtgaagga gagggtcctg ggtctttctc aaattctgat gattaattca    480

gaaaacattg ctaataatgc taatttgaca caagaagtaa agaagttgtt aactgaaatg    540

gttaatgaag aaatgcaaag tttgtcagat gtaatgattg actttgaaat tcctttagga    600

gaccctcgtg atcaagaaca atatatacat agaaaatgct atcaagaatt tgcaaattgt    660

tatttagtaa aatataaaga acccaaaccg tggcctaagg agggccttat agctgatcaa    720

tgcccattac caggttacca tgctggatta acctataata gacagtctat ttgggattac    780

tatattaaag tggagagtat tagacctgca aattggacaa caaagagtaa atatggacaa    840
```

```
gctagactag gaagttttta tattcctagc agtctgagac aaatcaatgt tagtcatgta    900

ctattctgta gtgatcaatt atattctaaa tggtataata tagaaaatac catagaacaa    960

aacgagcggt ttctgcttaa taaactaaat aaccttacat ctggaacctc agtattgaag   1020

aaaagagctc ttccgaagga ttggagttct caaggtaaaa atgctctgtt tagagaaatc   1080

aatgtgttag atatctgcag taaacctgaa tctgtaatac tattgaatac ttcatactat   1140

tccttctctt tatgggaagg agattgtaat tttactaaag atatgatttc tcagttggtt   1200

ccagaatgtg atggatttta taacaattct aagtggatgc atatgcatcc atatgcttgt   1260

agattctgga gaagtaagaa tgaaaaagaa gaaactaaat gtagagatgg ggaaactaag   1320

agatgtctgt attatccttt atgggacagt cccgaatcta catatgattt tggttattta   1380

gcataccaaa agaattttcc ttcccctatc tgtatagaac aacagaaaat tagagatcaa   1440

gattatgaag tttattcttt gtatcaagaa tgcaaaatag cttctaaagc atatggaatt   1500

gatacagttt tattctctct aaagaatttt cttaattata caggaactcc tgtaaatgaa   1560

atgcctaatg caagagcttt tgtaggccta atagatccca agtttcctcc ttcctatccc   1620

aatgttacta gggaacatta tacttcctgt aataatagga aaagaagaag tgttgataat   1680

aactatgcta agttaaggtc tatggggtat gcacttacag gagcagtgca aaccttatct   1740

caaatatcag atattaatga tgaaaactta cagcaaggaa tatatttatt aagggatcat   1800

gtaataacct taatggaagc tacattgcat gatatatctg ttatggaagg aatgtttgct   1860

gtacaacatt tgcatacaca tttgaatcat ttgaagacaa tgcttctaga aagaagaata   1920

gactggacct atatgtctag tacttggcta caacaacaat tacagaaatc tgatgatgag   1980

atgaaagtaa taaagagaat tgctagaagt ttggtatatt atgttaaaca aacccatagt   2040

tctcccacag ctacagcctg ggagattgga ttatattatg aattggttat acctaaacat   2100

atttacttga ataattggaa tgttgtcaat ataggtcact tagttaaatc agctggacaa   2160

ttgactcatg taactatagc tcatccttat gaaataatca ataaggaatg tgtagagact   2220

atatatctgc atcttgaaga ctgcacaaga caagattatg tcatatgtga tgtggtaaag   2280

atagtgcagc cttgtggcaa tagctcagac acgagtgatt gtcctgtctg ggctgaagct   2340

gtaaaagaac catttgtgca agtcaatcct ctgaaaaacg gaagttatct ggtttttggca   2400

agttccacag actgtcagat cccaccatat gttcctagca tcgtgactgt taatgaaaca   2460

acgtcatgct ttggactgga ctttaaaagg ccactggttg cggaagaaag attgagcttt   2520

gagccacgac tgccaaatct acaactaaga ttaccacatt tggttggaat tattgcaaaa   2580

atcaaaggga taaaaataga agtcacatcc tctggagaaa gtataaaaga gcagattgaa   2640

agagcaaaag ctgagctcct tcgactggac attcacgagg gagatactcc tgcctggata   2700

caacagctag ctgcagcaac aaaggacgtc tggccagcag cagcttctgc tctacaagga   2760

attgggaact tttatctgg gactgcccaa ggaatatttg gaactgcctt tagtctcttg   2820

ggatacttaa agcctatcct aataggagta ggggtcattc tcttggttat tcttatattt   2880

aaaattgtat cctggattcc tacgaaaaag aagaatcagt ag                      2922
```

<210> SEQ ID NO 17
<211> LENGTH: 2895
<212> TYPE: DNA
<213> ORGANISM: Artificial Sequence
<220> FEATURE:
<223> OTHER INFORMATION: Foamy Viral Envelope Gene EM228

<400> SEQUENCE: 17

```
atgacaacaa ctgtgactga acagcagcgc gaacaaatta tactggacat tcaaaatgaa     60
gaagtacaac caactaggag agatcgcttt agatatctgc tttatacttg ttgtgctact    120
agctcaagag tattggcctg gatgttttta gtttgtatat tgttaatcat tgttttggtt    180
tcatgctttg tgactatatc cagaatacaa tggaataagg atattcaggt attaggacct    240
gtaatagact ggaatgttac tcaaagagct gtttatcaac ccttacagac tagaaggatt    300
gcacgttccc ttagaatgca gcatcctgtt ccaaaatatg tggaggtaaa tatgactagt    360
attccacaag gtgtatacta tgaaccccat ccggaaccca tagtggtgaa ggagagggtc    420
ctgggtcttt ctcaaattct gatgattaat tcagaaaaca ttgctaataa tgctaatttg    480
acacaagaag taaagaagtt gttaactgaa atggttaatg aagaaatgca aagtttgtca    540
gatgtaatga ttgactttga aattccttta ggagaccctc gtgatcaaga acaatatata    600
catagaaaat gctatcaaga atttgcaaat tgttatttag taaaatataa agaacccaaa    660
ccgtggccta aggagggcct tatagctgat caatgcccat taccaggtta ccatgctgga    720
ttaacctata atagacagtc tatttgggat tactatatta aagtggagag tattagacct    780
gcaaattgga caacaaagag taaatatgga caagctagac taggaagttt ttatattcct    840
agcagtctga gacaaatcaa tgttagtcat gtactattct gtagtgatca attatattct    900
aaatggtata atatagaaaa taccatagaa caaaacgagc ggtttctgct taataaacta    960
aataacctta catctggaac ctcagtattg aagaaaagag ctcttccgaa ggattggagt   1020
tctcaaggta aaaatgctct gtttagagaa atcaatgtgt tagatatctg cagtaaacct   1080
gaatctgtaa tactattgaa tacttcatac tattccttct ctttatggga aggagattgt   1140
aattttacta aagatatgat ttctcagttg gttccagaat gtgatggatt ttataacaat   1200
tctaagtgga tgcatatgca tccatatgct tgtagattct ggagaagtaa gaatgaaaaa   1260
gaagaaacta aatgtagaga tggggaaact aagagatgtc tgtattatcc tttatgggac   1320
agtcccgaat ctacatatga ttttggttat ttagcatacc aaaagaattt tccttcccct   1380
atctgtatag aacaacagaa aattagagat caagattatg aagtttattc tttgtatcaa   1440
gaatgcaaaa tagcttctaa agcatatgga attgatacag ttttattctc tctaaagaat   1500
tttcttaatt atacaggaac tcctgtaaat gaaatgccta atgcaagagc ttttgtaggc   1560
ctaatagatc ccaagtttcc tccttcctat cccaatgtta ctagggaaca ttatacttcc   1620
tgtaataata ggaaaagaag aagtgttgat aataactatg ctaagttaag gtctatgggg   1680
tatgcactta caggagcagt gcaaacctta tctcaaatat cagatattaa tgatgaaaac   1740
ttacagcaag gaatatattt attaagggat catgtaataa ccttaatgga agctacattg   1800
catgatatat ctgttatgga aggaatgttt gctgtacaac atttgcatac acatttgaat   1860
catttgaaga caatgcttct agaaagaaga atagactgga cctatatgtc tagtacttgg   1920
ctacaacaac aattacagaa atctgatgat gagatgaaag taataaagag aattgctaga   1980
agtttggtat attatgttaa acaaacccat agttctccca cagctacagc ctgggagatt   2040
ggattatatt atgaattggt tatacctaaa catatttact tgaataattg gaatgttgtc   2100
aatataggtc acttagttaa atcagctgga caattgactc atgtaactat agctcatcct   2160
tatgaaataa tcaataagga atgtgtagag actatatatc tgcatcttga agactgcaca   2220
agacaagatt atgtcatatg tgatgtggta aagatagtgc agccttgtgg caatagctca   2280
gacacgagtg attgtcctgt ctgggctgaa gctgtaaaag aaccatttgt gcaagtcaat   2340
cctctgaaaa acggaagtta tctggttttg gcaagttcca cagactgtca gatcccacca   2400
```

```
tatgttccta gcatcgtgac tgttaatgaa acaacgtcat gctttggact ggactttaaa   2460

aggccactgg ttgcggaaga aagattgagc tttgagccac gactgccaaa tctacaacta   2520

agattaccac atttggttgg aattattgca aaaatcaaag ggataaaaat agaagtcaca   2580

tcctctggag aaagtataaa agagcagatt gaaagagcaa aagctgagct ccttcgactg   2640

gacattcacg agggagatac tcctgcctgg atacaacagc tagctgcagc aacaaaggac   2700

gtctggccag cagcagcttc tgctctacaa ggaattggga actttttatc tgggactgcc   2760

caaggaatat ttggaactgc ctttagtctc ttgggatact taaagcctat cctaatagga   2820

gtaggggtca ttctcttggt tattcttata tttaaaattg tatcctggat tcctacgaaa   2880

aagaagaatc agtag                                                    2895
```

```
<210> SEQ ID NO 18
<211> LENGTH: 2955
<212> TYPE: DNA
<213> ORGANISM: Artificial Sequence
<220> FEATURE:
<223> OTHER INFORMATION: Foamy Viral Envelope Gene SM04

<400> SEQUENCE: 18

atgacactgc aacaatggat catttggaga agaatgaata gagcgcatga ggcacttcaa     60

aatacaacaa ctgtgactga acagcagcgc gaacaaatta tactggacat tcaaaatgaa    120

gaagtacaac caactaggag agatcgcttt agatatctgc tttatacttg ttgtgctact    180

agctcaagag tattggcctg gatgttttta gtttgtatat tgttaatcat tgttttggtt    240

tcatgctttg tgactatatc cagaatacaa tggaataagg atattcaggt attaggacct    300

gtaatagact ggaatgttac tcaaagagct gtttatcaac ccttacagac tagaaggatt    360

gcacgttccc ttagaatgca gcatcctgtt ccaaaatatg tggaggtaaa tatgactagt    420

attccacaag gtgtatacta tgaaccccat ccggaaccca tagtggtgaa ggagagggtc    480

ctgggtcttt ctcaaattct gatgattaat tcagaaaaca ttgctaataa tgctaatttg    540

acacaagaag taaagaagtt gttaactgaa atggttaatg aagaaatgca aagtttgtca    600

gatgtaatga ttgactttga aattccttta ggagaccctc gtgatcaaga acaatatata    660

catagaaaat gctatcaaga atttgcaaat tgttatttag taaaatataa agaacccaaa    720

ccgtggccta aggagggcct tatagctgat caatgcccat taccaggtta ccatgctgga    780

ttaacctata atagacagtc tatttgggat tactatatta aagtggagag tattagacct    840

gcaaattgga caacaaagag taaatatgga caagctagac taggaagttt ttatattcct    900

agcagtctga gacaaatcaa tgttagtcat gtactattct gtagtgatca attatattct    960

aaatggtata atatagaaaa taccatagaa caaaacgagc ggtttctgct taataaacta   1020

aataacctta catctggaac ctcagtattg aagaaaagag ctcttccgaa ggattggagt   1080

tctcaaggta aaaatgctct gtttagagaa atcaatgtgt tagatatctg cagtaaacct   1140

gaatctgtaa tactattgaa tacttcatac tattccttct ctttatggga aggagattgt   1200

aattttacta aagatatgat ttctcagttg gttccagaat gtgatggatt ttataacaat   1260

tctaagtgga tgcatatgca tccatatgct tgtagattct ggagaagtaa gaatgaaaaa   1320

gaagaaacta aatgtagaga tggggaaact aagagatgtc tgtattatcc tttatgggac   1380

agtcccgaat ctacatatga ttttggttat ttagcatacc aaaagaattt tccttcccct   1440

atctgtatag aacaacagaa aattagagat caagattatg aagtttattc tttgtatcaa   1500

gaatgcaaaa tagcttctaa agcatatgga attgatacag ttttattctc tctaaagaat   1560
```

```
tttcttaatt atacaggaac tcctgtaaat gaaatgccta atgcaagagc ttttgtaggc   1620

ctaatagatc ccaagtttcc tccttcctat cccaatgtta ctagggaaca ttatacttcc   1680

tgtaataata ggaaaagaag aagtgttgat aataactatg ctaagttaag gtctatgggg   1740

tatgcactta caggagcagt gcaaacctta tctcaaatat cagatattaa tgatgaaaac   1800

ttacagcaag gaatatattt attaagggat catgtaataa ccttaatgga agctacattg   1860

catgatatat ctgttatgga aggaatgttt gctgtacaac atttgcatac acatttgaat   1920

catttgaaga caatgcttct agaaagaaga atagactgga cctatatgtc tagtacttgg   1980

ctacaacaac aattacagaa atctgatgat gagatgaaag taataaagag aattgctaga   2040

agtttggtat attatgttaa acaaacccat agttctccca cagctacagc ctgggagatt   2100

ggattatatt atgaattggt tatacctaaa catatttact tgaataattg gaatgttgtc   2160

aatataggtc acttagttaa atcagctgga caattgactc atgtaactat agctcatcct   2220

tatgaaataa tcaataagga atgtgtagag actatatatc tgcatcttga agactgcaca   2280

agacaagatt atgtcatatg tgatgtggta aagatagtgc agccttgtgg caatagctca   2340

gacacgagtg attgtcctgt ctgggctgaa gctgtaaaag aaccatttgt gcaagtcaat   2400

cctctgaaaa acggaagtta tctggttttg gcaagttcca cagactgtca gatcccacca   2460

tatgttccta gcatcgtgac tgttaatgaa acaacgtcat gctttggact ggactttaaa   2520

aggccactgg ttgcggaaga aagattgagc tttgagccac gactgccaaa tctacaacta   2580

agattaccac atttggttgg aattattgca aaaatcaaag ggataaaaat agaagtcaca   2640

tcctctggag aaagtataaa agagcagatt gaaagagcaa aagctgagct ccttcgactg   2700

gacattcacg agggagatac tcctgcctgg atacaacagc tagctgcagc aacaaaggac   2760

gtctggccag cagcagcttc tgctctacaa ggaattggga actttttatc tgggactgcc   2820

caaggaatat ttggaactgc ctttagtctc ttgggatact taaagcctat cctaatagga   2880

gtaggggtca ttctcttggt tattcttata tttaaaattg tatcctggat tcctacgaaa   2940

aagaagaatc agtag                                                    2955
```

<210> SEQ ID NO 19
<211> LENGTH: 2970
<212> TYPE: DNA
<213> ORGANISM: Artificial Sequence
<220> FEATURE:
<223> OTHER INFORMATION: Foamy Viral Envelope Gene EM134

<400> SEQUENCE: 19

```
atggcacctc caatgactct ggaacaatgg ctcttatgga ggaggatgag tcaagcacat     60

caagcacttg aaaatgtaac caccttgact gaggaacaga ggcaacaagt tataatagac    120

attcagcatg aagatgttgt tcctactagg atggacagat tgagatatct ggcctattca    180

tgctgcgcta ctagcacacg tgtattgtgc tggatagtgt tagtttgcgt cttgctatta    240

gttgtattta tatcctgctt tgtgacaatg tccaggatac aatggaataa ggatattgct    300

gtttttggtc cagtcattga ctggaatgtt agccaacaag ctgtgattca acaaataaga    360

gctaaaagat tagcaagatc aattagggtg gaacatgcta ctgagacata tgtagaggtc    420

aatatgacca gtatacctca aggggtgtta tatgtgcctc atccagaacc aataattctc    480

aaggagagga ttcttggttt atctcaggtc atgatgataa actctgaaaa tattgctaat    540

actgctaacc ttactcaaga aactaaggta ctgttagcag acatgattaa tgaagagatg    600

aatgatttag ctaatcaaat gatagatttt gaaatcccat taggagatcc cagagatcaa    660
```

```
aaacaatacc agcatcaaaa atgttttcaa gaatttgcac attgttattt agtaaaatat    720
aaaactacta aaggatggcc tagttctact gttatagcag atcaatgccc tttgcctggt    780
aaccatccta cagtacaata tgcacatcaa aatatatggg attattatgt cccctttgaa    840
caaattcggc cagaaggatg gaactcaaaa agttattatg aagatgctag aataggaggg    900
ttttatatac caaaatggtt acgaaatat tcctataccc atgtcttatt ttgttctgat    960
caaatttatg gaaaatggta taatattgat ctcacagccc aggagaggga aaatttatta   1020
gtccgaaaat taattaattt agctaaagga aattcatcac aattaaaaga tagagctatg   1080
ccagctgaat gggataaaca aggaaaagct gatctattta gacaaattaa tactttagat   1140
gtttgtaata gaccagaaat ggtatttttg ttaaattcct catattatga attttcccta   1200
tgggaaggag attgtggttt taccagacag aatgttacac aggctaattc cttatgtaaa   1260
gatttctata ataactcaaa atggcaaaaa ttacatccat attcgtgtag attttggaga   1320
tataaacaag agaaagaaga aactaaatgt agtaatggtg aaaagaaaaa atgtctttat   1380
tacccacaat gggatactcc tgaagcttta tatgactttg ggttcctagc atatttaaat   1440
tcttttcctt ctccaatctg tataaaaaat cagactataa gggaacctga gtataaaatc   1500
tcttctttat acctagaatg catgaatgct tcagacagac atggtataga tagtgcttta   1560
ttagctttga agacattttt aaactttact ggtcagtctg taaacgaaat gccattagct   1620
agagcctttg taggccttac tgaccctaaa tttccaccaa catatcccaa cattacaagg   1680
gaatcttctg gttgtaataa taacaaaaga aaaaggagaa gtgttaataa ttatgaaaga   1740
cttagatcta tgggatatgc tttaactgga gctgttcaaa ctttatctca aatatctgat   1800
attaatgatg agaggctgca acacggagta tatttactcc gggatcatgt ggtaaccctg   1860
atggaagctg cccttcatga tgtttcgatt atggaaggaa tgttagcaat tcaacatgtg   1920
catactcatc tcaatcatct caagaccatg cttttgatga gaaagattga ttggacattc   1980
atcagaagtg actggattca acagcaatta cagaagacag atgatgaaat gaaattgata   2040
cgaagaactg cacgaagtct agtctactat gtcacacaaa cctccagttc tcctacagct   2100
acttcctggg agattggaat atattatgaa atagtaattc ctaaacatat atatttaaat   2160
aattggcaag taatcaatgt aggtcattta ttggagtcag ctggtcatct gactcatgta   2220
aaggttaagc atccttatga aataattaat aaggaatgta gtgacactca atatttacat   2280
cttgaggaat gcattagaga ggattatgtg atttgtgaca tagtacaaat agttcaacca   2340
tgtggaaatg caacagaatt gagtgattgt ccagtaacag cattaaaggt gaagactcca   2400
tatattcaag tgtctcccct gaagaatgga agttatttag ttttatctag tactaaggat   2460
tgttctatac ctgcatatgt acctagtgtg gtcacagtca atgaaacagt taagtgcttt   2520
ggagtagagt ttcacaaacc actttatgct gaaacaaaaa ccagctatga accacaagtt   2580
ccgcatttga agcttcgttt accccacttg actgggatta ttgccagctt gcaatcactg   2640
gaaatagaag ttacttctac acaagagaat ataaaagacc agatcgaaag ggccaaagca   2700
cagcttctcc ggctggacat tcacgaagga gactttcctg actggctgaa acaagtcgcc   2760
tctgcaacca gggacgtttg gcctgctgca gcttccttta tacaaggagt agggaacttc   2820
ttatctaata ctgcccaggg gatattcggc tcagcggtaa gcctcctatc ctatgcaaaa   2880
cctattttga taggaatagg agttatactg cttattgccc ttctttttaa aataatatcg   2940
tggcttcctg ggaagcccaa gaagaattga                                   2970
```

<210> SEQ ID NO 20
<211> LENGTH: 2967
<212> TYPE: DNA
<213> ORGANISM: Artificial Sequence
<220> FEATURE:
<223> OTHER INFORMATION: Foamy Viral Envelope Gene EM140

<400> SEQUENCE: 20

```
atggcaccac caatgacact gcaacaatgg atcatttgga gaagaatgaa tagagcgcat     60
gaggcacttc aaaatacaac aactgtgact gaacagcaga aggaacaaat tatactggac    120
attcaaaatg aagaagtaca accaactagg agagataaat ttagatatct gctttatact    180
tgttgtgcta ctagctcaag agtattggcc tggatgtttt tagtttgtat attgttaatc    240
attgttttgg tttcatgctt tgtgactata tccagaatac aatggaataa ggatattcag    300
gtattaggac ctgtaataga ctggaatgtt actcaaagag ctgtttatca acccttacag    360
actagaagga ttgcacgttc ccttagaatg cagcatcctg ttccaaaata tgtggaggta    420
aatatgacta gtattccaca aggtgtatac tatgaacccc atccggaacc catagtggtg    480
aaggagaggg tcctgggtct ttctcaaatt ctgatgatta attcagaaaa cattgctaat    540
aatgctaatt tgacacaaga agtaaagaag ttgttaactg aaatggttaa tgaagaaatg    600
caaagtttgt cagatgtaat gattgacttt gaaattcctt taggagaccc tcgtgatcaa    660
gaacaatata tacatagaaa atgctatcaa gaatttgcaa attgttattt agtaaaatat    720
aaagaaccca aaccgtggcc taaggagggc cttatagctg atcaatgccc attaccaggt    780
taccatgctg gattaaccta taatagacag tctatttggg attactatat taaagtggag    840
agtattagac ctgcaaattg gacaacaaag agtaaatatg gacaagctag actaggaagt    900
ttttatattc ctagcagtct gagacaaatc aatgttagtc atgtactatt ctgtagtgat    960
caattatatt ctaaatggta taatatagaa aataccatag aacaaaacga gcggtttctg   1020
cttaataaac taaataacct tacatctgga acctcagtat tgaagaaaag agctcttccg   1080
aaggattgga gttctcaagg taaaaatgct ctgtttagag aaatcaatgt gttagatatc   1140
tgcagtaaac ctgaatctgt aatactattg aatacttcat actattcctt ctctttatgg   1200
gaaggagatt gtaattttac taaagatatg atttctcagt tggttccaga atgtgatgga   1260
ttttataaca attctaagtg gatgcatatg catccatatg cttgtagatt ctggagaagt   1320
aagaatgaaa aagaagaaac taaatgtaga gatggggaaa ctaagagatg tctgtattat   1380
cctttatggg acagtcccga atctacatat gattttggtt atttagcata ccaaaagaat   1440
tttccttccc ctatctgtat agaacaacag aaaattagag atcaagatta tgaagtttat   1500
tctttgtatc aagaatgcaa aatagcttct aaagcatatg gaattgatac agttttattc   1560
tctctaaaga attttcttaa ttatacagga actcctgtaa atgaaatgcc taatgcaaga   1620
gcttttgtag gcctaataga tcccaagttt cctccttcct atcccaatgt tactagggaa   1680
cattatactt cctgtaataa taggaaaaga agaagtgttg ataataacta tgctaagtta   1740
aggtctatgg ggtatgcact tacaggagca gtgcaaacct tatctcaaat atcagatatt   1800
aatgatgaaa acttacagca aggaatatat ttattaaggg atcatgtaat aaccttaatg   1860
gaagctacat tgcatgatat atctgttatg gaaggaatgt ttgctgtaca acatttgcat   1920
acacatttga atcatttgaa gacaatgctt ctagaaagaa gaatagactg gacctatatg   1980
tctagtactt ggctacaaca acaattacag aaatctgatg atgagatgaa agtaataaag   2040
agaattgcta gaagtttggt atattatgtt aaacaaaccc atagttctcc cacagctaca   2100
gcctgggaga ttggattata ttatgaattg gttataccta aacatattta cttgaataat   2160
```

```
tggaatgttg tcaatatagg tcacttagtt aaatcagctg gacaattgac tcatgtaact   2220

atagctcatc cttatgaaat aatcaataag gaatgtgtag agactatata tctgcatctt   2280

gaagactgca caagacaaga ttatgtcata tgtgatgtgg taaagatagt gcagccttgt   2340

ggcaatagct cagacacgag tgattgtcct gtctgggctg aagctgtaaa agaaccattt   2400

gtgcaagtca atcctctgaa aaacggaagt tatctggttt tggcaagttc cacagactgt   2460

cagatcccac catatgttcc tagcatcgtg actgttaatg aaacaacgtc atgctttgga   2520

ctggacttta aaaggccact ggttgcggaa gaaagattga gctttgagcc acgactgcca   2580

aatctacaac taagattacc acatttggtt ggaattattg caaaaatcaa agggataaaa   2640

atagaagtca catcctctgg agaaagtata aaagagcaga ttgaaagagc aaaagctgag   2700

ctccttcgac tggacattca cgagggagat actcctgcct ggatacaaca gctagctgca   2760

gcaacaaagg acgtctggcc agcagcagct tctgctctac aaggaattgg gaacttttta   2820

tctgggactg cccaaggaat atttggaact gcctttagtc tcttgggata cttaaagcct   2880

atcctaatag gagtaggggt cattctcttg gttattctta tatttaaaat tgtatcctgg   2940

attcctacga aaaagaagaa tcagtag                                        2967
```

<210> SEQ ID NO 21
<211> LENGTH: 2967
<212> TYPE: DNA
<213> ORGANISM: Artificial Sequence
<220> FEATURE:
<223> OTHER INFORMATION: Foamy Viral Envelope Gene pczHFV EM167

<400> SEQUENCE: 21

```
atggcaccac caatgacact gcaacaatgg atcatttgga gaagaatgaa tagagcgcat     60

gaggcacttc aaaatacaac aactgtgact gaacagcagc gcgaacaaat tatactggac    120

attcaaaatg aagaagtaca accaactagg agagatcgct ttagatatct gctttatact    180

tgttgtgcta ctagctcaag agtattggcc tggatgtttt tagtttgtat attgttaatc    240

attgttttgg tttcatgctt tgtgactata tccagaatac aatggaataa ggatattcag    300

gtattaggac ctgtaataga ctggaatgtt actcaaagag ctgtttatca acccttacag    360

actagaagga ttgcacgttc ccttagaatg cagcatcctg ttccaaaata tgtggaggta    420

aatatgacta gtattccaca aggtgtatac tatgaacccc atccggaacc catagtggtg    480

aaggagaggg tcctgggtct ttctcaaatt ctgatgatta attcagaaaa cattgctaat    540

aatgctaatt tgacacaaga agtaaagaag ttgttaactg aaatggttaa tgaagaaatg    600

caaagtttgt cagatgtaat gattgacttt gaaattcctt taggagaccc tcgtgatcaa    660

gaacaatata tacatagaaa atgctatcaa gaatttgcaa attgttattt agtaaaatat    720

aaagaaccca aaccgtggcc taaggagggc cttatagctg atcaatgccc attaccaggt    780

taccatgctg gattaaccta taatagacag tctatttggg attactatat taaagtggag    840

agtattagac ctgcaaattg gacaacaaag agtaaatatg gacaagctag actaggaagt    900

ttttatattc ctagcagtct gagacaaatc aatgttagtc atgtactatt ctgtagtgat    960

caattatatt ctaaatggta taatatagaa aataccatag aacaaaacga gcggtttctg   1020

cttaataaac taaataacct tacatctgga acctcagtat tgaagaaaag agctcttccg   1080

aaggattgga gttctcaagg taaaaatgct ctgtttagag aaatcaatgt gttagatatc   1140

tgcagtaaac ctgaatctgt aatactattg aatacttcat actattcctt ctctttatgg   1200

gaaggagatt gtaattttac taaagatatg atttctcagt tggttccaga atgtgatgga   1260
```

```
ttttataaca attctaagtg gatgcatatg catccatatg cttgtagatt ctggagaagt   1320

aagaatgaaa aagaagaaac taaatgtaga gatggggaaa ctaagagatg tctgtattat   1380

cctttatggg acagtcccga atctacatat gattttggtt atttagcata ccaaaagaat   1440

tttccttccc ctatctgtat agaacaacag aaaattagag atcaagatta tgaagtttat   1500

tctttgtatc aagaatgcaa aatagcttct aaagcatatg gaattgatac agttttattc   1560

tctctaaaga attttcttaa ttatacagga actcctgtaa atgaaatgcc taatgcaaga   1620

gcttttgtag gcctaataga tcccaagttt cctccttcct atcccaatgt tactagggaa   1680

cattatactt cctgtaataa taggaaaaga agaagtgttg ataataacta tgctaagtta   1740

aggtctatgg ggtatgcact tacaggagca gtgcaaacct tatctcaaat atcagatatt   1800

aatgatgaaa acttacagca aggaatatat ttattaaggg atcatgtaat aaccttaatg   1860

gaagctacat tgcatgatat atctgttatg gaaggaatgt ttgctgtaca acatttgcat   1920

acacatttga atcatttgaa gacaatgctt ctagaaagaa gaatagactg gacctatatg   1980

tctagtactt ggctacaaca acaattacag aaatctgatg atgagatgaa agtaataaag   2040

agaattgcta gaagtttggt atattatgtt aaacaaaccc atagttctcc cacagctaca   2100

gcctgggaga ttggattata ttatgaattg gttataccta aacatattta cttgaataat   2160

tggaatgttg tcaatatagg tcacttagtt aaatcagctg gacaattgac tcatgtaact   2220

atagctcatc cttatgaaat aatcaataag gaatgtgtag agactatata tctgcatctt   2280

gaagactgca caagacaaga ttatgtcata tgtgatgtgg taaagatagt gcagccttgt   2340

ggcaatagct cagacacgag tgattgtcct gtctgggctg aagctgtaaa agaaccattt   2400

gtgcaagtca atcctctgaa aaacggaagt tatctggttt tggcaagttc cacagactgt   2460

cagatcccac catatgttcc tagcatcgtg actgttaatg aaacaacgtc atgctttgga   2520

ctggacttta aaaggccact ggttgcggaa gaaagattga gctttgagcc acgactgcca   2580

aatctacaac taagattacc acatttggtt ggaattattg caaaaatcaa agggataaaa   2640

atagaagtca catcctctgg agaaagtata aaagagcaga ttgaaagagc aaaagctgag   2700

ctccttcgac tggacattca cgagggagat actcctgcct ggatacaaca gctagctgca   2760

gcaacaaagg acgtctggcc agcagcagct tctgctctac aaggaattgg gaacttttta   2820

tctgggactg cccaaggaat atttggaact gcctttagtc tcttgggata cttaaagcct   2880

atcctaatag gagtaggggt cattctcttg gttattctta tatttaaaat tgtatcctgg   2940

attcctacga aaaagaagaa tcagtag                                       2967
```

```
<210> SEQ ID NO 22
<211> LENGTH: 10916
<212> TYPE: DNA
<213> ORGANISM: Artificial Sequence
<220> FEATURE:
<223> OTHER INFORMATION: Foamy Viral Envelope Gene pczHFV EM168

<400> SEQUENCE: 22

gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360
```

```
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctaga    900
aaacctacgt ctcatcagaa tggcaccacc aatgacactg caacaatgga tcatttggag    960
aagaatgaat agagcgcatg aggcacttca aaatacaaca actgtgactg aacagcagcg   1020
cgaacaaatt atactggaca ttcaaaatga agaagtacaa ccaactagga gagatcgctt   1080
tagatatctg ctttatactt gttgtgctac tagctcaaga gtattggcct ggatgttttt   1140
agtttgtata ttgttaatca ttgttttggt ttcatgcttt gtgactatat ccagaataca   1200
atggaataag gatattcagg tattaggacc tgtaatagac tggaatgtta ctcaaagagc   1260
tgtttatcaa cccttacaga ctagaaggat tgcacgttcc cttagaatgc agcatcctgt   1320
tccaaaatat gtggaggtaa atatgactag tattccacaa ggtgtatact atgaacccca   1380
tccggaaccc atagtggtga aggagagggt cctgggtctt tctcaaattc tgatgattaa   1440
ttcagaaaac attgctaata atgctaattt gacacaagaa gtaaagaagt tgttaactga   1500
aatggttaat gaagaaatgc aaagtttgtc agatgtaatg attgactttg aaattccttt   1560
aggagaccct cgtgatcaag aacaatatat acatagaaaa tgctatcaag aatttgcaaa   1620
ttgttattta gtaaaatata aagaacccaa accgtggcct aaggagggcc ttatagctga   1680
tcaatgccca ttaccaggtt accatgctgg attaacctat aatagacagt ctatttggga   1740
ttactatatt aaagtggaga gtattagacc tgcaaattgg acaacaaaga gtaaatatgg   1800
acaagctaga ctaggaagtt tttatattcc tagcagtctg agacaaatca atgttagtca   1860
tgtactattc tgtagtgatc aattatattc taaatggtat aatatagaaa ataccataga   1920
acaaaacgag cggtttctgc ttaataaact aaataacctt acatctggaa cctcagtatt   1980
gaagaaaaga gctcttccga aggattggag ttctcaaggt aaaaatgctc tgtttagaga   2040
aatcaatgtg ttagatatct gcagtaaacc tgaatctgta atactattga atacttcata   2100
ctattccttc tctttatggg aaggagattg taattttact aaagatatga tttctcagtt   2160
ggttccagaa tgtgatggat tttataacaa ttctaagtgg atgcatatgc atccatatgc   2220
ttgtagattc tggagaagta agaatgaaaa agaagaaact aaatgtagag atggggaaac   2280
taagagatgt ctgtattatc ctttatggga cagtcccgaa tctacatatg attttggtta   2340
tttagcatac caaaagaatt ttccttcccc tatctgtata gaacaacaga aaattagaga   2400
tcaagattat gaagtttatt ctttgtatca agaatgcaaa atagcttcta aagcatatgg   2460
aattgataca gttttattct ctctaaagaa ttttcttaat tatacaggaa ctcctgtaaa   2520
tgaaatgcct aatgcaagag cttttgtagg cctaatagat cccaagtttc ctccttccta   2580
tcccaatgtt actagggaac attatacttc ctgtaataat aggaaaagaa gaagtgttga   2640
taataactat gctaagttaa ggtctatggg gtatgcactt acaggagcag tgcaaacctt   2700
atctcaaata tcagatatta atgatgaaaa cttacagcaa ggaatatatt tattaaggga   2760
```

```
tcatgtaata accttaatgg aagctacatt gcatgatata tctgttatgg aaggaatgtt   2820

tgctgtacaa catttgcata cacatttgaa tcatttgaag acaatgcttc tagaaagaag   2880

aatagactgg acctatatgt ctagtacttg gctacaacaa caattacaga aatctgatga   2940

tgagatgaaa gtaataaaga gaattgctag aagtttggta tattatgtta aacaaaccca   3000

tagttctccc acagctacag cctgggagat tggattatat tatgaattgg ttatacctaa   3060

acatatttac ttgaataatt ggaatgttgt caatataggt cacttagtta aatcagctgg   3120

acaattgact catgtaacta tagctcatcc ttatgaaata atcaataagg aatgtgtaga   3180

gactatatat ctgcatcttg aagactgcac aagacaagat tatgtcatat gtgatgtggt   3240

aaagatagtg cagccttgtg gcaatagctc agacacgagt gattgtcctg tctgggctga   3300

agctgtaaaa gaaccatttg tgcaagtcaa tcctctgaaa aacggaagtt atctggtttt   3360

ggcaagttcc acagactgtc agatcccacc atatgttcct agcatcgtga ctgttaatga   3420

aacaacgtca tgctttggac tggactttaa aaggccactg gttgcggaag aaagattgag   3480

ctttgagcca cgactgccaa atctacaact aagattacca catttggttg gaattattgc   3540

aaaaatcaaa gggataaaaa tagaagtcac atcctctgga gaaagtataa aagagcagat   3600

tgaaagagca aaagctgagc tccttcgact ggacattcac gagggagata ctcctgcctg   3660

gatacaacag ctagctgcag caacaaagga cgtctggcca gcagcagctt ctgctctaca   3720

aggaattggg aactttttat ctgggactgc ccaaggaata tttggaactg cctttagtct   3780

cttgggatac ttaaagccta tcctaatagg agtaggggtc attctcttgg ttattcttat   3840

atttaaaatt gtatcctgga ttcctacgag aaggaggaat cagtagaatt ctgcagatat   3900

ccagcacagt ggcggccgct cgagtctaga gggcccgttt aaacccgctg atcagcctcg   3960

actgtgcctt ctagttgcca gccatctgtt gtttgcccct cccccgtgcc ttccttgacc   4020

ctggaaggtg ccactcccac tgtcctttcc taataaaatg aggaaattgc atcgcattgt   4080

ctgagtaggt gtcattctat tctggggggt ggggtggggc aggacagcaa gggggaggat   4140

tgggaagaca atagcaggca tgctggggat gcggtgggct ctatggcttc tgaggcggaa   4200

agaaccagct ggggctctag ggggtatccc cacgcgccct gtagcggcgc attaagcgcg   4260

gcgggtgtgg tggttacgcg cagcgtgacc gctacacttg ccagcgccct agcgcccgct   4320

cctttcgctt tcttcccttc ctttctcgcc acgttcgccg gctttccccg tcaagctcta   4380

aatcggggca tccctttagg gttccgattt agtgctttac ggcacctcga ccccaaaaaa   4440

cttgattagg gtgatggttc acgtagtggg ccatcgccct gatagacggt ttttcgccct   4500

ttgacgttgg agtccacgtt ctttaatagt ggactcttgt tccaaactgg aacaacactc   4560

aaccctatct cggtctattc ttttgattta taagggattt tggggatttc ggcctattgg   4620

ttaaaaaatg agctgattta acaaaaattt aacgcgaatt aattctgtgg aatgtgtgtc   4680

agttagggtg tggaaagtcc ccaggctccc caggcaggca gaagtatgca aagcatgcat   4740

ctcaattagt cagcaaccag gtgtggaaag tccccaggct ccccagcagg cagaagtatg   4800

caaagcatgc atctcaatta gtcagcaacc atagtcccgc ccctaactcc gcccatcccg   4860

cccctaactc cgcccagttc cgcccattct ccgccccatg gctgactaat tttttttatt   4920

tatgcagagg ccgaggccgc ctctgcctct gagctattcc agaagtagtg aggaggcttt   4980

tttggaggcc taggcttttg caaaaagctc ccgggagctt gtatatccat tttcggatct   5040

gatcagcacg tgttgacaat taatcatcgg catagtatat cggcatagta taatacgaca   5100

aggtgaggaa ctaaaccatg gccaagttga ccagtgccgt tccggtgctc accgcgcgcg   5160
```

-continued acgtcgccgg agcggtcgag ttctggaccg accggctcgg gttctcccgg gacttcgtgg 5220
aggacgactt cgccggtgtg gtccgggacg acgtgaccct gttcatcagc gcggtccagg 5280
accaggtggt gccggacaac accctggcct gggtgtgggt gcgcggcctg gacgagctgt 5340
acgccgagtg gtcggaggtc gtgtccacga acttccggga cgcctccggg ccggccatga 5400
ccgagatcgg cgagcagccg tgggggcggg agttcgccct gcgcgacccg gccggcaact 5460
gcgtgcactt cgtggccgag gagcaggact gacacgtgct acgagatttc gattccaccg 5520
ccgccttcta tgaaaggttg ggcttcggaa tcgttttccg ggacgccggc tggatgatcc 5580
tccagcgcgg ggatctcatg ctggagttct tcgcccaccc caacttgttt attgcagctt 5640
ataatggtta caaataaagc aatagcatca caaatttcac aaataaagca tttttttcac 5700
tgcattctag ttgtggtttg tccaaactca tcaatgtatc ttatcatgtc tgtataccgt 5760
cgacctctag ctagagcttg gcgtaatcat ggtcatagct gtttcctgtg tgaaattgtt 5820
atccgctcac aattccacac aacatacgag ccggaagcat aaagtgtaaa gcctggggtg 5880
cctaatgagt gagctaactc acattaattg cgttgcgctc actgcccgct ttccagtcgg 5940
gaaacctgtc gtgccagctg cattaatgaa tcggccaacg cgcggggaga ggcggtttgc 6000
gtattgggcg ctcttccgct tcctcgctca ctgactcgct gcgctcggtc gttcggctgc 6060
ggcgagcggt atcagctcac tcaaaggcgg taatacggtt atccacagaa tcaggggata 6120
acgcaggaaa gaacatgtga gcaaaaggcc agcaaaaggc caggaaccgt aaaaaggccg 6180
cgttgctggc gtttttccat aggctccgcc cccctgacga gcatcacaaa aatcgacgct 6240
caagtcagag gtggcgaaac ccgacaggac tataaagata ccaggcgttt ccccctggaa 6300
gctccctcgt gcgctctcct gttccgaccc tgccgcttac cggatacctg tccgcctttc 6360
tcccttcggg aagcgtggcg ctttctcaat gctcacgctg taggtatctc agttcggtgt 6420
aggtcgttcg ctccaagctg ggctgtgtgc acgaaccccc cgttcagccc gaccgctgcg 6480
ccttatccgg taactatcgt cttgagtcca acccggtaag acacgactta tcgccactgg 6540
cagcagccac tggtaacagg attagcagag cgaggtatgt aggcggtgct acagagttct 6600
tgaagtggtg gcctaactac ggctacacta gaaggacagt atttggtatc tgcgctctgc 6660
tgaagccagt taccttcgga aaaagagttg gtagctcttg atccggcaaa caaaccaccg 6720
ctggtagcgg tggttttttt gtttgcaagc agcagattac gcgcagaaaa aaaggatctc 6780
aagaagatcc tttgatcttt tctacggggt ctgacgctca gtggaacgaa aactcacgtt 6840
aagggatttt ggtcatgaga ttatcaaaaa ggatcttcac ctagatcctt ttaaattaaa 6900
aatgaagttt taaatcaatc taaagtatat atgagtaaac ttggtctgac agttaccaat 6960
gcttaatcag tgaggcacct atctcagcga tctgtctatt tcgttcatcc atagttgcct 7020
gactccccgt cgtgtagata actacgatac gggagggctt accatctggc cccagtgctg 7080
caatgatacc gcgagaccca cgctcaccgg ctccagattt atcagcaata aaccagccag 7140
ccggaagggc cgagcgcaga agtggtcctg caactttatc cgcctccatc cagtctatta 7200
attgttgccg ggaagctaga gtaagtagtt cgccagttaa tagtttgcgc aacgttgttg 7260
ccattgctac aggcatcgtg gtgtcacgct cgtcgtttgg tatggcttca ttcagctccg 7320
gttcccaacg atcaaggcga gttacatgat cccccatgtt gtgcaaaaaa gcggttagct 7380
ccttcggtcc tccgatcgtt gtcagaagta agttggccgc agtgttatca ctcatggtta 7440
tggcagcact gcataattct cttactgtca tgccatccgt aagatgcttt tctgtgactg 7500
gtgagtactc aaccaagtca ttctgagaat agtgtatgcg gcgaccgagt tgctcttgcc 7560

```
cggcgtcaat acgggataat accgcgccac atagcagaac tttaaaagtg ctcatcattg   7620
gaaaacgttc ttcggggcga aaactctcaa ggatcttacc gctgttgaga tccagttcga   7680
tgtaacccac tcgtgcaccc aactgatctt cagcatcttt tactttcacc agcgtttctg   7740
ggtgagcaaa aacaggaagg caaaatgccg caaaaaaggg aataagggcg acacggaaat   7800
gttgaatact catactcttc ctttttcaat attattgaag catttatcag ggttattgtc   7860
tcatgagcgg atacatattt gaatgtattt agaaaaataa acaaataggg gttccgcgca   7920
catttccccg aaaagtgcca cctgacgtca tggcaccacc aatgacactg caacaatgga   7980
tcatttggag aagaatgaat agagcgcatg aggcacttca aaatacaaca actgtgactg   8040
aacagcagcg cgaacaaatt atactggaca ttcaaaatga agaagtacaa ccaactagga   8100
gagatcgctt tagatatctg ctttatactt gttgtgctac tagctcaaga gtattggcct   8160
ggatgttttt agtttgtata ttgttaatca ttgttttggt ttcatgcttt gtgactatat   8220
ccagaataca atggaataag gatattcagg tattaggacc tgtaatagac tggaatgtta   8280
ctcaaagagc tgtttatcaa cccttacaga ctagaaggat tgcacgttcc cttagaatgc   8340
agcatcctgt tccaaaatat gtggaggtaa atatgactag tattccacaa ggtgtatact   8400
atgaacccca tccggaaccc atagtggtga aggagagggt cctgggtctt tctcaaattc   8460
tgatgattaa ttcagaaaac attgctaata atgctaattt gacacaagaa gtaaagaagt   8520
tgttaactga aatggttaat gaagaaatgc aaagtttgtc agatgtaatg attgactttg   8580
aaattccttt aggagaccct cgtgatcaag aacaatatat acatagaaaa tgctatcaag   8640
aatttgcaaa ttgttattta gtaaaatata aagaacccaa accgtggcct aaggagggcc   8700
ttatagctga tcaatgccca ttaccaggtt accatgctgg attaacctat aatagacagt   8760
ctatttggga ttactatatt aaagtggaga gtattagacc tgcaaattgg acaacaaaga   8820
gtaaatatgg acaagctaga ctaggaagtt tttatattcc tagcagtctg agacaaatca   8880
atgttagtca tgtactattc tgtagtgatc aattatattc taaatggtat aatatagaaa   8940
ataccataga acaaaacgag cggtttctgc ttaataaact aaataacctt acatctggaa   9000
cctcagtatt gaagaaaaga gctcttccga aggattggag ttctcaaggt aaaaatgctc   9060
tgtttagaga aatcaatgtg ttagatatct gcagtaaacc tgaatctgta atactattga   9120
atacttcata ctattccttc tctttatggg aaggagattg taattttact aaagatatga   9180
tttctcagtt ggttccagaa tgtgatggat tttataacaa ttctaagtgg atgcatatgc   9240
atccatatgc ttgtagattc tggagaagta agaatgaaaa agaagaaact aaatgtagag   9300
atggggaaac taagagatgt ctgtattatc ctttatggga cagtcccgaa tctacatatg   9360
attttggtta tttagcatac caaaagaatt ttccttcccc tatctgtata gaacaacaga   9420
aaattagaga tcaagattat gaagtttatt ctttgtatca agaatgcaaa atagcttcta   9480
aagcatatgg aattgataca gttttattct ctctaaagaa ttttcttaat tatacaggaa   9540
ctcctgtaaa tgaaatgcct aatgcaagag cttttgtagg cctaatagat cccaagtttc   9600
ctccttccta tcccaatgtt actagggaac attatacttc ctgtaataat aggaaaagaa   9660
gaagtgttga taataactat gctaagttaa ggtctatggg gtatgcactt acaggagcag   9720
tgcaaacctt atctcaaata tcagatatta atgatgaaaa cttacagcaa ggaatatatt   9780
tattaaggga tcatgtaata accttaatgg aagctacatt gcatgatata tctgttatgg   9840
aaggaatgtt tgctgtacaa catttgcata cacatttgaa tcatttgaag acaatgcttc   9900
tagaaagaag aatagactgg acctatatgt ctagtacttg gctacaacaa caattacaga   9960
```

```
aatctgatga tgagatgaaa gtaataaaga gaattgctag aagtttggta tattatgtta  10020

aacaaaccca tagttctccc acagctacag cctgggagat tggattatat tatgaattgg  10080

ttatacctaa acatatttac ttgaataatt ggaatgttgt caatataggt cacttagtta  10140

aatcagctgg acaattgact catgtaacta tagctcatcc ttatgaaata atcaataagg  10200

aatgtgtaga gactatatat ctgcatcttg aagactgcac aagacaagat tatgtcatat  10260

gtgatgtggt aaagatagtg cagccttgtg gcaatagctc agacacgagt gattgtcctg  10320

tctgggctga agctgtaaaa gaaccatttg tgcaagtcaa tcctctgaaa aacggaagtt  10380

atctggtttt ggcaagttcc acagactgtc agatcccacc atatgttcct agcatcgtga  10440

ctgttaatga aacaacgtca tgctttggac tggactttaa aaggccactg gttgcggaag  10500

aaagattgag ctttgagcca cgactgccaa atctacaact aagattacca catttggttg  10560

gaattattgc aaaaatcaaa gggataaaaa tagaagtcac atcctctgga gaaagtataa  10620

aagagcagat tgaaagagca aaagctgagc tccttcgact ggacattcac gagggagata  10680

ctcctgcctg gatacaacag ctagctgcag caacaaagga cgtctggcca gcagcagctt  10740

ctgctctaca aggaattggg aactttttat ctgggactgc ccaaggaata tttggaactg  10800

cctttagtct cttgggatac ttaaagccta tcctaatagg agtaggggtc attctcttgg  10860

ttattcttat atttaaaatt gtatcctgga ttcctacgag aaggaggaat cagtag      10916
```

<210> SEQ ID NO 23
<211> LENGTH: 10916
<212> TYPE: DNA
<213> ORGANISM: Artificial Sequence
<220> FEATURE:
<223> OTHER INFORMATION: Foamy Viral Envelope Gene pczHFV EM225

<400> SEQUENCE: 23

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctaga    900

aaacctacgt ctcatcagaa tggcaccacc aatgacactg caacaatgga tcatttggag    960

aagaatgaat agagcgcatg aggcacttca aaatacaaca actgtgactg aacagcagcg   1020

cgaacaaatt atactggaca ttcaaaatga agaagtacaa ccaactagga gagatcgctt   1080

tagatatctg ctttatactt gttgtgctac tagctcaaga gtattggcct ggatgttttt   1140
```

```
agtttgtata ttgttaatca ttgttttggt ttcatgcttt gtgactatat ccagaataca   1200
atggaataag gatattcagg tattaggacc tgtaatagac tggaatgtta ctcaaagagc   1260
tgtttatcaa cccttacaga ctagaaggat tgcacgttcc cttagaatgc agcatcctgt   1320
tccaaaatat gtggaggtaa atatgactag tattccacaa ggtgtatact atgaacccca   1380
tccggaaccc atagtggtga aggagagggt cctgggtctt tctcaaattc tgatgattaa   1440
ttcagaaaac attgctaata atgctaattt gacacaagaa gtaaagaagt tgttaactga   1500
aatggttaat gaagaaatgc aaagtttgtc agatgtaatg attgactttg aaattccttt   1560
aggagaccct cgtgatcaag aacaatatat acatagaaaa tgctatcaag aatttgcaaa   1620
ttgttattta gtaaaatata aagaacccaa accgtggcct aaggagggcc ttatagctga   1680
tcaatgccca ttaccaggtt accatgctgg attaacctat aatagacagt ctatttggga   1740
ttactatatt aaagtggaga gtattagacc tgcaaattgg acaacaaaga gtaaatatgg   1800
acaagctaga ctaggaagtt tttatattcc tagcagtctg agacaaatca atgttagtca   1860
tgtactattc tgtagtgatc aattatattc taaatggtat aatatagaaa ataccataga   1920
acaaaacgag cggtttctgc ttaataaact aaataacctt acatctggaa cctcagtatt   1980
gaagaaaaga gctcttccga aggattggag ttctcaaggt aaaaatgctc tgtttagaga   2040
aatcaatgtg ttagatatct gcagtaaacc tgaatctgta atactattga atacttcata   2100
ctattccttc tctttatggg aaggagattg taattttact aaagatatga tttctcagtt   2160
ggttccagaa tgtgatggat tttataacaa ttctaagtgg atgcatatgc atccatatgc   2220
ttgtagattc tggagaagta agaatgaaaa agaagaaact aaatgtagag atggggaaac   2280
taagagatgt ctgtattatc ctttatggga cagtcccgaa tctacatatg attttggtta   2340
tttagcatac caaaagaatt ttccttcccc tatctgtata gaacaacaga aaattagaga   2400
tcaagattat gaagtttatt ctttgtatca agaatgcaaa atagcttcta aagcatatgg   2460
aattgataca gttttattct ctctaaagaa ttttcttaat tatacaggaa ctcctgtaaa   2520
tgaaatgcct aatgcaagag cttttgtagg cctaatagat cccaagtttc ctccttccta   2580
tcccaatgtt actagggaac attatacttc ctgtaataat aggaaaagaa gaagtgttga   2640
taataactat gctaagttaa ggtctatggg gtatgcactt acaggagcag tgcaaacctt   2700
atctcaaata tcagatatta atgatgaaaa cttacagcaa ggaatatatt tattaaggga   2760
tcatgtaata accttaatgg aagctacatt gcatgatata tctgttatgg aaggaatgtt   2820
tgctgtacaa catttgcata cacatttgaa tcatttgaag acaatgcttc tagaaagaag   2880
aatagactgg acctatatgt ctagtacttg gctacaacaa caattacaga aatctgatga   2940
tgagatgaaa gtaataaaga gaattgctag aagtttggta tattatgtta aacaaaccca   3000
tagttctccc acagctacag cctgggagat tggattatat tatgaattgg ttatacctaa   3060
acatatttac ttgaataatt ggaatgttgt caatataggt cacttagtta aatcagctgg   3120
acaattgact catgtaacta tagctcatcc ttatgaaata atcaataagg aatgtgtaga   3180
gactatatat ctgcatcttg aagactgcac aagacaagat tatgtcatat gtgatgtggt   3240
aaagatagtg cagccttgtg gcaatagctc agacacgagt gattgtcctg tctgggctga   3300
agctgtaaaa gaaccatttg tgcaagtcaa tcctctgaaa aacggaagtt atctggtttt   3360
ggcaagttcc acagactgtc agatcccacc atatgttcct agcatcgtga ctgttaatga   3420
aacaacgtca tgctttggac tggactttaa aaggccactg gttgcggaag aaagattgag   3480
ctttgagcca cgactgccaa atctacaact aagattacca catttggttg gaattattgc   3540
```

-continued aaaaatcaaa gggataaaaa tagaagtcac atcctctgga gaaagtataa aagagcagat 3600
tgaaagagca aaagctgagc tccttcgact ggacattcac gagggagata ctcctgcctg 3660
gatacaacag ctagctgcag caacaaagga cgtctggcca gcagcagctt ctgctctaca 3720
aggaattggg aactttttat ctgggactgc ccaaggaata tttggaactg cctttagtct 3780
cttgggatac ttaaggccta tcctaatagg agtaggggtc attctcttgg ttattcttat 3840
atttagaatt gtatcctgga ttcctacgag aaggaggaat cagtagaatt ctgcagatat 3900
ccagcacagt ggcggccgct cgagtctaga gggcccgttt aaacccgctg atcagcctcg 3960
actgtgcctt ctagttgcca gccatctgtt gtttgcccct cccccgtgcc ttccttgacc 4020
ctggaaggtg ccactcccac tgtcctttcc taataaaatg aggaaattgc atcgcattgt 4080
ctgagtaggt gtcattctat tctggggggt ggggtggggc aggacagcaa gggggaggat 4140
tgggaagaca atagcaggca tgctggggat gcggtgggct ctatggcttc tgaggcggaa 4200
agaaccagct ggggctctag ggggtatccc cacgcgccct gtagcggcgc attaagcgcg 4260
gcgggtgtgg tggttacgcg cagcgtgacc gctacacttg ccagcgccct agcgcccgct 4320
cctttcgctt tcttcccttc ctttctcgcc acgttcgccg gctttccccg tcaagctcta 4380
aatcggggca tccctttagg gttccgattt agtgctttac ggcacctcga ccccaaaaaa 4440
cttgattagg gtgatggttc acgtagtggg ccatcgccct gatagacggt ttttcgccct 4500
ttgacgttgg agtccacgtt ctttaatagt ggactcttgt tccaaactgg aacaacactc 4560
aaccctatct cggtctattc ttttgattta taagggattt tggggatttc ggcctattgg 4620
ttaaaaaatg agctgattta acaaaaattt aacgcgaatt aattctgtgg aatgtgtgtc 4680
agttagggtg tggaaagtcc ccaggctccc caggcaggca gaagtatgca aagcatgcat 4740
ctcaattagt cagcaaccag gtgtggaaag tccccaggct ccccagcagg cagaagtatg 4800
caaagcatgc atctcaatta gtcagcaacc atagtcccgc ccctaactcc gcccatcccg 4860
cccctaactc cgcccagttc cgcccattct ccgccccatg gctgactaat tttttttatt 4920
tatgcagagg ccgaggccgc ctctgcctct gagctattcc agaagtagtg aggaggcttt 4980
tttggaggcc taggcttttg caaaaagctc ccgggagctt gtatatccat tttcggatct 5040
gatcagcacg tgttgacaat taatcatcgg catagtatat cggcatagta taatacgaca 5100
aggtgaggaa ctaaaccatg gccaagttga ccagtgccgt tccggtgctc accgcgcgcg 5160
acgtcgccgg agcggtcgag ttctggaccg accggctcgg gttctcccgg gacttcgtgg 5220
aggacgactt cgccggtgtg gtccgggacg acgtgaccct gttcatcagc gcggtccagg 5280
accaggtggt gccggacaac accctggcct gggtgtgggt gcgcggcctg gacgagctgt 5340
acgccgagtg gtcggaggtc gtgtccacga acttccggga cgcctccggg ccggccatga 5400
ccgagatcgg cgagcagccg tgggggcggg agttcgccct gcgcgacccg gccggcaact 5460
gcgtgcactt cgtggccgag gagcaggact gacacgtgct acgagatttc gattccaccg 5520
ccgccttcta tgaaaggttg ggcttcggaa tcgttttccg ggacgccggc tggatgatcc 5580
tccagcgcgg ggatctcatg ctggagttct tcgcccaccc caacttgttt attgcagctt 5640
ataatggtta caaataaagc aatagcatca caaatttcac aaataaagca tttttttcac 5700
tgcattctag ttgtggtttg tccaaactca tcaatgtatc ttatcatgtc tgtataccgt 5760
cgacctctag ctagagcttg gcgtaatcat ggtcatagct gtttcctgtg tgaaattgtt 5820
atccgctcac aattccacac aacatacgag ccggaagcat aaagtgtaaa gcctggggtg 5880
cctaatgagt gagctaactc acattaattg cgttgcgctc actgcccgct ttccagtcgg 5940

```
gaaacctgtc gtgccagctg cattaatgaa tcggccaacg cgcggggaga ggcggtttgc   6000
gtattgggcg ctcttccgct tcctcgctca ctgactcgct gcgctcggtc gttcggctgc   6060
ggcgagcggt atcagctcac tcaaaggcgg taatacggtt atccacagaa tcaggggata   6120
acgcaggaaa gaacatgtga gcaaaaggcc agcaaaaggc caggaaccgt aaaaaggccg   6180
cgttgctggc gtttttccat aggctccgcc cccctgacga gcatcacaaa aatcgacgct   6240
caagtcagag gtggcgaaac ccgacaggac tataaagata ccaggcgttt ccccctggaa   6300
gctccctcgt gcgctctcct gttccgaccc tgccgcttac cggatacctg tccgcctttc   6360
tcccttcggg aagcgtggcg ctttctcaat gctcacgctg taggtatctc agttcggtgt   6420
aggtcgttcg ctccaagctg ggctgtgtgc acgaaccccc cgttcagccc gaccgctgcg   6480
ccttatccgg taactatcgt cttgagtcca acccggtaag acacgactta tcgccactgg   6540
cagcagccac tggtaacagg attagcagag cgaggtatgt aggcggtgct acagagttct   6600
tgaagtggtg gcctaactac ggctacacta gaaggacagt atttggtatc tgcgctctgc   6660
tgaagccagt taccttcgga aaaagagttg gtagctcttg atccggcaaa caaaccaccg   6720
ctggtagcgg tggttttttt gtttgcaagc agcagattac gcgcagaaaa aaaggatctc   6780
aagaagatcc tttgatcttt tctacggggt ctgacgctca gtggaacgaa aactcacgtt   6840
aagggatttt ggtcatgaga ttatcaaaaa ggatcttcac ctagatcctt ttaaattaaa   6900
aatgaagttt taaatcaatc taaagtatat atgagtaaac ttggtctgac agttaccaat   6960
gcttaatcag tgaggcacct atctcagcga tctgtctatt tcgttcatcc atagttgcct   7020
gactccccgt cgtgtagata actacgatac gggagggctt accatctggc cccagtgctg   7080
caatgatacc gcgagaccca cgctcaccgg ctccagattt atcagcaata aaccagccag   7140
ccggaagggc cgagcgcaga agtggtcctg caactttatc cgcctccatc cagtctatta   7200
attgttgccg ggaagctaga gtaagtagtt cgccagttaa tagtttgcgc aacgttgttg   7260
ccattgctac aggcatcgtg gtgtcacgct cgtcgtttgg tatggcttca ttcagctccg   7320
gttcccaacg atcaaggcga gttacatgat cccccatgtt gtgcaaaaaa gcggttagct   7380
ccttcggtcc tccgatcgtt gtcagaagta agttggccgc agtgttatca ctcatggtta   7440
tggcagcact gcataattct cttactgtca tgccatccgt aagatgcttt tctgtgactg   7500
gtgagtactc aaccaagtca ttctgagaat agtgtatgcg gcgaccgagt tgctcttgcc   7560
cggcgtcaat acgggataat accgcgccac atagcagaac tttaaaagtg ctcatcattg   7620
gaaaacgttc ttcggggcga aaactctcaa ggatcttacc gctgttgaga tccagttcga   7680
tgtaacccac tcgtgcaccc aactgatctt cagcatcttt tactttcacc agcgtttctg   7740
ggtgagcaaa aacaggaagg caaaatgccg caaaaaaggg aataagggcg acacggaaat   7800
gttgaatact catactcttc ctttttcaat attattgaag catttatcag ggttattgtc   7860
tcatgagcgg atacatattt gaatgtattt agaaaaataa acaaataggg gttccgcgca   7920
catttccccg aaaagtgcca cctgacgtca tggcaccacc aatgacactg caacaatgga   7980
tcatttggag aagaatgaat agagcgcatg aggcacttca aaatacaaca actgtgactg   8040
aacagcagcg cgaacaaatt atactggaca ttcaaaatga agaagtacaa ccaactagga   8100
gagatcgctt tagatatctg ctttatactt gttgtgctac tagctcaaga gtattggcct   8160
ggatgttttt agtttgtata ttgttaatca ttgttttggt ttcatgcttt gtgactatat   8220
ccagaataca atggaataag gatattcagg tattaggacc tgtaatagac tggaatgtta   8280
ctcaaagagc tgtttatcaa cccttacaga ctagaaggat tgcacgttcc cttagaatgc   8340
```

-continued

```
agcatcctgt tccaaaatat gtggaggtaa atatgactag tattccacaa ggtgtatact   8400
atgaacccca tccggaaccc atagtggtga aggagagggt cctgggtctt tctcaaattc   8460
tgatgattaa ttcagaaaac attgctaata atgctaattt gacacaagaa gtaaagaagt   8520
tgttaactga aatggttaat gaagaaatgc aaagtttgtc agatgtaatg attgactttg   8580
aaattccttt aggagaccct cgtgatcaag aacaatatat acatagaaaa tgctatcaag   8640
aatttgcaaa ttgttattta gtaaaatata aagaacccaa accgtggcct aaggagggcc   8700
ttatagctga tcaatgccca ttaccaggtt accatgctgg attaacctat aatagacagt   8760
ctatttggga ttactatatt aaagtggaga gtattagacc tgcaaattgg acaacaaaga   8820
gtaaatatgg acaagctaga ctaggaagtt tttatattcc tagcagtctg agacaaatca   8880
atgttagtca tgtactattc tgtagtgatc aattatattc taaatggtat aatatagaaa   8940
ataccataga acaaaacgag cggtttctgc ttaataaact aaataacctt acatctggaa   9000
cctcagtatt gaagaaaaga gctcttccga aggattggag ttctcaaggt aaaaatgctc   9060
tgtttagaga aatcaatgtg ttagatatct gcagtaaacc tgaatctgta atactattga   9120
atacttcata ctattccttc tctttatggg aaggagattg taattttact aaagatatga   9180
tttctcagtt ggttccagaa tgtgatggat tttataacaa ttctaagtgg atgcatatgc   9240
atccatatgc ttgtagattc tggagaagta agaatgaaaa agaagaaact aaatgtagag   9300
atggggaaac taagagatgt ctgtattatc ctttatggga cagtcccgaa tctacatatg   9360
attttggtta tttagcatac caaaagaatt ttccttcccc tatctgtata gaacaacaga   9420
aaattagaga tcaagattat gaagtttatt ctttgtatca agaatgcaaa atagcttcta   9480
aagcatatgg aattgataca gttttattct ctctaaagaa ttttcttaat tatacaggaa   9540
ctcctgtaaa tgaaatgcct aatgcaagag cttttgtagg cctaatagat cccaagtttc   9600
ctccttccta tcccaatgtt actagggaac attatacttc ctgtaataat aggaaaagaa   9660
gaagtgttga taataactat gctaagttaa ggtctatggg gtatgcactt acaggagcag   9720
tgcaaacctt atctcaaata tcagatatta atgatgaaaa cttacagcaa ggaatatatt   9780
tattaaggga tcatgtaata accttaatgg aagctacatt gcatgatata tctgttatgg   9840
aaggaatgtt tgctgtacaa catttgcata cacatttgaa tcatttgaag acaatgcttc   9900
tagaaagaag aatagactgg acctatatgt ctagtacttg gctacaacaa caattacaga   9960
aatctgatga tgagatgaaa gtaataaaga gaattgctag aagtttggta tattatgtta  10020
aacaaaccca tagttctccc acagctacag cctgggagat tggattatat tatgaattgg  10080
ttatacctaa acatatttac ttgaataatt ggaatgttgt caatataggt cacttagtta  10140
aatcagctgg acaattgact catgtaacta tagctcatcc ttatgaaata atcaataagg  10200
aatgtgtaga gactatatat ctgcatcttg aagactgcac aagacaagat tatgtcatat  10260
gtgatgtggt aaagatagtg cagccttgtg gcaatagctc agacacgagt gattgtcctg  10320
tctgggctga agctgtaaaa gaaccatttg tgcaagtcaa tcctctgaaa aacggaagtt  10380
atctggtttt ggcaagttcc acagactgtc agatcccacc atatgttcct agcatcgtga  10440
ctgttaatga aacaacgtca tgctttggac tggactttaa aaggccactg gttgcggaag  10500
aaagattgag ctttgagcca cgactgccaa atctacaact aagattacca catttggttg  10560
gaattattgc aaaaatcaaa gggataaaaa tagaagtcac atcctctgga gaaagtataa  10620
aagagcagat tgaaagagca aaagctgagc tccttcgact ggacattcac gagggagata  10680
ctcctgcctg gatacaacag ctagctgcag caacaaagga cgtctggcca gcagcagctt  10740
```

ctgctctaca aggaattggg aactttttat ctgggactgc ccaaggaata tttggaactg 10800
cctttagtct cttgggatac ttaaggccta tcctaatagg agtaggggtc attctcttgg 10860
ttattcttat atttagaatt gtatcctgga ttcctacgag aaggaggaat cagtag 10916

<210> SEQ ID NO 24
<211> LENGTH: 10902
<212> TYPE: DNA
<213> ORGANISM: Artificial Sequence
<220> FEATURE:
<223> OTHER INFORMATION: Foamy Viral Envelope Gene pciSFV-1 SM05

<400> SEQUENCE: 24
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctaga 900
ctgccatggc accaccaatg acactgcaac aatggatcat ttggaaaaaa atgaataaag 960
cgcatgaggc acttcaaaat acaacaactg tgactgaaca gcagaaggaa caaattatac 1020
tggacattca aaatgaagaa gtacaaccaa ctaggagaga taaatttaga tatctgcttt 1080
atacttgttg tgctactagc tcaagagtat tggcctggat gtttttagtt tgtatattgt 1140
taatcattgt tttggtttca tgctttgtga ctatatccag aatacaatgg aataaggata 1200
ttcaggtatt aggacctgta atagactgga atgttactca aagagctgtt tatcaaccct 1260
tacagactag aaggattgca cgttccctta gaatgcagca tcctgttcca aaatatgtgg 1320
aggtaaatat gactagtatt ccacaaggtg tgtactatga accccatccg gaacccatag 1380
tggtgaagga gagggtccta ggtctttctc aaattctgat gattaattca gaaaacattg 1440
ctaataatgc taatttgaca caagaagtaa agaagttgtt aactgaaatg gttaatgaag 1500
aaatgcaaag tttgtcagat gtaatgattg actttgaaat tcctttagga gaccctcgtg 1560
atcaagaaca atatatacat agaaaatgct atcaagaatt tgcaaattgt tatttagtaa 1620
aatataaaga acccaaaccg tggcctaagg agggccttat agctgatcaa tgcccattac 1680
caggttacca tgctggatta acctataata gacagtctat ttgggattac tatattaaag 1740
tggagagtat tagacctgca aattggacaa caaagagtaa atatggacaa gctagactag 1800
gaagttttta tattcctagc agtctgagac aaatcaatgt tagtcatgta ctattctgta 1860
gtgatcaatt atattctaaa tggtataata tagaaaatac catagaacaa aacgagcggt 1920
ttctgcttaa taaactaaat aaccttacat ctggaacctc agtattgaag aaaagagctc 1980
ttccgaagga ttggagttct caaggtaaaa atgctctgtt tagagaaatc aatgtgttag 2040
atatctgcag taaacctgaa tctgtaatac tattgaatac ttcatactat tccttctctt 2100
tatgggaagg agattgtaat tttactaaag atatgatttc tcagttggtt ccagaatgtg 2160
atggatttta taacaattct aagtggatgc atatgcatcc atatgcttgt agattctgga 2220
gaagtaagaa tgaaaaagaa gaaactaaat gtagagatgg ggaaactaag agatgtctgt 2280
attatccttt atgggacagt cccgaatcta catatgattt tggttattta gcataccaaa 2340
agaattttcc ttcccctatc tgtatagaac aacagaaaat tagagatcaa gattatgaag 2400
tttattcttt gtatcaagaa tgcaaaatag cttctaaagc atatggaatt gatacagttt 2460
tattctctct aaagaatttt cttaattata caggaactcc tgtaaatgaa atgcctaatg 2520
caagagcttt tgtaggccta atagatccca agtttcctcc ttcctatccc aatgttacta 2580
gggaacatta tacttcctgt aataatagga aaagaagaag tgttgataat aactatgcta 2640
agttaaggtc tatggggtat gcacttacag gagcagtgca aaccttatct caaatatcag 2700
atattaatga tgaaaactta cagcaaggaa tatatttatt aagggatcat gtaataacct 2760
taatggaagc tacattgcat gatatatctg ttatggaagg aatgtttgct gtacaacatt 2820
tgcatacaca tttgaatcat ttgaagacaa tgcttctaga aagaagaata gactggacct 2880
atatgtctag tacttggcta caacaacaat tacagaaatc tgatgatgag atgaaagtaa 2940
taaagagaat tgctagaagt ttggtatatt atgttaaaca aacccatagt tctcccacag 3000
ctacagcctg ggagattgga ttatattatg aattggttat acctaaacat atttacttga 3060
ataattggaa tgttgtcaat ataggtcact tagttaaatc agctggacaa ttgactcatg 3120
taactatagc tcatccttat gaaataatca ataaggaatg tgtagagact atatatctgc 3180
atcttgaaga ctgcacaaga caagattatg tcatatgtga tgtggtaaag atagtgcagc 3240
cttgtggcaa tagctcagac acgagtgatt gtcctgtctg ggctgaagct gtaaaagaac 3300
catttgtgca agtcaatcct ctgaaaaacg gaagttatct ggttttggca agttccacag 3360
actgtcagat cccaccatat gttcctagca tcgtgactgt taatgaaaca acgtcatgct 3420
ttggactgga ctttaaaagg ccactggttg cggaagaaag attgagcttt gagccacgac 3480
tgccaaatct acaactaaga ttaccacatt tggttggaat tattgcaaaa atcaaaggga 3540
taaaaataga agtcacatcc tctggagaaa gtataaaaga gcagattgaa agagcaaaag 3600
ctgagctcct tcgactggac attcacgagg gagatactcc tgcctggata caacagctag 3660
ctgcagcaac aaaggacgtc tggccagcag cagcttctgc tctacaagga attgggaact 3720
ttttatctgg gactgcccaa ggaatatttg gaactgcctt tagtctcttg ggatacttaa 3780
agcctatcct aataggagta ggggtcattc tcttggttat tcttatattt aaaattgtat 3840
cctggattcc tacgagaagg aggaatcagt agaattctgc agatatccag cacagtggcg 3900
gccgctcgag tctagagggc ccgtttaaac ccgctgatca gcctcgactg tgccttctag 3960
ttgccagcca tctgttgttt gcccctcccc cgtgccttcc ttgaccctgg aaggtgccac 4020
tcccactgtc ctttcctaat aaaatgagga aattgcatcg cattgtctga gtaggtgtca 4080
ttctattctg gggggtgggg tggggcagga cagcaagggg gaggattggg aagacaatag 4140
caggcatgct ggggatgcgg tgggctctat ggcttctgag gcggaaagaa ccagctgggg 4200
ctctaggggg tatccccacg cgccctgtag cggcgcatta agcgcggcgg gtgtggtggt 4260
tacgcgcagc gtgaccgcta cacttgccag cgccctagcg cccgctcctt tcgctttctt 4320

```
ccctccttt ctcgccacgt tcgccggctt tccccgtcaa gctctaaatc ggggcatccc   4380
tttagggttc cgatttagtg ctttacggca cctcgacccc aaaaaacttg attagggtga   4440
tggttcacgt agtgggccat cgccctgata gacggttttt cgccctttga cgttggagtc   4500
cacgttcttt aatagtggac tcttgttcca aactggaaca acactcaacc ctatctcggt   4560
ctattctttt gatttataag ggattttggg gatttcggcc tattggttaa aaaatgagct   4620
gatttaacaa aaatttaacg cgaattaatt ctgtggaatg tgtgtcagtt agggtgtgga   4680
aagtccccag gctccccagg caggcagaag tatgcaaagc atgcatctca attagtcagc   4740
aaccaggtgt ggaaagtccc caggctcccc agcaggcaga agtatgcaaa gcatgcatct   4800
caattagtca gcaaccatag tcccgcccct aactccgccc atcccgcccc taactccgcc   4860
cagttccgcc cattctccgc cccatggctg actaattttt tttatttatg cagaggccga   4920
ggccgcctct gcctctgagc tattccagaa gtagtgagga ggcttttttg gaggcctagg   4980
cttttgcaaa aagctcccgg gagcttgtat atccattttc ggatctgatc agcacgtgtt   5040
gacaattaat catcggcata gtatatcggc atagtataat acgacaaggt gaggaactaa   5100
accatggcca agttgaccag tgccgttccg gtgctcaccg cgcgcgacgt cgccggagcg   5160
gtcgagttct ggaccgaccg gctcgggttc tcccgggact tcgtggagga cgacttcgcc   5220
ggtgtggtcc gggacgacgt gaccctgttc atcagcgcgg tccaggacca ggtggtgccg   5280
gacaacaccc tggcctgggt gtgggtgcgc ggcctggacg agctgtacgc cgagtggtcg   5340
gaggtcgtgt ccacgaactt ccgggacgcc tccgggccgg ccatgaccga gatcggcgag   5400
cagccgtggg ggcgggagtt cgccctgcgc gacccggccg gcaactgcgt gcacttcgtg   5460
gccgaggagc aggactgaca cgtgctacga gatttcgatt ccaccgccgc cttctatgaa   5520
aggttgggct tcggaatcgt tttccgggac gccggctgga tgatcctcca gcgcggggat   5580
ctcatgctgg agttcttcgc ccaccccaac ttgtttattg cagcttataa tggttacaaa   5640
taaagcaata gcatcacaaa tttcacaaat aaagcatttt tttcactgca ttctagttgt   5700
ggtttgtcca aactcatcaa tgtatcttat catgtctgta taccgtcgac ctctagctag   5760
agcttggcgt aatcatggtc atagctgttt cctgtgtgaa attgttatcc gctcacaatt   5820
ccacacaaca tacgagccgg aagcataaag tgtaaagcct ggggtgccta atgagtgagc   5880
taactcacat taattgcgtt gcgctcactg cccgctttcc agtcgggaaa cctgtcgtgc   5940
cagctgcatt aatgaatcgg ccaacgcgcg gggagaggcg gtttgcgtat tgggcgctct   6000
tccgcttcct cgctcactga ctcgctgcgc tcggtcgttc ggctgcggcg agcggtatca   6060
gctcactcaa aggcggtaat acggttatcc acagaatcag gggataacgc aggaaagaac   6120
atgtgagcaa aaggccagca aaaggccagg aaccgtaaaa aggccgcgtt gctggcgttt   6180
ttccataggc tccgcccccc tgacgagcat cacaaaaatc gacgctcaag tcagaggtgg   6240
cgaaacccga caggactata aagataccag gcgtttcccc ctggaagctc cctcgtgcgc   6300
tctcctgttc cgaccctgcc gcttaccgga tacctgtccg cctttctccc ttcgggaagc   6360
gtggcgcttt ctcaatgctc acgctgtagg tatctcagtt cggtgtaggt cgttcgctcc   6420
aagctgggct gtgtgcacga accccccgtt cagcccgacc gctgcgcctt atccggtaac   6480
tatcgtcttg agtccaaccc ggtaagacac gacttatcgc cactggcagc agccactggt   6540
aacaggatta gcagagcgag gtatgtaggc ggtgctacag agttcttgaa gtggtggcct   6600
aactacggct acactagaag gacagtattt ggtatctgcg ctctgctgaa gccagttacc   6660
ttcggaaaaa gagttggtag ctcttgatcc ggcaaacaaa ccaccgctgg tagcggtggt   6720
```

```
tttttgttt gcaagcagca gattacgcgc agaaaaaaag gatctcaaga agatcctttg   6780
atcttttcta cggggtctga cgctcagtgg aacgaaaact cacgttaagg gattttggtc   6840
atgagattat caaaaaggat cttcacctag atccttttaa attaaaaatg aagttttaaa   6900
tcaatctaaa gtatatatga gtaaacttgg tctgacagtt accaatgctt aatcagtgag   6960
gcacctatct cagcgatctg tctatttcgt tcatccatag ttgcctgact ccccgtcgtg   7020
tagataacta cgatacggga gggcttacca tctggcccca gtgctgcaat gataccgcga   7080
gacccacgct caccggctcc agatttatca gcaataaacc agccagccgg aagggccgag   7140
cgcagaagtg gtcctgcaac tttatccgcc tccatccagt ctattaattg ttgccgggaa   7200
gctagagtaa gtagttcgcc agttaatagt ttgcgcaacg ttgttgccat tgctacaggc   7260
atcgtggtgt cacgctcgtc gtttggtatg gcttcattca gctccggttc ccaacgatca   7320
aggcgagtta catgatcccc catgttgtgc aaaaaagcgg ttagctcctt cggtcctccg   7380
atcgttgtca gaagtaagtt ggccgcagtg ttatcactca tggttatggc agcactgcat   7440
aattctctta ctgtcatgcc atccgtaaga tgcttttctg tgactggtga gtactcaacc   7500
aagtcattct gagaatagtg tatgcggcga ccgagttgct cttgcccggc gtcaatacgg   7560
gataataccg cgccacatag cagaacttta aaagtgctca tcattggaaa acgttcttcg   7620
gggcgaaaac tctcaaggat cttaccgctg ttgagatcca gttcgatgta acccactcgt   7680
gcacccaact gatcttcagc atcttttact ttcaccagcg tttctgggtg agcaaaaaca   7740
ggaaggcaaa atgccgcaaa aaagggaata agggcgacac ggaaatgttg aatactcata   7800
ctcttccttt ttcaatatta ttgaagcatt tatcagggtt attgtctcat gagcggatac   7860
atatttgaat gtatttagaa aaataaacaa ataggggttc cgcgcacatt tccccgaaaa   7920
gtgccacctg acgtcatggc accaccaatg acactgcaac aatggatcat ttggaaaaaa   7980
atgaataaag cgcatgaggc acttcaaaat acaacaactg tgactgaaca gcagaaggaa   8040
caaattatac tggacattca aaatgaagaa gtacaaccaa ctaggagaga taaatttaga   8100
tatctgcttt atacttgttg tgctactagc tcaagagtat tggcctggat gtttttagtt   8160
tgtatattgt taatcattgt tttggtttca tgctttgtga ctatatccag aatacaatgg   8220
aataaggata ttcaggtatt aggacctgta atagactgga atgttactca aagagctgtt   8280
tatcaaccct tacagactag aaggattgca cgttccctta gaatgcagca tcctgttcca   8340
aaatatgtgg aggtaaatat gactagtatt ccacaaggtg tgtactatga accccatccg   8400
gaacccatag tggtgaagga gagggtccta ggtctttctc aaattctgat gattaattca   8460
gaaaacattg ctaataatgc taatttgaca caagaagtaa agaagttgtt aactgaaatg   8520
gttaatgaag aaatgcaaag tttgtcagat gtaatgattg actttgaaat tcctttagga   8580
gaccctcgtg atcaagaaca atatatacat agaaaatgct atcaagaatt tgcaaattgt   8640
tatttagtaa aatataaaga acccaaaccg tggcctaagg agggccttat agctgatcaa   8700
tgcccattac caggttacca tgctggatta acctataata gacagtctat ttgggattac   8760
tatattaaag tggagagtat tagacctgca aattggacaa caaagagtaa atatggacaa   8820
gctagactag gaagttttta tattcctagc agtctgagac aaatcaatgt tagtcatgta   8880
ctattctgta gtgatcaatt atattctaaa tggtataata tagaaaatac catagaacaa   8940
aacgagcggt ttctgcttaa taaactaaat aaccttacat ctggaacctc agtattgaag   9000
aaaagagctc ttccgaagga ttggagttct caaggtaaaa atgctctgtt tagagaaatc   9060
aatgtgttag atatctgcag taaacctgaa tctgtaatac tattgaatac ttcatactat   9120
```

```
tccttctctt tatgggaagg agattgtaat tttactaaag atatgatttc tcagttggtt   9180

ccagaatgtg atggatttta taacaattct aagtggatgc atatgcatcc atatgcttgt   9240

agattctgga gaagtaagaa tgaaaaagaa gaaactaaat gtagagatgg ggaaactaag   9300

agatgtctgt attatccttt atgggacagt cccgaatcta catatgattt tggttattta   9360

gcataccaaa agaattttcc ttcccctatc tgtatagaac aacagaaaat tagagatcaa   9420

gattatgaag tttattcttt gtatcaagaa tgcaaaatag cttctaaagc atatggaatt   9480

gatacagttt tattctctct aaagaatttt cttaattata caggaactcc tgtaaatgaa   9540

atgcctaatg caagagcttt tgtaggccta atagatccca agtttcctcc ttcctatccc   9600

aatgttacta gggaacatta tacttcctgt aataatagga aaagaagaag tgttgataat   9660

aactatgcta agttaaggtc tatggggtat gcacttacag gagcagtgca aaccttatct   9720

caaatatcag atattaatga tgaaaactta cagcaaggaa tatatttatt aagggatcat   9780

gtaataacct taatggaagc tacattgcat gatatatctg ttatggaagg aatgtttgct   9840

gtacaacatt tgcatacaca tttgaatcat ttgaagacaa tgcttctaga aagaagaata   9900

gactggacct atatgtctag tacttggcta caacaacaat tacagaaatc tgatgatgag   9960

atgaaagtaa taaagagaat tgctagaagt ttggtatatt atgttaaaca aacccatagt  10020

tctcccacag ctacagcctg ggagattgga ttatattatg aattggttat acctaaacat  10080

atttacttga ataattggaa tgttgtcaat ataggtcact tagttaaatc agctggacaa  10140

ttgactcatg taactatagc tcatccttat gaaataatca ataaggaatg tgtagagact  10200

atatatctgc atcttgaaga ctgcacaaga caagattatg tcatatgtga tgtggtaaag  10260

atagtgcagc cttgtggcaa tagctcagac acgagtgatt gtcctgtctg ggctgaagct  10320

gtaaaagaac catttgtgca agtcaatcct ctgaaaaacg gaagttatct ggttttggca  10380

agttccacag actgtcagat cccaccatat gttcctagca tcgtgactgt taatgaaaca  10440

acgtcatgct ttggactgga ctttaaaagg ccactggttg cggaagaaag attgagcttt  10500

gagccacgac tgccaaatct acaactaaga ttaccacatt tggttggaat tattgcaaaa  10560

atcaaaggga taaaaataga agtcacatcc tctggagaaa gtataaaaga gcagattgaa  10620

agagcaaaag ctgagctcct tcgactggac attcacgagg gagatactcc tgcctggata  10680

caacagctag ctgcagcaac aaaggacgtc tggccagcag cagcttctgc tctacaagga  10740

attgggaact ttttatctgg gactgcccaa ggaatatttg gaactgcctt tagtctcttg  10800

ggatacttaa agcctatcct aataggagta ggggtcattc tcttggttat tcttatattt  10860

aaaattgtat cctggattcc tacgagaagg aggaatcagt ag                     10902
```

<210> SEQ ID NO 25
<211> LENGTH: 9982
<212> TYPE: DNA
<213> ORGANISM: Artificial Sequence
<220> FEATURE:
<223> OTHER INFORMATION: Foamy Viral Envelope Gene pciSFV-1 SM06

<400> SEQUENCE: 25

```
tcaatattgg ccattagcca tattattcat tggttatata gcataaatca atattggcta     60

ttggccattg catacgttgt atctatatca taatatgtac atttatattg gctcatgtcc    120

aatatgaccg ccatgttggc attgattatt gactagttat taatagtaat caattacggg    180

gtcattagtt catagcccat atatggagtt ccgcgttaca taacttacgg taaatggccc    240

gcctggctga ccgcccaacg acccccgccc attgacgtca ataatgacgt atgttcccat    300
```

```
agtaacgcca atagggactt tccattgacg tcaatgggtg gagtatttac ggtaaactgc    360
ccacttggca gtacatcaag tgtatcatat gccaagtccg ccccctattg acgtcaatga    420
cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaataaccc    660
cgccccgttg acgcaaatgg gcggtaggcg tgtacggtgg gaggtctata taagcagagc    720
tcgtttagtg aaccgtcaga tcactagaag ctttattgcg gtagtttatc acagttaaat    780
tgctaacgca gtcagtgctt ctgacacaac agtctcgaac ttaagctgca gaagttggtc    840
gtgaggcact gggcaggtaa gtatcaaggt tacaagacag gtttaaggag accaatagaa    900
actgggcttg tcgagacaga gaagactctt gcgtttctga taggcaccta ttggtcttac    960
tgacatccac tttgcctttc tctccacagg tgtccactcc cagttcaatt acagctctta   1020
aggctagagt acttaatacg actcactata ggctagcctc gagaattctg cagatatcca   1080
gcacagtggc ggccgctcga gtctagactg ccatggcacc tccaatgact ctggaacaat   1140
ggctcttatg gaggaggatg agtcaagcac atcaagcact tgaaaatgta accaccttga   1200
ctgaggaaca gaggcaacaa gttataatag acattcagca tgaagatgtt gttcctacta   1260
ggatggacag attgagatat ctggcctatt catgctgcgc tactagcaca cgtgtattgt   1320
gctggatagt gttagtttgc gtcttgctat tagttgtatt tatatcctgc tttgtgacaa   1380
tgtccaggat acaatggaat aaggatattg ctgtttttgg tccagtcatt gactggaatg   1440
ttagccaaca agctgtgatt caacaaataa gagctaaaag attagcaaga tcaattaggg   1500
tggaacatgc tactgagaca tatgtagagg tcaatatgac cagtatacct caaggggtgt   1560
tatatgtgcc tcatccagaa ccaataattc tcaaggagag gattcttggt ttatctcagg   1620
tcatgatgat aaactctgaa aatattgcta atactgctaa ccttactcaa gaaactaagg   1680
tactgttagc agacatgatt aatgaagaga tgaatgattt agctaatcaa atgatagatt   1740
ttgaaatccc attaggagat cccagagatc aaaaacaata ccagcatcaa aaatgttttc   1800
aagaatttgc acattgttat ttagtaaaat ataaaactac taaaggatgg cctagttcta   1860
ctgttatagc agatcaatgc cctttgcctg gtaaccatcc tacagtacaa tatgcacatc   1920
aaaatatatg ggattattat gtccccttttg aacaaattcg gccagaagga tggaactcaa   1980
aaagttatta tgaagatgct agaataggag ggttttatat accaaaatgg ttacgaaata   2040
attcctatac ccatgtctta ttttgttctg atcaaattta tggaaaatgg tataatattg   2100
atctcacagc ccaggagagg gaaaatttat tagtccgaaa attaattaat ttagctaaag   2160
gaaattcatc acaattaaaa gatagagcta tgccagctga atgggataaa caaggaaaag   2220
ctgatctatt tagacaaatt aatactttag atgtttgtaa tagaccagaa atggtatttt   2280
tgttaaattc ctcatattat gaattttccc tatgggaagg agattgtggt tttaccagac   2340
agaatgttac acaggctaat tccttatgta aagatttcta taataactca aaatggcaaa   2400
aattacatcc atattcgtgt agattttgga gatataaaca agagaaagaa gaaactaaat   2460
gtagtaatgg tgaaaagaaa aaatgtcttt attacccaca atgggatact cctgaagctt   2520
tatatgactt tgggttccta gcatatttaa attcttttcc ttctccaatc tgtataaaaa   2580
atcagactat aagggaacct gagtataaaa tctcttcttt atacctagaa tgcatgaatg   2640
cttcagacag acatggtata gatagtgctt tattagcttt gaagacattt ttaaacttta   2700
```

```
ctggtcagtc tgtaaacgaa atgccattag ctagagcctt tgtaggcctt actgacccta   2760
aatttccacc aacatatccc aacattacaa gggaatcttc tggttgtaat aataacaaaa   2820
gaaaaaggag aagtgttaat aattatgaaa gacttagatc tatgggatat gctttaactg   2880
gagctgttca aactttatct caaatatctg atattaatga tgagaggctg caacacggag   2940
tatatttact ccgggatcat gtggtaaccc tgatggaagc tgcccttcat gatgtttcga   3000
ttatggaagg aatgttagca attcaacatg tgcatactca tctcaatcat ctcaagacca   3060
tgcttttgat gagaaagatt gattggacat tcatcagaag tgactggatt caacagcaat   3120
tacagaagac agatgatgaa atgaaattga tacgaagaac tgcacgaagt ctagtctact   3180
atgtcacaca aacctccagt tctcctacag ctacttcctg ggagattgga atatattatg   3240
aaatagtaat tcctaaacat atatatttaa ataattggca agtaatcaat gtaggtcatt   3300
tattggagtc agctggtcat ctgactcatg taaaggttaa gcatccttat gaaataatta   3360
ataaggaatg tagtgacact caatatttac atcttgagga atgcattaga gaggattatg   3420
tgatttgtga catagtacaa atagttcaac catgtggaaa tgcaacagaa ttgagtgatt   3480
gtccagtaac agcattaaag gtgaagactc catatattca agtgtctccc ctgaagaatg   3540
gaagttattt agttttatct agtactaagg attgttctat acctgcatat gtacctagtg   3600
tggtcacagt caatgaaaca gttaagtgct ttggagtaga gtttcacaaa ccactttatg   3660
ctgaaacaaa aaccagctat gaaccacaag ttccgcattt gaagcttcgt ttaccccact   3720
tgactgggat tattgccagc ttgcaatcac tggaaataga agttacttct acacaagaga   3780
atataaaaga ccagatcgaa agggccaaag cacagcttct ccggctggac attcacgaag   3840
gagactttcc tgactggctg aaacaagtcg cctctgcaac cagggacgtt tggcctgctg   3900
cagcttcctt tatacaagga gtagggaact tcttatctaa tactgcccag ggggatattcg  3960
gctcagcggt aagcctccta tcctatgcaa aacctatttt gataggaata ggagttatac   4020
tgcttattgc ccttcttttt aaaataatat cgtggcttcc tgggaggccc aggaggaatt   4080
gatctagagg gcccgtttgg gcggccgctt cgagcagaca tgataagata cattgatgag   4140
tttggacaaa ccacaactag aatgcagtga aaaaaatgct ttatttgtga aatttgtgat   4200
gctattgctt tatttgtaac cattataagc tgcaataaac aagttaacaa caacaattgc   4260
attcatttta tgtttcaggt tcagggggag atgtgggagg tttttaaag caagtaaaac    4320
ctctacaaat gtggtaaaat cgataaggat ccgggctggc gtaatagcga agaggcccgc   4380
accgatcgcc cttcccaaca gttgcgcagc ctgaatggcg aatggacgcg ccctgtagcg   4440
gcgcattaag cgcggcgggt gtggtggtta cgcgcagcgt gaccgctaca cttgccagcg   4500
ccctagcgcc cgctcctttc gctttcttcc cttcctttct cgccacgttc gccggctttc   4560
cccgtcaagc tctaaatcgg gggctccctt tagggttccg atttagagct ttacggcacc   4620
tcgaccgcaa aaaacttgat ttgggtgatg gttcacgtag tgggccatcg ccctgataga   4680
cggtttttcg ccctttgacg ttggagtcca cgttctttaa tagtggactc ttgttccaaa   4740
ctggaacaac actcaaccct atctcggtct attcttttga tttataaggg attttgccga   4800
tttcggccta ttggttaaaa aatgagctga tttaacaaat atttaacgcg aattttaaca   4860
aaatattaac gtttacaatt tcgcctgatg cggtattttc tccttacgca tctgtgcggt   4920
atttcacacc gcatatggtg cactctcagt acaatctgct ctgatgccgc atagttaagc   4980
cagccccgac acccgccaac acccgctgac gcgccctgac gggcttgtct gctcccggca   5040
tccgcttaca gacaagctgt gaccgtctcc gggagctgca tgtgtcagag gttttcaccg   5100
```

```
tcatcaccga aacgcgcgag acgaaagggc ctcgtgatac gcctattttt ataggttaat   5160
gtcatgataa taatggtttc ttagacgtca ggtggcactt ttcggggaaa tgtgcgcgga   5220
acccctattt gtttattttt ctaaatacat tcaaatatgt atccgctcat gagacaataa   5280
ccctgataaa tgcttcaata atattgaaaa aggaagagta tgagtattca acatttccgt   5340
gtcgccctta ttcccttttt tgcggcattt tgccttcctg tttttgctca cccagaaacg   5400
ctggtgaaag taaaagatgc tgaagatcag ttgggtgcac gagtgggtta catcgaactg   5460
gatctcaaca gcggtaagat ccttgagagt tttcgccccg aagaacgttt tccaatgatg   5520
agcactttta aagttctgct atgtggcgcg gtattatccc gtattgacgc cgggcaagag   5580
caactcggtc gccgcataca ctattctcag aatgacttgg ttgagtactc accagtcaca   5640
gaaaagcatc ttacggatgg catgacagta agagaattat gcagtgctgc cataaccatg   5700
agtgataaca ctgcggccaa cttacttctg acaacgatcg gaggaccgaa ggagctaacc   5760
gcttttttgc acaacatggg ggatcatgta actcgccttg atcgttggga accggagctg   5820
aatgaagcca taccaaacga cgagcgtgac accacgatgc ctgtagcaat ggcaacaacg   5880
ttgcgcaaac tattaactgg cgaactactt actctagctt cccggcaaca attaatagac   5940
tggatggagg cggataaagt tgcaggacca cttctgcgct cggcccttcc ggctggctgg   6000
tttattgctg ataaatctgg agccggtgag cgtgggtctc gcggtatcat tgcagcactg   6060
gggccagatg gtaagccctc ccgtatcgta gttatctaca cgacggggag tcaggcaact   6120
atggatgaac gaaatagaca gatcgctgag ataggtgcct cactgattaa gcattggtaa   6180
ctgtcagacc aagtttactc atatatactt tagattgatt taaaacttca tttttaattt   6240
aaaaggatct aggtgaagat cctttttgat aatctcatga ccaaaatccc ttaacgtgag   6300
ttttcgttcc actgagcgtc agaccccgta gaaaagatca aaggatcttc ttgagatcct   6360
ttttttctgc gcgtaatctg ctgcttgcaa acaaaaaaac caccgctacc agcggtggtt   6420
tgtttgccgg atcaagagct accaactctt tttccgaagg taactggctt cagcagagcg   6480
cagataccaa atactgtcct tctagtgtag ccgtagttag gccaccactt caagaactct   6540
gtagcaccgc ctacatacct cgctctgcta atcctgttac cagtggctgc tgccagtggc   6600
gataagtcgt gtcttaccgg gttggactca agacgatagt taccggataa ggcgcagcgg   6660
tcgggctgaa cggggggttc gtgcacacag cccagcttgg agcgaacgac ctacaccgaa   6720
ctgagatacc tacagcgtga gctatgagaa agcgccacgc ttcccgaagg gagaaaggcg   6780
gacaggtatc cggtaagcgg cagggtcgga acaggagagc gcacgaggga gcttccaggg   6840
ggaaacgcct ggtatcttta tagtcctgtc gggtttcgcc acctctgact tgagcgtcga   6900
tttttgtgat gctcgtcagg ggggcggagc ctatggaaaa acgccagcaa cgcggccttt   6960
ttacggttcc tggccttttg ctggcctttt gctcacatgg ctcgacagat ctatggcacc   7020
tccaatgact ctggaacaat ggctcttatg gaggaggatg agtcaagcac atcaagcact   7080
tgaaaatgta accaccttga ctgaggaaca gaggcaacaa gttataatag acattcagca   7140
tgaagatgtt gttcctacta ggatggacag attgagatat ctggcctatt catgctgcgc   7200
tactagcaca cgtgtattgt gctggatagt gttagtttgc gtcttgctat tagttgtatt   7260
tatatcctgc tttgtgacaa tgtccaggat acaatggaat aaggatattg ctgtttttgg   7320
tccagtcatt gactggaatg ttagccaaca agctgtgatt caacaaataa gagctaaaag   7380
attagcaaga tcaattaggg tggaacatgc tactgagaca tatgtagagg tcaatatgac   7440
cagtatacct caaggggtgt tatatgtgcc tcatccagaa ccaataattc tcaaggagag   7500
```

```
gattcttggt ttatctcagg tcatgatgat aaactctgaa aatattgcta atactgctaa   7560
ccttactcaa gaaactaagg tactgttagc agacatgatt aatgaagaga tgaatgattt   7620
agctaatcaa atgatagatt ttgaaatccc attaggagat cccagagatc aaaaacaata   7680
ccagcatcaa aaatgttttc aagaatttgc acattgttat ttagtaaaat ataaaactac   7740
taaaggatgg cctagttcta ctgttatagc agatcaatgc cctttgcctg gtaaccatcc   7800
tacagtacaa tatgcacatc aaaatatatg ggattattat gtccccttg aacaaattcg   7860
gccagaagga tggaactcaa aaagttatta tgaagatgct agaataggag ggttttatat   7920
accaaaatgg ttacgaaata attcctatac ccatgtctta ttttgttctg atcaaattta   7980
tggaaaatgg tataatattg atctcacagc ccaggagagg gaaaatttat tagtccgaaa   8040
attaattaat ttagctaaag gaaattcatc acaattaaaa gatagagcta tgccagctga   8100
atgggataaa caaggaaaag ctgatctatt tagacaaatt aatactttag atgtttgtaa   8160
tagaccagaa atggtatttt tgttaaattc ctcatattat gaattttccc tatgggaagg   8220
agattgtggt tttaccagac agaatgttac acaggctaat tccttatgta aagatttcta   8280
taataactca aaatggcaaa aattacatcc atattcgtgt agattttgga gatataaaca   8340
agagaaagaa gaaactaaat gtagtaatgg tgaaaagaaa aaatgtcttt attacccaca   8400
atgggatact cctgaagctt tatatgactt tgggttccta gcatatttaa attcttttcc   8460
ttctccaatc tgtataaaaa atcagactat aagggaacct gagtataaaa tctcttcttt   8520
atacctagaa tgcatgaatg cttcagacag acatggtata gatagtgctt tattagcttt   8580
gaagacattt ttaaacttta ctggtcagtc tgtaaacgaa atgccattag ctagagcctt   8640
tgtaggcctt actgacccta aatttccacc aacatatccc aacattacaa gggaatcttc   8700
tggttgtaat aataacaaaa gaaaaaggag aagtgttaat aattatgaaa gacttagatc   8760
tatgggatat gctttaactg gagctgttca aactttatct caaatatctg atattaatga   8820
tgagaggctg caacacggag tatatttact ccgggatcat gtggtaaccc tgatggaagc   8880
tgcccttcat gatgtttcga ttatggaagg aatgttagca attcaacatg tgcatactca   8940
tctcaatcat ctcaagacca tgcttttgat gagaaagatt gattggacat tcatcagaag   9000
tgactggatt caacagcaat tacagaagac agatgatgaa atgaaattga tacgaagaac   9060
tgcacgaagt ctagtctact atgtcacaca aacctccagt tctcctacag ctacttcctg   9120
ggagattgga atatattatg aaatagtaat tcctaaacat atatatttaa ataattggca   9180
agtaatcaat gtaggtcatt tattggagtc agctggtcat ctgactcatg taaaggttaa   9240
gcatccttat gaaataatta ataaggaatg tagtgacact caatatttac atcttgagga   9300
atgcattaga gaggattatg tgatttgtga catagtacaa atagttcaac catgtggaaa   9360
tgcaacagaa ttgagtgatt gtccagtaac agcattaaag gtgaagactc catatattca   9420
agtgtctccc ctgaagaatg gaagttattt agttttatct agtactaagg attgttctat   9480
acctgcatat gtacctagtg tggtcacagt caatgaaaca gttaagtgct ttggagtaga   9540
gtttcacaaa ccactttatg ctgaaacaaa aaccagctat gaaccacaag ttccgcattt   9600
gaagcttcgt ttaccccact tgactgggat tattgccagc ttgcaatcac tggaaataga   9660
agttacttct acacaagaga atataaaaga ccagatcgaa agggccaaag cacagcttct   9720
ccggctggac attcacgaag gagactttcc tgactggctg aaacaagtcg cctctgcaac   9780
cagggacgtt tggcctgctg cagcttcctt tatacaagga gtagggaact tcttatctaa   9840
tactgcccag ggatattcgg gctcagcggt aagcctccta tcctatgcaa aacctatttt   9900
```

```
gataggaata ggagttatac tgcttattgc ccttcttttt aaaataatat cgtggcttcc   9960

tgggaggccc aggaggaatt ga                                             9982


<210> SEQ ID NO 26
<211> LENGTH: 9982
<212> TYPE: DNA
<213> ORGANISM: Artificial Sequence
<220> FEATURE:
<223> OTHER INFORMATION: Foamy Viral Envelope Gene pczHFV EM236

<400> SEQUENCE: 26

tcaatattgg ccattagcca tattattcat tggttatata gcataaatca atattggcta     60

ttggccattg catacgttgt atctatatca taatatgtac atttatattg gctcatgtcc    120

aatatgaccg ccatgttggc attgattatt gactagttat taatagtaat caattacggg    180

gtcattagtt catagcccat atatggagtt ccgcgttaca taacttacgg taaatggccc    240

gcctggctga ccgcccaacg acccccgccc attgacgtca ataatgacgt atgttcccat    300

agtaacgcca atagggactt tccattgacg tcaatgggtg gagtatttac ggtaaactgc    360

ccacttggca gtacatcaag tgtatcatat gccaagtccg ccccctattg acgtcaatga    420

cggtaaatgg cccgcctggc attatgccca gtacatgacc ttacgggact ttcctacttg    480

gcagtacatc tacgtattag tcatcgctat taccatggtg atgcggtttt ggcagtacac    540

caatgggcgt ggatagcggt ttgactcacg gggatttcca agtctccacc ccattgacgt    600

caatgggagt ttgttttggc accaaaatca acgggacttt ccaaaatgtc gtaataaccc    660

cgccccgttg acgcaaatgg gcggtaggcg tgtacggtgg gaggtctata taagcagagc    720

tcgtttagtg aaccgtcaga tcactagaag ctttattgcg gtagtttatc acagttaaat    780

tgctaacgca gtcagtgctt ctgacacaac agtctcgaac ttaagctgca gaagttggtc    840

gtgaggcact gggcaggtaa gtatcaaggt tacaagacag gtttaaggag accaatagaa    900

actgggcttg tcgagacaga gaagactctt gcgtttctga taggcaccta ttggtcttac    960

tgacatccac tttgcctttc tctccacagg tgtccactcc cagttcaatt acagctctta   1020

aggctagagt acttaatacg actcactata ggctagcctc gagaattctg cagatatcca   1080

gcacagtggc ggccgctcga gtctagactg ccatggcacc tccaatgact ctggaacaat   1140

ggctcttatg gaggaggatg agtcaagcac atcaagcact tgaaaatgta accaccttga   1200

ctgaggaaca gaggcaacaa gttataatag acattcagca tgaagatgtt gttcctacta   1260

ggatggacag attgagatat ctggcctatt catgctgcgc tactagcaca cgtgtattgt   1320

gctggatagt gttagtttgc gtcttgctat tagttgtatt tatatcctgc tttgtgacaa   1380

tgtccaggat acaatggaat aaggatattg ctgtttttgg tccagtcatt gactggaatg   1440

ttagccaaca agctgtgatt caacaaataa gagctaaaag attagcaaga tcaattaggg   1500

tggaacatgc tactgagaca tatgtagagg tcaatatgac cagtatacct caaggggtgt   1560

tatatgtgcc tcatccagaa ccaataattc tcaaggagag gattcttggt ttatctcagg   1620

tcatgatgat aaactctgaa aatattgcta atactgctaa ccttactcaa gaaactaagg   1680

tactgttagc agacatgatt aatgaagaga tgaatgattt agctaatcaa atgatagatt   1740

ttgaaatccc attaggagat cccagagatc aaaaacaata ccagcatcaa aaatgttttc   1800

aagaatttgc acattgttat ttagtaaaat ataaaactac taaaggatgg cctagttcta   1860

ctgttatagc agatcaatgc cctttgcctg gtaaccatcc tacagtacaa tatgcacatc   1920

aaaatatatg ggattattat gtcccctttg aacaaattcg gccagaagga tggaactcaa   1980
```

```
aaagttatta tgaagatgct agaataggag ggttttatat accaaaatgg ttacgaaata   2040

attcctatac ccatgtctta ttttgttctg atcaaattta tggaaaatgg tataatattg   2100

atctcacagc ccaggagagg gaaaatttat tagtccgaaa attaattaat ttagctaaag   2160

gaaattcatc acaattaaaa gatagagcta tgccagctga atgggataaa caaggaaaag   2220

ctgatctatt tagacaaatt aatactttag atgtttgtaa tagaccagaa atggtatttt   2280

tgttaaattc ctcatattat gaattttccc tatgggaagg agattgtggt tttaccagac   2340

agaatgttac acaggctaat tccttatgta aagatttcta taataactca aaatggcaaa   2400

aattacatcc atattcgtgt agattttgga gatataaaca agagaaagaa gaaactaaat   2460

gtagtaatgg tgaaaagaaa aaatgtcttt attacccaca atgggatact cctgaagctt   2520

tatatgactt tgggttccta gcatatttaa attcttttcc ttctccaatc tgtataaaaa   2580

atcagactat aagggaacct gagtataaaa tctcttcttt atacctagaa tgcatgaatg   2640

cttcagacag acatggtata gatagtgctt tattagcttt gaagacattt ttaaacttta   2700

ctggtcagtc tgtaaacgaa atgccattag ctagagcctt tgtaggcctt actgacccta   2760

aatttccacc aacatatccc aacattacaa gggaatcttc tggttgtaat aataacaaaa   2820

gaaaaaggag aagtgttaat aattatgaaa gacttagatc tatgggatat gctttaactg   2880

gagctgttca aactttatct caaatatctg atattaatga tgagaggctg caacacggag   2940

tatatttact ccgggatcat gtggtaaccc tgatggaagc tgcccttcat gatgtttcga   3000

ttatggaagg aatgttagca attcaacatg tgcatactca tctcaatcat ctcaagacca   3060

tgcttttgat gagaaagatt gattggacat tcatcagaag tgactggatt caacagcaat   3120

tacagaagac agatgatgaa atgaaattga tacgaagaac tgcacgaagt ctagtctact   3180

atgtcacaca aacctccagt tctcctacag ctacttcctg ggagattgga atatattatg   3240

aaatagtaat tcctaaacat atatatttaa ataattggca agtaatcaat gtaggtcatt   3300

tattggagtc agctggtcat ctgactcatg taaaggttaa gcatccttat gaaataatta   3360

ataaggaatg tagtgacact caatatttac atcttgagga atgcattaga gaggattatg   3420

tgatttgtga catagtacaa atagttcaac catgtggaaa tgcaacagaa ttgagtgatt   3480

gtccagtaac agcattaaag gtgaagactc catatattca agtgtctccc ctgaagaatg   3540

gaagttattt agttttatct agtactaagg attgttctat acctgcatat gtacctagtg   3600

tggtcacagt caatgaaaca gttaagtgct ttggagtaga gtttcacaaa ccactttatg   3660

ctgaaacaaa aaccagctat gaaccacaag ttccgcattt gaagcttcgt ttaccccact   3720

tgactgggat tattgccagc ttgcaatcac tggaaataga agttacttct acacaagaga   3780

atataaaaga ccagatcgaa agggccaaag cacagcttct ccggctggac attcacgaag   3840

gagactttcc tgactggctg aaacaagtcg cctctgcaac cagggacgtt tggcctgctg   3900

cagcttcctt tatacaagga gtagggaact tcttatctaa tactgcccag ggatattcg    3960

gctcagcggt aagcctccta ttctatgcaa gacctatttt gataggaata ggagttatac   4020

tgcttattgc ccttcttttt agaataatat cgtggcttcc tgggaggccc aggaggaatt   4080

gatctagagg gcccgtttgg gcggccgctt cgagcagaca tgataagata cattgatgag   4140

tttggacaaa ccacaactag aatgcagtga aaaaaatgct ttatttgtga aatttgtgat   4200

gctattgctt tatttgtaac cattataagc tgcaataaac aagttaacaa caacaattgc   4260

attcatttta tgtttcaggt tcagggggag atgtgggagg ttttttaaag caagtaaaac   4320

ctctacaaat gtggtaaaat cgataaggat ccgggctggc gtaatagcga agaggcccgc   4380
```

```
accgatcgcc cttcccaaca gttgcgcagc ctgaatggcg aatggacgcg ccctgtagcg   4440
gcgcattaag cgcggcgggt gtggtggtta cgcgcagcgt gaccgctaca cttgccagcg   4500
ccctagcgcc cgctcctttc gctttcttcc cttcctttct cgccacgttc gccggctttc   4560
cccgtcaagc tctaaatcgg gggctccctt tagggttccg atttagagct ttacggcacc   4620
tcgaccgcaa aaaacttgat ttgggtgatg gttcacgtag tgggccatcg ccctgataga   4680
cggtttttcg ccctttgacg ttggagtcca cgttctttaa tagtggactc ttgttccaaa   4740
ctggaacaac actcaaccct atctcggtct attcttttga tttataaggg attttgccga   4800
tttcggccta ttggttaaaa aatgagctga tttaacaaat atttaacgcg aattttaaca   4860
aaatattaac gtttacaatt tcgcctgatg cggtattttc tccttacgca tctgtgcggt   4920
atttcacacc gcatatggtg cactctcagt acaatctgct ctgatgccgc atagttaagc   4980
cagccccgac acccgccaac acccgctgac gcgccctgac gggcttgtct gctcccggca   5040
tccgcttaca gacaagctgt gaccgtctcc gggagctgca tgtgtcagag gttttcaccg   5100
tcatcaccga aacgcgcgag acgaaagggc ctcgtgatac gcctattttt ataggttaat   5160
gtcatgataa taatggtttc ttagacgtca ggtggcactt ttcggggaaa tgtgcgcgga   5220
acccctattt gtttattttt ctaaatacat tcaaatatgt atccgctcat gagacaataa   5280
ccctgataaa tgcttcaata atattgaaaa aggaagagta tgagtattca acatttccgt   5340
gtcgccctta ttcccttttt tgcggcattt tgccttcctg tttttgctca cccagaaacg   5400
ctggtgaaag taaaagatgc tgaagatcag ttgggtgcac gagtgggtta catcgaactg   5460
gatctcaaca gcggtaagat ccttgagagt tttcgccccg aagaacgttt tccaatgatg   5520
agcactttta aagttctgct atgtggcgcg gtattatccc gtattgacgc cgggcaagag   5580
caactcggtc gccgcataca ctattctcag aatgacttgg ttgagtactc accagtcaca   5640
gaaaagcatc ttacggatgg catgacagta agagaattat gcagtgctgc cataaccatg   5700
agtgataaca ctgcggccaa cttacttctg acaacgatcg gaggaccgaa ggagctaacc   5760
gcttttttgc acaacatggg ggatcatgta actcgccttg atcgttggga accggagctg   5820
aatgaagcca taccaaacga cgagcgtgac accacgatgc ctgtagcaat ggcaacaacg   5880
ttgcgcaaac tattaactgg cgaactactt actctagctt cccggcaaca attaatagac   5940
tggatggagg cggataaagt tgcaggacca cttctgcgct cggcccttcc ggctggctgg   6000
tttattgctg ataaatctgg agccggtgag cgtgggtctc gcggtatcat tgcagcactg   6060
gggccagatg gtaagccctc ccgtatcgta gttatctaca cgacggggag tcaggcaact   6120
atggatgaac gaaatagaca gatcgctgag ataggtgcct cactgattaa gcattggtaa   6180
ctgtcagacc aagtttactc atatatactt tagattgatt taaaacttca tttttaattt   6240
aaaaggatct aggtgaagat cctttttgat aatctcatga ccaaaatccc ttaacgtgag   6300
ttttcgttcc actgagcgtc agaccccgta gaaaagatca aaggatcttc ttgagatcct   6360
ttttttctgc gcgtaatctg ctgcttgcaa acaaaaaaac caccgctacc agcggtggtt   6420
tgtttgccgg atcaagagct accaactctt tttccgaagg taactggctt cagcagagcg   6480
cagataccaa atactgtcct tctagtgtag ccgtagttag gccaccactt caagaactct   6540
gtagcaccgc ctacatacct cgctctgcta atcctgttac cagtggctgc tgccagtggc   6600
gataagtcgt gtcttaccgg gttggactca agacgatagt taccggataa ggcgcagcgg   6660
tcgggctgaa cggggggttc gtgcacacag cccagcttgg agcgaacgac ctacaccgaa   6720
ctgagatacc tacagcgtga gctatgagaa agcgccacgc ttcccgaagg gagaaaggcg   6780
```

```
gacaggtatc cggtaagcgg cagggtcgga acaggagagc gcacgaggga gcttccaggg   6840
ggaaacgcct ggtatcttta tagtcctgtc gggtttcgcc acctctgact tgagcgtcga   6900
tttttgtgat gctcgtcagg ggggcggagc ctatggaaaa acgccagcaa cgcggccttt   6960
ttacggttcc tggccttttg ctggcctttt gctcacatgg ctcgacagat ctatggcacc   7020
tccaatgact ctggaacaat ggctcttatg gaggaggatg agtcaagcac atcaagcact   7080
tgaaaatgta accaccttga ctgaggaaca gaggcaacaa gttataatag acattcagca   7140
tgaagatgtt gttcctacta ggatggacag attgagatat ctggcctatt catgctgcgc   7200
tactagcaca cgtgtattgt gctggatagt gttagtttgc gtcttgctat tagttgtatt   7260
tatatcctgc tttgtgacaa tgtccaggat acaatggaat aaggatattg ctgtttttgg   7320
tccagtcatt gactggaatg ttagccaaca agctgtgatt caacaaataa gagctaaaag   7380
attagcaaga tcaattaggg tggaacatgc tactgagaca tatgtagagg tcaatatgac   7440
cagtatacct caaggggtgt tatatgtgcc tcatccagaa ccaataattc tcaaggagag   7500
gattcttggt ttatctcagg tcatgatgat aaactctgaa aatattgcta atactgctaa   7560
ccttactcaa gaaactaagg tactgttagc agacatgatt aatgaagaga tgaatgattt   7620
agctaatcaa atgatagatt ttgaaatccc attaggagat cccagagatc aaaaacaata   7680
ccagcatcaa aaatgttttc aagaatttgc acattgttat ttagtaaaat ataaaactac   7740
taaaggatgg cctagttcta ctgttatagc agatcaatgc cctttgcctg gtaaccatcc   7800
tacagtacaa tatgcacatc aaaatatatg ggattattat gtccccttg aacaaattcg   7860
gccagaagga tggaactcaa aaagttatta tgaagatgct agaataggag ggttttatat   7920
accaaaatgg ttacgaaata attcctatac ccatgtctta ttttgttctg atcaaattta   7980
tggaaaatgg tataatattg atctcacagc ccaggagagg gaaaatttat tagtccgaaa   8040
attaattaat ttagctaaag gaaattcatc acaattaaaa gatagagcta tgccagctga   8100
atgggataaa caaggaaaag ctgatctatt tagacaaatt aatactttag atgtttgtaa   8160
tagaccagaa atggtatttt tgttaaattc ctcatattat gaattttccc tatgggaagg   8220
agattgtggt tttaccagac agaatgttac acaggctaat tccttatgta aagatttcta   8280
taataactca aaatggcaaa aattacatcc atattcgtgt agattttgga gatataaaca   8340
agagaaagaa gaaactaaat gtagtaatgg tgaaaagaaa aaatgtcttt attacccaca   8400
atgggatact cctgaagctt tatatgactt tgggttccta gcatatttaa attcttttcc   8460
ttctccaatc tgtataaaaa atcagactat aagggaacct gagtataaaa tctcttcttt   8520
atacctagaa tgcatgaatg cttcagacag acatggtata gatagtgctt tattagcttt   8580
gaagacattt ttaaacttta ctggtcagtc tgtaaacgaa atgccattag ctagagcctt   8640
tgtaggcctt actgacccta aatttccacc aacatatccc aacattacaa gggaatcttc   8700
tggttgtaat aataacaaaa gaaaaaggag aagtgttaat aattatgaaa gacttagatc   8760
tatgggatat gctttaactg gagctgttca aactttatct caaatatctg atattaatga   8820
tgagaggctg caacacggag tatatttact ccgggatcat gtggtaaccc tgatggaagc   8880
tgcccttcat gatgtttcga ttatggaagg aatgttagca attcaacatg tgcatactca   8940
tctcaatcat ctcaagacca tgcttttgat gagaaagatt gattggacat tcatcagaag   9000
tgactggatt caacagcaat tacagaagac agatgatgaa atgaaattga tacgaagaac   9060
tgcacgaagt ctagtctact atgtcacaca aacctccagt tctcctacag ctacttcctg   9120
ggagattgga atatattatg aaatagtaat tcctaaacat atatatttaa ataattggca   9180
```

```
agtaatcaat gtaggtcatt tattggagtc agctggtcat ctgactcatg taaaggttaa   9240

gcatccttat gaaataatta ataaggaatg tagtgacact caatatttac atcttgagga   9300

atgcattaga gaggattatg tgatttgtga catagtacaa atagttcaac catgtggaaa   9360

tgcaacagaa ttgagtgatt gtccagtaac agcattaaag gtgaagactc catatattca   9420

agtgtctccc ctgaagaatg gaagttattt agttttatct agtactaagg attgttctat   9480

acctgcatat gtacctagtg tggtcacagt caatgaaaca gttaagtgct ttggagtaga   9540

gtttcacaaa ccactttatg ctgaaacaaa aaccagctat gaaccacaag ttccgcattt   9600

gaagcttcgt ttaccccact tgactgggat tattgccagc ttgcaatcac tggaaataga   9660

agttacttct acacaagaga atataaaaga ccagatcgaa agggccaaag cacagcttct   9720

ccggctggac attcacgaag gagactttcc tgactggctg aaacaagtcg cctctgcaac   9780

cagggacgtt tggcctgctg cagcttcctt tatacaagga gtagggaact tcttatctaa   9840

tactgcccag gggatattcg gctcagcggt aagcctccta ttctatgcaa gacctatttt   9900

gataggaata ggagttatac tgcttattgc ccttcttttt agaataatat cgtggcttcc   9960

tgggaggccc aggaggaatt ga                                            9982
```

<210> SEQ ID NO 27
<211> LENGTH: 12453
<212> TYPE: DNA
<213> ORGANISM: Artificial Sequence
<220> FEATURE:
<223> OTHER INFORMATION: Foamy Viral Envelope Gene pczHFV EM238

<400> SEQUENCE: 27

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctaga    900

aaacctacgt ctcatcagca tgggatccca cgtgagcaag ggcgaggagg ataacatggc    960

catcatcaag gagttcatgc gcttcaaggt gcacatggag ggctccgtga acggccacga   1020

gttcgagatc gagggcgagg gcgagggccg cccctacgag ggcacccaga ccgccaagct   1080

gaaggtgacc aagggtggcc ccctgccctt cgcctgggac atcctgtccc ctcagttcat   1140

gtacggctcc aaggcctacg tgaagcaccc cgccgacatc cccgactact tgaagctgtc   1200

cttccccgag ggcttcaagt gggagcgcgt gatgaacttc gaggacggcg gcgtggtgac   1260
```

```
cgtgacccag gactcctccc tgcaggacgg cgagttcatc tacaaggtga agctgcgcgg   1320
caccaacttc ccctccgacg gccccgtaat gcagaagaag accatgggct gggaggcctc   1380
ctccgagcgg atgtaccccg aggacggcgc cctgaagggc gagatcaagc agaggctgaa   1440
gctgaaggac ggcggccact acgacgctga ggtcaagacc acctacaagg ccaagaagcc   1500
cgtgcagctg cccggcgcct acaacgtcaa catcaagttg gacatcacct cccacaacga   1560
ggactacacc atcgtggaac agtacgaacg cgccgagggc cgccactcca ccggcggcat   1620
ggacgagctg tacaagagat ctggcggcgg cagcggcggg ggcgggagcg gcggcggggg   1680
atccgcacca ccaatgacac tgcaacaatg gatcatttgg agaagaatga atagagcgca   1740
tgaggcactt caaaatacaa caactgtgac tgaacagcag cgcgaacaaa ttatactgga   1800
cattcaaaat gaagaagtac aaccaactag gagagatcgc tttagatatc tgctttatac   1860
ttgttgtgct actagctcaa gagtattggc ctggatgttt ttagtttgta tattgttaat   1920
cattgttttg gtttcatgct ttgtgactat atccagaata caatggaata aggatattca   1980
ggtattagga cctgtaatag actggaatgt tactcaaaga gctgtttatc aacccttaca   2040
gactagaagg attgcacgtt cccttagaat gcagcatcct gttccaaaat atgtggaggt   2100
aaatatgact agtattccac aaggtgtata ctatgaaccc catccggaac ccatagtggt   2160
gaaggagagg gtcctgggtc tttctcaaat tctgatgatt aattcagaaa acattgctaa   2220
taatgctaat ttgacacaag aagtaaagaa gttgttaact gaaatggtta atgaagaaat   2280
gcaaagtttg tcagatgtaa tgattgactt tgaaattcct ttaggagacc ctcgtgatca   2340
agaacaatat atacatagaa aatgctatca agaatttgca aattgttatt tagtaaaata   2400
taaagaaccc aaaccgtggc ctaaggaggg ccttatagct gatcaatgcc cattaccagg   2460
ttaccatgct ggattaacct ataatagaca gtctatttgg gattactata ttaaagtgga   2520
gagtattaga cctgcaaatt ggacaacaaa gagtaaatat ggacaagcta gactaggaag   2580
tttttatatt cctagcagtc tgagacaaat caatgttagt catgtactat tctgtagtga   2640
tcaattatat tctaaatggt ataatataga aaataccata gaacaaaacg agcggtttct   2700
gcttaataaa ctaaataacc ttacatctgg aacctcagta ttgaagaaaa gagctcttcc   2760
gaaggattgg agttctcaag gtaaaaatgc tctgtttaga gaaatcaatg tgttagatat   2820
ctgcagtaaa cctgaatctg taatactatt gaatacttca tactattcct tctctttatg   2880
ggaaggagat tgtaatttta ctaaagatat gatttctcag ttggttccag aatgtgatgg   2940
attttataac aattctaagt ggatgcatat gcatccatat gcttgtagat tctggagaag   3000
taagaatgaa aaagaagaaa ctaaatgtag agatggggaa actaagagat gtctgtatta   3060
tcctttatgg gacagtcccg aatctacata tgattttggt tatttagcat accaaaagaa   3120
ttttccttcc cctatctgta tagaacaaca gaaaattaga gatcaagatt atgaagttta   3180
ttctttgtat caagaatgca aaatagcttc taaagcatat ggaattgata cagttttatt   3240
ctctctaaag aattttctta attatacagg aactcctgta aatgaaatgc ctaatgcaag   3300
agcttttgta ggcctaatag atcccaagtt tcctccttcc tatcccaatg ttactaggga   3360
acattatact tcctgtaata ataggaaaag aagaagtgtt gataataact atgctaagtt   3420
aaggtctatg ggtatgcac ttacaggagc agtgcaaacc ttatctcaaa tatcagatat   3480
taatgatgaa aacttacagc aaggaatata tttattaagg gatcatgtaa taaccttaat   3540
ggaagctaca ttgcatgata tatctgttat ggaaggaatg tttgctgtac aacatttgca   3600
tacacatttg aatcatttga agacaatgct tctagaaaga agaatagact ggacctatat   3660
```

```
gtctagtact tggctacaac aacaattaca gaaatctgat gatgagatga aagtaataaa   3720
gagaattgct agaagtttgg tatattatgt taaacaaacc catagttctc ccacagctac   3780
agcctgggag attggattat attatgaatt ggttatacct aaacatattt acttgaataa   3840
ttggaatgtt gtcaatatag gtcacttagt taaatcagct ggacaattga ctcatgtaac   3900
tatagctcat ccttatgaaa taatcaataa ggaatgtgta gagactatat atctgcatct   3960
tgaagactgc acaagacaag attatgtcat atgtgatgtg gtaaagatag tgcagccttg   4020
tggcaatagc tcagacacga gtgattgtcc tgtctgggct gaagctgtaa aagaaccatt   4080
tgtgcaagtc aatcctctga aaaacggaag ttatctggtt ttggcaagtt ccacagactg   4140
tcagatccca ccatatgttc ctagcatcgt gactgttaat gaaacaacgt catgctttgg   4200
actggacttt aaaaggccac tggttgcgga agaaagattg agctttgagc cacgactgcc   4260
aaatctacaa ctaagattac cacatttggt tggaattatt gcaaaaatca aagggataaa   4320
aatagaagtc acatcctctg gagaaagtat aaaagagcag attgaaagag caaaagctga   4380
gctccttcga ctggacattc acgagggaga tactcctgcc tggatacaac agctagctgc   4440
agcaacaaag gacgtctggc cagcagcagc ttctgctcta caaggaattg ggaacttttt   4500
atctgggact gcccaaggaa tatttggaac tgcctttagt ctcttgggat acttaaagcc   4560
tatcctaata ggagtagggg tcattctctt ggttattctt atatttaaaa ttgtatcctg   4620
gattcctacg aaaaagaaga atcagtagcc tccacctctg gaattctgca gatatccagc   4680
acagtggcgg ccgctcgagt ctagagggcc cgtttaaacc cgctgatcag cctcgactgt   4740
gccttctagt tgccagccat ctgttgtttg cccctccccc gtgccttcct tgaccctgga   4800
aggtgccact cccactgtcc tttcctaata aaatgaggaa attgcatcgc attgtctgag   4860
taggtgtcat tctattctgg ggggtggggt ggggcaggac agcaaggggg aggattggga   4920
agacaatagc aggcatgctg gggatgcggt gggctctatg gcttctgagg cggaaagaac   4980
cagctggggc tctagggggt atccccacgc gccctgtagc ggcgcattaa gcgcggcggg   5040
tgtggtggtt acgcgcagcg tgaccgctac acttgccagc gccctagcgc ccgctccttt   5100
cgctttcttc ccttcctttc tcgccacgtt cgccggcttt ccccgtcaag ctctaaatcg   5160
ggcatccct ttagggttcc gatttagtgc tttacggcac ctcgacccca aaaaacttga   5220
ttagggtgat ggttcacgta gtgggccatc gccctgatag acggtttttc gccctttgac   5280
gttggagtcc acgttcttta atagtggact cttgttccaa actggaacaa cactcaaccc   5340
tatctcggtc tattcttttg atttataagg gattttgggg atttcggcct attggttaaa   5400
aaatgagctg atttaacaaa aatttaacgc gaattaattc tgtggaatgt gtgtcagtta   5460
gggtgtggaa agtccccagg ctccccaggc aggcagaagt atgcaaagca tgcatctcaa   5520
ttagtcagca accaggtgtg gaaagtcccc aggctcccca gcaggcagaa gtatgcaaag   5580
catgcatctc aattagtcag caaccatagt cccgccccta actccgccca tcccgcccct   5640
aactccgccc agttccgccc attctccgcc ccatggctga ctaatttttt ttatttatgc   5700
agaggccgag gccgcctctg cctctgagct attccagaag tagtgaggag gcttttttgg   5760
aggcctaggc ttttgcaaaa agctcccggg agcttgtata tccattttcg gatctgatca   5820
gcacgtgttg acaattaatc atcggcatag tatatcggca tagtataata cgacaaggtg   5880
aggaactaaa ccatggccaa gttgaccagt gccgttccgg tgctcaccgc gcgcgacgtc   5940
gccggagcgg tcgagttctg gaccgaccgg ctcgggttct cccgggactt cgtggaggac   6000
gacttcgccg gtgtggtccg ggacgacgtg accctgttca tcagcgcggt ccaggaccag   6060
```

```
gtggtgccgg acaacaccct ggcctgggtg tgggtgcgcg gcctggacga gctgtacgcc   6120
gagtggtcgg aggtcgtgtc cacgaacttc cgggacgcct ccgggccggc catgaccgag   6180
atcggcgagc agccgtgggg gcgggagttc gccctgcgcg acccggccgg caactgcgtg   6240
cacttcgtgg ccgaggagca ggactgacac gtgctacgag atttcgattc caccgccgcc   6300
ttctatgaaa ggttgggctt cggaatcgtt ttccgggacg ccggctggat gatcctccag   6360
cgcggggatc tcatgctgga gttcttcgcc caccccaact tgtttattgc agcttataat   6420
ggttacaaat aaagcaatag catcacaaat ttcacaaata aagcattttt ttcactgcat   6480
tctagttgtg gtttgtccaa actcatcaat gtatcttatc atgtctgtat accgtcgacc   6540
tctagctaga gcttggcgta atcatggtca tagctgtttc ctgtgtgaaa ttgttatccg   6600
ctcacaattc cacacaacat acgagccgga agcataaagt gtaaagcctg gggtgcctaa   6660
tgagtgagct aactcacatt aattgcgttg cgctcactgc ccgctttcca gtcgggaaac   6720
ctgtcgtgcc agctgcatta atgaatcggc caacgcgcgg ggagaggcgg tttgcgtatt   6780
gggcgctctt ccgcttcctc gctcactgac tcgctgcgct cggtcgttcg gctgcggcga   6840
gcggtatcag ctcactcaaa ggcggtaata cggttatcca cagaatcagg ggataacgca   6900
ggaaagaaca tgtgagcaaa aggccagcaa aaggccagga accgtaaaaa ggccgcgttg   6960
ctggcgtttt tccataggct ccgcccccct gacgagcatc acaaaaatcg acgctcaagt   7020
cagaggtggc gaaacccgac aggactataa agataccagg cgtttccccc tggaagctcc   7080
ctcgtgcgct ctcctgttcc gaccctgccg cttaccggat acctgtccgc ctttctccct   7140
tcgggaagcg tggcgctttc tcaatgctca cgctgtaggt atctcagttc ggtgtaggtc   7200
gttcgctcca agctgggctg tgtgcacgaa ccccccgttc agcccgaccg ctgcgcctta   7260
tccggtaact atcgtcttga gtccaacccg gtaagacacg acttatcgcc actggcagca   7320
gccactggta acaggattag cagagcgagg tatgtaggcg gtgctacaga gttcttgaag   7380
tggtggccta actacggcta cactagaagg acagtatttg gtatctgcgc tctgctgaag   7440
ccagttacct tcggaaaaag agttggtagc tcttgatccg gcaaacaaac caccgctggt   7500
agcggtggtt tttttgtttg caagcagcag attacgcgca gaaaaaaagg atctcaagaa   7560
gatcctttga tcttttctac ggggtctgac gctcagtgga acgaaaactc acgttaaggg   7620
attttggtca tgagattatc aaaaaggatc ttcacctaga tccttttaaa ttaaaaatga   7680
agttttaaat caatctaaag tatatatgag taaacttggt ctgacagtta ccaatgctta   7740
atcagtgagg cacctatctc agcgatctgt ctatttcgtt catccatagt tgcctgactc   7800
cccgtcgtgt agataactac gatacgggag ggcttaccat ctggccccag tgctgcaatg   7860
ataccgcgag acccacgctc accggctcca gatttatcag caataaacca gccagccgga   7920
agggccgagc gcagaagtgg tcctgcaact ttatccgcct ccatccagtc tattaattgt   7980
tgccgggaag ctagagtaag tagttcgcca gttaatagtt tgcgcaacgt tgttgccatt   8040
gctacaggca tcgtggtgtc acgctcgtcg tttggtatgg cttcattcag ctccggttcc   8100
caacgatcaa ggcgagttac atgatccccc atgttgtgca aaaaagcggt tagctccttc   8160
ggtcctccga tcgttgtcag aagtaagttg gccgcagtgt tatcactcat ggttatggca   8220
gcactgcata attctcttac tgtcatgcca tccgtaagat gcttttctgt gactggtgag   8280
tactcaacca agtcattctg agaatagtgt atgcggcgac cgagttgctc ttgcccggcg   8340
tcaatacggg ataataccgc gccacatagc agaactttaa aagtgctcat cattggaaaa   8400
cgttcttcgg ggcgaaaact ctcaaggatc ttaccgctgt tgagatccag ttcgatgtaa   8460
```

```
cccactcgtg cacccaactg atcttcagca tcttttactt tcaccagcgt ttctgggtga   8520
gcaaaaacag gaaggcaaaa tgccgcaaaa aagggaataa gggcgacacg gaaatgttga   8580
atactcatac tcttcctttt tcaatattat tgaagcattt atcagggtta ttgtctcatg   8640
agcggataca tatttgaatg tatttagaaa aataaacaaa taggggttcc gcgcacattt   8700
ccccgaaaag tgccacctga cgtcatggga tcccacgtga gcaagggcga ggaggataac   8760
atggccatca tcaaggagtt catgcgcttc aaggtgcaca tggagggctc cgtgaacggc   8820
cacgagttcg agatcgaggg cgagggcgag ggccgcccct acgagggcac ccagaccgcc   8880
aagctgaagg tgaccaaggg tggcccctg cccttcgcct gggacatcct gtcccctcag   8940
ttcatgtacg gctccaaggc ctacgtgaag caccccgccg acatccccga ctacttgaag   9000
ctgtccttcc ccgagggctt caagtgggag cgcgtgatga acttcgagga cggcggcgtg   9060
gtgaccgtga cccaggactc ctccctgcag gacggcgagt tcatctacaa ggtgaagctg   9120
cgcggcacca acttcccctc cgacggcccc gtaatgcaga agaagaccat gggctgggag   9180
gcctcctccg agcggatgta ccccgaggac ggcgccctga agggcgagat caagcagagg   9240
ctgaagctga aggacggcgg ccactacgac gctgaggtca agaccaccta caaggccaag   9300
aagcccgtgc agctgcccgg cgcctacaac gtcaacatca agttggacat cacctcccac   9360
aacgaggact acaccatcgt ggaacagtac gaacgcgccg agggccgcca ctccaccggc   9420
ggcatggacg agctgtacaa gagatctggc ggcggcagcg gcgggggcgg gagcggcggc   9480
gggggatccg caccaccaat gacactgcaa caatggatca tttggagaag aatgaataga   9540
gcgcatgagg cacttcaaaa tacaacaact gtgactgaac agcagcgcga acaaattata   9600
ctggacattc aaaatgaaga agtacaacca actaggagag atcgctttag atatctgctt   9660
tatacttgtt gtgctactag ctcaagagta ttggcctgga tgtttttagt ttgtatattg   9720
ttaatcattg ttttggtttc atgctttgtg actatatcca gaatacaatg gaataaggat   9780
attcaggtat taggacctgt aatagactgg aatgttactc aaagagctgt ttatcaaccc   9840
ttacagacta gaaggattgc acgttccctt agaatgcagc atcctgttcc aaaatatgtg   9900
gaggtaaata tgactagtat tccacaaggt gtatactatg aaccccatcc ggaacccata   9960
gtggtgaagg agagggtcct gggtctttct caaattctga tgattaattc agaaaacatt  10020
gctaataatg ctaatttgac acaagaagta aagaagttgt taactgaaat ggttaatgaa  10080
gaaatgcaaa gtttgtcaga tgtaatgatt gactttgaaa ttcctttagg agaccctcgt  10140
gatcaagaac aatatataca tagaaaatgc tatcaagaat ttgcaaattg ttatttagta  10200
aaatataaag aacccaaacc gtggcctaag gagggcctta tagctgatca atgcccatta  10260
ccaggttacc atgctggatt aacctataat agacagtcta tttgggatta ctatattaaa  10320
gtggagagta ttagacctgc aaattggaca acaaagagta aatatggaca agctagacta  10380
ggaagttttt atattcctag cagtctgaga caaatcaatg ttagtcatgt actattctgt  10440
agtgatcaat tatattctaa atggtataat atagaaaata ccatagaaca aaacgagcgg  10500
tttctgctta ataaactaaa taaccttaca tctggaacct cagtattgaa gaaaagagct  10560
cttccgaagg attggagttc tcaaggtaaa aatgctctgt ttagagaaat caatgtgtta  10620
gatatctgca gtaaacctga atctgtaata ctattgaata cttcatacta ttccttctct  10680
ttatgggaag gagattgtaa ttttactaaa gatatgattt ctcagttggt tccagaatgt  10740
gatggatttt ataacaattc taagtggatg catatgcatc catatgcttg tagattctgg  10800
agaagtaaga atgaaaaaga agaaactaaa tgtagagatg ggaaactaag gagatgtctg  10860
```

```
tattatcctt tatgggacag tcccgaatct acatatgatt ttggttattt agcataccaa  10920

aagaattttc cttcccctat ctgtatagaa caacagaaaa ttagagatca agattatgaa  10980

gtttattctt tgtatcaaga atgcaaaata gcttctaaag catatggaat tgatacagtt  11040

ttattctctc taaagaattt tcttaattat acaggaactc ctgtaaatga aatgcctaat  11100

gcaagagctt ttgtaggcct aatagatccc aagtttcctc cttcctatcc caatgttact  11160

agggaacatt atacttcctg taataatagg aaaagaagaa gtgttgataa taactatgct  11220

aagttaaggt ctatggggta tgcacttaca ggagcagtgc aaaccttatc tcaaatatca  11280

gatattaatg atgaaaactt acagcaagga atatatttat taagggatca tgtaataacc  11340

ttaatggaag ctacattgca tgatatatct gttatggaag gaatgtttgc tgtacaacat  11400

ttgcatacac atttgaatca tttgaagaca atgcttctag aaagaagaat agactggacc  11460

tatatgtcta gtacttggct acaacaacaa ttacagaaat ctgatgatga gatgaaagta  11520

ataaagagaa ttgctagaag tttggtatat tatgttaaac aaacccatag ttctcccaca  11580

gctacagcct gggagattgg attatattat gaattggtta tacctaaaca tatttacttg  11640

aataattgga atgttgtcaa tataggtcac ttagttaaat cagctggaca attgactcat  11700

gtaactatag ctcatcctta tgaaataatc aataaggaat gtgtagagac tatatatctg  11760

catcttgaag actgcacaag acaagattat gtcatatgtg atgtggtaaa gatagtgcag  11820

ccttgtggca atagctcaga cacgagtgat tgtcctgtct gggctgaagc tgtaaaagaa  11880

ccatttgtgc aagtcaatcc tctgaaaaac ggaagttatc tggttttggc aagttccaca  11940

gactgtcaga tcccaccata tgttcctagc atcgtgactg ttaatgaaac aacgtcatgc  12000

tttggactgg actttaaaag gccactggtt gcggaagaaa gattgagctt tgagccacga  12060

ctgccaaatc tacaactaag attaccacat ttggttggaa ttattgcaaa aatcaaaggg  12120

ataaaaatag aagtcacatc ctctggagaa agtataaaag agcagattga aagagcaaaa  12180

gctgagctcc ttcgactgga cattcacgag ggagatactc ctgcctggat acaacagcta  12240

gctgcagcaa caaaggacgt ctggccagca gcagcttctg ctctacaagg aattgggaac  12300

tttttatctg ggactgccca aggaatattt ggaactgcct ttagtctctt gggatactta  12360

aagcctatcc taataggagt aggggtcatt ctcttggtta ttcttatatt taaaattgta  12420

tcctggattc ctacgaaaaa gaagaatcag tag                               12453
```

<210> SEQ ID NO 28
<211> LENGTH: 12453
<212> TYPE: DNA
<213> ORGANISM: Artificial Sequence
<220> FEATURE:
<223> OTHER INFORMATION: Foamy Viral Envelope Gene pczHFV EM261

<400> SEQUENCE: 28

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480
```

```
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctaga    900
aaacctacgt ctcatcagca tgaccggtca cgtgagcaag ggcgaggagg ataacatggc    960
catcatcaag gagttcatgc gcttcaaggt gcacatggag ggctccgtga acggccacga   1020
gttcgagatc gagggcgagg gcgagggccg cccctacgag ggcacccaga ccgccaagct   1080
gaaggtgacc aagggtggcc ccctgccctt cgcctgggac atcctgtccc ctcagttcat   1140
gtacggctcc aaggcctacg tgaagcaccc cgccgacatc cccgactact tgaagctgtc   1200
cttccccgag ggcttcaagt gggagcgcgt gatgaacttc gaggacggcg gcgtggtgac   1260
cgtgacccag gactcctccc tgcaggacgg cgagttcatc tacaaggtga agctgcgcgg   1320
caccaacttc ccctccgacg gccccgtaat gcagaagaag accatgggct gggaggcctc   1380
ctccgagcgg atgtaccccg aggacggcgc cctgaagggc gagatcaagc agaggctgaa   1440
gctgaaggac ggcggccact acgacgctga ggtcaagacc acctacaagg ccaagaagcc   1500
cgtgcagctg cccggcgcct acaacgtcaa catcaagttg gacatcacct cccacaacga   1560
ggactacacc atcgtggaac agtacgaacg cgccgagggc cgccactcca ccggcggcat   1620
ggacgagctg tacaagagat ctggcggcgg cagcggcggg ggcgggagcg gcggcggggg   1680
atccgcacca ccaatgacac tgcaacaatg gatcatttgg aaaaaaatga ataaagcgca   1740
tgaggcactt caaaatacaa caactgtgac tgaacagcag aaggaacaaa ttatactgga   1800
cattcaaaat gaagaagtac aaccaactag gagagataaa tttagatatc tgctttatac   1860
ttgttgtgct actagctcaa gagtattggc ctggatgttt ttagtttgta tattgttaat   1920
cattgttttg gtttcatgct ttgtgactat atccagaata caatggaata aggatattca   1980
ggtattagga cctgtaatag actggaatgt tactcaaaga gctgtttatc aacccttaca   2040
gactagaagg attgcacgtt cccttagaat gcagcatcct gttccaaaat atgtggaggt   2100
aaatatgact agtattccac aaggtgtata ctatgaaccc catccggaac ccatagtggt   2160
gaaggagagg gtcctgggtc tttctcaaat tctgatgatt aattcagaaa acattgctaa   2220
taatgctaat ttgacacaag aagtaaagaa gttgttaact gaaatggtta atgaagaaat   2280
gcaaagtttg tcagatgtaa tgattgactt tgaaattcct ttaggagacc ctcgtgatca   2340
agaacaatat atacatagaa aatgctatca agaatttgca aattgttatt tagtaaaata   2400
taaagaaccc aaaccgtggc ctaaggaggg ccttatagct gatcaatgcc cattaccagg   2460
ttaccatgct ggattaacct ataatagaca gtctatttgg gattactata ttaaagtgga   2520
gagtattaga cctgcaaatt ggacaacaaa gagtaaatat ggacaagcta gactaggaag   2580
tttttatatt cctagcagtc tgagacaaat caatgttagt catgtactat tctgtagtga   2640
tcaattatat tctaaatggt ataatataga aaataccata gaacaaaacg agcggtttct   2700
gcttaataaa ctaaataacc ttacatctgg aacctcagta ttgaagaaaa gagctcttcc   2760
gaaggattgg agttctcaag gtaaaaatgc tctgtttaga gaaatcaatg tgttagatat   2820
ctgcagtaaa cctgaatctg taatactatt gaatacttca tactattcct tctctttatg   2880
```

```
ggaaggagat tgtaatttta ctaaagatat gatttctcag ttggttccag aatgtgatgg   2940
attttataac aattctaagt ggatgcatat gcatccatat gcttgtagat tctggagaag   3000
taagaatgaa aaagaagaaa ctaaatgtag agatggggaa actaagagat gtctgtatta   3060
tcctttatgg gacagtcccg aatctacata tgattttggt tatttagcat accaaaagaa   3120
ttttccttcc cctatctgta tagaacaaca gaaaattaga gatcaagatt atgaagttta   3180
ttctttgtat caagaatgca aaatagcttc taaagcatat ggaattgata cagttttatt   3240
ctctctaaag aattttctta attatacagg aactcctgta aatgaaatgc ctaatgcaag   3300
agcttttgta ggcctaatag atcccaagtt tcctccttcc tatcccaatg ttactaggga   3360
acattatact tcctgtaata ataggaaaag aagaagtgtt gataataact atgctaagtt   3420
aaggtctatg ggtatgcac ttacaggagc agtgcaaacc ttatctcaaa tatcagatat    3480
taatgatgaa aacttacagc aaggaatata tttattaagg gatcatgtaa taaccttaat   3540
ggaagctaca ttgcatgata tatctgttat ggaaggaatg tttgctgtac aacatttgca   3600
tacacatttg aatcatttga agacaatgct tctagaaaga agaatagact ggacctatat   3660
gtctagtact tggctacaac aacaattaca gaaatctgat gatgagatga aagtaataaa   3720
gagaattgct agaagtttgg tatattatgt taaacaaacc catagttctc ccacagctac   3780
agcctgggag attggattat attatgaatt ggttatacct aaacatattt acttgaataa   3840
ttggaatgtt gtcaatatag gtcacttagt taaatcagct ggacaattga ctcatgtaac   3900
tatagctcat ccttatgaaa taatcaataa ggaatgtgta gagactatat atctgcatct   3960
tgaagactgc acaagacaag attatgtcat atgtgatgtg gtaaagatag tgcagccttg   4020
tggcaatagc tcagacacga gtgattgtcc tgtctgggct gaagctgtaa aagaaccatt   4080
tgtgcaagtc aatcctctga aaaacggaag ttatctggtt ttggcaagtt ccacagactg   4140
tcagatccca ccatatgttc ctagcatcgt gactgttaat gaaacaacgt catgctttgg   4200
actggacttt aaaaggccac tggttgcgga agaaagattg agctttgagc cacgactgcc   4260
aaatctacaa ctaagattac cacatttggt tggaattatt gcaaaaatca aagggataaa   4320
aatagaagtc acatcctctg gagaaagtat aaaagagcag attgaaagag caaaagctga   4380
gctccttcga ctggacattc acgagggaga tactcctgcc tggatacaac agctagctgc   4440
agcaacaaag gacgtctggc cagcagcagc ttctgctcta caaggaattg ggaacttttt   4500
atctgggact gcccaaggaa tatttggaac tgcctttagt ctcttgggat acttaaagcc   4560
tatcctaata ggagtagggg tcattctctt ggttattctt atatttaaaa ttgtatcctg   4620
gattcctacg aaaaagaaga atcagtagcc tccacctctg gaattctgca gatatccagc   4680
acagtggcgg ccgctcgagt ctagagggcc cgtttaaacc cgctgatcag cctcgactgt   4740
gccttctagt tgccagccat ctgttgtttg cccctccccc gtgccttcct tgaccctgga   4800
aggtgccact cccactgtcc tttcctaata aaatgaggaa attgcatcgc attgtctgag   4860
taggtgtcat tctattctgg ggggtggggt ggggcaggac agcaaggggg aggattggga   4920
agacaatagc aggcatgctg gggatgcggt gggctctatg gcttctgagg cggaaagaac   4980
cagctggggc tctagggggt atccccacgc gccctgtagc ggcgcattaa gcgcggcggg   5040
tgtggtggtt acgcgcagcg tgaccgctac acttgccagc gccctagcgc ccgctccttt   5100
cgctttcttc ccttcctttc tcgccacgtt cgccggcttt ccccgtcaag ctctaaatcg   5160
ggcatccct ttagggttcc gatttagtgc tttacggcac ctcgacccca aaaaacttga    5220
ttagggtgat ggttcacgta gtgggccatc gccctgatag acggtttttc gccctttgac   5280
```

gttggagtcc acgttcttta atagtggact cttgttccaa actggaacaa cactcaaccc 5340
tatctcggtc tattcttttg atttataagg gattttgggg atttcggcct attggttaaa 5400
aaatgagctg atttaacaaa aatttaacgc gaattaattc tgtggaatgt gtgtcagtta 5460
gggtgtggaa agtccccagg ctccccaggc aggcagaagt atgcaaagca tgcatctcaa 5520
ttagtcagca accaggtgtg gaaagtcccc aggctcccca gcaggcagaa gtatgcaaag 5580
catgcatctc aattagtcag caaccatagt cccgccccta actccgccca tcccgcccct 5640
aactccgccc agttccgccc attctccgcc ccatggctga ctaatttttt ttatttatgc 5700
agaggccgag gccgcctctg cctctgagct attccagaag tagtgaggag gcttttttgg 5760
aggcctaggc ttttgcaaaa agctcccggg agcttgtata tccattttcg gatctgatca 5820
gcacgtgttg acaattaatc atcggcatag tatatcggca tagtataata cgacaaggtg 5880
aggaactaaa ccatggccaa gttgaccagt gccgttccgg tgctcaccgc gcgcgacgtc 5940
gccggagcgg tcgagttctg gaccgaccgg ctcgggttct cccgggactt cgtggaggac 6000
gacttcgccg gtgtggtccg ggacgacgtg accctgttca tcagcgcggt ccaggaccag 6060
gtggtgccgg acaacaccct ggcctgggtg tgggtgcgcg gcctggacga gctgtacgcc 6120
gagtggtcgg aggtcgtgtc cacgaacttc cgggacgcct ccgggccggc catgaccgag 6180
atcggcgagc agccgtgggg gcgggagttc gccctgcgcg acccggccgg caactgcgtg 6240
cacttcgtgg ccgaggagca ggactgacac gtgctacgag atttcgattc caccgccgcc 6300
ttctatgaaa ggttgggctt cggaatcgtt ttccgggacg ccggctggat gatcctccag 6360
cgcggggatc tcatgctgga gttcttcgcc caccccaact tgtttattgc agcttataat 6420
ggttacaaat aaagcaatag catcacaaat ttcacaaata aagcattttt ttcactgcat 6480
tctagttgtg gtttgtccaa actcatcaat gtatcttatc atgtctgtat accgtcgacc 6540
tctagctaga gcttggcgta atcatggtca tagctgtttc ctgtgtgaaa ttgttatccg 6600
ctcacaattc cacacaacat acgagccgga agcataaagt gtaaagcctg gggtgcctaa 6660
tgagtgagct aactcacatt aattgcgttg cgctcactgc ccgctttcca gtcgggaaac 6720
ctgtcgtgcc agctgcatta atgaatcggc caacgcgcgg ggagaggcgg tttgcgtatt 6780
gggcgctctt ccgcttcctc gctcactgac tcgctgcgct cggtcgttcg gctgcggcga 6840
gcggtatcag ctcactcaaa ggcggtaata cggttatcca cagaatcagg ggataacgca 6900
ggaaagaaca tgtgagcaaa aggccagcaa aaggccagga accgtaaaaa ggccgcgttg 6960
ctggcgtttt tccataggct ccgcccccct gacgagcatc acaaaaatcg acgctcaagt 7020
cagaggtggc gaaacccgac aggactataa agataccagg cgtttccccc tggaagctcc 7080
ctcgtgcgct ctcctgttcc gaccctgccg cttaccggat acctgtccgc ctttctccct 7140
tcgggaagcg tggcgctttc tcaatgctca cgctgtaggt atctcagttc ggtgtaggtc 7200
gttcgctcca agctgggctg tgtgcacgaa ccccccgttc agcccgaccg ctgcgcctta 7260
tccggtaact atcgtcttga gtccaacccg gtaagacacg acttatcgcc actggcagca 7320
gccactggta acaggattag cagagcgagg tatgtaggcg gtgctacaga gttcttgaag 7380
tggtggccta actacggcta cactagaagg acagtatttg gtatctgcgc tctgctgaag 7440
ccagttacct tcggaaaaag agttggtagc tcttgatccg gcaaacaaac caccgctggt 7500
agcggtggtt tttttgtttg caagcagcag attacgcgca gaaaaaaagg atctcaagaa 7560
gatcctttga tcttttctac ggggtctgac gctcagtgga acgaaaactc acgttaaggg 7620
attttggtca tgagattatc aaaaaggatc ttcacctaga tccttttaaa ttaaaaatga 7680

```
agttttaaat caatctaaag tatatatgag taaacttggt ctgacagtta ccaatgctta   7740
atcagtgagg cacctatctc agcgatctgt ctatttcgtt catccatagt tgcctgactc   7800
cccgtcgtgt agataactac gatacgggag ggcttaccat ctggccccag tgctgcaatg   7860
ataccgcgag acccacgctc accggctcca gatttatcag caataaacca gccagccgga   7920
agggccgagc gcagaagtgg tcctgcaact ttatccgcct ccatccagtc tattaattgt   7980
tgccgggaag ctagagtaag tagttcgcca gttaatagtt tgcgcaacgt tgttgccatt   8040
gctacaggca tcgtggtgtc acgctcgtcg tttggtatgg cttcattcag ctccggttcc   8100
caacgatcaa ggcgagttac atgatccccc atgttgtgca aaaaagcggt tagctccttc   8160
ggtcctccga tcgttgtcag aagtaagttg gccgcagtgt tatcactcat ggttatggca   8220
gcactgcata attctcttac tgtcatgcca tccgtaagat gcttttctgt gactggtgag   8280
tactcaacca agtcattctg agaatagtgt atgcggcgac cgagttgctc ttgcccggcg   8340
tcaatacggg ataataccgc gccacatagc agaactttaa aagtgctcat cattggaaaa   8400
cgttcttcgg ggcgaaaact ctcaaggatc ttaccgctgt tgagatccag ttcgatgtaa   8460
cccactcgtg cacccaactg atcttcagca tcttttactt tcaccagcgt ttctgggtga   8520
gcaaaaacag gaaggcaaaa tgccgcaaaa aagggaataa gggcgacacg gaaatgttga   8580
atactcatac tcttcctttt tcaatattat tgaagcattt atcagggtta ttgtctcatg   8640
agcggataca tatttgaatg tatttagaaa aataaacaaa taggggttcc gcgcacattt   8700
ccccgaaaag tgccacctga cgtcatgacc ggtcacgtga gcaagggcga ggaggataac   8760
atggccatca tcaaggagtt catgcgcttc aaggtgcaca tggagggctc cgtgaacggc   8820
cacgagttcg agatcgaggg cgagggcgag ggccgcccct acgagggcac ccagaccgcc   8880
aagctgaagg tgaccaaggg tggcccccctg cccttcgcct gggacatcct gtcccctcag   8940
ttcatgtacg gctccaaggc ctacgtgaag caccccgccg acatccccga ctacttgaag   9000
ctgtccttcc ccgagggctt caagtgggag cgcgtgatga acttcgagga cggcggcgtg   9060
gtgaccgtga cccaggactc ctccctgcag gacggcgagt tcatctacaa ggtgaagctg   9120
cgcggcacca acttcccctc cgacggcccc gtaatgcaga agaagaccat gggctgggag   9180
gcctcctccg agcggatgta ccccgaggac ggcgccctga agggcgagat caagcagagg   9240
ctgaagctga aggacggcgg ccactacgac gctgaggtca agaccaccta caaggccaag   9300
aagcccgtgc agctgcccgg cgcctacaac gtcaacatca agttggacat cacctcccac   9360
aacgaggact acaccatcgt ggaacagtac gaacgcgccg agggccgcca ctccaccggc   9420
ggcatggacg agctgtacaa gagatctggc ggcggcagcg gcgggggcgg gagcggcggc   9480
gggggatccg caccaccaat gacactgcaa caatggatca tttggaaaaa aatgaataaa   9540
gcgcatgagg cacttcaaaa tacaacaact gtgactgaac agcagaagga acaaattata   9600
ctggacattc aaaatgaaga agtacaacca actaggagag ataaatttag atatctgctt   9660
tatacttgtt gtgctactag ctcaagagta ttggcctgga tgtttttagt ttgtatattg   9720
ttaatcattg ttttggtttc atgctttgtg actatatcca gaatacaatg gaataaggat   9780
attcaggtat taggacctgt aatagactgg aatgttactc aaagagctgt ttatcaaccc   9840
ttacagacta gaaggattgc acgttccctt agaatgcagc atcctgttcc aaaatatgtg   9900
gaggtaaata tgactagtat tccacaaggt gtatactatg aaccccatcc ggaacccata   9960
gtggtgaagg agagggtcct gggtctttct caaattctga tgattaattc agaaaacatt  10020
gctaataatg ctaatttgac acaagaagta aagaagttgt taactgaaat ggttaatgaa  10080
```

```
gaaatgcaaa gtttgtcaga tgtaatgatt gactttgaaa ttcctttagg agaccctcgt  10140

gatcaagaac aatatataca tagaaaatgc tatcaagaat ttgcaaattg ttatttagta  10200

aaatataaag aacccaaacc gtggcctaag gagggcctta tagctgatca atgcccatta  10260

ccaggttacc atgctggatt aacctataat agacagtcta tttgggatta ctatattaaa  10320

gtggagagta ttagacctgc aaattggaca acaaagagta aatatggaca agctagacta  10380

ggaagttttt atattcctag cagtctgaga caaatcaatg ttagtcatgt actattctgt  10440

agtgatcaat tatattctaa atggtataat atagaaaata ccatagaaca aaacgagcgg  10500

tttctgctta ataaactaaa taaccttaca tctggaacct cagtattgaa gaaaagagct  10560

cttccgaagg attggagttc tcaaggtaaa aatgctctgt ttagagaaat caatgtgtta  10620

gatatctgca gtaaacctga atctgtaata ctattgaata cttcatacta ttccttctct  10680

ttatgggaag gagattgtaa ttttactaaa gatatgattt ctcagttggt tccagaatgt  10740

gatggatttt ataacaattc taagtggatg catatgcatc catatgcttg tagattctgg  10800

agaagtaaga atgaaaaaga agaaactaaa tgtagagatg ggaaactaa gagatgtctg  10860

tattatcctt tatgggacag tcccgaatct acatatgatt ttggttattt agcataccaa  10920

aagaattttc cttcccctat ctgtatagaa caacagaaaa ttagagatca agattatgaa  10980

gtttattctt tgtatcaaga atgcaaaata gcttctaaag catatggaat tgatacagtt  11040

ttattctctc taaagaattt tcttaattat acaggaactc ctgtaaatga aatgcctaat  11100

gcaagagctt ttgtaggcct aatagatccc aagtttcctc cttcctatcc caatgttact  11160

agggaacatt atacttcctg taataatagg aaaagaagaa gtgttgataa taactatgct  11220

aagttaaggt ctatggggta tgcacttaca ggagcagtgc aaaccttatc tcaaatatca  11280

gatattaatg atgaaaactt acagcaagga atatatttat taagggatca tgtaataacc  11340

ttaatggaag ctacattgca tgatatatct gttatggaag gaatgtttgc tgtacaacat  11400

ttgcatacac atttgaatca tttgaagaca atgcttctag aaagaagaat agactggacc  11460

tatatgtcta gtacttggct acaacaacaa ttacagaaat ctgatgatga gatgaaagta  11520

ataaagagaa ttgctagaag tttggtatat tatgttaaac aaacccatag ttctcccaca  11580

gctacagcct gggagattgg attatattat gaattggtta tacctaaaca tatttacttg  11640

aataattgga atgttgtcaa tataggtcac ttagttaaat cagctggaca attgactcat  11700

gtaactatag ctcatcctta tgaaataatc aataaggaat gtgtagagac tatatatctg  11760

catcttgaag actgcacaag acaagattat gtcatatgtg atgtggtaaa gatagtgcag  11820

ccttgtggca atagctcaga cacgagtgat tgtcctgtct gggctgaagc tgtaaaagaa  11880

ccatttgtgc aagtcaatcc tctgaaaaac ggaagttatc tggttttggc aagttccaca  11940

gactgtcaga tcccaccata tgttcctagc atcgtgactg ttaatgaaac aacgtcatgc  12000

tttggactgg actttaaaag gccactggtt gcggaagaaa gattgagctt tgagccacga  12060

ctgccaaatc tacaactaag attaccacat ttggttggaa ttattgcaaa aatcaaaggg  12120

ataaaaatag aagtcacatc ctctggagaa agtataaaag agcagattga aagagcaaaa  12180

gctgagctcc ttcgactgga cattcacgag ggagatactc ctgcctggat acaacagcta  12240

gctgcagcaa caaaggacgt ctggccagca gcagcttctg ctctacaagg aattgggaac  12300

tttttatctg ggactgccca aggaatattt ggaactgcct ttagtctctt gggatactta  12360

aagcctatcc taataggagt aggggtcatt ctcttggtta ttcttatatt taaaattgta  12420

tcctggattc ctacgaaaaa gaagaatcag tag                               12453
```

<210> SEQ ID NO 29
<211> LENGTH: 12477
<212> TYPE: DNA
<213> ORGANISM: Artificial Sequence
<220> FEATURE:
<223> OTHER INFORMATION: Foamy Viral Envelope Gene pczHFV EM170

<400> SEQUENCE: 29

```
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctaga    900
aaacctacgt ctcatcagca tggccagatc tgtgagcaag ggcgaggagc tgttcaccgg    960
ggtggtgccc atcctggtcg agctggacgg cgacgtaaac ggccacaagt tcagcgtgtc   1020
cggcgagggc gagggcgatg ccacctacgg caagctgacc ctgaagttca tctgcaccac   1080
cggcaagctg cccgtgccct ggcccaccct cgtgaccacc ttcggctacg gcctgcagtg   1140
cttcgcccgc taccccgacc acatgaagca gcacgacttc ttcaagtccg ccatgcccga   1200
aggctacgtc caggagcgca ccatcttctt caaggacgac ggcaactaca agacccgcgc   1260
cgaggtgaag ttcgagggcg acaccctggt gaaccgcatc gagctgaagg gcatcgactt   1320
caaggaggac ggcaacatcc tggggcacaa gctggagtac aactacaaca gccacaacgt   1380
ctatatcatg gccgacaagc agaagaacgg catcaaggtg aacttcaaga tccgccacaa   1440
catcgaggac ggcagcgtgc agctcgccga ccactaccag cagaacaccc ccatcggcga   1500
cggccccgtg ctgctgcccg acaaccacta cctgagctac cagtccgccc tgagcaaaga   1560
ccccaacgag aagcgcgatc acatggtcct gctggagttc gtgaccgccg ccgggatcac   1620
tctcggcatg gacgagctgt acaagacctt cgaaggcggc ggcagcggcg ggggcgggag   1680
cggcggcggg ggatccgcac caccaatgac actgcaacaa tggatcattt ggaaaaaaat   1740
gaataaagcg catgaggcac ttcaaaatac aacaactgtg actgaacagc agaaggaaca   1800
aattatactg gacattcaaa atgaagaagt acaaccaact aggagagata aatttagata   1860
tctgctttat acttgttgtg ctactagctc aagagtattg gcctggatgt ttttagtttg   1920
tatattgtta atcattgttt tggtttcatg ctttgtgact atatccagaa tacaatggaa   1980
taaggatatt caggtattag gacctgtaat agactggaat gttactcaaa gagctgttta   2040
tcaaccctta cagactagaa ggattgcacg ttcccttaga atgcagcatc ctgttccaaa   2100
```

```
atatgtggag gtaaatatga ctagtattcc acaaggtgta tactatgaac cccatccgga   2160
acccatagtg gtgaaggaga gggtcctggg tctttctcaa attctgatga ttaattcaga   2220
aaacattgct aataatgcta atttgacaca agaagtaaag aagttgttaa ctgaaatggt   2280
taatgaagaa atgcaaagtt tgtcagatgt aatgattgac tttgaaattc ctttaggaga   2340
ccctcgtgat caagaacaat atatacatag aaaatgctat caagaatttg caaattgtta   2400
tttagtaaaa tataaagaac ccaaaccgtg gcctaaggag ggccttatag ctgatcaatg   2460
cccattacca ggttaccatg ctggattaac ctataataga cagtctattt gggattacta   2520
tattaaagtg gagagtatta gacctgcaaa ttggacaaca aagagtaaat atggacaagc   2580
tagactagga agtttttata ttcctagcag tctgagacaa atcaatgtta gtcatgtact   2640
attctgtagt gatcaattat attctaaatg gtataatata gaaaatacca tagaacaaaa   2700
cgagcggttt ctgcttaata aactaaataa ccttacatct ggaacctcag tattgaagaa   2760
aagagctctt ccgaaggatt ggagttctca aggtaaaaat gctctgttta gagaaatcaa   2820
tgtgttagat atctgcagta aacctgaatc tgtaatacta ttgaatactt catactattc   2880
cttctcttta tgggaaggag attgtaattt tactaaagat atgatttctc agttggttcc   2940
agaatgtgat ggattttata acaattctaa gtggatgcat atgcatccat atgcttgtag   3000
attctggaga agtaagaatg aaaaagaaga aactaaatgt agagatgggg aaactaagag   3060
atgtctgtat tatcctttat gggacagtcc cgaatctaca tatgattttg gttatttagc   3120
ataccaaaag aattttcctt cccctatctg tatagaacaa cagaaaatta gagatcaaga   3180
ttatgaagtt tattctttgt atcaagaatg caaaatagct tctaaagcat atggaattga   3240
tacagtttta ttctctctaa agaattttct taattataca ggaactcctg taaatgaaat   3300
gcctaatgca agagcttttg taggcctaat agatcccaag tttcctcctt cctatcccaa   3360
tgttactagg gaacattata cttcctgtaa taataggaaa agaagaagtg ttgataataa   3420
ctatgctaag ttaaggtcta tggggtatgc acttacagga gcagtgcaaa ccttatctca   3480
aatatcagat attaatgatg aaaacttaca gcaaggaata tatttattaa gggatcatgt   3540
aataacctta atggaagcta cattgcatga tatatctgtt atggaaggaa tgtttgctgt   3600
acaacatttg catacacatt tgaatcattt gaagacaatg cttctagaaa gaagaataga   3660
ctggacctat atgtctagta cttggctaca acaacaatta cagaaatctg atgatgagat   3720
gaaagtaata aagagaattg ctagaagttt ggtatattat gttaaacaaa cccatagttc   3780
tcccacagct acagcctggg agattggatt atattatgaa ttggttatac ctaaacatat   3840
ttacttgaat aattggaatg ttgtcaatat aggtcactta gttaaatcag ctggacaatt   3900
gactcatgta actatagctc atccttatga aataatcaat aaggaatgtg tagagactat   3960
atatctgcat cttgaagact gcacaagaca agattatgtc atatgtgatg tggtaaagat   4020
agtgcagcct tgtggcaata gctcagacac gagtgattgt cctgtctggg ctgaagctgt   4080
aaaagaacca tttgtgcaag tcaatcctct gaaaaacgga agttatctgg ttttggcaag   4140
ttccacagac tgtcagatcc caccatatgt tcctagcatc gtgactgtta atgaaacaac   4200
gtcatgcttt ggactggact ttaaaaggcc actggttgcg gaagaaagat tgagctttga   4260
gccacgactg ccaaatctac aactaagatt accacatttg gttggaatta ttgcaaaaat   4320
caaagggata aaaatagaag tcacatcctc tggagaaagt ataaaagagc agattgaaag   4380
agcaaaagct gagctccttc gactggacat tcacgaggga gatactcctg cctggataca   4440
acagctagct gcagcaacaa aggacgtctg gccagcagca gcttctgctc tacaaggaat   4500
```

```
tgggaacttt ttatctggga ctgcccaagg aatatttgga actgccttta gtctcttggg   4560
atacttaaag cctatcctaa taggagtagg ggtcattctc ttggttattc ttatatttaa   4620
aattgtatcc tggattccta cgaaaaagaa gaatcagtag cctccacctc tggaattctg   4680
cagatatcca gcacagtggc ggccgctcga gtctagaggg cccgtttaaa cccgctgatc   4740
agcctcgact gtgccttcta gttgccagcc atctgttgtt tgcccctccc ccgtgccttc   4800
cttgaccctg gaaggtgcca ctcccactgt cctttcctaa taaaatgagg aaattgcatc   4860
gcattgtctg agtaggtgtc attctattct ggggggtggg gtggggcagg acagcaaggg   4920
ggaggattgg gaagacaata gcaggcatgc tggggatgcg gtgggctcta tggcttctga   4980
ggcggaaaga accagctggg gctctagggg gtatccccac gcgccctgta gcggcgcatt   5040
aagcgcggcg ggtgtggtgg ttacgcgcag cgtgaccgct acacttgcca gcgccctagc   5100
gcccgctcct ttcgctttct tcccttcctt tctcgccacg ttcgccggct ttccccgtca   5160
agctctaaat cggggcatcc ctttagggtt ccgatttagt gctttacggc acctcgaccc   5220
caaaaaactt gattagggtg atggttcacg tagtgggcca tcgccctgat agacggtttt   5280
tcgccctttg acgttggagt ccacgttctt taatagtgga ctcttgttcc aaactggaac   5340
aacactcaac cctatctcgg tctattcttt tgatttataa gggattttgg ggatttcggc   5400
ctattggtta aaaaatgagc tgatttaaca aaaatttaac gcgaattaat tctgtggaat   5460
gtgtgtcagt tagggtgtgg aaagtcccca ggctccccag gcaggcagaa gtatgcaaag   5520
catgcatctc aattagtcag caaccaggtg tggaaagtcc ccaggctccc cagcaggcag   5580
aagtatgcaa agcatgcatc tcaattagtc agcaaccata gtcccgcccc taactccgcc   5640
catcccgccc ctaactccgc ccagttccgc ccattctccg ccccatggct gactaatttt   5700
ttttatttat gcagaggccg aggccgcctc tgcctctgag ctattccaga agtagtgagg   5760
aggctttttt ggaggcctag gcttttgcaa aaagctcccg ggagcttgta tatccatttt   5820
cggatctgat cagcacgtgt tgacaattaa tcatcggcat agtatatcgg catagtataa   5880
tacgacaagg tgaggaacta aaccatggcc aagttgacca gtgccgttcc ggtgctcacc   5940
gcgcgcgacg tcgccggagc ggtcgagttc tggaccgacc ggctcgggtt ctcccgggac   6000
ttcgtggagg acgacttcgc cggtgtggtc cgggacgacg tgaccctgtt catcagcgcg   6060
gtccaggacc aggtggtgcc ggacaacacc ctggcctggg tgtgggtgcg cggcctggac   6120
gagctgtacg ccgagtggtc ggaggtcgtg tccacgaact tccgggacgc ctccgggccg   6180
gccatgaccg agatcggcga gcagccgtgg gggcgggagt tcgccctgcg cgacccggcc   6240
ggcaactgcg tgcacttcgt ggccgaggag caggactgac acgtgctacg agatttcgat   6300
tccaccgccg ccttctatga aaggttgggc ttcggaatcg ttttccggga cgccggctgg   6360
atgatcctcc agcgcgggga tctcatgctg gagttcttcg cccaccccaa cttgtttatt   6420
gcagcttata atggttacaa ataaagcaat agcatcacaa atttcacaaa taaagcattt   6480
ttttcactgc attctagttg tggtttgtcc aaactcatca atgtatctta tcatgtctgt   6540
ataccgtcga cctctagcta gagcttggcg taatcatggt catagctgtt tcctgtgtga   6600
aattgttatc cgctcacaat tccacacaac atacgagccg gaagcataaa gtgtaaagcc   6660
tggggtgcct aatgagtgag ctaactcaca ttaattgcgt tgcgctcact gcccgctttc   6720
cagtcgggaa acctgtcgtg ccagctgcat taatgaatcg gccaacgcgc ggggagaggc   6780
ggtttgcgta ttgggcgctc ttccgcttcc tcgctcactg actcgctgcg ctcggtcgtt   6840
cggctgcggc gagcggtatc agctcactca aaggcggtaa tacggttatc cacagaatca   6900
```

```
ggggataacg caggaaagaa catgtgagca aaaggccagc aaaaggccag gaaccgtaaa   6960
aaggccgcgt tgctggcgtt tttccatagg ctccgccccc ctgacgagca tcacaaaaat   7020
cgacgctcaa gtcagaggtg gcgaaacccg acaggactat aaagatacca ggcgtttccc   7080
cctggaagct ccctcgtgcg ctctcctgtt ccgaccctgc cgcttaccgg atacctgtcc   7140
gcctttctcc cttcgggaag cgtggcgctt tctcaatgct cacgctgtag gtatctcagt   7200
tcggtgtagg tcgttcgctc caagctgggc tgtgtgcacg aaccccccgt tcagcccgac   7260
cgctgcgcct tatccggtaa ctatcgtctt gagtccaacc cggtaagaca cgacttatcg   7320
ccactggcag cagccactgg taacaggatt agcagagcga ggtatgtagg cggtgctaca   7380
gagttcttga agtggtggcc taactacggc tacactagaa ggacagtatt tggtatctgc   7440
gctctgctga agccagttac cttcggaaaa agagttggta gctcttgatc cggcaaacaa   7500
accaccgctg gtagcggtgg tttttttgtt tgcaagcagc agattacgcg cagaaaaaaa   7560
ggatctcaag aagatccttt gatcttttct acggggtctg acgctcagtg gaacgaaaac   7620
tcacgttaag ggattttggt catgagatta tcaaaaagga tcttcaccta gatcctttta   7680
aattaaaaat gaagttttaa atcaatctaa agtatatatg agtaaacttg gtctgacagt   7740
taccaatgct taatcagtga ggcacctatc tcagcgatct gtctatttcg ttcatccata   7800
gttgcctgac tccccgtcgt gtagataact acgatacggg agggcttacc atctggcccc   7860
agtgctgcaa tgataccgcg agacccacgc tcaccggctc cagatttatc agcaataaac   7920
cagccagccg gaagggccga gcgcagaagt ggtcctgcaa ctttatccgc ctccatccag   7980
tctattaatt gttgccggga agctagagta agtagttcgc cagttaatag tttgcgcaac   8040
gttgttgcca ttgctacagg catcgtggtg tcacgctcgt cgtttggtat ggcttcattc   8100
agctccggtt cccaacgatc aaggcgagtt acatgatccc ccatgttgtg caaaaaagcg   8160
gttagctcct tcggtcctcc gatcgttgtc agaagtaagt tggccgcagt gttatcactc   8220
atggttatgg cagcactgca taattctctt actgtcatgc catccgtaag atgcttttct   8280
gtgactggtg agtactcaac caagtcattc tgagaatagt gtatgcggcg accgagttgc   8340
tcttgcccgg cgtcaatacg ggataatacc gcgccacata gcagaacttt aaaagtgctc   8400
atcattggaa aacgttcttc ggggcgaaaa ctctcaagga tcttaccgct gttgagatcc   8460
agttcgatgt aacccactcg tgcacccaac tgatcttcag catcttttac tttcaccagc   8520
gtttctgggt gagcaaaaac aggaaggcaa aatgccgcaa aaaagggaat aagggcgaca   8580
cggaaatgtt gaatactcat actcttcctt tttcaatatt attgaagcat ttatcagggt   8640
tattgtctca tgagcggata catatttgaa tgtatttaga aaaataaaca aataggggtt   8700
ccgcgcacat ttccccgaaa agtgccacct gacgtcatgg ccagatctgt gagcaagggc   8760
gaggagctgt tcaccggggt ggtgcccatc ctggtcgagc tggacggcga cgtaaacggc   8820
cacaagttca gcgtgtccgg cgagggcgag ggcgatgcca cctacggcaa gctgaccctg   8880
aagttcatct gcaccaccgg caagctgccc gtgccctggc ccaccctcgt gaccaccttc   8940
ggctacggcc tgcagtgctt cgcccgctac cccgaccaca tgaagcagca cgacttcttc   9000
aagtccgcca tgcccgaagg ctacgtccag gagcgcacca tcttcttcaa ggacgacggc   9060
aactacaaga cccgcgccga ggtgaagttc gagggcgaca ccctggtgaa ccgcatcgag   9120
ctgaagggca tcgacttcaa ggaggacggc aacatcctgg ggcacaagct ggagtacaac   9180
tacaacagcc acaacgtcta tatcatggcc gacaagcaga agaacggcat caaggtgaac   9240
ttcaagatcc gccacaacat cgaggacggc agcgtgcagc tcgccgacca ctaccagcag   9300
```

```
aacaccccca tcggcgacgg ccccgtgctg ctgcccgaca accactacct gagctaccag   9360
tccgccctga gcaaagaccc caacgagaag cgcgatcaca tggtcctgct ggagttcgtg   9420
accgccgccg ggatcactct cggcatggac gagctgtaca agaccttcga aggcggcggc   9480
agcggcgggg gcgggagcgg cggcgggga tccgcaccac caatgacact gcaacaatgg    9540
atcatttgga aaaaaatgaa taaagcgcat gaggcacttc aaaatacaac aactgtgact   9600
gaacagcaga aggaacaaat tatactggac attcaaaatg aagaagtaca accaactagg   9660
agagataaat ttagatatct gctttatact tgttgtgcta ctagctcaag agtattggcc   9720
tggatgtttt tagtttgtat attgttaatc attgttttgg tttcatgctt tgtgactata   9780
tccagaatac aatggaataa ggatattcag gtattaggac ctgtaataga ctggaatgtt   9840
actcaaagag ctgtttatca acccttacag actagaagga ttgcacgttc ccttagaatg   9900
cagcatcctg ttccaaaata tgtggaggta aatatgacta gtattccaca aggtgtatac   9960
tatgaacccc atccggaacc catagtggtg aaggagaggg tcctgggtct ttctcaaatt  10020
ctgatgatta attcagaaaa cattgctaat aatgctaatt tgacacaaga agtaaagaag  10080
ttgttaactg aaatggttaa tgaagaaatg caaagtttgt cagatgtaat gattgacttt  10140
gaaattcctt taggagaccc tcgtgatcaa gaacaatata tacatagaaa atgctatcaa  10200
gaatttgcaa attgttattt agtaaaatat aaagaaccca aaccgtggcc taaggagggc  10260
cttatagctg atcaatgccc attaccaggt taccatgctg gattaaccta taatagacag  10320
tctatttggg attactatat taaagtggag agtattagac ctgcaaattg gacaacaaag  10380
agtaaatatg gacaagctag actaggaagt tttatattc ctagcagtct gagacaaatc   10440
aatgttagtc atgtactatt ctgtagtgat caattatatt ctaaatggta taatatagaa  10500
aataccatag aacaaaacga gcggtttctg cttaataaac taaataacct tacatctgga  10560
acctcagtat tgaagaaaag agctcttccg aaggattgga gttctcaagg taaaaatgct  10620
ctgtttagag aaatcaatgt gttagatatc tgcagtaaac ctgaatctgt aatactattg  10680
aatacttcat actattcctt ctctttatgg gaaggagatt gtaattttac taaagatatg  10740
atttctcagt tggttccaga atgtgatgga ttttataaca attctaagtg gatgcatatg  10800
catccatatg cttgtagatt ctggagaagt aagaatgaaa aagaagaaac taaatgtaga  10860
gatggggaaa ctaagagatg tctgtattat cctttatggg acagtcccga atctacatat  10920
gattttggtt atttagcata ccaaaagaat tttccttccc ctatctgtat agaacaacag  10980
aaaattagag atcaagatta tgaagtttat tctttgtatc aagaatgcaa aatagcttct  11040
aaagcatatg gaattgatac agttttattc tctctaaaga attttcttaa ttatacagga  11100
actcctgtaa atgaaatgcc taatgcaaga gcttttgtag gcctaataga tcccaagttt  11160
cctccttcct atcccaatgt tactagggaa cattatactt cctgtaataa taggaaaaga  11220
agaagtgttg ataataacta tgctaagtta aggtctatgg ggtatgcact tacaggagca  11280
gtgcaaacct tatctcaaat atcagatatt aatgatgaaa acttacagca aggaatatat  11340
ttattaaggg atcatgtaat aaccttaatg gaagctacat tgcatgatat atctgttatg  11400
gaaggaatgt ttgctgtaca acatttgcat acacatttga atcatttgaa gacaatgctt  11460
ctagaaagaa gaatagactg gacctatatg tctagtactt ggctacaaca acaattacag  11520
aaatctgatg atgagatgaa agtaataaag agaattgcta gaagtttggt atattatgtt  11580
aaacaaaccc atagttctcc cacagctaca gcctgggaga ttggattata ttatgaattg  11640
gttataccta aacatattta cttgaataat tggaatgttg tcaatatagg tcacttagtt  11700
```

```
aaatcagctg gacaattgac tcatgtaact atagctcatc cttatgaaat aatcaataag  11760

gaatgtgtag agactatata tctgcatctt gaagactgca caagacaaga ttatgtcata  11820

tgtgatgtgg taaagatagt gcagccttgt ggcaatagct cagacacgag tgattgtcct  11880

gtctgggctg aagctgtaaa agaaccattt gtgcaagtca atcctctgaa aaacggaagt  11940

tatctggttt tggcaagttc cacagactgt cagatcccac catatgttcc tagcatcgtg  12000

actgttaatg aaacaacgtc atgctttgga ctggacttta aaaggccact ggttgcggaa  12060

gaaagattga gctttgagcc acgactgcca aatctacaac taagattacc acatttggtt  12120

ggaattattg caaaaatcaa agggataaaa atagaagtca catcctctgg agaaagtata  12180

aaagagcaga ttgaaagagc aaaagctgag ctccttcgac tggacattca cgagggagat  12240

actcctgcct ggatacaaca gctagctgca gcaacaaagg acgtctggcc agcagcagct  12300

tctgctctac aaggaattgg gaacttttta tctgggactg cccaaggaat atttggaact  12360

gcctttagtc tcttgggata cttaaagcct atcctaatag gagtaggggt cattctcttg  12420

gttattctta tatttaaaat tgtatcctgg attcctacga aaaagaagaa tcagtag     12477
```

<210> SEQ ID NO 30
<211> LENGTH: 10826
<212> TYPE: DNA
<213> ORGANISM: Artificial Sequence
<220> FEATURE:
<223> OTHER INFORMATION: Foamy Viral Envelope Gene pczHFV EM171

<400> SEQUENCE: 30

```
gacggatcgg gagatctccc gatcccctat ggtcgactct cagtacaatc tgctctgatg    60

ccgcatagtt aagccagtat ctgctccctg cttgtgtgtt ggaggtcgct gagtagtgcg   120

cgagcaaaat ttaagctaca acaaggcaag gcttgaccga caattgcatg aagaatctgc   180

ttagggttag gcgttttgcg ctgcttcgcg atgtacgggc cagatatacg cgttgacatt   240

gattattgac tagttattaa tagtaatcaa ttacggggtc attagttcat agcccatata   300

tggagttccg cgttacataa cttacggtaa atggcccgcc tggctgaccg cccaacgacc   360

cccgcccatt gacgtcaata atgacgtatg ttcccatagt aacgccaata gggactttcc   420

attgacgtca atgggtggac tatttacggt aaactgccca cttggcagta catcaagtgt   480

atcatatgcc aagtacgccc cctattgacg tcaatgacgg taaatggccc gcctggcatt   540

atgcccagta catgacctta tgggactttc ctacttggca gtacatctac gtattagtca   600

tcgctattac catggtgatg cggttttggc agtacatcaa tgggcgtgga tagcggtttg   660

actcacgggg atttccaagt ctccacccca ttgacgtcaa tgggagtttg ttttggcacc   720

aaaatcaacg ggactttcca aaatgtcgta acaactccgc cccattgacg caaatgggcg   780

gtaggcgtgt acggtgggag gtctatataa gcagagctct ctggctaact agagaaccca   840

ctgcttactg gcttatcgaa attaatacga ctcactatag ggagacccaa gctgggctag   900

actgccatga atagagcgca tgaggcactt caaaatacaa caactgtgac tgaacagcag   960

cgcgaacaaa ttatactgga cattcaaaat gaagaagtac aaccaactag gagagatcgc  1020

tttagatatc tgctttatac ttgttgtgct actagctcaa gagtattggc ctggatcttt  1080

ttagtttgta tattgttaat cattgttttg gtttcatgct ttgtgactat atccagaata  1140

caatggaata aggatattca ggtattagga cctgtaatag actggaatgt tactcaaaga  1200

gctgtttatc aacccttaca gactagaagg attgcacgtt cccttagaat gcagcatcct  1260

gttccaaaat atgtggaggt aaatatgact agtattccac aaggtgtata ctatgaaccc  1320
```

-continued

```
catccggaac ccatagtggt gaaggagagg gtcctgggtc tttctcaaat tctgatgatt   1380
aattcagaaa acattgctaa taatgctaat ttgacacaag aagtaaagaa gttgttaact   1440
gaaatggtta atgaagaaat gcaaagtttg tcagatgtaa tgattgactt tgaaattcct   1500
ttaggagacc ctcgtgatca agaacaatat atacatagaa aatgctatca agaatttgca   1560
aattgttatt tagtaaaata taaagaaccc aaaccgtggc ctaaggaggg ccttatagct   1620
gatcaatgcc cattaccagg ttaccatgct ggattaacct ataatagaca gtctatttgg   1680
gattactata ttaaagtgga gagtattaga cctgcaaatt ggacaacaaa gagtaaatat   1740
ggacaagcta gactaggaag tttttatatt cctagcagtc tgagacaaat caatgttagt   1800
catgtactat tctgtagtga tcaattatat tctaaatggt ataatataga aaataccata   1860
gaacaaaacg agcggtttct gcttaataaa ctaaataacc ttacatctgg aacctcagta   1920
ttgaagaaaa gagctcttcc gaaggattgg agttctcaag gtaaaaatgc tctgtttaga   1980
gaaatcaatg tgttagatat ctgcagtaaa cctgaatctg taatactatt gaatacttca   2040
tactattcct tctctttatg ggaaggagat tgtaatttta ctaaagatat gatttctcag   2100
ttggttccag aatgtgatgg attttataac aattctaagt ggatgcatat gcatccatat   2160
gcttgtagat tctggagaag taagaatgaa aaagaagaaa ctaaatgtag agatggggaa   2220
actaagagat gtctgtatta tcctttatgg gacagtcccg aatctacata tgattttggt   2280
tatttagcat accaaaagaa ttttccttcc cctatctgta tagaacaaca gaaaattaga   2340
gatcaagatt atgaagttta ttctttgtat caagaatgca aaatagcttc taaagcatat   2400
ggaattgata cagttttatt ctctctaaag aattttctta attatacagg aactcctgta   2460
aatgaaatgc ctaatgcaag agcttttgta ggcctaatag atcccaagtt tcctccttcc   2520
tatcccaatg ttactaggga acattatact tcctgtaata ataggaaaag aagaagtgtt   2580
gataataact atgctaagtt aaggtctatg ggtatgcac ttacaggagc agtgcaaacc   2640
ttatctcaaa tatcagatat taatgatgaa aacttacagc aaggaatata tttattaagg   2700
gatcatgtaa taaccttaat ggaagctaca ttgcatgata tatctgttat ggaaggaatg   2760
tttgctgtac aacatttgca tacacatttg aatcatttga agacaatgct tctagaaaga   2820
agaatagact ggacctatat gtctagtact tggctacaac aacaattaca gaaatctgat   2880
gatgagatga aagtaataaa gagaattgct agaagtttgg tatattatgt taaacaaacc   2940
catagttctc ccacagctac agcctgggag attggattat attatgaatt ggttatacct   3000
aaacatattt acttgaataa ttggaatgtt gtcaatatag gtcacttagt taaatcagct   3060
ggacaattga ctcatgtaac tatagctcat ccttatgaaa taatcaataa ggaatgtgta   3120
gagactatat atctgcatct tgaagactgc acaagacaag attatgtcat atgtgatgtg   3180
gtaaagatag tgcagccttg tggcaatagc tcagacacga gtgattgtcc tgtctgggct   3240
gaagctgtaa aagaaccatt tgtgcaagtc aatcctctga aaaacggaag ttatctggtt   3300
ttggcaagtt ccacagactg tcagatccca ccatatgttc ctagcatcgt gactgttaat   3360
gaaacaacgt catgctttgg actggacttt aaaaggccac tggttgcgga agaaagattg   3420
agctttgagc cacgactgcc aaatctacaa ctaagattac cacatttggt tggaattatt   3480
gcaaaaatca aagggataaa aatagaagtc acatcctctg gagaaagtat aaaagagcag   3540
attgaaagag caaaagctga gctccttcga ctggacattc acgagggaga tactcctgcc   3600
tggatacaac agctagctgc agcaacaaag gacgtctggc cagcagcagc ttctgctcta   3660
caaggaattg ggaacttttt atctgggact gcccaaggaa tatttggaac tgcctttagt   3720
```

```
ctcttgggat acttaaagcc tatcctaata ggagtagggg tcattctctt ggttattctt   3780

atatttaaaa ttgtatcctg gattcctacg aaaaagaaga atcagtagcc tccacctctg   3840

gaattctgca gatatccagc acagtggcgg ccgctcgagt ctagagggcc cgtttaaacc   3900

cgctgatcag cctcgactgt gccttctagt tgccagccat ctgttgtttg cccctccccc   3960

gtgccttcct tgaccctgga aggtgccact cccactgtcc tttcctaata aaatgaggaa   4020

attgcatcgc attgtctgag taggtgtcat tctattctgg ggggtggggt ggggcaggac   4080

agcaaggggg aggattggga agacaatagc aggcatgctg gggatgcggt gggctctatg   4140

gcttctgagg cggaaagaac cagctggggc tctagggggt atccccacgc gccctgtagc   4200

ggcgcattaa gcgcggcggg tgtggtggtt acgcgcagcg tgaccgctac acttgccagc   4260

gccctagcgc ccgctccttt cgctttcttc ccttcctttc tcgccacgtt cgccggcttt   4320

ccccgtcaag ctctaaatcg ggcatccct ttagggttcc gatttagtgc tttacggcac    4380

ctcgacccca aaaaacttga ttagggtgat ggttcacgta gtgggccatc gccctgatag   4440

acggtttttc gccctttgac gttggagtcc acgttcttta atagtggact cttgttccaa   4500

actggaacaa cactcaaccc tatctcggtc tattcttttg atttataagg gattttgggg   4560

atttcggcct attggttaaa aaatgagctg atttaacaaa aatttaacgc gaattaattc   4620

tgtggaatgt gtgtcagtta gggtgtggaa agtccccagg ctccccaggc aggcagaagt   4680

atgcaaagca tgcatctcaa ttagtcagca accaggtgtg gaaagtcccc aggctcccca   4740

gcaggcagaa gtatgcaaag catgcatctc aattagtcag caaccatagt cccgccccta   4800

actccgccca tcccgcccct aactccgccc agttccgccc attctccgcc ccatggctga   4860

ctaatttttt ttatttatgc agaggccgag gccgcctctg cctctgagct attccagaag   4920

tagtgaggag gcttttttgg aggcctaggc ttttgcaaaa agctcccggg agcttgtata   4980

tccattttcg gatctgatca gcacgtgttg acaattaatc atcggcatag tatatcggca   5040

tagtataata cgacaaggtg aggaactaaa ccatggccaa gttgaccagt gccgttccgg   5100

tgctcaccgc gcgcgacgtc gccggagcgg tcgagttctg gaccgaccgg ctcgggttct   5160

cccgggactt cgtggaggac gacttcgccg gtgtggtccg ggacgacgtg accctgttca   5220

tcagcgcggt ccaggaccag gtggtgccgg acaacaccct ggcctgggtg tgggtgcgcg   5280

gcctggacga gctgtacgcc gagtggtcgg aggtcgtgtc cacgaacttc cgggacgcct   5340

ccgggccggc catgaccgag atcggcgagc agccgtgggg gcgggagttc gccctgcgcg   5400

acccggccgg caactgcgtg cacttcgtgg ccgaggagca ggactgacac gtgctacgag   5460

atttcgattc caccgccgcc ttctatgaaa ggttgggctt cggaatcgtt ttccgggacg   5520

ccggctggat gatcctccag cgcggggatc tcatgctgga gttcttcgcc caccccaact   5580

tgtttattgc agcttataat ggttacaaat aaagcaatag catcacaaat ttcacaaata   5640

aagcattttt ttcactgcat tctagttgtg gtttgtccaa actcatcaat gtatcttatc   5700

atgtctgtat accgtcgacc tctagctaga gcttggcgta atcatggtca tagctgtttc   5760

ctgtgtgaaa ttgttatccg ctcacaattc cacacaacat acgagccgga agcataaagt   5820

gtaaagcctg gggtgcctaa tgagtgagct aactcacatt aattgcgttg cgctcactgc   5880

ccgctttcca gtcgggaaac ctgtcgtgcc agctgcatta atgaatcggc caacgcgcgg   5940

ggagaggcgg tttgcgtatt gggcgctctt ccgcttcctc gctcactgac tcgctgcgct   6000

cggtcgttcg gctgcggcga gcggtatcag ctcactcaaa ggcggtaata cggttatcca   6060

cagaatcagg ggataacgca ggaaagaaca tgtgagcaaa aggccagcaa aaggccagga   6120
```

```
accgtaaaaa ggccgcgttg ctggcgtttt tccataggct ccgcccccct gacgagcatc   6180
acaaaaatcg acgctcaagt cagaggtggc gaaacccgac aggactataa agataccagg   6240
cgtttccccc tggaagctcc ctcgtgcgct ctcctgttcc gaccctgccg cttaccggat   6300
acctgtccgc ctttctccct tcgggaagcg tggcgctttc tcaatgctca cgctgtaggt   6360
atctcagttc ggtgtaggtc gttcgctcca agctgggctg tgtgcacgaa ccccccgttc   6420
agcccgaccg ctgcgcctta tccggtaact atcgtcttga gtccaacccg gtaagacacg   6480
acttatcgcc actggcagca gccactggta acaggattag cagagcgagg tatgtaggcg   6540
gtgctacaga gttcttgaag tggtggccta actacggcta cactagaagg acagtatttg   6600
gtatctgcgc tctgctgaag ccagttacct tcggaaaaag agttggtagc tcttgatccg   6660
gcaaacaaac caccgctggt agcggtggtt tttttgtttg caagcagcag attacgcgca   6720
gaaaaaaagg atctcaagaa gatcctttga tcttttctac ggggtctgac gctcagtgga   6780
acgaaaactc acgttaaggg attttggtca tgagattatc aaaaaggatc ttcacctaga   6840
tccttttaaa ttaaaaatga agttttaaat caatctaaag tatatatgag taaacttggt   6900
ctgacagtta ccaatgctta atcagtgagg cacctatctc agcgatctgt ctatttcgtt   6960
catccatagt tgcctgactc cccgtcgtgt agataactac gatacgggag ggcttaccat   7020
ctggccccag tgctgcaatg ataccgcgag acccacgctc accggctcca gatttatcag   7080
caataaacca gccagccgga agggccgagc gcagaagtgg tcctgcaact ttatccgcct   7140
ccatccagtc tattaattgt tgccgggaag ctagagtaag tagttcgcca gttaatagtt   7200
tgcgcaacgt tgttgccatt gctacaggca tcgtggtgtc acgctcgtcg tttggtatgg   7260
cttcattcag ctccggttcc caacgatcaa ggcgagttac atgatccccc atgttgtgca   7320
aaaaagcggt tagctccttc ggtcctccga tcgttgtcag aagtaagttg gccgcagtgt   7380
tatcactcat ggttatggca gcactgcata attctcttac tgtcatgcca tccgtaagat   7440
gcttttctgt gactggtgag tactcaacca agtcattctg agaatagtgt atgcggcgac   7500
cgagttgctc ttgcccggcg tcaatacggg ataataccgc gccacatagc agaactttaa   7560
aagtgctcat cattggaaaa cgttcttcgg ggcgaaaact ctcaaggatc ttaccgctgt   7620
tgagatccag ttcgatgtaa cccactcgtg cacccaactg atcttcagca tcttttactt   7680
tcaccagcgt ttctgggtga gcaaaaacag gaaggcaaaa tgccgcaaaa aagggaataa   7740
gggcgacacg gaaatgttga atactcatac tcttcctttt tcaatattat tgaagcattt   7800
atcagggtta ttgtctcatg agcggataca tatttgaatg tatttagaaa aataaacaaa   7860
taggggttcc gcgcacattt ccccgaaaag tgccacctga cgtcatgaat agagcgcatg   7920
aggcacttca aaatacaaca actgtgactg aacagcagcg cgaacaaatt atactggaca   7980
ttcaaaatga agaagtacaa ccaactagga gagatcgctt tagatatctg ctttatactt   8040
gttgtgctac tagctcaaga gtattggcct ggatcttttt agtttgtata ttgttaatca   8100
ttgttttggt ttcatgcttt gtgactatat ccagaataca atggaataag gatattcagg   8160
tattaggacc tgtaatagac tggaatgtta ctcaaagagc tgtttatcaa cccttacaga   8220
ctagaaggat tgcacgttcc cttagaatgc agcatcctgt tccaaaatat gtggaggtaa   8280
atatgactag tattccacaa ggtgtatact atgaacccca tccggaaccc atagtggtga   8340
aggagagggt cctgggtctt tctcaaattc tgatgattaa ttcagaaaac attgctaata   8400
atgctaattt gacacaagaa gtaaagaagt tgttaactga aatggttaat gaagaaatgc   8460
aaagtttgtc agatgtaatg attgactttg aaattccttt aggagaccct cgtgatcaag   8520
```

```
aacaatatat acatagaaaa tgctatcaag aatttgcaaa ttgttattta gtaaaatata   8580
aagaacccaa accgtggcct aaggagggcc ttatagctga tcaatgccca ttaccaggtt   8640
accatgctgg attaacctat aatagacagt ctatttggga ttactatatt aaagtggaga   8700
gtattagacc tgcaaattgg acaacaaaga gtaaatatgg acaagctaga ctaggaagtt   8760
tttatattcc tagcagtctg agacaaatca atgttagtca tgtactattc tgtagtgatc   8820
aattatattc taaatggtat aatatagaaa ataccataga acaaaacgag cggtttctgc   8880
ttaataaact aaataacctt acatctggaa cctcagtatt gaagaaaaga gctcttccga   8940
aggattggag ttctcaaggt aaaaatgctc tgtttagaga aatcaatgtg ttagatatct   9000
gcagtaaacc tgaatctgta atactattga atacttcata ctattccttc tctttatggg   9060
aaggagattg taattttact aaagatatga tttctcagtt ggttccagaa tgtgatggat   9120
tttataacaa ttctaagtgg atgcatatgc atccatatgc ttgtagattc tggagaagta   9180
agaatgaaaa agaagaaact aaatgtagag atggggaaac taagagatgt ctgtattatc   9240
ctttatggga cagtcccgaa tctacatatg attttggtta tttagcatac caaaagaatt   9300
ttccttcccc tatctgtata gaacaacaga aaattagaga tcaagattat gaagtttatt   9360
ctttgtatca agaatgcaaa atagcttcta aagcatatgg aattgataca gttttattct   9420
ctctaaagaa ttttcttaat tatacaggaa ctcctgtaaa tgaaatgcct aatgcaagag   9480
cttttgtagg cctaatagat cccaagtttc ctccttccta tcccaatgtt actagggaac   9540
attatacttc ctgtaataat aggaaaagaa gaagtgttga taataactat gctaagttaa   9600
ggtctatggg gtatgcactt acaggagcag tgcaaacctt atctcaaata tcagatatta   9660
atgatgaaaa cttacagcaa ggaatatatt tattaaggga tcatgtaata accttaatgg   9720
aagctacatt gcatgatata tctgttatgg aaggaatgtt tgctgtacaa catttgcata   9780
cacatttgaa tcatttgaag acaatgcttc tagaaagaag aatagactgg acctatatgt   9840
ctagtacttg gctacaacaa caattacaga aatctgatga tgagatgaaa gtaataaaga   9900
gaattgctag aagtttggta tattatgtta aacaaaccca tagttctccc acagctacag   9960
cctgggagat tggattatat tatgaattgg ttatacctaa acatatttac ttgaataatt  10020
ggaatgttgt caatataggt cacttagtta aatcagctgg acaattgact catgtaacta  10080
tagctcatcc ttatgaaata atcaataagg aatgtgtaga gactatatat ctgcatcttg  10140
aagactgcac aagacaagat tatgtcatat gtgatgtggt aaagatagtg cagccttgtg  10200
gcaatagctc agacacgagt gattgtcctg tctgggctga agctgtaaaa gaaccatttg  10260
tgcaagtcaa tcctctgaaa aacggaagtt atctggtttt ggcaagttcc acagactgtc  10320
agatcccacc atatgttcct agcatcgtga ctgttaatga aacaacgtca tgctttggac  10380
tggactttaa aaggccactg gttgcggaag aaagattgag ctttgagcca cgactgccaa  10440
atctacaact aagattacca catttggttg gaattattgc aaaaatcaaa gggataaaaa  10500
tagaagtcac atcctctgga gaaagtataa aagagcagat tgaaagagca aaagctgagc  10560
tccttcgact ggacattcac gagggagata ctcctgcctg gatacaacag ctagctgcag  10620
caacaaagga cgtctggcca gcagcagctt ctgctctaca aggaattggg aactttttat  10680
ctgggactgc ccaaggaata tttggaactg cctttagtct cttgggatac ttaaagccta  10740
tcctaatagg agtaggggtc attctcttgg ttattcttat atttaaaatt gtatcctgga  10800
ttcctacgaa aaagaagaat cagtag                                       10826
```

<210> SEQ ID NO 31
<211> LENGTH: 10771
<212> TYPE: DNA
<213> ORGANISM: Artificial Sequence
<220> FEATURE:
<223> OTHER INFORMATION: Foamy Viral Envelope Gene pczHFV EM228

<400> SEQUENCE: 31

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctaga    900

ctgccatgac aacaactgtg actgaacagc agcgcgaaca aattatactg gacattcaaa    960

atgaagaagt acaaccaact aggagagatc gctttagata tctgctttat acttgttgtg   1020

ctactagctc aagagtattg gcctggatgt ttttagtttg tatattgtta atcattgttt   1080

tggtttcatg ctttgtgact atatccagaa tacaatggaa taaggatatt caggtattag   1140

gacctgtaat agactggaat gttactcaaa gagctgttta tcaaccctta cagactagaa   1200

ggattgcacg ttcccttaga atgcagcatc ctgttccaaa atatgtggag gtaaatatga   1260

ctagtattcc acaaggtgta tactatgaac ccatccgga acccatagtg gtgaaggaga    1320

gggtcctggg tctttctcaa attctgatga ttaattcaga aaacattgct aataatgcta   1380

atttgacaca agaagtaaag aagttgttaa ctgaaatggt taatgaagaa atgcaaagtt   1440

tgtcagatgt aatgattgac tttgaaattc ctttaggaga ccctcgtgat caagaacaat   1500

atatacatag aaaatgctat caagaatttg caaattgtta tttagtaaaa tataaagaac   1560

ccaaaccgtg gcctaaggag ggccttatag ctgatcaatg cccattacca ggttaccatg   1620

ctggattaac ctataataga cagtctattt gggattacta tattaaagtg gagagtatta   1680

gacctgcaaa ttggacaaca aagagtaaat atggacaagc tagactagga agtttttata   1740

ttcctagcag tctgagacaa atcaatgtta gtcatgtact attctgtagt gatcaattat   1800

attctaaatg gtataatata gaaaatacca tagaacaaaa cgagcggttt ctgcttaata   1860

aactaaataa ccttacatct ggaacctcag tattgaagaa aagagctctt ccgaaggatt   1920

ggagttctca aggtaaaaat gctctgttta gagaaatcaa tgtgttagat atctgcagta   1980

aacctgaatc tgtaatacta ttgaatactt catactattc cttctcttta tgggaaggag   2040

attgtaattt tactaaagat atgatttctc agttggttcc agaatgtgat ggattttata   2100

acaattctaa gtggatgcat atgcatccat atgcttgtag attctggaga agtaagaatg   2160
```

```
aaaaagaaga aactaaatgt agagatgggg aaactaagag atgtctgtat tatcctttat   2220
gggacagtcc cgaatctaca tatgattttg gttatttagc ataccaaaag aattttcctt   2280
cccctatctg tatagaacaa cagaaaatta gagatcaaga ttatgaagtt tattctttgt   2340
atcaagaatg caaaatagct tctaaagcat atggaattga tacagtttta ttctctctaa   2400
agaattttct taattataca ggaactcctg taaatgaaat gcctaatgca agagcttttg   2460
taggcctaat agatcccaag tttcctcctt cctatcccaa tgttactagg gaacattata   2520
cttcctgtaa taataggaaa agaagaagtg ttgataataa ctatgctaag ttaaggtcta   2580
tggggtatgc acttacagga gcagtgcaaa ccttatctca aatatcagat attaatgatg   2640
aaaacttaca gcaaggaata tatttattaa gggatcatgt aataacctta atggaagcta   2700
cattgcatga tatatctgtt atggaaggaa tgtttgctgt acaacatttg catacacatt   2760
tgaatcattt gaagacaatg cttctagaaa gaagaataga ctggacctat atgtctagta   2820
cttggctaca acaacaatta cagaaatctg atgatgagat gaaagtaata aagagaattg   2880
ctagaagttt ggtatattat gttaaacaaa cccatagttc tcccacagct acagcctggg   2940
agattggatt atattatgaa ttggttatac ctaaacatat ttacttgaat aattggaatg   3000
ttgtcaatat aggtcactta gttaaatcag ctggacaatt gactcatgta actatagctc   3060
atccttatga aataatcaat aaggaatgtg tagagactat atatctgcat cttgaagact   3120
gcacaagaca agattatgtc atatgtgatg tggtaaagat agtgcagcct tgtggcaata   3180
gctcagacac gagtgattgt cctgtctggg ctgaagctgt aaaagaacca tttgtgcaag   3240
tcaatcctct gaaaaacgga agttatctgg ttttggcaag ttccacagac tgtcagatcc   3300
caccatatgt tcctagcatc gtgactgtta atgaaacaac gtcatgcttt ggactggact   3360
ttaaaaggcc actggttgcg gaagaaagat tgagctttga gccacgactg ccaaatctac   3420
aactaagatt accacatttg gttggaatta ttgcaaaaat caaagggata aaaatagaag   3480
tcacatcctc tggagaaagt ataaaagagc agattgaaag agcaaaagct gagctccttc   3540
gactggacat tcacgaggga gatactcctg cctggataca acagctagct gcagcaacaa   3600
aggacgtctg gccagcagca gcttctgctc tacaaggaat tgggaacttt ttatctggga   3660
ctgcccaagg aatatttgga actgccttta gtctcttggg atacttaaag cctatcctaa   3720
taggagtagg ggtcattctc ttggttattc ttatatttaa aattgtatcc tggattccta   3780
cgaaaaagaa gaatcagtag cctccacctc tggaattctg cagatatcca gcacagtggc   3840
ggccgctcga gtctagaggg cccgtttaaa cccgctgatc agcctcgact gtgccttcta   3900
gttgccagcc atctgttgtt tgcccctccc ccgtgccttc cttgaccctg gaaggtgcca   3960
ctcccactgt cctttcctaa taaaatgagg aaattgcatc gcattgtctg agtaggtgtc   4020
attctattct ggggggtggg gtggggcagg acagcaaggg ggaggattgg gaagacaata   4080
gcaggcatgc tggggatgcg gtgggctcta tggcttctga ggcggaaaga accagctggg   4140
gctctagggg gtatccccac gcgccctgta gcggcgcatt aagcgcggcg ggtgtggtgg   4200
ttacgcgcag cgtgaccgct acacttgcca gcgccctagc gcccgctcct ttcgctttct   4260
tcccttcctt tctcgccacg ttcgccggct ttccccgtca agctctaaat cggggcatcc   4320
ctttagggtt ccgatttagt gctttacggc acctcgaccc caaaaaactt gattagggtg   4380
atggttcacg tagtgggcca tcgccctgat agacggtttt tcgccctttg acgttggagt   4440
ccacgttctt taatagtgga ctcttgttcc aaactggaac aacactcaac cctatctcgg   4500
tctattcttt tgatttataa gggattttgg ggatttcggc ctattggtta aaaaatgagc   4560
```

```
tgatttaaca aaaatttaac gcgaattaat tctgtggaat gtgtgtcagt tagggtgtgg   4620
aaagtcccca ggctccccag gcaggcagaa gtatgcaaag catgcatctc aattagtcag   4680
caaccaggtg tggaaagtcc ccaggctccc cagcaggcag aagtatgcaa agcatgcatc   4740
tcaattagtc agcaaccata gtcccgcccc taactccgcc catcccgccc ctaactccgc   4800
ccagttccgc ccattctccg ccccatggct gactaatttt ttttatttat gcagaggccg   4860
aggccgcctc tgcctctgag ctattccaga agtagtgagg aggctttttt ggaggcctag   4920
gcttttgcaa aaagctcccg ggagcttgta tatccatttt cggatctgat cagcacgtgt   4980
tgacaattaa tcatcggcat agtatatcgg catagtataa tacgacaagg tgaggaacta   5040
aaccatggcc aagttgacca gtgccgttcc ggtgctcacc gcgcgcgacg tcgccggagc   5100
ggtcgagttc tggaccgacc ggctcgggtt ctcccgggac ttcgtggagg acgacttcgc   5160
cggtgtggtc cgggacgacg tgaccctgtt catcagcgcg gtccaggacc aggtggtgcc   5220
ggacaacacc ctggcctggg tgtgggtgcg cggcctggac gagctgtacg ccgagtggtc   5280
ggaggtcgtg tccacgaact tccgggacgc ctccgggccg gccatgaccg agatcggcga   5340
gcagccgtgg gggcgggagt tcgccctgcg cgacccggcc ggcaactgcg tgcacttcgt   5400
ggccgaggag caggactgac acgtgctacg agatttcgat tccaccgccg ccttctatga   5460
aaggttgggc ttcggaatcg ttttccggga cgccggctgg atgatcctcc agcgcgggga   5520
tctcatgctg gagttcttcg cccaccccaa cttgtttatt gcagcttata atggttacaa   5580
ataaagcaat agcatcacaa atttcacaaa taaagcattt ttttcactgc attctagttg   5640
tggtttgtcc aaactcatca atgtatctta tcatgtctgt ataccgtcga cctctagcta   5700
gagcttggcg taatcatggt catagctgtt tcctgtgtga aattgttatc cgctcacaat   5760
tccacacaac atacgagccg gaagcataaa gtgtaaagcc tggggtgcct aatgagtgag   5820
ctaactcaca ttaattgcgt tgcgctcact gcccgctttc cagtcgggaa acctgtcgtg   5880
ccagctgcat taatgaatcg gccaacgcgc ggggagaggc ggtttgcgta ttgggcgctc   5940
ttccgcttcc tcgctcactg actcgctgcg ctcggtcgtt cggctgcggc gagcggtatc   6000
agctcactca aaggcggtaa tacggttatc cacagaatca ggggataacg caggaaagaa   6060
catgtgagca aaaggccagc aaaaggccag gaaccgtaaa aaggccgcgt tgctggcgtt   6120
tttccatagg ctccgccccc ctgacgagca tcacaaaaat cgacgctcaa gtcagaggtg   6180
gcgaaacccg acaggactat aaagatacca ggcgtttccc cctggaagct ccctcgtgcg   6240
ctctcctgtt ccgaccctgc cgcttaccgg atacctgtcc gcctttctcc cttcgggaag   6300
cgtggcgctt tctcaatgct cacgctgtag gtatctcagt tcggtgtagg tcgttcgctc   6360
caagctgggc tgtgtgcacg aaccccccgt tcagcccgac cgctgcgcct tatccggtaa   6420
ctatcgtctt gagtccaacc cggtaagaca cgacttatcg ccactggcag cagccactgg   6480
taacaggatt agcagagcga ggtatgtagg cggtgctaca gagttcttga agtggtggcc   6540
taactacggc tacactagaa ggacagtatt tggtatctgc gctctgctga agccagttac   6600
cttcggaaaa agagttggta gctcttgatc cggcaaacaa accaccgctg gtagcggtgg   6660
tttttttgtt tgcaagcagc agattacgcg cagaaaaaaa ggatctcaag aagatccttt   6720
gatcttttct acggggtctg acgctcagtg gaacgaaaac tcacgttaag ggattttggt   6780
catgagatta tcaaaaagga tcttcaccta gatcctttta aattaaaaat gaagttttaa   6840
atcaatctaa agtatatatg agtaaacttg gtctgacagt taccaatgct taatcagtga   6900
ggcacctatc tcagcgatct gtctatttcg ttcatccata gttgcctgac tccccgtcgt   6960
```

```
gtagataact acgatacggg agggcttacc atctggcccc agtgctgcaa tgataccgcg   7020
agacccacgc tcaccggctc cagatttatc agcaataaac cagccagccg gaagggccga   7080
gcgcagaagt ggtcctgcaa ctttatccgc ctccatccag tctattaatt gttgccggga   7140
agctagagta agtagttcgc cagttaatag tttgcgcaac gttgttgcca ttgctacagg   7200
catcgtggtg tcacgctcgt cgtttggtat ggcttcattc agctccggtt cccaacgatc   7260
aaggcgagtt acatgatccc ccatgttgtg caaaaaagcg gttagctcct tcggtcctcc   7320
gatcgttgtc agaagtaagt tggccgcagt gttatcactc atggttatgg cagcactgca   7380
taattctctt actgtcatgc catccgtaag atgcttttct gtgactggtg agtactcaac   7440
caagtcattc tgagaatagt gtatgcggcg accgagttgc tcttgcccgg cgtcaatacg   7500
ggataatacc gcgccacata gcagaacttt aaaagtgctc atcattggaa aacgttcttc   7560
ggggcgaaaa ctctcaagga tcttaccgct gttgagatcc agttcgatgt aacccactcg   7620
tgcacccaac tgatcttcag catcttttac tttcaccagc gtttctgggt gagcaaaaac   7680
aggaaggcaa aatgccgcaa aaaagggaat aagggcgaca cggaaatgtt gaatactcat   7740
actcttcctt tttcaatatt attgaagcat ttatcagggt tattgtctca tgagcggata   7800
catatttgaa tgtatttaga aaaataaaca aataggggtt ccgcgcacat ttccccgaaa   7860
agtgccacct gacgtcatga caacaactgt gactgaacag cagcgcgaac aaattatact   7920
ggacattcaa aatgaagaag tacaaccaac taggagagat cgctttagat atctgcttta   7980
tacttgttgt gctactagct caagagtatt ggcctggatg tttttagttt gtatattgtt   8040
aatcattgtt ttggtttcat gctttgtgac tatatccaga atacaatgga ataaggatat   8100
tcaggtatta ggacctgtaa tagactggaa tgttactcaa agagctgttt atcaaccctt   8160
acagactaga aggattgcac gttcccttag aatgcagcat cctgttccaa aatatgtgga   8220
ggtaaatatg actagtattc cacaaggtgt atactatgaa ccccatccgg aacccatagt   8280
ggtgaaggag agggtcctgg gtctttctca aattctgatg attaattcag aaaacattgc   8340
taataatgct aatttgacac aagaagtaaa gaagttgtta actgaaatgg ttaatgaaga   8400
aatgcaaagt ttgtcagatg taatgattga ctttgaaatt cctttaggag accctcgtga   8460
tcaagaacaa tatatacata gaaaatgcta tcaagaattt gcaaattgtt atttagtaaa   8520
atataaagaa cccaaaccgt ggcctaagga gggccttata gctgatcaat gcccattacc   8580
aggttaccat gctggattaa cctataatag acagtctatt tgggattact atattaaagt   8640
ggagagtatt agacctgcaa attggacaac aaagagtaaa tatggacaag ctagactagg   8700
aagtttttat attcctagca gtctgagaca aatcaatgtt agtcatgtac tattctgtag   8760
tgatcaatta tattctaaat ggtataatat agaaaatacc atagaacaaa acgagcggtt   8820
tctgcttaat aaactaaata accttacatc tggaacctca gtattgaaga aaagagctct   8880
tccgaaggat tggagttctc aaggtaaaaa tgctctgttt agagaaatca atgtgttaga   8940
tatctgcagt aaacctgaat ctgtaatact attgaatact tcatactatt ccttctcttt   9000
atgggaagga gattgtaatt ttactaaaga tatgatttct cagttggttc cagaatgtga   9060
tggattttat aacaattcta agtggatgca tatgcatcca tatgcttgta gattctggag   9120
aagtaagaat gaaaaagaag aaactaaatg tagagatggg gaaactaaga gatgtctgta   9180
ttatccttta tgggacagtc ccgaatctac atatgatttt ggttatttag cataccaaaa   9240
gaattttcct tcccctatct gtatagaaca acagaaaatt agagatcaag attatgaagt   9300
ttattctttg tatcaagaat gcaaaatagc ttctaaagca tatggaattg atacagtttt   9360
```

attctctcta aagaattttc ttaattatac aggaactcct gtaaatgaaa tgcctaatgc 9420
aagagctttt gtaggcctaa tagatcccaa gtttcctcct tcctatccca atgttactag 9480
ggaacattat acttcctgta ataataggaa aagaagaagt gttgataata actatgctaa 9540
gttaaggtct atggggtatg cacttacagg agcagtgcaa accttatctc aaatatcaga 9600
tattaatgat gaaaacttac agcaaggaat atatttatta agggatcatg taataacctt 9660
aatggaagct acattgcatg atatatctgt tatggaagga atgtttgctg tacaacattt 9720
gcatacacat ttgaatcatt tgaagacaat gcttctagaa agaagaatag actggaccta 9780
tatgtctagt acttggctac aacaacaatt acagaaatct gatgatgaga tgaaagtaat 9840
aaagagaatt gctagaagtt tggtatatta tgttaaacaa acccatagtt ctcccacagc 9900
tacagcctgg gagattggat tatattatga attggttata cctaaacata tttacttgaa 9960
taattggaat gttgtcaata taggtcactt agttaaatca gctggacaat tgactcatgt 10020
aactatagct catccttatg aaataatcaa taaggaatgt gtagagacta tatatctgca 10080
tcttgaagac tgcacaagac aagattatgt catatgtgat gtggtaaaga tagtgcagcc 10140
ttgtggcaat agctcagaca cgagtgattg tcctgtctgg gctgaagctg taaaagaacc 10200
atttgtgcaa gtcaatcctc tgaaaaacgg aagttatctg gttttggcaa gttccacaga 10260
ctgtcagatc ccaccatatg ttcctagcat cgtgactgtt aatgaaacaa cgtcatgctt 10320
tggactggac tttaaaaggc cactggttgc ggaagaaaga ttgagctttg agccacgact 10380
gccaaatcta caactaagat taccacattt ggttggaatt attgcaaaaa tcaaagggat 10440
aaaaatagaa gtcacatcct ctggagaaag tataaaagag cagattgaaa gagcaaaagc 10500
tgagctcctt cgactggaca ttcacgaggg agatactcct gcctggatac aacagctagc 10560
tgcagcaaca aaggacgtct ggccagcagc agcttctgct ctacaaggaa ttgggaactt 10620
tttatctggg actgcccaag gaatatttgg aactgccttt agtctcttgg gatacttaaa 10680
gcctatccta ataggagtag gggtcattct cttggttatt cttatattta aaattgtatc 10740
ctggattcct acgaaaaaga agaatcagta g 10771

<210> SEQ ID NO 32
<211> LENGTH: 10904
<212> TYPE: DNA
<213> ORGANISM: Artificial Sequence
<220> FEATURE:
<223> OTHER INFORMATION: Foamy Viral Envelope Gene pciSFV-1 SM04

<400> SEQUENCE: 32
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660

```
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctaga    900
aaacctacgt ctcatcagat gacactgcaa caatggatca tttggagaag aatgaataga    960
gcgcatgagg cacttcaaaa tacaacaact gtgactgaac agcagcgcga acaaattata   1020
ctggacattc aaaatgaaga agtacaacca actaggagag atcgctttag atatctgctt   1080
tatacttgtt gtgctactag ctcaagagta ttggcctgga tgtttttagt ttgtatattg   1140
ttaatcattg ttttggtttc atgctttgtg actatatcca gaatacaatg gaataaggat   1200
attcaggtat taggacctgt aatagactgg aatgttactc aaagagctgt ttatcaaccc   1260
ttacagacta gaaggattgc acgttccctt agaatgcagc atcctgttcc aaaatatgtg   1320
gaggtaaata tgactagtat tccacaaggt gtatactatg aaccccatcc ggaacccata   1380
gtggtgaagg agagggtcct gggtctttct caaattctga tgattaattc agaaaacatt   1440
gctaataatg ctaatttgac acaagaagta aagaagttgt taactgaaat ggttaatgaa   1500
gaaatgcaaa gtttgtcaga tgtaatgatt gactttgaaa ttcctttagg agaccctcgt   1560
gatcaagaac aatatataca tagaaaatgc tatcaagaat ttgcaaattg ttatttagta   1620
aaatataaag aacccaaacc gtggcctaag gagggcctta tagctgatca atgcccatta   1680
ccaggttacc atgctggatt aacctataat agacagtcta tttgggatta ctatattaaa   1740
gtggagagta ttagacctgc aaattggaca acaaagagta aatatggaca agctagacta   1800
ggaagttttt atattcctag cagtctgaga caaatcaatg ttagtcatgt actattctgt   1860
agtgatcaat tatattctaa atggtataat atagaaaata ccatagaaca aaacgagcgg   1920
tttctgctta ataaactaaa taaccttaca tctggaacct cagtattgaa gaaaagagct   1980
cttccgaagg attggagttc tcaaggtaaa aatgctctgt ttagagaaat caatgtgtta   2040
gatatctgca gtaaacctga atctgtaata ctattgaata cttcatacta ttccttctct   2100
ttatgggaag gagattgtaa ttttactaaa gatatgattt ctcagttggt tccagaatgt   2160
gatggatttt ataacaattc taagtggatg catatgcatc catatgcttg tagattctgg   2220
agaagtaaga atgaaaaaga agaaactaaa tgtagagatg gggaaactaa gagatgtctg   2280
tattatcctt tatgggacag tcccgaatct acatatgatt ttggttattt agcataccaa   2340
aagaattttc cttcccctat ctgtatagaa caacagaaaa ttagagatca agattatgaa   2400
gtttattctt tgtatcaaga atgcaaaata gcttctaaag catatggaat tgatacagtt   2460
ttattctctc taaagaattt tcttaattat acaggaactc ctgtaaatga aatgcctaat   2520
gcaagagctt ttgtaggcct aatagatccc aagtttcctc cttcctatcc caatgttact   2580
agggaacatt atacttcctg taataatagg aaaagaagaa gtgttgataa taactatgct   2640
aagttaaggt ctatggggta tgcacttaca ggagcagtgc aaaccttatc tcaaatatca   2700
gatattaatg atgaaaactt acagcaagga atatatttat taagggatca tgtaataacc   2760
ttaatggaag ctacattgca tgatatatct gttatggaag gaatgtttgc tgtacaacat   2820
ttgcatacac atttgaatca tttgaagaca atgcttctag aaagaagaat agactggacc   2880
tatatgtcta gtacttggct acaacaacaa ttacagaaat ctgatgatga gatgaaagta   2940
ataaagagaa ttgctagaag tttggtatat tatgttaaac aaacccatag ttctcccaca   3000
gctacagcct gggagattgg attatattat gaattggtta tacctaaaca tatttacttg   3060
```

```
aataattgga atgttgtcaa tataggtcac ttagttaaat cagctggaca attgactcat   3120
gtaactatag ctcatcctta tgaaataatc aataaggaat gtgtagagac tatatatctg   3180
catcttgaag actgcacaag acaagattat gtcatatgtg atgtggtaaa gatagtgcag   3240
ccttgtggca atagctcaga cacgagtgat tgtcctgtct gggctgaagc tgtaaaagaa   3300
ccatttgtgc aagtcaatcc tctgaaaaac ggaagttatc tggttttggc aagttccaca   3360
gactgtcaga tcccaccata tgttcctagc atcgtgactg ttaatgaaac aacgtcatgc   3420
tttggactgg actttaaaag gccactggtt gcggaagaaa gattgagctt tgagccacga   3480
ctgccaaatc tacaactaag attaccacat ttggttggaa ttattgcaaa aatcaaaggg   3540
ataaaaatag aagtcacatc ctctggagaa agtataaaag agcagattga aagagcaaaa   3600
gctgagctcc ttcgactgga cattcacgag ggagatactc ctgcctggat acaacagcta   3660
gctgcagcaa caaaggacgt ctggccagca gcagcttctg ctctacaagg aattgggaac   3720
tttttatctg ggactgccca aggaatattt ggaactgcct ttagtctctt gggatactta   3780
aagcctatcc taataggagt aggggtcatt ctcttggtta ttcttatatt taaaattgta   3840
tcctggattc ctacgaaaaa gaagaatcag tagcctccac ctctggaatt ctgcagatat   3900
ccagcacagt ggcggccgct cgagtctaga gggcccgttt aaacccgctg atcagcctcg   3960
actgtgcctt ctagttgcca gccatctgtt gtttgcccct cccccgtgcc ttccttgacc   4020
ctggaaggtg ccactcccac tgtcctttcc taataaaatg aggaaattgc atcgcattgt   4080
ctgagtaggt gtcattctat tctggggggt ggggtggggc aggacagcaa gggggaggat   4140
tgggaagaca atagcaggca tgctggggat gcggtgggct ctatggcttc tgaggcggaa   4200
agaaccagct ggggctctag ggggtatccc cacgcgccct gtagcggcgc attaagcgcg   4260
gcgggtgtgg tggttacgcg cagcgtgacc gctacacttg ccagcgccct agcgcccgct   4320
cctttcgctt tcttcccttc ctttctcgcc acgttcgccg gctttccccg tcaagctcta   4380
aatcggggca tccctttagg gttccgattt agtgctttac ggcacctcga ccccaaaaaa   4440
cttgattagg gtgatggttc acgtagtggg ccatcgccct gatagacggt ttttcgccct   4500
ttgacgttgg agtccacgtt ctttaatagt ggactcttgt tccaaactgg aacaacactc   4560
aaccctatct cggtctattc ttttgattta taagggattt tggggatttc ggcctattgg   4620
ttaaaaaatg agctgattta acaaaaattt aacgcgaatt aattctgtgg aatgtgtgtc   4680
agttagggtg tggaaagtcc ccaggctccc caggcaggca gaagtatgca aagcatgcat   4740
ctcaattagt cagcaaccag gtgtggaaag tccccaggct ccccagcagg cagaagtatg   4800
caaagcatgc atctcaatta gtcagcaacc atagtcccgc ccctaactcc gcccatcccg   4860
cccctaactc cgcccagttc cgcccattct ccgccccatg gctgactaat tttttttatt   4920
tatgcagagg ccgaggccgc ctctgcctct gagctattcc agaagtagtg aggaggcttt   4980
tttggaggcc taggcttttg caaaaagctc ccgggagctt gtatatccat tttcggatct   5040
gatcagcacg tgttgacaat taatcatcgg catagtatat cggcatagta taatacgaca   5100
aggtgaggaa ctaaaccatg gccaagttga ccagtgccgt tccggtgctc accgcgcgcg   5160
acgtcgccgg agcggtcgag ttctggaccg accggctcgg gttctcccgg gacttcgtgg   5220
aggacgactt cgccggtgtg gtccgggacg acgtgaccct gttcatcagc gcggtccagg   5280
accaggtggt gccggacaac accctggcct gggtgtgggt gcgcggcctg gacgagctgt   5340
acgccgagtg gtcggaggtc gtgtccacga acttccggga cgcctccggg ccggccatga   5400
ccgagatcgg cgagcagccg tgggggcggg agttcgccct gcgcgacccg gccggcaact   5460
```

```
gcgtgcactt cgtggccgag gagcaggact gacacgtgct acgagatttc gattccaccg   5520
ccgccttcta tgaaaggttg ggcttcggaa tcgttttccg ggacgccggc tggatgatcc   5580
tccagcgcgg ggatctcatg ctggagttct tcgcccaccc caacttgttt attgcagctt   5640
ataatggtta caaataaagc aatagcatca caaatttcac aaataaagca tttttttcac   5700
tgcattctag ttgtggtttg tccaaactca tcaatgtatc ttatcatgtc tgtataccgt   5760
cgacctctag ctagagcttg gcgtaatcat ggtcatagct gtttcctgtg tgaaattgtt   5820
atccgctcac aattccacac aacatacgag ccggaagcat aaagtgtaaa gcctggggtg   5880
cctaatgagt gagctaactc acattaattg cgttgcgctc actgcccgct ttccagtcgg   5940
gaaacctgtc gtgccagctg cattaatgaa tcggccaacg cgcggggaga ggcggtttgc   6000
gtattgggcg ctcttccgct tcctcgctca ctgactcgct gcgctcggtc gttcggctgc   6060
ggcgagcggt atcagctcac tcaaaggcgg taatacggtt atccacagaa tcaggggata   6120
acgcaggaaa gaacatgtga gcaaaaggcc agcaaaaggc caggaaccgt aaaaaggccg   6180
cgttgctggc gtttttccat aggctccgcc cccctgacga gcatcacaaa aatcgacgct   6240
caagtcagag gtggcgaaac ccgacaggac tataaagata ccaggcgttt ccccctggaa   6300
gctccctcgt gcgctctcct gttccgaccc tgccgcttac cggatacctg tccgcctttc   6360
tcccttcggg aagcgtggcg ctttctcaat gctcacgctg taggtatctc agttcggtgt   6420
aggtcgttcg ctccaagctg ggctgtgtgc acgaaccccc cgttcagccc gaccgctgcg   6480
ccttatccgg taactatcgt cttgagtcca acccggtaag acacgactta tcgccactgg   6540
cagcagccac tggtaacagg attagcagag cgaggtatgt aggcggtgct acagagttct   6600
tgaagtggtg gcctaactac ggctacacta gaaggacagt atttggtatc tgcgctctgc   6660
tgaagccagt taccttcgga aaaagagttg gtagctcttg atccggcaaa caaaccaccg   6720
ctggtagcgg tggttttttt gtttgcaagc agcagattac gcgcagaaaa aaaggatctc   6780
aagaagatcc tttgatcttt tctacggggt ctgacgctca gtggaacgaa aactcacgtt   6840
aagggatttt ggtcatgaga ttatcaaaaa ggatcttcac ctagatcctt ttaaattaaa   6900
aatgaagttt taaatcaatc taaagtatat atgagtaaac ttggtctgac agttaccaat   6960
gcttaatcag tgaggcacct atctcagcga tctgtctatt tcgttcatcc atagttgcct   7020
gactccccgt cgtgtagata actacgatac gggagggctt accatctggc cccagtgctg   7080
caatgatacc gcgagaccca cgctcaccgg ctccagattt atcagcaata aaccagccag   7140
ccggaagggc cgagcgcaga agtggtcctg caactttatc cgcctccatc cagtctatta   7200
attgttgccg ggaagctaga gtaagtagtt cgccagttaa tagtttgcgc aacgttgttg   7260
ccattgctac aggcatcgtg gtgtcacgct cgtcgtttgg tatggcttca ttcagctccg   7320
gttcccaacg atcaaggcga gttacatgat cccccatgtt gtgcaaaaaa gcggttagct   7380
ccttcggtcc tccgatcgtt gtcagaagta agttggccgc agtgttatca ctcatggtta   7440
tggcagcact gcataattct cttactgtca tgccatccgt aagatgcttt tctgtgactg   7500
gtgagtactc aaccaagtca ttctgagaat agtgtatgcg gcgaccgagt tgctcttgcc   7560
cggcgtcaat acgggataat accgcgccac atagcagaac tttaaaagtg ctcatcattg   7620
gaaaacgttc ttcggggcga aaactctcaa ggatcttacc gctgttgaga tccagttcga   7680
tgtaacccac tcgtgcaccc aactgatctt cagcatcttt tactttcacc agcgtttctg   7740
ggtgagcaaa aacaggaagg caaaatgccg caaaaaaggg aataagggcg acacggaaat   7800
gttgaatact catactcttc ctttttcaat attattgaag catttatcag ggttattgtc   7860
```

```
tcatgagcgg atacatattt gaatgtattt agaaaaataa acaaataggg gttccgcgca   7920
catttccccg aaaagtgcca cctgacgtca tgacactgca acaatggatc atttggagaa   7980
gaatgaatag agcgcatgag gcacttcaaa atacaacaac tgtgactgaa cagcagcgcg   8040
aacaaattat actggacatt caaaatgaag aagtacaacc aactaggaga gatcgcttta   8100
gatatctgct ttatacttgt tgtgctacta gctcaagagt attggcctgg atgtttttag   8160
tttgtatatt gttaatcatt gttttggttt catgctttgt gactatatcc agaatacaat   8220
ggaataagga tattcaggta ttaggacctg taatagactg gaatgttact caaagagctg   8280
tttatcaacc cttacagact agaaggattg cacgttccct tagaatgcag catcctgttc   8340
caaaatatgt ggaggtaaat atgactagta ttccacaagg tgtatactat gaaccccatc   8400
cggaacccat agtggtgaag gagagggtcc tgggtctttc tcaaattctg atgattaatt   8460
cagaaaacat tgctaataat gctaatttga cacaagaagt aaagaagttg ttaactgaaa   8520
tggttaatga agaaatgcaa agtttgtcag atgtaatgat tgactttgaa attcctttag   8580
gagaccctcg tgatcaagaa caatatatac atagaaaatg ctatcaagaa tttgcaaatt   8640
gttatttagt aaaatataaa gaacccaaac cgtggcctaa ggagggcctt atagctgatc   8700
aatgcccatt accaggttac catgctggat taacctataa tagacagtct atttgggatt   8760
actatattaa agtggagagt attagacctg caaattggac aacaaagagt aaatatggac   8820
aagctagact aggaagtttt tatattccta gcagtctgag acaaatcaat gttagtcatg   8880
tactattctg tagtgatcaa ttatattcta aatggtataa tatagaaaat accatagaac   8940
aaaacgagcg gtttctgctt aataaactaa ataaccttac atctggaacc tcagtattga   9000
agaaaagagc tcttccgaag gattggagtt ctcaaggtaa aaatgctctg tttagagaaa   9060
tcaatgtgtt agatatctgc agtaaacctg aatctgtaat actattgaat acttcatact   9120
attccttctc tttatgggaa ggagattgta attttactaa agatatgatt tctcagttgg   9180
ttccagaatg tgatggattt tataacaatt ctaagtggat gcatatgcat ccatatgctt   9240
gtagattctg gagaagtaag aatgaaaaag aagaaactaa atgtagagat ggggaaacta   9300
agagatgtct gtattatcct ttatgggaca gtcccgaatc tacatatgat tttggttatt   9360
tagcatacca aaagaatttt ccttccccta tctgtataga acaacagaaa attagagatc   9420
aagattatga agtttattct ttgtatcaag aatgcaaaat agcttctaaa gcatatggaa   9480
ttgatacagt tttattctct ctaaagaatt ttcttaatta tacaggaact cctgtaaatg   9540
aaatgcctaa tgcaagagct tttgtaggcc taatagatcc caagtttcct ccttcctatc   9600
ccaatgttac tagggaacat tatacttcct gtaataatag gaaaagaaga agtgttgata   9660
ataactatgc taagttaagg tctatggggt atgcacttac aggagcagtg caaaccttat   9720
ctcaaatatc agatattaat gatgaaaact tacagcaagg aatatattta ttaagggatc   9780
atgtaataac cttaatggaa gctacattgc atgatatatc tgttatggaa ggaatgtttg   9840
ctgtacaaca tttgcataca catttgaatc atttgaagac aatgcttcta gaaagaagaa   9900
tagactggac ctatatgtct agtacttggc tacaacaaca attacagaaa tctgatgatg   9960
agatgaaagt aataaagaga attgctagaa gtttggtata ttatgttaaa caaacccata  10020
gttctcccac agctacagcc tgggagattg gattatatta tgaattggtt atacctaaac  10080
atatttactt gaataattgg aatgttgtca atataggtca cttagttaaa tcagctggac  10140
aattgactca tgtaactata gctcatcctt atgaaataat caataaggaa tgtgtagaga  10200
ctatatatct gcatcttgaa gactgcacaa gacaagatta tgtcatatgt gatgtggtaa  10260
```

```
agatagtgca gccttgtggc aatagctcag acacgagtga ttgtcctgtc tgggctgaag  10320

ctgtaaaaga accatttgtg caagtcaatc ctctgaaaaa cggaagttat ctggttttgg  10380

caagttccac agactgtcag atcccaccat atgttcctag catcgtgact gttaatgaaa  10440

caacgtcatg ctttggactg gactttaaaa ggccactggt tgcggaagaa agattgagct  10500

ttgagccacg actgccaaat ctacaactaa gattaccaca tttggttgga attattgcaa  10560

aaatcaaagg gataaaaata gaagtcacat cctctggaga aagtataaaa gagcagattg  10620

aaagagcaaa agctgagctc cttcgactgg acattcacga gggagatact cctgcctgga  10680

tacaacagct agctgcagca acaaaggacg tctggccagc agcagcttct gctctacaag  10740

gaattgggaa ctttttatct gggactgccc aaggaatatt tggaactgcc tttagtctct  10800

tgggatactt aaagcctatc ctaataggag taggggtcat tctcttggtt attcttatat  10860

ttaaaattgt atcctggatt cctacgaaaa agaagaatca gtag                  10904
```

```
<210> SEQ ID NO 33
<211> LENGTH: 9982
<212> TYPE: DNA
<213> ORGANISM: Artificial Sequence
<220> FEATURE:
<223> OTHER INFORMATION: Foamy Viral Envelope Gene pczHFV EM140

<400> SEQUENCE: 33
```

```
tcaatattgg ccattagcca tattattcat tggttatata gcataaatca atattggcta     60

ttggccattg catacgttgt atctatatca taatatgtac atttatattg gctcatgtcc    120

aatatgaccg ccatgttggc attgattatt gactagttat taatagtaat caattacggg    180

gtcattagtt catagcccat atatggagtt ccgcgttaca taacttacgg taaatggccc    240

gcctggctga ccgcccaacg acccccgccc attgacgtca ataatgacgt atgttcccat    300

agtaacgcca atagggactt tccattgacg tcaatgggtg gagtatttac ggtaaactgc    360

ccacttggca gtacatcaag tgtatcatat gccaagtccg ccccctattg acgtcaatga    420

cggtaaatgg cccgcctggc attatgccca gtacatgacc ttacgggact ttcctacttg    480

gcagtacatc tacgtattag tcatcgctat taccatggtg atgcggtttt ggcagtacac    540

caatgggcgt ggatagcggt ttgactcacg gggatttcca agtctccacc ccattgacgt    600

caatgggagt ttgttttggc accaaaatca acgggacttt ccaaaatgtc gtaataaccc    660

cgccccgttg acgcaaatgg gcggtaggcg tgtacggtgg gaggtctata taagcagagc    720

tcgtttagtg aaccgtcaga tcactagaag ctttattgcg gtagtttatc acagttaaat    780

tgctaacgca gtcagtgctt ctgacacaac agtctcgaac ttaagctgca gaagttggtc    840

gtgaggcact gggcaggtaa gtatcaaggt tacaagacag gtttaaggag accaatagaa    900

actgggcttg tcgagacaga gaagactctt gcgtttctga taggcaccta ttggtcttac    960

tgacatccac tttgcctttc tctccacagg tgtccactcc cagttcaatt acagctctta   1020

aggctagagt acttaatacg actcactata ggctagcctc gagaattctg cagatatcca   1080

gcacagtggc ggccgctcga gtctagactg ccatggcacc tccaatgact ctggaacaat   1140

ggctcttatg gaggaggatg agtcaagcac atcaagcact tgaaaatgta accaccttga   1200

ctgaggaaca gaggcaacaa gttataatag acattcagca tgaagatgtt gttcctacta   1260

ggatggacag attgagatat ctggcctatt catgctgcgc tactagcaca cgtgtattgt   1320

gctggatagt gttagtttgc gtcttgctat tagttgtatt tatatcctgc tttgtgacaa   1380

tgtccaggat acaatggaat aaggatattg ctgtttttgg tccagtcatt gactggaatg   1440
```

```
ttagccaaca agctgtgatt caacaaataa gagctaaaag attagcaaga tcaattaggg   1500
tggaacatgc tactgagaca tatgtagagg tcaatatgac cagtatacct caaggggtgt   1560
tatatgtgcc tcatccagaa ccaataattc tcaaggagag gattcttggt ttatctcagg   1620
tcatgatgat aaactctgaa aatattgcta atactgctaa ccttactcaa gaaactaagg   1680
tactgttagc agacatgatt aatgaagaga tgaatgattt agctaatcaa atgatagatt   1740
ttgaaatccc attaggagat cccagagatc aaaaacaata ccagcatcaa aaatgttttc   1800
aagaatttgc acattgttat ttagtaaaat ataaaactac taaaggatgg cctagttcta   1860
ctgttatagc agatcaatgc cctttgcctg gtaaccatcc tacagtacaa tatgcacatc   1920
aaaatatatg ggattattat gtccccttg  aacaaattcg gccagaagga tggaactcaa   1980
aaagttatta tgaagatgct agaataggag ggttttatat accaaaatgg ttacgaaata   2040
attcctatac ccatgtctta ttttgttctg atcaaattta tggaaaatgg tataatattg   2100
atctcacagc ccaggagagg gaaaatttat tagtccgaaa attaattaat ttagctaaag   2160
gaaattcatc acaattaaaa gatagagcta tgccagctga atgggataaa caaggaaaag   2220
ctgatctatt tagacaaatt aatactttag atgtttgtaa tagaccagaa atggtatttt   2280
tgttaaattc ctcatattat gaattttccc tatgggaagg agattgtggt tttaccagac   2340
agaatgttac acaggctaat tccttatgta aagatttcta taataactca aaatggcaaa   2400
aattacatcc atattcgtgt agattttgga gatataaaca agagaaagaa gaaactaaat   2460
gtagtaatgg tgaaaagaaa aaatgtcttt attacccaca atgggatact cctgaagctt   2520
tatatgactt tgggttccta gcatatttaa attcttttcc ttctccaatc tgtataaaaa   2580
atcagactat aagggaacct gagtataaaa tctcttcttt atacctagaa tgcatgaatg   2640
cttcagacag acatggtata gatagtgctt tattagcttt gaagacattt ttaaacttta   2700
ctggtcagtc tgtaaacgaa atgccattag ctagagcctt tgtaggcctt actgacccta   2760
aatttccacc aacatatccc aacattacaa gggaatcttc tggttgtaat aataacaaaa   2820
gaaaaaggag aagtgttaat aattatgaaa gacttagatc tatgggatat gctttaactg   2880
gagctgttca aactttatct caaatatctg atattaatga tgagaggctg caacacggag   2940
tatatttact ccgggatcat gtggtaaccc tgatggaagc tgcccttcat gatgtttcga   3000
ttatggaagg aatgttagca attcaacatg tgcatactca tctcaatcat ctcaagacca   3060
tgcttttgat gagaaagatt gattggacat tcatcagaag tgactggatt caacagcaat   3120
tacagaagac agatgatgaa atgaaattga tacgaagaac tgcacgaagt ctagtctact   3180
atgtcacaca aacctccagt tctcctacag ctacttcctg ggagattgga atatattatg   3240
aaatagtaat tcctaaacat atatatttaa ataattggca agtaatcaat gtaggtcatt   3300
tattggagtc agctggtcat ctgactcatg taaaggttaa gcatccttat gaaataatta   3360
ataaggaatg tagtgacact caatatttac atcttgagga atgcattaga gaggattatg   3420
tgatttgtga catagtacaa atagttcaac catgtggaaa tgcaacagaa ttgagtgatt   3480
gtccagtaac agcattaaag gtgaagactc catatattca agtgtctccc ctgaagaatg   3540
gaagttattt agttttatct agtactaagg attgttctat acctgcatat gtacctagtg   3600
tggtcacagt caatgaaaca gttaagtgct ttggagtaga gtttcacaaa ccactttatg   3660
ctgaaacaaa aaccagctat gaaccacaag ttccgcattt gaagcttcgt ttaccccact   3720
tgactgggat tattgccagc ttgcaatcac tggaaataga agttacttct acacaagaga   3780
atataaaaga ccagatcgaa agggccaaag cacagcttct ccggctggac attcacgaag   3840
```

```
gagactttcc tgactggctg aaacaagtcg cctctgcaac cagggacgtt tggcctgctg   3900
cagcttcctt tatacaagga gtagggaact tcttatctaa tactgcccag ggatattcg    3960
gctcagcggt aagcctccta tcctatgcaa aacctatttt gataggaata ggagttatac   4020
tgcttattgc ccttcttttt aaaataatat cgtggcttcc tgggaagccc aagaagaatt   4080
gatctagagg gcccgtttgg gcggccgctt cgagcagaca tgataagata cattgatgag   4140
tttggacaaa ccacaactag aatgcagtga aaaaaatgct ttatttgtga aatttgtgat   4200
gctattgctt tatttgtaac cattataagc tgcaataaac aagttaacaa caacaattgc   4260
attcatttta tgtttcaggt tcagggggag atgtgggagg tttttaaag caagtaaaac    4320
ctctacaaat gtggtaaaat cgataaggat ccgggctggc gtaatagcga agaggcccgc   4380
accgatcgcc cttcccaaca gttgcgcagc ctgaatggcg aatggacgcg ccctgtagcg   4440
gcgcattaag cgcggcgggt gtggtggtta cgcgcagcgt gaccgctaca cttgccagcg   4500
ccctagcgcc cgctcctttc gctttcttcc cttcctttct cgccacgttc gccggctttc   4560
cccgtcaagc tctaaatcgg gggctccctt tagggttccg atttagagct ttacggcacc   4620
tcgaccgcaa aaaacttgat ttgggtgatg gttcacgtag tgggccatcg ccctgataga   4680
cggtttttcg ccctttgacg ttggagtcca cgttctttaa tagtggactc ttgttccaaa   4740
ctggaacaac actcaaccct atctcggtct attcttttga tttataaggg attttgccga   4800
tttcggccta ttggttaaaa aatgagctga tttaacaaat atttaacgcg aattttaaca   4860
aaatattaac gtttacaatt tcgcctgatg cggtattttc tccttacgca tctgtgcggt   4920
atttcacacc gcatatggtg cactctcagt acaatctgct ctgatgccgc atagttaagc   4980
cagccccgac acccgccaac acccgctgac gcgccctgac gggcttgtct gctcccggca   5040
tccgcttaca gacaagctgt gaccgtctcc gggagctgca tgtgtcagag gttttcaccg   5100
tcatcaccga aacgcgcgag acgaaagggc ctcgtgatac gcctattttt ataggttaat   5160
gtcatgataa taatggtttc ttagacgtca ggtggcactt ttcggggaaa tgtgcgcgga   5220
acccctattt gtttattttt ctaaatacat tcaaatatgt atccgctcat gagacaataa   5280
ccctgataaa tgcttcaata atattgaaaa aggaagagta tgagtattca acatttccgt   5340
gtcgccctta ttcccttttt tgcggcattt tgccttcctg tttttgctca cccagaaacg   5400
ctggtgaaag taaaagatgc tgaagatcag ttgggtgcac gagtgggtta catcgaactg   5460
gatctcaaca gcggtaagat ccttgagagt tttcgccccg aagaacgttt tccaatgatg   5520
agcactttta aagttctgct atgtggcgcg gtattatccc gtattgacgc cgggcaagag   5580
caactcggtc gccgcataca ctattctcag aatgacttgg ttgagtactc accagtcaca   5640
gaaaagcatc ttacggatgg catgacagta agagaattat gcagtgctgc cataaccatg   5700
agtgataaca ctgcggccaa cttacttctg acaacgatcg gaggaccgaa ggagctaacc   5760
gcttttttgc acaacatggg ggatcatgta actcgccttg atcgttggga accggagctg   5820
aatgaagcca taccaaacga cgagcgtgac accacgatgc ctgtagcaat ggcaacaacg   5880
ttgcgcaaac tattaactgg cgaactactt actctagctt cccggcaaca attaatagac   5940
tggatggagg cggataaagt tgcaggacca cttctgcgct cggcccttcc ggctggctgg   6000
tttattgctg ataaatctgg agccggtgag cgtgggtctc gcggtatcat tgcagcactg   6060
gggccagatg gtaagccctc ccgtatcgta gttatctaca cgacggggag tcaggcaact   6120
atggatgaac gaaatagaca gatcgctgag ataggtgcct cactgattaa gcattggtaa   6180
ctgtcagacc aagtttactc atatatactt tagattgatt taaaacttca tttttaattt   6240
```

```
aaaaggatct aggtgaagat cctttttgat aatctcatga ccaaaatccc ttaacgtgag   6300
ttttcgttcc actgagcgtc agaccccgta gaaaagatca aaggatcttc ttgagatcct   6360
tttttctgc gcgtaatctg ctgcttgcaa acaaaaaaac caccgctacc agcggtggtt   6420
tgtttgccgg atcaagagct accaactctt tttccgaagg taactggctt cagcagagcg   6480
cagataccaa atactgtcct tctagtgtag ccgtagttag gccaccactt caagaactct   6540
gtagcaccgc ctacatacct cgctctgcta atcctgttac cagtggctgc tgccagtggc   6600
gataagtcgt gtcttaccgg gttggactca agacgatagt taccggataa ggcgcagcgg   6660
tcgggctgaa cggggggttc gtgcacacag cccagcttgg agcgaacgac ctacaccgaa   6720
ctgagatacc tacagcgtga gctatgagaa agcgccacgc ttcccgaagg gagaaaggcg   6780
gacaggtatc cggtaagcgg cagggtcgga acaggagagc gcacgaggga gcttccaggg   6840
ggaaacgcct ggtatcttta tagtcctgtc gggtttcgcc acctctgact tgagcgtcga   6900
tttttgtgat gctcgtcagg ggggcggagc ctatggaaaa acgccagcaa cgcggccttt   6960
ttacggttcc tggccttttg ctggcctttt gctcacatgg ctcgacagat ctatggcacc   7020
tccaatgact ctggaacaat ggctcttatg gaggaggatg agtcaagcac atcaagcact   7080
tgaaaatgta accaccttga ctgaggaaca gaggcaacaa gttataatag acattcagca   7140
tgaagatgtt gttcctacta ggatggacag attgagatat ctggcctatt catgctgcgc   7200
tactagcaca cgtgtattgt gctggatagt gttagtttgc gtcttgctat tagttgtatt   7260
tatatcctgc tttgtgacaa tgtccaggat acaatggaat aaggatattg ctgtttttgg   7320
tccagtcatt gactggaatg ttagccaaca agctgtgatt caacaaataa gagctaaaag   7380
attagcaaga tcaattaggg tggaacatgc tactgagaca tatgtagagg tcaatatgac   7440
cagtatacct caaggggtgt tatatgtgcc tcatccagaa ccaataattc tcaaggagag   7500
gattcttggt ttatctcagg tcatgatgat aaactctgaa aatattgcta atactgctaa   7560
ccttactcaa gaaactaagg tactgttagc agacatgatt aatgaagaga tgaatgattt   7620
agctaatcaa atgatagatt ttgaaatccc attaggagat cccagagatc aaaaacaata   7680
ccagcatcaa aaatgttttc aagaatttgc acattgttat ttagtaaaat ataaaactac   7740
taaaggatgg cctagttcta ctgttatagc agatcaatgc cctttgcctg gtaaccatcc   7800
tacagtacaa tatgcacatc aaaatatatg ggattattat gtccccttg aacaaattcg   7860
gccagaagga tggaactcaa aaagttatta tgaagatgct agaataggag ggttttatat   7920
accaaaatgg ttacgaaata attcctatac ccatgtctta ttttgttctg atcaaattta   7980
tggaaaatgg tataatattg atctcacagc ccaggagagg gaaaatttat tagtccgaaa   8040
attaattaat ttagctaaag gaaattcatc acaattaaaa gatagagcta tgccagctga   8100
atgggataaa caaggaaaag ctgatctatt tagacaaatt aatactttag atgtttgtaa   8160
tagaccagaa atggtatttt tgttaaattc ctcatattat gaattttccc tatgggaagg   8220
agattgtggt tttaccagac agaatgttac acaggctaat tccttatgta aagatttcta   8280
taataactca aaatggcaaa aattacatcc atattcgtgt agattttgga gatataaaca   8340
agagaaagaa gaaactaaat gtagtaatgg tgaaaagaaa aaatgtcttt attacccaca   8400
atgggatact cctgaagctt tatatgactt tgggttccta gcatatttaa attcttttcc   8460
ttctccaatc tgtataaaaa atcagactat aagggaacct gagtataaaa tctcttcttt   8520
atacctagaa tgcatgaatg cttcagacag acatggtata gatagtgctt tattagcttt   8580
gaagacattt ttaaacttta ctggtcagtc tgtaaacgaa atgccattag ctagagcctt   8640
```

```
tgtaggcctt actgacccta aatttccacc aacatatccc aacattacaa gggaatcttc   8700

tggttgtaat aataacaaaa gaaaaaggag aagtgttaat aattatgaaa gacttagatc   8760

tatgggatat gctttaactg gagctgttca aactttatct caaatatctg atattaatga   8820

tgagaggctg caacacggag tatatttact ccgggatcat gtggtaaccc tgatggaagc   8880

tgcccttcat gatgtttcga ttatggaagg aatgttagca attcaacatg tgcatactca   8940

tctcaatcat ctcaagacca tgcttttgat gagaaagatt gattggacat tcatcagaag   9000

tgactggatt caacagcaat tacagaagac agatgatgaa atgaaattga tacgaagaac   9060

tgcacgaagt ctagtctact atgtcacaca aacctccagt tctcctacag ctacttcctg   9120

ggagattgga atatattatg aaatagtaat tcctaaacat atatatttaa ataattggca   9180

agtaatcaat gtaggtcatt tattggagtc agctggtcat ctgactcatg taaaggttaa   9240

gcatccttat gaaataatta ataaggaatg tagtgacact caatatttac atcttgagga   9300

atgcattaga gaggattatg tgatttgtga catagtacaa atagttcaac catgtggaaa   9360

tgcaacagaa ttgagtgatt gtccagtaac agcattaaag gtgaagactc catatattca   9420

agtgtctccc ctgaagaatg gaagttattt agttttatct agtactaagg attgttctat   9480

acctgcatat gtacctagtg tggtcacagt caatgaaaca gttaagtgct ttggagtaga   9540

gtttcacaaa ccactttatg ctgaaacaaa aaccagctat gaaccacaag ttccgcattt   9600

gaagcttcgt ttaccccact tgactgggat tattgccagc ttgcaatcac tggaaataga   9660

agttacttct acacaagaga atataaaaga ccagatcgaa agggccaaag cacagcttct   9720

ccggctggac attcacgaag gagactttcc tgactggctg aaacaagtcg cctctgcaac   9780

cagggacgtt tggcctgctg cagcttcctt tatacaagga gtagggaact tcttatctaa   9840

tactgcccag gggatattcg gctcagcggt aagcctccta tcctatgcaa aacctatttt   9900

gataggaata ggagttatac tgcttattgc ccttcttttt aaaataatat cgtggcttcc   9960

tgggaagccc aagaagaatt ga                                            9982
```

```
<210> SEQ ID NO 34
<211> LENGTH: 10929
<212> TYPE: DNA
<213> ORGANISM: Artificial Sequence
<220> FEATURE:
<223> OTHER INFORMATION: Foamy Viral Envelope Gene pczHFV EM002

<400> SEQUENCE: 34
```

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720
```

```
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctaga    900
aaacctacgt ctcatcagaa tggcaccacc aatgacactg caacaatgga tcatttggag    960
aagaatgaat agagcgcatg aggcacttca aaatacaaca actgtgactg aacagcagcg   1020
cgaacaaatt atactggaca ttcaaaatga agaagtacaa ccaactagga gagatcgctt   1080
tagatatctg ctttatactt gttgtgctac tagctcaaga gtattggcct ggatgttttt   1140
agtttgtata ttgttaatca ttgttttggt ttcatgcttt gtgactatat ccagaataca   1200
atggaataag gatattcagg tattaggacc tgtaatagac tggaatgtta ctcaaagagc   1260
tgtttatcaa cccttacaga ctagaaggat tgcacgttcc cttagaatgc agcatcctgt   1320
tccaaaatat gtggaggtaa atatgactag tattccacaa ggtgtatact atgaacccca   1380
tccggaaccc atagtggtga aggagagggt cctgggtctt tctcaaattc tgatgattaa   1440
ttcagaaaac attgctaata atgctaattt gacacaagaa gtaaagaagt tgttaactga   1500
aatggttaat gaagaaatgc aaagtttgtc agatgtaatg attgactttg aaattccttt   1560
aggagaccct cgtgatcaag aacaatatat acatagaaaa tgctatcaag aatttgcaaa   1620
ttgttattta gtaaaatata aagaacccaa accgtggcct aaggagggcc ttatagctga   1680
tcaatgccca ttaccaggtt accatgctgg attaacctat aatagacagt ctatttggga   1740
ttactatatt aaagtggaga gtattagacc tgcaaattgg acaacaaaga gtaaatatgg   1800
acaagctaga ctaggaagtt tttatattcc tagcagtctg agacaaatca atgttagtca   1860
tgtactattc tgtagtgatc aattatattc taaatggtat aatatagaaa ataccataga   1920
acaaaacgag cggtttctgc ttaataaact aaataacctt acatctggaa cctcagtatt   1980
gaagaaaaga gctcttccga aggattggag ttctcaaggt aaaaatgctc tgtttagaga   2040
aatcaatgtg ttagatatct gcagtaaacc tgaatctgta atactattga atacttcata   2100
ctattccttc tctttatggg aaggagattg taattttact aaagatatga tttctcagtt   2160
ggttccagaa tgtgatggat tttataacaa ttctaagtgg atgcatatgc atccatatgc   2220
ttgtagattc tggagaagta agaatgaaaa agaagaaact aaatgtagag atggggaaac   2280
taagagatgt ctgtattatc ctttatggga cagtcccgaa tctacatatg attttggtta   2340
tttagcatac caaaagaatt ttccttcccc tatctgtata gaacaacaga aaattagaga   2400
tcaagattat gaagtttatt ctttgtatca agaatgcaaa atagcttcta aagcatatgg   2460
aattgataca gttttattct ctctaaagaa ttttcttaat tatacaggaa ctcctgtaaa   2520
tgaaatgcct aatgcaagag cttttgtagg cctaatagat cccaagtttc ctccttccta   2580
tcccaatgtt actagggaac attatacttc ctgtaataat aggaaaagaa gaagtgttga   2640
taataactat gctaagttaa ggtctatggg gtatgcactt acaggagcag tgcaaacctt   2700
atctcaaata tcagatatta atgatgaaaa cttacagcaa ggaatatatt tattaaggga   2760
tcatgtaata accttaatgg aagctacatt gcatgatata tctgttatgg aaggaatgtt   2820
tgctgtacaa catttgcata cacatttgaa tcatttgaag acaatgcttc tagaaagaag   2880
aatagactgg acctatatgt ctagtacttg gctacaacaa caattacaga aatctgatga   2940
tgagatgaaa gtaataaaga gaattgctag aagtttggta tattatgtta aacaaaccca   3000
tagttctccc acagctacag cctgggagat tggattatat tatgaattgg ttatacctaa   3060
acatatttac ttgaataatt ggaatgttgt caatataggt cacttagtta aatcagctgg   3120
```

-continued

```
acaattgact catgtaacta tagctcatcc ttatgaaata atcaataagg aatgtgtaga   3180
gactatatat ctgcatcttg aagactgcac aagacaagat tatgtcatat gtgatgtggt   3240
aaagatagtg cagccttgtg gcaatagctc agacacgagt gattgtcctg tctgggctga   3300
agctgtaaaa gaaccatttg tgcaagtcaa tcctctgaaa aacggaagtt atctggtttt   3360
ggcaagttcc acagactgtc agatcccacc atatgttcct agcatcgtga ctgttaatga   3420
aacaacgtca tgctttggac tggactttaa aaggccactg gttgcggaag aaagattgag   3480
ctttgagcca cgactgccaa atctacaact aagattacca catttggttg gaattattgc   3540
aaaaatcaaa gggataaaaa tagaagtcac atcctctgga gaaagtataa aagagcagat   3600
tgaaagagca aaagctgagc tccttcgact ggacattcac gagggagata ctcctgcctg   3660
gatacaacag ctagctgcag caacaaagga cgtctggcca gcagcagctt ctgctctaca   3720
aggaattggg aactttttat ctgggactgc ccaaggaata tttggaactg cctttagtct   3780
cttgggatac ttaaagccta tcctaatagg agtaggggtc attctcttgg ttattcttat   3840
atttaaaatt gtatcctgga ttcctacgaa aaagaagaat cagtagcctc cacctctgga   3900
attctgcaga tatccagcac agtggcggcc gctcgagtct agagggcccg tttaaacccg   3960
ctgatcagcc tcgactgtgc cttctagttg ccagccatct gttgtttgcc cctcccccgt   4020
gccttccttg accctggaag gtgccactcc cactgtcctt tcctaataaa atgaggaaat   4080
tgcatcgcat tgtctgagta ggtgtcattc tattctgggg ggtggggtgg ggcaggacag   4140
caagggggag gattgggaag acaatagcag gcatgctggg gatgcggtgg gctctatggc   4200
ttctgaggcg gaaagaacca gctggggctc taggggggtat ccccacgcgc cctgtagcgg   4260
cgcattaagc gcggcgggtg tggtggttac gcgcagcgtg accgctacac ttgccagcgc   4320
cctagcgccc gctcctttcg ctttcttccc ttcctttctc gccacgttcg ccggctttcc   4380
ccgtcaagct ctaaatcggg gcatcccttt agggttccga tttagtgctt tacggcacct   4440
cgaccccaaa aaacttgatt agggtgatgg ttcacgtagt gggccatcgc cctgatagac   4500
ggtttttcgc cctttgacgt tggagtccac gttctttaat agtggactct tgttccaaac   4560
tggaacaaca ctcaacccta tctcggtcta ttcttttgat ttataaggga ttttggggat   4620
ttcggcctat tggttaaaaa atgagctgat ttaacaaaaa tttaacgcga attaattctg   4680
tggaatgtgt gtcagttagg gtgtggaaag tccccaggct ccccaggcag gcagaagtat   4740
gcaaagcatg catctcaatt agtcagcaac caggtgtgga aagtccccag gctccccagc   4800
aggcagaagt atgcaaagca tgcatctcaa ttagtcagca accatagtcc cgcccctaac   4860
tccgcccatc ccgcccctaa ctccgcccag ttccgcccat tctccgcccc atggctgact   4920
aattttttttt atttatgcag aggccgaggc cgcctctgcc tctgagctat tccagaagta   4980
gtgaggaggc ttttttggag gcctaggctt ttgcaaaaag ctcccgggag cttgtatatc   5040
cattttcgga tctgatcagc acgtgttgac aattaatcat cggcatagta tatcggcata   5100
gtataatacg acaaggtgag gaactaaacc atggccaagt tgaccagtgc cgttccggtg   5160
ctcaccgcgc gcgacgtcgc cggagcggtc gagttctgga ccgaccggct cgggttctcc   5220
cgggacttcg tggaggacga cttcgccggt gtggtccggg acgacgtgac cctgttcatc   5280
agcgcggtcc aggaccaggt ggtgccggac aacaccctgg cctgggtgtg ggtgcgcggc   5340
ctggacgagc tgtacgccga gtggtcggag gtcgtgtcca cgaacttccg ggacgcctcc   5400
gggccggcca tgaccgagat cggcgagcag ccgtgggggc gggagttcgc cctgcgcgac   5460
ccggccggca actgcgtgca cttcgtggcc gaggagcagg actgacacgt gctacgagat   5520
```

ttcgattcca ccgccgcctt ctatgaaagg ttgggcttcg gaatcgtttt ccgggacgcc 5580
ggctggatga tcctccagcg cggggatctc atgctggagt tcttcgccca ccccaacttg 5640
tttattgcag cttataatgg ttacaaataa agcaatagca tcacaaattt cacaaataaa 5700
gcattttttt cactgcattc tagttgtggt ttgtccaaac tcatcaatgt atcttatcat 5760
gtctgtatac cgtcgacctc tagctagagc ttggcgtaat catggtcata gctgtttcct 5820
gtgtgaaatt gttatccgct cacaattcca cacaacatac gagccggaag cataaagtgt 5880
aaagcctggg gtgcctaatg agtgagctaa ctcacattaa ttgcgttgcg ctcactgccc 5940
gctttccagt cgggaaacct gtcgtgccag ctgcattaat gaatcggcca acgcgcgggg 6000
agaggcggtt tgcgtattgg gcgctcttcc gcttcctcgc tcactgactc gctgcgctcg 6060
gtcgttcggc tgcggcgagc ggtatcagct cactcaaagg cggtaatacg gttatccaca 6120
gaatcagggg ataacgcagg aaagaacatg tgagcaaaag gccagcaaaa ggccaggaac 6180
cgtaaaaagg ccgcgttgct ggcgtttttc cataggctcc gcccccctga cgagcatcac 6240
aaaaatcgac gctcaagtca gaggtggcga aacccgacag gactataaag ataccaggcg 6300
tttccccctg gaagctccct cgtgcgctct cctgttccga ccctgccgct taccggatac 6360
ctgtccgcct ttctcccttc gggaagcgtg gcgctttctc aatgctcacg ctgtaggtat 6420
ctcagttcgg tgtaggtcgt tcgctccaag ctgggctgtg tgcacgaacc ccccgttcag 6480
cccgaccgct gcgccttatc cggtaactat cgtcttgagt ccaacccggt aagacacgac 6540
ttatcgccac tggcagcagc cactggtaac aggattagca gagcgaggta tgtaggcggt 6600
gctacagagt tcttgaagtg gtggcctaac tacggctaca ctagaaggac agtatttggt 6660
atctgcgctc tgctgaagcc agttaccttc ggaaaaagag ttggtagctc ttgatccggc 6720
aaacaaacca ccgctggtag cggtggtttt tttgtttgca agcagcagat tacgcgcaga 6780
aaaaaaggat ctcaagaaga tcctttgatc ttttctacgg ggtctgacgc tcagtggaac 6840
gaaaactcac gttaagggat tttggtcatg agattatcaa aaaggatctt cacctagatc 6900
cttttaaatt aaaaatgaag ttttaaatca atctaaagta tatatgagta aacttggtct 6960
gacagttacc aatgcttaat cagtgaggca cctatctcag cgatctgtct atttcgttca 7020
tccatagttg cctgactccc cgtcgtgtag ataactacga tacgggaggg cttaccatct 7080
ggccccagtg ctgcaatgat accgcgagac ccacgctcac cggctccaga tttatcagca 7140
ataaaccagc cagccggaag ggccgagcgc agaagtggtc ctgcaacttt atccgcctcc 7200
atccagtcta ttaattgttg ccgggaagct agagtaagta gttcgccagt taatagtttg 7260
cgcaacgttg ttgccattgc tacaggcatc gtggtgtcac gctcgtcgtt tggtatggct 7320
tcattcagct ccggttccca acgatcaagg cgagttacat gatcccccat gttgtgcaaa 7380
aaagcggtta gctccttcgg tcctccgatc gttgtcagaa gtaagttggc cgcagtgtta 7440
tcactcatgg ttatggcagc actgcataat tctcttactg tcatgccatc cgtaagatgc 7500
ttttctgtga ctggtgagta ctcaaccaag tcattctgag aatagtgtat gcggcgaccg 7560
agttgctctt gcccggcgtc aatacgggat aataccgcgc cacatagcag aactttaaaa 7620
gtgctcatca ttggaaaacg ttcttcgggg cgaaaactct caaggatctt accgctgttg 7680
agatccagtt cgatgtaacc cactcgtgca cccaactgat cttcagcatc ttttactttc 7740
accagcgttt ctgggtgagc aaaaacagga aggcaaaatg ccgcaaaaaa gggaataagg 7800
gcgacacgga aatgttgaat actcatactc ttcctttttc aatattattg aagcatttat 7860
cagggttatt gtctcatgag cggatacata tttgaatgta tttagaaaaa taaacaaata 7920

```
ggggttccgc gcacatttcc ccgaaaagtg ccacctgacg tcatggcacc accaatgaca   7980
ctgcaacaat ggatcatttg gagaagaatg aatagagcgc atgaggcact tcaaaataca   8040
acaactgtga ctgaacagca gcgcgaacaa attatactgg acattcaaaa tgaagaagta   8100
caaccaacta ggagagatcg ctttagatat ctgctttata cttgttgtgc tactagctca   8160
agagtattgg cctggatgtt tttagtttgt atattgttaa tcattgtttt ggtttcatgc   8220
tttgtgacta tatccagaat acaatggaat aaggatattc aggtattagg acctgtaata   8280
gactggaatg ttactcaaag agctgtttat caacccttac agactagaag gattgcacgt   8340
tcccttagaa tgcagcatcc tgttccaaaa tatgtggagg taaatatgac tagtattcca   8400
caaggtgtat actatgaacc ccatccggaa cccatagtgg tgaaggagag ggtcctgggt   8460
ctttctcaaa ttctgatgat taattcagaa aacattgcta ataatgctaa tttgacacaa   8520
gaagtaaaga agttgttaac tgaaatggtt aatgaagaaa tgcaaagttt gtcagatgta   8580
atgattgact ttgaaattcc tttaggagac cctcgtgatc aagaacaata tatacataga   8640
aaatgctatc aagaatttgc aaattgttat ttagtaaaat ataaagaacc caaaccgtgg   8700
cctaaggagg gccttatagc tgatcaatgc ccattaccag gttaccatgc tggattaacc   8760
tataatagac agtctatttg ggattactat attaaagtgg agagtattag acctgcaaat   8820
tggacaacaa agagtaaata tggacaagct agactaggaa gtttttatat tcctagcagt   8880
ctgagacaaa tcaatgttag tcatgtacta ttctgtagtg atcaattata ttctaaatgg   8940
tataatatag aaaataccat agaacaaaac gagcggtttc tgcttaataa actaaataac   9000
cttacatctg gaacctcagt attgaagaaa agagctcttc cgaaggattg gagttctcaa   9060
ggtaaaaatg ctctgtttag agaaatcaat gtgttagata tctgcagtaa acctgaatct   9120
gtaatactat tgaatacttc atactattcc ttctctttat gggaaggaga ttgtaatttt   9180
actaaagata tgatttctca gttggttcca gaatgtgatg gattttataa caattctaag   9240
tggatgcata tgcatcccata tgcttgtaga ttctggagaa gtaagaatga aaaagaagaa   9300
actaaatgta gagatgggga aactaagaga tgtctgtatt atcctttatg ggacagtccc   9360
gaatctacat atgattttgg ttatttagca taccaaaaga atttccttc ccctatctgt   9420
atagaacaac agaaaattag agatcaagat tatgaagttt attctttgta tcaagaatgc   9480
aaaatagctt ctaaagcata tggaattgat acagttttat tctctctaaa gaattttctt   9540
aattatacag gaactcctgt aaatgaaatg cctaatgcaa gagcttttgt aggcctaata   9600
gatcccaagt ttcctccttc ctatcccaat gttactaggg aacattatac ttcctgtaat   9660
aataggaaaa gaagaagtgt tgataataac tatgctaagt taaggtctat ggggtatgca   9720
cttacaggag cagtgcaaac cttatctcaa atatcagata ttaatgatga aaacttacag   9780
caaggaatat atttattaag ggatcatgta ataaccttaa tggaagctac attgcatgat   9840
atatctgtta tggaaggaat gtttgctgta caacatttgc atacacattt gaatcatttg   9900
aagacaatgc ttctagaaag aagaatagac tggacctata tgtctagtac ttggctacaa   9960
caacaattac agaaatctga tgatgagatg aaagtaataa agagaattgc tagaagtttg  10020
gtatattatg ttaaacaaac ccatagttct cccacagcta cagcctggga gattggatta  10080
tattatgaat tggttatacc taaacatatt tacttgaata attggaatgt tgtcaatata  10140
ggtcacttag ttaaatcagc tggacaattg actcatgtaa ctatagctca tccttatgaa  10200
ataatcaata aggaatgtgt agagactata tatctgcatc ttgaagactg cacaagacaa  10260
gattatgtca tatgtgatgt ggtaaagata gtgcagcctt gtggcaatag ctcagacacg  10320
```

```
agtgattgtc ctgtctgggc tgaagctgta aaagaaccat ttgtgcaagt caatcctctg  10380

aaaaacggaa gttatctggt tttggcaagt tccacagact gtcagatccc accatatgtt  10440

cctagcatcg tgactgttaa tgaaacaacg tcatgctttg gactggactt taaaaggcca  10500

ctggttgcgg aagaaagatt gagctttgag ccacgactgc caaatctaca actaagatta  10560

ccacatttgg ttggaattat tgcaaaaatc aaagggataa aaatagaagt cacatcctct  10620

ggagaaagta taaaagagca gattgaaaga gcaaaagctg agctccttcg actggacatt  10680

cacgagggag atactcctgc ctggatacaa cagctagctg cagcaacaaa ggacgtctgg  10740

ccagcagcag cttctgctct acaaggaatt gggaactttt tatctgggac tgcccaagga  10800

atatttggaa ctgcctttag tctcttggga tacttaaagc ctatcctaat aggagtaggg  10860

gtcattctct tggttattct tatatttaaa attgtatcct ggattcctac gaaaaagaag  10920

aatcagtag                                                          10929
```

```
<210> SEQ ID NO 35
<211> LENGTH: 10915
<212> TYPE: DNA
<213> ORGANISM: Artificial Sequence
<220> FEATURE:
<223> OTHER INFORMATION: Foamy Viral Envelope Gene pczHFV EM134

<400> SEQUENCE: 35

gacggatcgg gagatctccc gatcccctat ggtcgactct cagtacaatc tgctctgatg    60

ccgcatagtt aagccagtat ctgctccctg cttgtgtgtt ggaggtcgct gagtagtgcg   120

cgagcaaaat ttaagctaca acaaggcaag gcttgaccga caattgcatg aagaatctgc   180

ttagggttag gcgttttgcg ctgcttcgcg atgtacgggc cagatatacg cgttgacatt   240

gattattgac tagttattaa tagtaatcaa ttacggggtc attagttcat agcccatata   300

tggagttccg cgttacataa cttacggtaa atggcccgcc tggctgaccg cccaacgacc   360

cccgcccatt gacgtcaata atgacgtatg ttcccatagt aacgccaata gggactttcc   420

attgacgtca atgggtggac tatttacggt aaactgccca cttggcagta catcaagtgt   480

atcatatgcc aagtacgccc cctattgacg tcaatgacgg taaatggccc gcctggcatt   540

atgcccagta catgacctta tgggactttc ctacttggca gtacatctac gtattagtca   600

tcgctattac catggtgatg cggttttggc agtacatcaa tgggcgtgga tagcggtttg   660

actcacgggg atttccaagt ctccacccca ttgacgtcaa tgggagtttg ttttggcacc   720

aaaatcaacg ggactttcca aaatgtcgta acaactccgc cccattgacg caaatgggcg   780

gtaggcgtgt acggtgggag gtctatataa gcagagctct ctggctaact agagaaccca   840

ctgcttactg gcttatcgaa attaatacga ctcactatag ggagacccaa gctggctaga   900

ctgccatggc accaccaatg acactgcaac aatggatcat ttggaaaaaa atgaataaag   960

cgcatgaggc acttcaaaat acaacaactg tgactgaaca gcagaaggaa caaattatac  1020

tggacattca aaatgaagaa gtacaaccaa ctaggagaga taaatttaga tatctgcttt  1080

atacttgttg tgctactagc tcaagagtat tggcctggat gtttttagtt tgtatattgt  1140

taatcattgt tttggtttca tgctttgtga ctatatccag aatacaatgg aataaggata  1200

ttcaggtatt aggacctgta atagactgga atgttactca aagagctgtt tatcaaccct  1260

tacagactag aaggattgca cgttccctta gaatgcagca tcctgttcca aaatatgtgg  1320

aggtaaatat gactagtatt ccacaaggtg tatactatga accccatccg gaacccatag  1380

tggtgaagga gagggtcctg ggtctttctc aaattctgat gattaattca gaaaacattg  1440
```

```
ctaataatgc taatttgaca caagaagtaa agaagttgtt aactgaaatg gttaatgaag   1500
aaatgcaaag tttgtcagat gtaatgattg actttgaaat tcctttagga gaccctcgtg   1560
atcaagaaca atatatacat agaaaatgct atcaagaatt tgcaaattgt tatttagtaa   1620
aatataaaga acccaaaccg tggcctaagg agggccttat agctgatcaa tgcccattac   1680
caggttacca tgctggatta acctataata gacagtctat ttgggattac tatattaaag   1740
tggagagtat tagacctgca aattggacaa caaagagtaa atatggacaa gctagactag   1800
gaagttttta tattcctagc agtctgagac aaatcaatgt tagtcatgta ctattctgta   1860
gtgatcaatt atattctaaa tggtataata tagaaaatac catagaacaa aacgagcggt   1920
ttctgcttaa taaactaaat aaccttacat ctggaacctc agtattgaag aaaagagctc   1980
ttccgaagga ttggagttct caaggtaaaa atgctctgtt tagagaaatc aatgtgttag   2040
atatctgcag taaacctgaa tctgtaatac tattgaatac ttcatactat tccttctctt   2100
tatgggaagg agattgtaat tttactaaag atatgatttc tcagttggtt ccagaatgtg   2160
atggatttta taacaattct aagtggatgc atatgcatcc atatgcttgt agattctgga   2220
gaagtaagaa tgaaaaagaa gaaactaaat gtagagatgg ggaaactaag agatgtctgt   2280
attatccttt atgggacagt cccgaatcta catatgattt tggttattta gcataccaaa   2340
agaattttcc ttcccctatc tgtatagaac aacagaaaat tagagatcaa gattatgaag   2400
tttattcttt gtatcaagaa tgcaaaatag cttctaaagc atatggaatt gatacagttt   2460
tattctctct aaagaatttt cttaattata caggaactcc tgtaaatgaa atgcctaatg   2520
caagagcttt tgtaggccta atagatccca agtttcctcc ttcctatccc aatgttacta   2580
gggaacatta tacttcctgt aataatagga aaagaagaag tgttgataat aactatgcta   2640
agttaaggtc tatggggtat gcacttacag gagcagtgca aaccttatct caaatatcag   2700
atattaatga tgaaaactta cagcaaggaa tatatttatt aagggatcat gtaataacct   2760
taatggaagc tacattgcat gatatatctg ttatggaagg aatgtttgct gtacaacatt   2820
tgcatacaca tttgaatcat ttgaagacaa tgcttctaga aagaagaata gactggacct   2880
atatgtctag tacttggcta caacaacaat tacagaaatc tgatgatgag atgaaagtaa   2940
taaagagaat tgctagaagt ttggtatatt atgttaaaca aacccatagt tctcccacag   3000
ctacagcctg ggagattgga ttatattatg aattggttat acctaaacat atttacttga   3060
ataattggaa tgttgtcaat ataggtcact tagttaaatc agctggacaa ttgactcatg   3120
taactatagc tcatccttat gaaataatca ataaggaatg tgtagagact atatatctgc   3180
atcttgaaga ctgcacaaga caagattatg tcatatgtga tgtggtaaag atagtgcagc   3240
cttgtggcaa tagctcagac acgagtgatt gtcctgtctg ggctgaagct gtaaaagaac   3300
catttgtgca agtcaatcct ctgaaaaacg gaagttatct ggttttggca agttccacag   3360
actgtcagat cccaccatat gttcctagca tcgtgactgt taatgaaaca acgtcatgct   3420
ttggactgga ctttaaaagg ccactggttg cggaagaaag attgagcttt gagccacgac   3480
tgccaaatct acaactaaga ttaccacatt tggttggaat tattgcaaaa atcaaaggga   3540
taaaaataga agtcacatcc tctggagaaa gtataaaaga gcagattgaa agagcaaaag   3600
ctgagctcct tcgactggac attcacgagg gagatactcc tgcctggata caacagctag   3660
ctgcagcaac aaaggacgtc tggccagcag cagcttctgc tctacaagga attgggaact   3720
ttttatctgg gactgcccaa ggaatatttg gaactgcctt tagtctcttg ggatacttaa   3780
agcctatcct aataggagta ggggtcattc tcttggttat tcttatattt aaaattgtat   3840
```

```
cctggattcc tacgaaaaag aagaatcagt agcctccacc tctggaattc tgcagatatc   3900
cagcacagtg gcggccgctc gagtctagag ggcccgttta aacccgctga tcagcctcga   3960
ctgtgccttc tagttgccag ccatctgttg tttgcccctc ccccgtgcct tccttgaccc   4020
tggaaggtgc cactcccact gtcctttcct aataaaatga ggaaattgca tcgcattgtc   4080
tgagtaggtg tcattctatt ctggggggtg gggtggggca ggacagcaag ggggaggatt   4140
gggaagacaa tagcaggcat gctggggatg cggtgggctc tatggcttct gaggcggaaa   4200
gaaccagctg gggctctagg gggtatcccc acgcgccctg tagcggcgca ttaagcgcgg   4260
cgggtgtggt ggttacgcgc agcgtgaccg ctacacttgc cagcgcccta gcgcccgctc   4320
ctttcgcttt cttcccttcc tttctcgcca cgttcgccgg ctttccccgt caagctctaa   4380
atcgggggct ccctttaggg ttccgattta gtgctttacg gcacctcgac cccaaaaaac   4440
ttgattaggg tgatggttca cgtagtgggc catcgccctg atagacggtt tttcgccctt   4500
tgacgttgga gtccacgttc tttaatagtg gactcttgtt ccaaactgga acaacactca   4560
accctatctc ggtctattct tttgatttat aagggatttt ggggatttcg gcctattggt   4620
taaaaaatga gctgatttaa caaaaattta acgcgaatta attctgtgga atgtgtgtca   4680
gttagggtgt ggaaagtccc caggctcccc aggcaggcag aagtatgcaa agcatgcatc   4740
tcaattagtc agcaaccagg tgtggaaagt ccccaggctc cccagcaggc agaagtatgc   4800
aaagcatgca tctcaattag tcagcaacca tagtcccgcc cctaactccg cccatcccgc   4860
ccctaactcc gcccagttcc gcccattctc cgccccatgg ctgactaatt ttttttattt   4920
atgcagaggc cgaggccgcc tctgcctctg agctattcca gaagtagtga ggaggctttt   4980
ttggaggcct aggcttttgc aaaaagctcc cgggagcttg tatatccatt ttcggatctg   5040
atcagcacgt gttgacaatt aatcatcggc atagtatatc ggcatagtat aatacgacaa   5100
ggtgaggaac taaaccatgg ccaagttgac cagtgccgtt ccggtgctca ccgcgcgcga   5160
cgtcgccgga gcggtcgagt tctggaccga ccggctcggg ttctcccggg acttcgtgga   5220
ggacgacttc gccggtgtgg tccgggacga cgtgaccctg ttcatcagcg cggtccagga   5280
ccaggtggtg ccggacaaca ccctggcctg ggtgtgggtg cgcggcctgg acgagctgta   5340
cgccgagtgg tcggaggtcg tgtccacgaa cttccgggac gcctccgggc cggccatgac   5400
cgagatcggc gagcagccgt gggggcggga gttcgccctg cgcgacccgg ccggcaactg   5460
cgtgcacttc gtggccgagg agcaggactg acacgtgcta cgagatttcg attccaccgc   5520
cgccttctat gaaaggttgg gcttcggaat cgttttccgg gacgccggct ggatgatcct   5580
ccagcgcggg gatctcatgc tggagttctt cgcccacccc aacttgttta ttgcagctta   5640
taatggttac aaataaagca atagcatcac aaatttcaca aataaagcat ttttttcact   5700
gcattctagt tgtggtttgt ccaaactcat caatgtatct tatcatgtct gtataccgtc   5760
gacctctagc tagagcttgg cgtaatcatg gtcatagctg tttcctgtgt gaaattgtta   5820
tccgctcaca attccacaca acatacgagc cggaagcata aagtgtaaag cctggggtgc   5880
ctaatgagtg agctaactca cattaattgc gttgcgctca ctgcccgctt tccagtcggg   5940
aaacctgtcg tgccagctgc attaatgaat cggccaacgc gcggggagag gcggtttgcg   6000
tattgggcgc tcttccgctt cctcgctcac tgactcgctg cgctcggtcg ttcggctgcg   6060
gcgagcggta tcagctcact caaaggcggt aatacggtta tccacagaat caggggataa   6120
cgcaggaaag aacatgtgag caaaaggcca gcaaaaggcc aggaaccgta aaaaggccgc   6180
gttgctggcg tttttccata ggctccgccc ccctgacgag catcacaaaa atcgacgctc   6240
```

```
aagtcagagg tggcgaaacc cgacaggact ataaagatac caggcgtttc cccctggaag   6300

ctccctcgtg cgctctcctg ttccgaccct gccgcttacc ggatacctgt ccgcctttct   6360

cccttcggga agcgtggcgc tttctcaatg ctcacgctgt aggtatctca gttcggtgta   6420

ggtcgttcgc tccaagctgg gctgtgtgca cgaacccccc gttcagcccg accgctgcgc   6480

cttatccggt aactatcgtc ttgagtccaa cccggtaaga cacgacttat cgccactggc   6540

agcagccact ggtaacagga ttagcagagc gaggtatgta ggcggtgcta cagagttctt   6600

gaagtggtgg cctaactacg gctacactag aaggacagta tttggtatct gcgctctgct   6660

gaagccagtt accttcggaa aaagagttgg tagctcttga tccggcaaac aaaccaccgc   6720

tggtagcggt ggtttttttg tttgcaagca gcagattacg cgcagaaaaa aaggatctca   6780

agaagatcct ttgatctttt ctacggggtc tgacgctcag tggaacgaaa actcacgtta   6840

agggattttg gtcatgagat tatcaaaaag gatcttcacc tagatccttt taaattaaaa   6900

atgaagtttt aaatcaatct aaagtatata tgagtaaact tggtctgaca gttaccaatg   6960

cttaatcagt gaggcaccta tctcagcgat ctgtctattt cgttcatcca tagttgcctg   7020

actccccgtc gtgtagataa ctacgatacg ggagggctta ccatctggcc ccagtgctgc   7080

aatgataccg cgagacccac gctcaccggc tccagattta tcagcaataa accagccagc   7140

cggaagggcc gagcgcagaa gtggtcctgc aactttatcc gcctccatcc agtctattaa   7200

ttgttgccgg gaagctagag taagtagttc gccagttaat agtttgcgca acgttgttgc   7260

cattgctaca ggcatcgtgg tgtcacgctc gtcgtttggt atggcttcat tcagctccgg   7320

ttcccaacga tcaaggcgag ttacatgatc ccccatgttg tgcaaaaaag cggttagctc   7380

cttcggtcct ccgatcgttg tcagaagtaa gttggccgca gtgttatcac tcatggttat   7440

ggcagcactg cataattctc ttactgtcat gccatccgta agatgctttt ctgtgactgg   7500

tgagtactca accaagtcat tctgagaata gtgtatgcgg cgaccgagtt gctcttgccc   7560

ggcgtcaata cgggataata ccgcgccaca tagcagaact ttaaaagtgc tcatcattgg   7620

aaaacgttct tcggggcgaa aactctcaag gatcttaccg ctgttgagat ccagttcgat   7680

gtaacccact cgtgcaccca actgatcttc agcatctttt actttcacca gcgtttctgg   7740

gtgagcaaaa acaggaaggc aaaatgccgc aaaaaaggga ataagggcga cacggaaatg   7800

ttgaatactc atactcttcc tttttcaata ttattgaagc atttatcagg gttattgtct   7860

catgagcgga tacatatttg aatgtattta gaaaaataaa caaatagggg ttccgcgcac   7920

atttccccga aaagtgccac ctgacgtcat ggcaccacca atgacactgc aacaatggat   7980

catttggaaa aaaatgaata aagcgcatga ggcacttcaa aatacaacaa ctgtgactga   8040

acagcagaag gaacaaatta tactggacat tcaaaatgaa gaagtacaac caactaggag   8100

agataaattt agatatctgc tttatacttg ttgtgctact agctcaagag tattggcctg   8160

gatgttttta gtttgtatat tgttaatcat tgttttggtt tcatgctttg tgactatatc   8220

cagaatacaa tggaataagg atattcaggt attaggacct gtaatagact ggaatgttac   8280

tcaaagagct gtttatcaac ccttacagac tagaaggatt gcacgttccc ttagaatgca   8340

gcatcctgtt ccaaaatatg tggaggtaaa tatgactagt attccacaag gtgtatacta   8400

tgaaccccat ccggaaccca tagtggtgaa ggagagggtc ctgggtcttt ctcaaattct   8460

gatgattaat tcagaaaaca ttgctaataa tgctaatttg acacaagaag taaagaagtt   8520

gttaactgaa atggttaatg aagaaatgca aagtttgtca gatgtaatga ttgactttga   8580

aattccttta ggagaccctc gtgatcaaga acaatatata catagaaaat gctatcaaga   8640
```

```
atttgcaaat tgttatttag taaaatataa agaacccaaa ccgtggccta aggagggcct   8700
tatagctgat caatgcccat taccaggtta ccatgctgga ttaacctata atagacagtc   8760
tatttgggat tactatatta aagtggagag tattagacct gcaaattgga caacaaagag   8820
taaatatgga caagctagac taggaagttt ttatattcct agcagtctga gacaaatcaa   8880
tgttagtcat gtactattct gtagtgatca attatattct aaatggtata atatagaaaa   8940
taccatagaa caaaacgagc ggtttctgct taataaacta aataacctta catctggaac   9000
ctcagtattg aagaaaagag ctcttccgaa ggattggagt tctcaaggta aaaatgctct   9060
gtttagagaa atcaatgtgt tagatatctg cagtaaacct gaatctgtaa tactattgaa   9120
tacttcatac tattccttct ctttatggga aggagattgt aattttacta aagatatgat   9180
ttctcagttg gttccagaat gtgatggatt ttataacaat tctaagtgga tgcatatgca   9240
tccatatgct tgtagattct ggagaagtaa gaatgaaaaa gaagaaacta aatgtagaga   9300
tggggaaact aagagatgtc tgtattatcc tttatgggac agtcccgaat ctacatatga   9360
ttttggttat ttagcatacc aaaagaattt tccttcccct atctgtatag aacaacagaa   9420
aattagagat caagattatg aagtttattc tttgtatcaa gaatgcaaaa tagcttctaa   9480
agcatatgga attgatacag ttttattctc tctaaagaat tttcttaatt atacaggaac   9540
tcctgtaaat gaaatgccta atgcaagagc ttttgtaggc ctaatagatc ccaagtttcc   9600
tccttcctat cccaatgtta ctagggaaca ttatacttcc tgtaataata ggaaaagaag   9660
aagtgttgat aataactatg ctaagttaag gtctatgggg tatgcactta caggagcagt   9720
gcaaacctta tctcaaatat cagatattaa tgatgaaaac ttacagcaag gaatatattt   9780
attaagggat catgtaataa ccttaatgga agctacattg catgatatat ctgttatgga   9840
aggaatgttt gctgtacaac atttgcatac acatttgaat catttgaaga caatgcttct   9900
agaaagaaga atagactgga cctatatgtc tagtacttgg ctacaacaac aattacagaa   9960
atctgatgat gagatgaaag taataaagag aattgctaga agtttggtat attatgttaa  10020
acaaacccat agttctccca cagctacagc ctgggagatt ggattatatt atgaattggt  10080
tatacctaaa catatttact tgaataattg gaatgttgtc aatataggtc acttagttaa  10140
atcagctgga caattgactc atgtaactat agctcatcct tatgaaataa tcaataagga  10200
atgtgtagag actatatatc tgcatcttga agactgcaca agacaagatt atgtcatatg  10260
tgatgtggta aagatagtgc agccttgtgg caatagctca gacacgagtg attgtcctgt  10320
ctgggctgaa gctgtaaaag aaccatttgt gcaagtcaat cctctgaaaa acggaagtta  10380
tctggttttg gcaagttcca cagactgtca gatcccacca tatgttccta gcatcgtgac  10440
tgttaatgaa acaacgtcat gctttggact ggactttaaa aggccactgg ttgcggaaga  10500
aagattgagc tttgagccac gactgccaaa tctacaacta agattaccac atttggttgg  10560
aattattgca aaaatcaaag ggataaaaat agaagtcaca tcctctggag aaagtataaa  10620
agagcagatt gaaagagcaa aagctgagct ccttcgactg gacattcacg agggagatac  10680
tcctgcctgg atacaacagc tagctgcagc aacaaaggac gtctggccag cagcagcttc  10740
tgctctacaa ggaattggga actttttatc tgggactgcc caaggaatat ttggaactgc  10800
ctttagtctc ttgggatact taaagcctat cctaatagga gtaggggtca ttctcttggt  10860
tattcttata tttaaaattg tatcctggat tcctacgaaa aagaagaatc agtag       10915
```

<210> SEQ ID NO 36
<211> LENGTH: 10929

<212> TYPE: DNA
<213> ORGANISM: Artificial Sequence
<220> FEATURE:
<223> OTHER INFORMATION: Foamy Viral Envelope Gene pczHFV EM043

<400> SEQUENCE: 36

```
gacggatcgg gagatctccc gatcccctat ggtcgactct cagtacaatc tgctctgatg      60

ccgcatagtt aagccagtat ctgctccctg cttgtgtgtt ggaggtcgct gagtagtgcg     120

cgagcaaaat ttaagctaca acaaggcaag gcttgaccga caattgcatg aagaatctgc     180

ttagggttag gcgttttgcg ctgcttcgcg atgtacgggc cagatatacg cgttgacatt     240

gattattgac tagttattaa tagtaatcaa ttacggggtc attagttcat agcccatata     300

tggagttccg cgttacataa cttacggtaa atggcccgcc tggctgaccg cccaacgacc     360

cccgcccatt gacgtcaata atgacgtatg ttcccatagt aacgccaata gggactttcc     420

attgacgtca atgggtggac tatttacggt aaactgccca cttggcagta catcaagtgt     480

atcatatgcc aagtacgccc cctattgacg tcaatgacgg taaatggccc gcctggcatt     540

atgcccagta catgacctta tgggactttc ctacttggca gtacatctac gtattagtca     600

tcgctattac catggtgatg cggttttggc agtacatcaa tgggcgtgga tagcggtttg     660

actcacgggg atttccaagt ctccacccca ttgacgtcaa tgggagtttg ttttggcacc     720

aaaatcaacg ggactttcca aaatgtcgta acaactccgc cccattgacg caaatgggcg     780

gtaggcgtgt acggtgggag gtctatataa gcagagctct ctggctaact agagaaccca     840

ctgcttactg gcttatcgaa attaatacga ctcactatag ggagacccaa gctggctaga     900

aaacctacgt ctcatcagaa tggcaccacc aatgacactg caacaatgga tcatttggag     960

aagaatgaat agagcgcatg aggcacttca aaatacaaca actgtgactg aacagcagaa    1020

ggaacaaatt atactggaca ttcaaaatga agaagtacaa ccaactagga gagataaatt    1080

tagatatctg ctttatactt gttgtgctac tagctcaaga gtattggcct ggatgttttt    1140

agtttgtata ttgttaatca ttgttttggt ttcatgcttt gtgactatat ccagaataca    1200

atggaataag gatattcagg tattaggacc tgtaatagac tggaatgtta ctcaaagagc    1260

tgtttatcaa cccttacaga ctagaaggat tgcacgttcc cttagaatgc agcatcctgt    1320

tccaaaatat gtggaggtaa atatgactag tattccacaa ggtgtatact atgaacccca    1380

tccggaaccc atagtggtga aggagagggt cctgggtctt tctcaaattc tgatgattaa    1440

ttcagaaaac attgctaata atgctaattt gacacaagaa gtaaagaagt tgttaactga    1500

aatggttaat gaagaaatgc aaagtttgtc agatgtaatg attgactttg aaattccttt    1560

aggagaccct cgtgatcaag aacaatatat acatagaaaa tgctatcaag aatttgcaaa    1620

ttgttattta gtaaaatata aagaacccaa accgtggcct aaggagggcc ttatagctga    1680

tcaatgccca ttaccaggtt accatgctgg attaacctat aatagacagt ctatttggga    1740

ttactatatt aaagtggaga gtattagacc tgcaaattgg acaacaaaga gtaaatatgg    1800

acaagctaga ctaggaagtt tttatattcc tagcagtctg agacaaatca atgttagtca    1860

tgtactattc tgtagtgatc aattatattc taaatggtat aatatagaaa ataccataga    1920

acaaaacgag cggtttctgc ttaataaact aaataacctt acatctggaa cctcagtatt    1980

gaagaaaaga gctcttccga aggattggag ttctcaaggt aaaaatgctc tgtttagaga    2040

aatcaatgtg ttagatatct gcagtaaacc tgaatctgta atactattga atacttcata    2100

ctattccttc tctttatggg aaggagattg taattttact aaagatatga tttctcagtt    2160

ggttccagaa tgtgatggat tttataacaa ttctaagtgg atgcatatgc atccatatgc    2220
```

```
ttgtagattc tggagaagta agaatgaaaa agaagaaact aaatgtagag atggggaaac   2280
taagagatgt ctgtattatc ctttatggga cagtcccgaa tctacatatg attttggtta   2340
tttagcatac caaaagaatt ttccttcccc tatctgtata gaacaacaga aaattagaga   2400
tcaagattat gaagtttatt ctttgtatca agaatgcaaa atagcttcta aagcatatgg   2460
aattgataca gttttattct ctctaaagaa ttttcttaat tatacaggaa ctcctgtaaa   2520
tgaaatgcct aatgcaagag cttttgtagg cctaatagat cccaagtttc ctccttccta   2580
tcccaatgtt actagggaac attatacttc ctgtaataat aggaaaagaa gaagtgttga   2640
taataactat gctaagttaa ggtctatggg gtatgcactt acaggagcag tgcaaacctt   2700
atctcaaata tcagatatta atgatgaaaa cttacagcaa ggaatatatt tattaaggga   2760
tcatgtaata accttaatgg aagctacatt gcatgatata tctgttatgg aaggaatgtt   2820
tgctgtacaa catttgcata cacatttgaa tcatttgaag acaatgcttc tagaaagaag   2880
aatagactgg acctatatgt ctagtacttg gctacaacaa caattacaga aatctgatga   2940
tgagatgaaa gtaataaaga gaattgctag aagtttggta tattatgtta aacaaaccca   3000
tagttctccc acagctacag cctgggagat tggattatat tatgaattgg ttatacctaa   3060
acatatttac ttgaataatt ggaatgttgt caatataggt cacttagtta aatcagctgg   3120
acaattgact catgtaacta tagctcatcc ttatgaaata atcaataagg aatgtgtaga   3180
gactatatat ctgcatcttg aagactgcac aagacaagat tatgtcatat gtgatgtggt   3240
aaagatagtg cagccttgtg gcaatagctc agacacgagt gattgtcctg tctgggctga   3300
agctgtaaaa gaaccatttg tgcaagtcaa tcctctgaaa aacggaagtt atctggtttt   3360
ggcaagttcc acagactgtc agatcccacc atatgttcct agcatcgtga ctgttaatga   3420
aacaacgtca tgctttggac tggactttaa aaggccactg gttgcggaag aaagattgag   3480
ctttgagcca cgactgccaa atctacaact aagattacca catttggttg gaattattgc   3540
aaaaatcaaa gggataaaaa tagaagtcac atcctctgga gaaagtataa aagagcagat   3600
tgaaagagca aaagctgagc tccttcgact ggacattcac gagggagata ctcctgcctg   3660
gatacaacag ctagctgcag caacaaagga cgtctggcca gcagcagctt ctgctctaca   3720
aggaattggg aactttttat ctgggactgc ccaaggaata tttggaactg cctttagtct   3780
cttgggatac ttaaagccta tcctaatagg agtaggggtc attctcttgg ttattcttat   3840
atttaaaatt gtatcctgga ttcctacgaa aaagaagaat cagtagcctc cacctctgga   3900
attctgcaga tatccagcac agtggcggcc gctcgagtct agagggcccg tttaaacccg   3960
ctgatcagcc tcgactgtgc cttctagttg ccagccatct gttgtttgcc cctcccccgt   4020
gccttccttg accctggaag gtgccactcc cactgtcctt tcctaataaa atgaggaaat   4080
tgcatcgcat tgtctgagta ggtgtcattc tattctgggg ggtggggtgg ggcaggacag   4140
caagggggag gattgggaag acaatagcag gcatgctggg gatgcggtgg gctctatggc   4200
ttctgaggcg gaaagaacca gctggggctc tagggggtat ccccacgcgc cctgtagcgg   4260
cgcattaagc gcggcgggtg tggtggttac gcgcagcgtg accgctacac ttgccagcgc   4320
cctagcgccc gctcctttcg ctttcttccc ttcctttctc gccacgttcg ccggctttcc   4380
ccgtcaagct ctaaatcggg gcatcccttt agggttccga tttagtgctt tacggcacct   4440
cgaccccaaa aaacttgatt agggtgatgg ttcacgtagt gggccatcgc cctgatagac   4500
ggtttttcgc cctttgacgt tggagtccac gttctttaat agtggactct tgttccaaac   4560
tggaacaaca ctcaacccta tctcggtcta ttcttttgat ttataaggga ttttggggat   4620
```

```
ttcggcctat tggttaaaaa atgagctgat ttaacaaaaa tttaacgcga attaattctg   4680
tggaatgtgt gtcagttagg gtgtggaaag tccccaggct ccccaggcag gcagaagtat   4740
gcaaagcatg catctcaatt agtcagcaac caggtgtgga aagtccccag gctccccagc   4800
aggcagaagt atgcaaagca tgcatctcaa ttagtcagca accatagtcc cgcccctaac   4860
tccgcccatc ccgcccctaa ctccgcccag ttccgcccat tctccgcccc atggctgact   4920
aattttttttt atttatgcag aggccgaggc cgcctctgcc tctgagctat tccagaagta   4980
gtgaggaggc ttttttggag gcctaggctt ttgcaaaaag ctcccgggag cttgtatatc   5040
cattttcgga tctgatcagc acgtgttgac aattaatcat cggcatagta tatcggcata   5100
gtataatacg acaaggtgag gaactaaacc atggccaagt tgaccagtgc cgttccggtg   5160
ctcaccgcgc gcgacgtcgc cggagcggtc gagttctgga ccgaccggct cgggttctcc   5220
cgggacttcg tggaggacga cttcgccggt gtggtccggg acgacgtgac cctgttcatc   5280
agcgcggtcc aggaccaggt ggtgccggac aacaccctgg cctgggtgtg ggtgcgcggc   5340
ctggacgagc tgtacgccga gtggtcggag gtcgtgtcca cgaacttccg ggacgcctcc   5400
gggccggcca tgaccgagat cggcgagcag ccgtgggggc gggagttcgc cctgcgcgac   5460
ccggccggca actgcgtgca cttcgtggcc gaggagcagg actgacacgt gctacgagat   5520
ttcgattcca ccgccgcctt ctatgaaagg ttgggcttcg gaatcgtttt ccgggacgcc   5580
ggctggatga tcctccagcg cggggatctc atgctggagt tcttcgccca ccccaacttg   5640
tttattgcag cttataatgg ttacaaataa agcaatagca tcacaaattt cacaaataaa   5700
gcattttttt cactgcattc tagttgtggt ttgtccaaac tcatcaatgt atcttatcat   5760
gtctgtatac cgtcgacctc tagctagagc ttggcgtaat catggtcata gctgtttcct   5820
gtgtgaaatt gttatccgct cacaattcca cacaacatac gagccggaag cataaagtgt   5880
aaagcctggg gtgcctaatg agtgagctaa ctcacattaa ttgcgttgcg ctcactgccc   5940
gctttccagt cgggaaacct gtcgtgccag ctgcattaat gaatcggcca acgcgcgggg   6000
agaggcggtt tgcgtattgg gcgctcttcc gcttcctcgc tcactgactc gctgcgctcg   6060
gtcgttcggc tgcggcgagc ggtatcagct cactcaaagg cggtaatacg gttatccaca   6120
gaatcagggg ataacgcagg aaagaacatg tgagcaaaag gccagcaaaa ggccaggaac   6180
cgtaaaaagg ccgcgttgct ggcgtttttc cataggctcc gcccccctga cgagcatcac   6240
aaaaatcgac gctcaagtca gaggtggcga aacccgacag gactataaag ataccaggcg   6300
tttccccctg gaagctccct cgtgcgctct cctgttccga ccctgccgct taccggatac   6360
ctgtccgcct ttctcccttc gggaagcgtg gcgctttctc aatgctcacg ctgtaggtat   6420
ctcagttcgg tgtaggtcgt tcgctccaag ctgggctgtg tgcacgaacc ccccgttcag   6480
cccgaccgct gcgccttatc cggtaactat cgtcttgagt ccaacccggt aagacacgac   6540
ttatcgccac tggcagcagc cactggtaac aggattagca gagcgaggta tgtaggcggt   6600
gctacagagt tcttgaagtg gtggcctaac tacggctaca ctagaaggac agtatttggt   6660
atctgcgctc tgctgaagcc agttaccttc ggaaaaagag ttggtagctc ttgatccggc   6720
aaacaaacca ccgctggtag cggtggtttt tttgtttgca agcagcagat tacgcgcaga   6780
aaaaaaggat ctcaagaaga tcctttgatc ttttctacgg ggtctgacgc tcagtggaac   6840
gaaaactcac gttaagggat tttggtcatg agattatcaa aaaggatctt cacctagatc   6900
cttttaaatt aaaaatgaag ttttaaatca atctaaagta tatatgagta aacttggtct   6960
gacagttacc aatgcttaat cagtgaggca cctatctcag cgatctgtct atttcgttca   7020
```

```
tccatagttg cctgactccc cgtcgtgtag ataactacga tacgggaggg cttaccatct   7080
ggccccagtg ctgcaatgat accgcgagac ccacgctcac cggctccaga tttatcagca   7140
ataaaccagc cagccggaag ggccgagcgc agaagtggtc ctgcaacttt atccgcctcc   7200
atccagtcta ttaattgttg ccgggaagct agagtaagta gttcgccagt taatagtttg   7260
cgcaacgttg ttgccattgc tacaggcatc gtggtgtcac gctcgtcgtt tggtatggct   7320
tcattcagct ccggttccca acgatcaagg cgagttacat gatcccccat gttgtgcaaa   7380
aaagcggtta gctccttcgg tcctccgatc gttgtcagaa gtaagttggc cgcagtgtta   7440
tcactcatgg ttatggcagc actgcataat tctcttactg tcatgccatc cgtaagatgc   7500
ttttctgtga ctggtgagta ctcaaccaag tcattctgag aatagtgtat gcggcgaccg   7560
agttgctctt gcccggcgtc aatacgggat aataccgcgc cacatagcag aactttaaaa   7620
gtgctcatca ttggaaaacg ttcttcgggg cgaaaactct caaggatctt accgctgttg   7680
agatccagtt cgatgtaacc cactcgtgca cccaactgat cttcagcatc ttttactttc   7740
accagcgttt ctgggtgagc aaaaacagga aggcaaaatg ccgcaaaaaa gggaataagg   7800
gcgacacgga aatgttgaat actcatactc ttcctttttc aatattattg aagcatttat   7860
cagggttatt gtctcatgag cggatacata tttgaatgta tttagaaaaa taaacaaata   7920
ggggttccgc gcacatttcc ccgaaaagtg ccacctgacg tcatggcacc accaatgaca   7980
ctgcaacaat ggatcatttg gagaagaatg aatagagcgc atgaggcact tcaaaataca   8040
acaactgtga ctgaacagca gaaggaacaa attatactgg acattcaaaa tgaagaagta   8100
caaccaacta ggagagataa atttagatat ctgctttata cttgttgtgc tactagctca   8160
agagtattgg cctggatgtt tttagtttgt atattgttaa tcattgtttt ggtttcatgc   8220
tttgtgacta tatccagaat acaatggaat aaggatattc aggtattagg acctgtaata   8280
gactggaatg ttactcaaag agctgtttat caacccttac agactagaag gattgcacgt   8340
tcccttagaa tgcagcatcc tgttccaaaa tatgtggagg taaatatgac tagtattcca   8400
caaggtgtat actatgaacc ccatccggaa cccatagtgg tgaaggagag ggtcctgggt   8460
ctttctcaaa ttctgatgat taattcagaa aacattgcta ataatgctaa tttgacacaa   8520
gaagtaaaga agttgttaac tgaaatggtt aatgaagaaa tgcaaagttt gtcagatgta   8580
atgattgact ttgaaattcc tttaggagac cctcgtgatc aagaacaata tatacataga   8640
aaatgctatc aagaatttgc aaattgttat ttagtaaaat ataaagaacc caaaccgtgg   8700
cctaaggagg gccttatagc tgatcaatgc ccattaccag gttaccatgc tggattaacc   8760
tataatagac agtctatttg ggattactat attaaagtgg agagtattag acctgcaaat   8820
tggacaacaa agagtaaata tggacaagct agactaggaa gtttttatat tcctagcagt   8880
ctgagacaaa tcaatgttag tcatgtacta ttctgtagtg atcaattata ttctaaatgg   8940
tataatatag aaaataccat agaacaaaac gagcggtttc tgcttaataa actaaataac   9000
cttacatctg gaacctcagt attgaagaaa agagctcttc cgaaggattg gagttctcaa   9060
ggtaaaaatg ctctgtttag agaaatcaat gtgttagata tctgcagtaa acctgaatct   9120
gtaatactat tgaatacttc atactattcc ttctctttat gggaaggaga ttgtaatttt   9180
actaaagata tgatttctca gttggttcca gaatgtgatg gattttataa caattctaag   9240
tggatgcata tgcatccata tgcttgtaga ttctggagaa gtaagaatga aaaagaagaa   9300
actaaatgta gagatgggga aactaagaga tgtctgtatt atcctttatg ggacagtccc   9360
gaatctacat atgattttgg ttatttagca taccaaaaga atttccttc ccctatctgt   9420
```

atagaacaac agaaaattag agatcaagat tatgaagttt attctttgta tcaagaatgc 9480
aaaatagctt ctaaagcata tggaattgat acagttttat tctctctaaa gaattttctt 9540
aattatacag gaactcctgt aaatgaaatg cctaatgcaa gagcttttgt aggcctaata 9600
gatcccaagt ttcctccttc ctatcccaat gttactaggg aacattatac ttcctgtaat 9660
aataggaaaa gaagaagtgt tgataataac tatgctaagt taaggtctat ggggtatgca 9720
cttacaggag cagtgcaaac cttatctcaa atatcagata ttaatgatga aaacttacag 9780
caaggaatat atttattaag ggatcatgta ataaccttaa tggaagctac attgcatgat 9840
atatctgtta tggaaggaat gtttgctgta caacatttgc atacacattt gaatcatttg 9900
aagacaatgc ttctagaaag aagaatagac tggacctata tgtctagtac ttggctacaa 9960
caacaattac agaaatctga tgatgagatg aaagtaataa agagaattgc tagaagtttg 10020
gtatattatg ttaaacaaac ccatagttct cccacagcta cagcctggga gattggatta 10080
tattatgaat tggttatacc taaacatatt tacttgaata attggaatgt tgtcaatata 10140
ggtcacttag ttaaatcagc tggacaattg actcatgtaa ctatagctca tccttatgaa 10200
ataatcaata aggaatgtgt agagactata tatctgcatc ttgaagactg cacaagacaa 10260
gattatgtca tatgtgatgt ggtaaagata gtgcagcctt gtggcaatag ctcagacacg 10320
agtgattgtc ctgtctgggc tgaagctgta aaagaaccat ttgtgcaagt caatcctctg 10380
aaaaacggaa gttatctggt tttggcaagt tccacagact gtcagatccc accatatgtt 10440
cctagcatcg tgactgttaa tgaaacaacg tcatgctttg gactggactt taaaaggcca 10500
ctggttgcgg aagaaagatt gagctttgag ccacgactgc caaatctaca actaagatta 10560
ccacatttgg ttggaattat tgcaaaaatc aaagggataa aaatagaagt cacatcctct 10620
ggagaaagta taaaagagca gattgaaaga gcaaaagctg agctccttcg actggacatt 10680
cacgagggag atactcctgc ctggatacaa cagctagctg cagcaacaaa ggacgtctgg 10740
ccagcagcag cttctgctct acaaggaatt gggaactttt tatctgggac tgcccaagga 10800
atatttggaa ctgcctttag tctcttggga tacttaaagc ctatcctaat aggagtaggg 10860
gtcattctct tggttattct tatatttaaa attgtatcct ggattcctac gaaaaagaag 10920
aatcagtag 10929

<210> SEQ ID NO 37
<211> LENGTH: 10826
<212> TYPE: DNA
<213> ORGANISM: Artificial Sequence
<220> FEATURE:
<223> OTHER INFORMATION: Foamy Viral Envelope Gene pczHFV EM070

<400> SEQUENCE: 37
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540

```
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctgggctag    900
actgccatga ataaagcgca tgaggcactt caaaatacaa caactgtgac tgaacagcag    960
aaggaacaaa ttatactgga cattcaaaat gaagaagtac aaccaactag gagagataaa   1020
tttagatatc tgctttatac ttgttgtgct actagctcaa gagtattggc ctggatcttt   1080
ttagtttgta tattgttaat cattgttttg gtttcatgct ttgtgactat atccagaata   1140
caatggaata aggatattca ggtattagga cctgtaatag actggaatgt tactcaaaga   1200
gctgtttatc aacccttaca gactagaagg attgcacgtt cccttagaat gcagcatcct   1260
gttccaaaat atgtggaggt aaatatgact agtattccac aaggtgtata ctatgaaccc   1320
catccggaac ccatagtggt gaaggagagg gtcctgggtc tttctcaaat tctgatgatt   1380
aattcagaaa acattgctaa taatgctaat ttgacacaag aagtaaagaa gttgttaact   1440
gaaatggtta atgaagaaat gcaaagtttg tcagatgtaa tgattgactt tgaaattcct   1500
ttaggagacc ctcgtgatca agaacaatat atacatagaa aatgctatca agaatttgca   1560
aattgttatt tagtaaaata taaagaaccc aaaccgtggc ctaaggaggg ccttatagct   1620
gatcaatgcc cattaccagg ttaccatgct ggattaacct ataatagaca gtctatttgg   1680
gattactata ttaaagtgga gagtattaga cctgcaaatt ggacaacaaa gagtaaatat   1740
ggacaagcta gactaggaag tttttatatt cctagcagtc tgagacaaat caatgttagt   1800
catgtactat tctgtagtga tcaattatat tctaaatggt ataatataga aaataccata   1860
gaacaaaacg agcggtttct gcttaataaa ctaaataacc ttacatctgg aacctcagta   1920
ttgaagaaaa gagctcttcc gaaggattgg agttctcaag gtaaaaatgc tctgtttaga   1980
gaaatcaatg tgttagatat ctgcagtaaa cctgaatctg taatactatt gaatacttca   2040
tactattcct tctctttatg ggaaggagat tgtaatttta ctaaagatat gatttctcag   2100
ttggttccag aatgtgatgg attttataac aattctaagt ggatgcatat gcatccatat   2160
gcttgtagat tctggagaag taagaatgaa aaagaagaaa ctaaatgtag agatggggaa   2220
actaagagat gtctgtatta tcctttatgg gacagtcccg aatctacata tgattttggt   2280
tatttagcat accaaaagaa ttttccttcc cctatctgta tagaacaaca gaaaattaga   2340
gatcaagatt atgaagttta ttctttgtat caagaatgca aaatagcttc taaagcatat   2400
ggaattgata cagttttatt ctctctaaag aattttctta attatacagg aactcctgta   2460
aatgaaatgc ctaatgcaag agcttttgta ggcctaatag atcccaagtt tcctccttcc   2520
tatcccaatg ttactaggga acattatact tcctgtaata ataggaaaag aagaagtgtt   2580
gataataact atgctaagtt aaggtctatg ggtatgcac ttacaggagc agtgcaaacc   2640
ttatctcaaa tatcagatat taatgatgaa aacttacagc aaggaatata tttattaagg   2700
gatcatgtaa taaccttaat ggaagctaca ttgcatgata tatctgttat ggaaggaatg   2760
tttgctgtac aacatttgca tacacatttg aatcatttga agacaatgct tctagaaaga   2820
agaatagact ggacctatat gtctagtact tggctacaac aacaattaca gaaatctgat   2880
gatgagatga aagtaataaa gagaattgct agaagtttgg tatattatgt taaacaaacc   2940
```

```
catagttctc ccacagctac agcctgggag attggattat attatgaatt ggttatacct   3000
aaacatattt acttgaataa ttggaatgtt gtcaatatag gtcacttagt taaatcagct   3060
ggacaattga ctcatgtaac tatagctcat ccttatgaaa taatcaataa ggaatgtgta   3120
gagactatat atctgcatct tgaagactgc acaagacaag attatgtcat atgtgatgtg   3180
gtaaagatag tgcagccttg tggcaatagc tcagacacga gtgattgtcc tgtctgggct   3240
gaagctgtaa aagaaccatt tgtgcaagtc aatcctctga aaaacggaag ttatctggtt   3300
ttggcaagtt ccacagactg tcagatccca ccatatgttc ctagcatcgt gactgttaat   3360
gaaacaacgt catgctttgg actggacttt aaaaggccac tggttgcgga agaaagattg   3420
agctttgagc cacgactgcc aaatctacaa ctaagattac cacatttggt tggaattatt   3480
gcaaaaatca aagggataaa aatagaagtc acatcctctg gagaaagtat aaaagagcag   3540
attgaaagag caaaagctga gctccttcga ctggacattc acgagggaga tactcctgcc   3600
tggatacaac agctagctgc agcaacaaag gacgtctggc cagcagcagc ttctgctcta   3660
caaggaattg ggaacttttt atctgggact gcccaaggaa tatttggaac tgcctttagt   3720
ctcttgggat acttaaagcc tatcctaata ggagtagggg tcattctctt ggttattctt   3780
atatttaaaa ttgtatcctg gattcctacg aaaaagaaga atcagtagcc tccacctctg   3840
gaattctgca gatatccagc acagtggcgg ccgctcgagt ctagagggcc cgtttaaacc   3900
cgctgatcag cctcgactgt gccttctagt tgccagccat ctgttgtttg cccctccccc   3960
gtgccttcct tgaccctgga aggtgccact cccactgtcc tttcctaata aaatgaggaa   4020
attgcatcgc attgtctgag taggtgtcat tctattctgg ggggtggggt ggggcaggac   4080
agcaaggggg aggattggga agacaatagc aggcatgctg gggatgcggt gggctctatg   4140
gcttctgagg cggaaagaac cagctggggc tctagggggt atccccacgc gccctgtagc   4200
ggcgcattaa gcgcggcggg tgtggtggtt acgcgcagcg tgaccgctac acttgccagc   4260
gccctagcgc ccgctccttt cgctttcttc ccttcctttc tcgccacgtt cgccggcttt   4320
ccccgtcaag ctctaaatcg ggcatccct ttagggttcc gatttagtgc tttacggcac   4380
ctcgacccca aaaaacttga ttagggtgat ggttcacgta gtgggccatc gccctgatag   4440
acggtttttc gccctttgac gttggagtcc acgttcttta atagtggact cttgttccaa   4500
actggaacaa cactcaaccc tatctcggtc tattcttttg atttataagg gattttgggg   4560
atttcggcct attggttaaa aaatgagctg atttaacaaa aatttaacgc gaattaattc   4620
tgtggaatgt gtgtcagtta gggtgtggaa agtccccagg ctccccaggc aggcagaagt   4680
atgcaaagca tgcatctcaa ttagtcagca accaggtgtg gaaagtcccc aggctcccca   4740
gcaggcagaa gtatgcaaag catgcatctc aattagtcag caaccatagt cccgccccta   4800
actccgccca tcccgcccct aactccgccc agttccgccc attctccgcc ccatggctga   4860
ctaatttttt ttatttatgc agaggccgag gccgcctctg cctctgagct attccagaag   4920
tagtgaggag gcttttttgg aggcctaggc ttttgcaaaa agctcccggg agcttgtata   4980
tccattttcg gatctgatca gcacgtgttg acaattaatc atcggcatag tatatcggca   5040
tagtataata cgacaaggtg aggaactaaa ccatggccaa gttgaccagt gccgttccgg   5100
tgctcaccgc gcgcgacgtc gccggagcgg tcgagttctg gaccgaccgg ctcgggttct   5160
cccgggactt cgtggaggac gacttcgccg gtgtggtccg ggacgacgtg accctgttca   5220
tcagcgcggt ccaggaccag gtggtgccgg acaacaccct ggcctgggtg tgggtgcgcg   5280
gcctggacga gctgtacgcc gagtggtcgg aggtcgtgtc cacgaacttc cgggacgcct   5340
```

```
ccgggccggc catgaccgag atcggcgagc agccgtgggg gcgggagttc gccctgcgcg   5400
acccggccgg caactgcgtg cacttcgtgg ccgaggagca ggactgacac gtgctacgag   5460
atttcgattc caccgccgcc ttctatgaaa ggttgggctt cggaatcgtt ttccgggacg   5520
ccggctggat gatcctccag cgcggggatc tcatgctgga gttcttcgcc caccccaact   5580
tgtttattgc agcttataat ggttacaaat aaagcaatag catcacaaat ttcacaaata   5640
aagcattttt ttcactgcat tctagttgtg gtttgtccaa actcatcaat gtatcttatc   5700
atgtctgtat accgtcgacc tctagctaga gcttggcgta atcatggtca tagctgtttc   5760
ctgtgtgaaa ttgttatccg ctcacaattc cacacaacat acgagccgga agcataaagt   5820
gtaaagcctg gggtgcctaa tgagtgagct aactcacatt aattgcgttg cgctcactgc   5880
ccgctttcca gtcgggaaac ctgtcgtgcc agctgcatta atgaatcggc caacgcgcgg   5940
ggagaggcgg tttgcgtatt gggcgctctt ccgcttcctc gctcactgac tcgctgcgct   6000
cggtcgttcg gctgcggcga gcggtatcag ctcactcaaa ggcggtaata cggttatcca   6060
cagaatcagg ggataacgca ggaaagaaca tgtgagcaaa aggccagcaa aaggccagga   6120
accgtaaaaa ggccgcgttg ctggcgtttt tccataggct ccgcccccct gacgagcatc   6180
acaaaaatcg acgctcaagt cagaggtggc gaaacccgac aggactataa agataccagg   6240
cgtttccccc tggaagctcc ctcgtgcgct ctcctgttcc gaccctgccg cttaccggat   6300
acctgtccgc ctttctccct tcgggaagcg tggcgctttc tcaatgctca cgctgtaggt   6360
atctcagttc ggtgtaggtc gttcgctcca agctgggctg tgtgcacgaa ccccccgttc   6420
agcccgaccg ctgcgcctta tccggtaact atcgtcttga gtccaacccg gtaagacacg   6480
acttatcgcc actggcagca gccactggta acaggattag cagagcgagg tatgtaggcg   6540
gtgctacaga gttcttgaag tggtggccta actacggcta cactagaagg acagtatttg   6600
gtatctgcgc tctgctgaag ccagttacct tcggaaaaag agttggtagc tcttgatccg   6660
gcaaacaaac caccgctggt agcggtggtt tttttgtttg caagcagcag attacgcgca   6720
gaaaaaaagg atctcaagaa gatcctttga tcttttctac ggggtctgac gctcagtgga   6780
acgaaaactc acgttaaggg attttggtca tgagattatc aaaaaggatc ttcacctaga   6840
tccttttaaa ttaaaaatga agttttaaat caatctaaag tatatatgag taaacttggt   6900
ctgacagtta ccaatgctta atcagtgagg cacctatctc agcgatctgt ctatttcgtt   6960
catccatagt tgcctgactc cccgtcgtgt agataactac gatacgggag ggcttaccat   7020
ctggccccag tgctgcaatg ataccgcgag acccacgctc accggctcca gatttatcag   7080
caataaacca gccagccgga agggccgagc gcagaagtgg tcctgcaact ttatccgcct   7140
ccatccagtc tattaattgt tgccgggaag ctagagtaag tagttcgcca gttaatagtt   7200
tgcgcaacgt tgttgccatt gctacaggca tcgtggtgtc acgctcgtcg tttggtatgg   7260
cttcattcag ctccggttcc caacgatcaa ggcgagttac atgatccccc atgttgtgca   7320
aaaaagcggt tagctccttc ggtcctccga tcgttgtcag aagtaagttg gccgcagtgt   7380
tatcactcat ggttatggca gcactgcata attctcttac tgtcatgcca tccgtaagat   7440
gcttttctgt gactggtgag tactcaacca agtcattctg agaatagtgt atgcggcgac   7500
cgagttgctc ttgcccggcg tcaatacggg ataataccgc gccacatagc agaactttaa   7560
aagtgctcat cattggaaaa cgttcttcgg ggcgaaaact ctcaaggatc ttaccgctgt   7620
tgagatccag ttcgatgtaa cccactcgtg cacccaactg atcttcagca tcttttactt   7680
tcaccagcgt ttctgggtga gcaaaaacag gaaggcaaaa tgccgcaaaa aagggaataa   7740
```

```
gggcgacacg gaaatgttga atactcatac tcttcctttt tcaatattat tgaagcattt   7800
atcagggtta ttgtctcatg agcggataca tatttgaatg tatttagaaa aataaacaaa   7860
taggggttcc gcgcacattt ccccgaaaag tgccacctga cgtcatgaat aaagcgcatg   7920
aggcacttca aaatacaaca actgtgactg aacagcagaa ggaacaaatt atactggaca   7980
ttcaaaatga agaagtacaa ccaactagga gagataaatt tagatatctg ctttatactt   8040
gttgtgctac tagctcaaga gtattggcct ggatcttttt agtttgtata ttgttaatca   8100
ttgttttggt ttcatgcttt gtgactatat ccagaataca atggaataag gatattcagg   8160
tattaggacc tgtaatagac tggaatgtta ctcaaagagc tgtttatcaa cccttacaga   8220
ctagaaggat tgcacgttcc cttagaatgc agcatcctgt tccaaaatat gtggaggtaa   8280
atatgactag tattccacaa ggtgtatact atgaacccca tccggaaccc atagtggtga   8340
aggagagggt cctgggtctt tctcaaattc tgatgattaa ttcagaaaac attgctaata   8400
atgctaattt gacacaagaa gtaaagaagt tgttaactga aatggttaat gaagaaatgc   8460
aaagtttgtc agatgtaatg attgactttg aaattccttt aggagaccct cgtgatcaag   8520
aacaatatat acatagaaaa tgctatcaag aatttgcaaa ttgttattta gtaaaatata   8580
aagaacccaa accgtggcct aaggagggcc ttatagctga tcaatgccca ttaccaggtt   8640
accatgctgg attaacctat aatagacagt ctatttggga ttactatatt aaagtggaga   8700
gtattagacc tgcaaattgg acaacaaaga gtaaatatgg acaagctaga ctaggaagtt   8760
tttatattcc tagcagtctg agacaaatca atgttagtca tgtactattc tgtagtgatc   8820
aattatattc taaatggtat aatatagaaa ataccataga acaaaacgag cggtttctgc   8880
ttaataaact aaataacctt acatctggaa cctcagtatt gaagaaaaga gctcttccga   8940
aggattggag ttctcaaggt aaaaatgctc tgtttagaga aatcaatgtg ttagatatct   9000
gcagtaaacc tgaatctgta atactattga atacttcata ctattccttc tctttatggg   9060
aaggagattg taattttact aaagatatga tttctcagtt ggttccagaa tgtgatggat   9120
tttataacaa ttctaagtgg atgcatatgc atccatatgc ttgtagattc tggagaagta   9180
agaatgaaaa agaagaaact aaatgtagag atggggaaac taagagatgt ctgtattatc   9240
ctttatggga cagtcccgaa tctacatatg attttggtta tttagcatac caaaagaatt   9300
ttccttcccc tatctgtata gaacaacaga aaattagaga tcaagattat gaagtttatt   9360
ctttgtatca agaatgcaaa atagcttcta aagcatatgg aattgataca gttttattct   9420
ctctaaagaa ttttcttaat tatacaggaa ctcctgtaaa tgaaatgcct aatgcaagag   9480
cttttgtagg cctaatagat cccaagtttc ctccttccta tcccaatgtt actagggaac   9540
attatacttc ctgtaataat aggaaaagaa gaagtgttga taataactat gctaagttaa   9600
ggtctatggg gtatgcactt acaggagcag tgcaaacctt atctcaaata tcagatatta   9660
atgatgaaaa cttacagcaa ggaatatatt tattaaggga tcatgtaata accttaatgg   9720
aagctacatt gcatgatata tctgttatgg aaggaatgtt tgctgtacaa catttgcata   9780
cacatttgaa tcatttgaag acaatgcttc tagaaagaag aatagactgg acctatatgt   9840
ctagtacttg gctacaacaa caattacaga aatctgatga tgagatgaaa gtaataaaga   9900
gaattgctag aagtttggta tattatgtta aacaaaccca tagttctccc acagctacag   9960
cctgggagat tggattatat tatgaattgg ttatacctaa acatatttac ttgaataatt  10020
ggaatgttgt caatataggt cacttagtta aatcagctgg acaattgact catgtaacta  10080
tagctcatcc ttatgaaata atcaataagg aatgtgtaga gactatatat ctgcatcttg  10140
```

```
aagactgcac aagacaagat tatgtcatat gtgatgtggt aaagatagtg cagccttgtg  10200

gcaatagctc agacacgagt gattgtcctg tctgggctga agctgtaaaa gaaccatttg  10260

tgcaagtcaa tcctctgaaa aacggaagtt atctggtttt ggcaagttcc acagactgtc  10320

agatcccacc atatgttcct agcatcgtga ctgttaatga aacaacgtca tgctttggac  10380

tggactttaa aggccactgg gttgcggaag aaagattgag ctttgagcca cgactgccaa  10440

atctacaact aagattacca catttggttg gaattattgc aaaaatcaaa gggataaaaa  10500

tagaagtcac atcctctgga gaaagtataa aagagcagat tgaaagagca aaagctgagc  10560

tccttcgact ggacattcac gagggagata ctcctgcctg gatacaacag ctagctgcag  10620

caacaaagga cgtctggcca gcagcagctt ctgctctaca aggaattggg aactttttat  10680

ctgggactgc ccaaggaata tttggaactg cctttagtct cttgggatac ttaaagccta  10740

tcctaatagg agtaggggtc attctcttgg ttattcttat atttaaaatt gtatcctgga  10800

ttcctacgaa aaagaagaat cagtag                                      10826
```

```
<210> SEQ ID NO 38
<211> LENGTH: 10771
<212> TYPE: DNA
<213> ORGANISM: Artificial Sequence
<220> FEATURE:
<223> OTHER INFORMATION: Foamyvirus

<400> SEQUENCE: 38

gacggatcgg gagatctccc gatcccctat ggtcgactct cagtacaatc tgctctgatg    60

ccgcatagtt aagccagtat ctgctccctg cttgtgtgtt ggaggtcgct gagtagtgcg   120

cgagcaaaat ttaagctaca acaaggcaag gcttgaccga caattgcatg aagaatctgc   180

ttagggttag gcgttttgcg ctgcttcgcg atgtacgggc cagatatacg cgttgacatt   240

gattattgac tagttattaa tagtaatcaa ttacggggtc attagttcat agcccatata   300

tggagttccg cgttacataa cttacggtaa atggcccgcc tggctgaccg cccaacgacc   360

cccgcccatt gacgtcaata atgacgtatg ttcccatagt aacgccaata gggactttcc   420

attgacgtca atgggtggac tatttacggt aaactgccca cttggcagta catcaagtgt   480

atcatatgcc aagtacgccc cctattgacg tcaatgacgg taaatggccc gcctggcatt   540

atgcccagta catgacctta tgggactttc ctacttggca gtacatctac gtattagtca   600

tcgctattac catggtgatg cggttttggc agtacatcaa tgggcgtgga tagcggtttg   660

actcacgggg atttccaagt ctccacccca ttgacgtcaa tgggagtttg ttttggcacc   720

aaaatcaacg ggactttcca aaatgtcgta acaactccgc cccattgacg caaatgggcg   780

gtaggcgtgt acggtgggag gtctatataa gcagagctct ctggctaact agagaaccca   840

ctgcttactg gcttatcgaa attaatacga ctcactatag ggagacccaa gctggctaga   900

ctgccatgac aacaactgtg actgaacagc agaaggaaca aattatactg gacattcaaa   960

atgaagaagt acaaccaact aggagagata aatttagata tctgctttat acttgttgtg  1020

ctactagctc aagagtattg gcctggatgt ttttagtttg tatattgtta atcattgttt  1080

tggtttcatg ctttgtgact atatccagaa tacaatggaa taaggatatt caggtattag  1140

gacctgtaat agactggaat gttactcaaa gagctgttta tcaaccctta cagactagaa  1200

ggattgcacg ttcccttaga atgcagcatc ctgttccaaa atatgtggag gtaaatatga  1260

ctagtattcc acaaggtgta tactatgaac cccatccgga acccatagtg gtgaaggaga  1320

gggtcctggg tctttctcaa attctgatga ttaattcaga aaacattgct aataatgcta  1380
```

```
atttgacaca agaagtaaag aagttgttaa ctgaaatggt taatgaagaa atgcaaagtt   1440

tgtcagatgt aatgattgac tttgaaattc ctttaggaga ccctcgtgat caagaacaat   1500

atatacatag aaaatgctat caagaatttg caaattgtta tttagtaaaa tataaagaac   1560

ccaaaccgtg gcctaaggag ggccttatag ctgatcaatg cccattacca ggttaccatg   1620

ctggattaac ctataataga cagtctattt gggattacta tattaaagtg gagagtatta   1680

gacctgcaaa ttggacaaca aagagtaaat atggacaagc tagactagga agtttttata   1740

ttcctagcag tctgagacaa atcaatgtta gtcatgtact attctgtagt gatcaattat   1800

attctaaatg gtataatata gaaaatacca tagaacaaaa cgagcggttt ctgcttaata   1860

aactaaataa ccttacatct ggaacctcag tattgaagaa aagagctctt ccgaaggatt   1920

ggagttctca aggtaaaaat gctctgttta gagaaatcaa tgtgttagat atctgcagta   1980

aacctgaatc tgtaatacta ttgaatactt catactattc cttctcttta tgggaaggag   2040

attgtaattt tactaaagat atgatttctc agttggttcc agaatgtgat ggattttata   2100

acaattctaa gtggatgcat atgcatccat atgcttgtag attctggaga agtaagaatg   2160

aaaaagaaga aactaaatgt agagatgggg aaactaagag atgtctgtat tatcctttat   2220

gggacagtcc cgaatctaca tatgattttg gttatttagc ataccaaaag aattttcctt   2280

cccctatctg tatagaacaa cagaaaatta gagatcaaga ttatgaagtt tattctttgt   2340

atcaagaatg caaaatagct tctaaagcat atggaattga tacagtttta ttctctctaa   2400

agaattttct taattataca ggaactcctg taaatgaaat gcctaatgca agagcttttg   2460

taggcctaat agatcccaag tttcctcctt cctatcccaa tgttactagg gaacattata   2520

cttcctgtaa taataggaaa agaagaagtg ttgataataa ctatgctaag ttaaggtcta   2580

tggggtatgc acttacagga gcagtgcaaa ccttatctca aatatcagat attaatgatg   2640

aaaacttaca gcaaggaata tatttattaa gggatcatgt aataacctta atggaagcta   2700

cattgcatga tatatctgtt atggaaggaa tgtttgctgt acaacatttg catacacatt   2760

tgaatcattt gaagacaatg cttctagaaa gaagaataga ctggacctat atgtctagta   2820

cttggctaca acaacaatta cagaaatctg atgatgagat gaaagtaata aagagaattg   2880

ctagaagttt ggtatattat gttaaacaaa cccatagttc tcccacagct acagcctggg   2940

agattggatt atattatgaa ttggttatac ctaaacatat ttacttgaat aattggaatg   3000

ttgtcaatat aggtcactta gttaaatcag ctggacaatt gactcatgta actatagctc   3060

atccttatga aataatcaat aaggaatgtg tagagactat atatctgcat cttgaagact   3120

gcacaagaca agattatgtc atatgtgatg tggtaaagat agtgcagcct tgtggcaata   3180

gctcagacac gagtgattgt cctgtctggg ctgaagctgt aaaagaacca tttgtgcaag   3240

tcaatcctct gaaaaacgga agttatctgg ttttggcaag ttccacagac tgtcagatcc   3300

caccatatgt tcctagcatc gtgactgtta atgaaacaac gtcatgcttt ggactggact   3360

ttaaaaggcc actggttgcg gaagaaagat tgagctttga gccacgactg ccaaatctac   3420

aactaagatt accacatttg gttggaatta ttgcaaaaat caaagggata aaaatagaag   3480

tcacatcctc tggagaaagt ataaaagagc agattgaaag agcaaaagct gagctccttc   3540

gactggacat tcacgaggga gatactcctg cctggataca acagctagct gcagcaacaa   3600

aggacgtctg gccagcagca gcttctgctc tacaaggaat tgggaacttt ttatctggga   3660

ctgcccaagg aatatttgga actgccttta gtctcttggg atacttaaag cctatcctaa   3720

taggagtagg ggtcattctc ttggttattc ttatatttaa aattgtatcc tggattccta   3780
```

```
cgaaaaagaa gaatcagtag cctccacctc tggaattctg cagatatcca gcacagtggc   3840
ggccgctcga gtctagaggg cccgtttaaa cccgctgatc agcctcgact gtgccttcta   3900
gttgccagcc atctgttgtt tgcccctccc ccgtgccttc cttgaccctg gaaggtgcca   3960
ctcccactgt cctttcctaa taaaatgagg aaattgcatc gcattgtctg agtaggtgtc   4020
attctattct ggggggtggg gtggggcagg acagcaaggg ggaggattgg gaagacaata   4080
gcaggcatgc tggggatgcg gtgggctcta tggcttctga ggcggaaaga accagctggg   4140
gctctagggg gtatccccac gcgccctgta gcggcgcatt aagcgcggcg ggtgtggtgg   4200
ttacgcgcag cgtgaccgct acacttgcca gcgccctagc gcccgctcct ttcgctttct   4260
tcccttcctt tctcgccacg ttcgccggct ttccccgtca agctctaaat cggggcatcc   4320
ctttagggtt ccgatttagt gctttacggc acctcgaccc caaaaaactt gattagggtg   4380
atggttcacg tagtgggcca tcgccctgat agacggtttt tcgccctttg acgttggagt   4440
ccacgttctt taatagtgga ctcttgttcc aaactggaac aacactcaac cctatctcgg   4500
tctattcttt tgatttataa gggattttgg ggatttcggc ctattggtta aaaaatgagc   4560
tgatttaaca aaaatttaac gcgaattaat tctgtggaat gtgtgtcagt tagggtgtgg   4620
aaagtcccca ggctccccag gcaggcagaa gtatgcaaag catgcatctc aattagtcag   4680
caaccaggtg tggaaagtcc ccaggctccc cagcaggcag aagtatgcaa agcatgcatc   4740
tcaattagtc agcaaccata gtcccgcccc taactccgcc catcccgccc ctaactccgc   4800
ccagttccgc ccattctccg ccccatggct gactaatttt ttttatttat gcagaggccg   4860
aggccgcctc tgcctctgag ctattccaga agtagtgagg aggctttttt ggaggcctag   4920
gcttttgcaa aaagctcccg ggagcttgta tatccatttt cggatctgat cagcacgtgt   4980
tgacaattaa tcatcggcat agtatatcgg catagtataa tacgacaagg tgaggaacta   5040
aaccatggcc aagttgacca gtgccgttcc ggtgctcacc gcgcgcgacg tcgccggagc   5100
ggtcgagttc tggaccgacc ggctcgggtt ctcccgggac ttcgtggagg acgacttcgc   5160
cggtgtggtc cgggacgacg tgaccctgtt catcagcgcg gtccaggacc aggtggtgcc   5220
ggacaacacc ctggcctggg tgtgggtgcg cggcctggac gagctgtacg ccgagtggtc   5280
ggaggtcgtg tccacgaact tccgggacgc ctccgggccg gccatgaccg agatcggcga   5340
gcagccgtgg gggcgggagt tcgccctgcg cgacccggcc ggcaactgcg tgcacttcgt   5400
ggccgaggag caggactgac acgtgctacg agatttcgat tccaccgccg ccttctatga   5460
aaggttgggc ttcggaatcg ttttccggga cgccggctgg atgatcctcc agcgcgggga   5520
tctcatgctg gagttcttcg cccaccccaa cttgtttatt gcagcttata atggttacaa   5580
ataaagcaat agcatcacaa atttcacaaa taaagcattt ttttcactgc attctagttg   5640
tggtttgtcc aaactcatca atgtatctta tcatgtctgt ataccgtcga cctctagcta   5700
gagcttggcg taatcatggt catagctgtt tcctgtgtga aattgttatc cgctcacaat   5760
tccacacaac atacgagccg gaagcataaa gtgtaaagcc tggggtgcct aatgagtgag   5820
ctaactcaca ttaattgcgt tgcgctcact gcccgctttc cagtcgggaa acctgtcgtg   5880
ccagctgcat taatgaatcg gccaacgcgc ggggagaggc ggtttgcgta ttgggcgctc   5940
ttccgcttcc tcgctcactg actcgctgcg ctcggtcgtt cggctgcggc gagcggtatc   6000
agctcactca aaggcggtaa tacggttatc cacagaatca ggggataacg caggaaagaa   6060
catgtgagca aaaggccagc aaaaggccag gaaccgtaaa aaggccgcgt tgctggcgtt   6120
tttccatagg ctccgccccc ctgacgagca tcacaaaaat cgacgctcaa gtcagaggtg   6180
```

```
gcgaaacccg acaggactat aaagatacca ggcgtttccc cctggaagct ccctcgtgcg   6240
ctctcctgtt ccgaccctgc cgcttaccgg atacctgtcc gcctttctcc cttcgggaag   6300
cgtggcgctt tctcaatgct cacgctgtag gtatctcagt tcggtgtagg tcgttcgctc   6360
caagctgggc tgtgtgcacg aaccccccgt tcagcccgac cgctgcgcct tatccggtaa   6420
ctatcgtctt gagtccaacc cggtaagaca cgacttatcg ccactggcag cagccactgg   6480
taacaggatt agcagagcga ggtatgtagg cggtgctaca gagttcttga agtggtggcc   6540
taactacggc tacactagaa ggacagtatt tggtatctgc gctctgctga agccagttac   6600
cttcggaaaa agagttggta gctcttgatc cggcaaacaa accaccgctg gtagcggtgg   6660
tttttttgtt tgcaagcagc agattacgcg cagaaaaaaa ggatctcaag aagatccttt   6720
gatcttttct acggggtctg acgctcagtg gaacgaaaac tcacgttaag ggattttggt   6780
catgagatta tcaaaaagga tcttcaccta gatcctttta aattaaaaat gaagttttaa   6840
atcaatctaa agtatatatg agtaaacttg gtctgacagt taccaatgct taatcagtga   6900
ggcacctatc tcagcgatct gtctatttcg ttcatccata gttgcctgac tccccgtcgt   6960
gtagataact acgatacggg agggcttacc atctggcccc agtgctgcaa tgataccgcg   7020
agacccacgc tcaccggctc cagatttatc agcaataaac cagccagccg gaagggccga   7080
gcgcagaagt ggtcctgcaa ctttatccgc ctccatccag tctattaatt gttgccggga   7140
agctagagta agtagttcgc cagttaatag tttgcgcaac gttgttgcca ttgctacagg   7200
catcgtggtg tcacgctcgt cgtttggtat ggcttcattc agctccggtt cccaacgatc   7260
aaggcgagtt acatgatccc ccatgttgtg caaaaaagcg gttagctcct tcggtcctcc   7320
gatcgttgtc agaagtaagt tggccgcagt gttatcactc atggttatgg cagcactgca   7380
taattctctt actgtcatgc catccgtaag atgcttttct gtgactggtg agtactcaac   7440
caagtcattc tgagaatagt gtatgcggcg accgagttgc tcttgcccgg cgtcaatacg   7500
ggataatacc gcgccacata gcagaacttt aaaagtgctc atcattggaa aacgttcttc   7560
ggggcgaaaa ctctcaagga tcttaccgct gttgagatcc agttcgatgt aacccactcg   7620
tgcacccaac tgatcttcag catcttttac tttcaccagc gtttctgggt gagcaaaaac   7680
aggaaggcaa aatgccgcaa aaaagggaat aagggcgaca cggaaatgtt gaatactcat   7740
actcttcctt tttcaatatt attgaagcat ttatcagggt tattgtctca tgagcggata   7800
catatttgaa tgtatttaga aaaataaaca aataggggtt ccgcgcacat ttccccgaaa   7860
agtgccacct gacgtcatga caacaactgt gactgaacag cagaaggaac aaattatact   7920
ggacattcaa aatgaagaag tacaaccaac taggagagat aaatttagat atctgcttta   7980
tacttgttgt gctactagct caagagtatt ggcctggatg tttttagttt gtatattgtt   8040
aatcattgtt ttggtttcat gctttgtgac tatatccaga atacaatgga ataaggatat   8100
tcaggtatta ggacctgtaa tagactggaa tgttactcaa agagctgttt atcaaccctt   8160
acagactaga aggattgcac gttcccttag aatgcagcat cctgttccaa aatatgtgga   8220
ggtaaatatg actagtattc cacaaggtgt atactatgaa ccccatccgg aacccatagt   8280
ggtgaaggag agggtcctgg gtctttctca aattctgatg attaattcag aaaacattgc   8340
taataatgct aatttgacac aagaagtaaa gaagttgtta actgaaatgg ttaatgaaga   8400
aatgcaaagt ttgtcagatg taatgattga ctttgaaatt cctttaggag accctcgtga   8460
tcaagaacaa tatatacata gaaaatgcta tcaagaattt gcaaattgtt atttagtaaa   8520
atataaagaa cccaaaccgt ggcctaagga gggccttata gctgatcaat gcccattacc   8580
```

```
aggttaccat gctggattaa cctataatag acagtctatt tgggattact atattaaagt   8640
ggagagtatt agacctgcaa attggacaac aaagagtaaa tatggacaag ctagactagg   8700
aagtttttat attcctagca gtctgagaca aatcaatgtt agtcatgtac tattctgtag   8760
tgatcaatta tattctaaat ggtataatat agaaaatacc atagaacaaa acgagcggtt   8820
tctgcttaat aaactaaata accttacatc tggaacctca gtattgaaga aaagagctct   8880
tccgaaggat tggagttctc aaggtaaaaa tgctctgttt agagaaatca atgtgttaga   8940
tatctgcagt aaacctgaat ctgtaatact attgaatact tcatactatt ccttctcttt   9000
atgggaagga gattgtaatt ttactaaaga tatgatttct cagttggttc cagaatgtga   9060
tggattttat aacaattcta agtggatgca tatgcatcca tatgcttgta gattctggag   9120
aagtaagaat gaaaaagaag aaactaaatg tagagatggg gaaactaaga gatgtctgta   9180
ttatccttta tgggacagtc ccgaatctac atatgatttt ggttatttag cataccaaaa   9240
gaattttcct tcccctatct gtatagaaca acagaaaatt agagatcaag attatgaagt   9300
ttattctttg tatcaagaat gcaaaatagc ttctaaagca tatggaattg atacagtttt   9360
attctctcta aagaatttct ttaattatac aggaactcct gtaaatgaaa tgcctaatgc   9420
aagagctttt gtaggcctaa tagatcccaa gtttcctcct tcctatccca atgttactag   9480
ggaacattat acttcctgta ataataggaa aagaagaagt gttgataata actatgctaa   9540
gttaaggtct atggggtatg cacttacagg agcagtgcaa accttatctc aaatatcaga   9600
tattaatgat gaaaacttac agcaaggaat atatttatta agggatcatg taataacctt   9660
aatggaagct acattgcatg atatatctgt tatggaagga atgtttgctg tacaacattt   9720
gcatacacat ttgaatcatt tgaagacaat gcttctagaa agaagaatag actggaccta   9780
tatgtctagt acttggctac aacaacaatt acagaaatct gatgatgaga tgaaagtaat   9840
aaagagaatt gctagaagtt tggtatatta tgttaaacaa acccatagtt ctcccacagc   9900
tacagcctgg gagattggat tatattatga attggttata cctaaacata tttacttgaa   9960
taattggaat gttgtcaata taggtcactt agttaaatca gctggacaat tgactcatgt  10020
aactatagct catccttatg aaataatcaa taaggaatgt gtagagacta tatatctgca  10080
tcttgaagac tgcacaagac aagattatgt catatgtgat gtggtaaaga tagtgcagcc  10140
ttgtggcaat agctcagaca cgagtgattg tcctgtctgg gctgaagctg taaaagaacc  10200
atttgtgcaa gtcaatcctc tgaaaaacgg aagttatctg gttttggcaa gttccacaga  10260
ctgtcagatc ccaccatatg ttcctagcat cgtgactgtt aatgaaacaa cgtcatgctt  10320
tggactggac tttaaaaggc cactggttgc ggaagaaaga ttgagctttg agccacgact  10380
gccaaatcta caactaagat taccacattt ggttggaatt attgcaaaaa tcaaagggat  10440
aaaaatagaa gtcacatcct ctggagaaag tataaaagag cagattgaaa gagcaaaagc  10500
tgagctcctt cgactggaca ttcacgaggg agatactcct gcctggatac aacagctagc  10560
tgcagcaaca aaggacgtct ggccagcagc agcttctgct ctacaaggaa ttgggaactt  10620
tttatctggg actgcccaag gaatatttgg aactgccttt agtctcttgg gatacttaaa  10680
gcctatccta ataggagtag gggtcattct cttggttatt cttatattta aaattgtatc  10740
ctggattcct acgaaaaaga agaatcagta g                                 10771
```

<210> SEQ ID NO 39
<211> LENGTH: 10902
<212> TYPE: DNA
<213> ORGANISM: Artificial Sequence
<220> FEATURE:
<223> OTHER INFORMATION: Foamyvirus

<400> SEQUENCE: 39

```
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctaga    900
ctgccatggc accaccaatg acactgcaac aatggatcat ttggaaaaaa atgaataaag    960
cgcatgaggc acttcaaaat acaacaactg tgactgaaca gcagaaggaa caaattatac   1020
tggacattca aaatgaagaa gtacaaccaa ctaggagaga taaatttaga tatctgcttt   1080
atacttgttg tgctactagc tcaagagtat tggcctggat gtttttagtt tgtatattgt   1140
taatcattgt tttggtttca tgctttgtga ctatatccag aatacaatgg aataaggata   1200
ttcaggtatt aggacctgta atagactgga atgttactca aagagctgtt tatcaaccct   1260
tacagactag aaggattgca cgttccctta gaatgcagca tcctgttcca aaatatgtgg   1320
aggtaaatat gactagtatt ccacaaggtg tatactatga accccatccg gaacccatag   1380
tggtgaagga gagggtcctg ggtctttctc aaattctgat gattaattca gaaaacattg   1440
ctaataatgc taatttgaca caagaagtaa agaagttgtt aactgaaatg gttaatgaag   1500
aaatgcaaag tttgtcagat gtaatgattg actttgaaat tcctttagga gaccctcgtg   1560
atcaagaaca atatatacat agaaaatgct atcaagaatt tgcaaattgt tatttagtaa   1620
aatataaaga acccaaaccg tggcctaagg agggccttat agctgatcaa tgcccattac   1680
caggttacca tgctggatta acctataata gacagtctat ttgggattac tatattaaag   1740
tggagagtat tagacctgca aattggacaa caaagagtaa atatggacaa gctagactag   1800
gaagttttta tattcctagc agtctgagac aaatcaatgt tagtcatgta ctattctgta   1860
gtgatcaatt atattctaaa tggtataata tagaaaatac catagaacaa aacgagcggt   1920
ttctgcttaa taaactaaat aaccttacat ctggaacctc agtattgaag aaaagagctc   1980
ttccgaagga ttggagttct caaggtaaaa atgctctgtt tagagaaatc aatgtgttag   2040
atatctgcag taaacctgaa tctgtaatac tattgaatac ttcatactat tccttctctt   2100
tatgggaagg agattgtaat tttactaaag atatgatttc tcagttggtt ccagaatgtg   2160
atggatttta taacaattct aagtggatgc atatgcatcc atatgcttgt agattctgga   2220
gaagtaagaa tgaaaaagaa gaaactaaat gtagagatgg ggaaactaag agatgtctgt   2280
```

```
attatccttt atgggacagt cccgaatcta catatgattt tggttattta gcataccaaa   2340
agaattttcc ttcccctatc tgtatagaac aacagaaaat tagagatcaa gattatgaag   2400
tttattcttt gtatcaagaa tgcaaaatag cttctaaagc atatggaatt gatacagttt   2460
tattctctct aaagaatttt cttaattata caggaactcc tgtaaatgaa atgcctaatg   2520
caagagcttt tgtaggccta atagatccca agtttcctcc ttcctatccc aatgttacta   2580
gggaacatta tacttcctgt aataatagga aaagaagaag tgttgataat aactatgcta   2640
agttaaggtc tatggggtat gcacttacag gagcagtgca aaccttatct caaatatcag   2700
atattaatga tgaaaactta cagcaaggaa tatatttatt aagggatcat gtaataacct   2760
taatggaagc tacattgcat gatatatctg ttatggaagg aatgtttgct gtacaacatt   2820
tgcatacaca tttgaatcat ttgaagacaa tgcttctaga aagaagaata gactggacct   2880
atatgtctag tacttggcta caacaacaat tacagaaatc tgatgatgag atgaaagtaa   2940
taaagagaat tgctagaagt ttggtatatt atgttaaaca aacccatagt tctcccacag   3000
ctacagcctg ggagattgga ttatattatg aattggttat acctaaacat atttacttga   3060
ataattggaa tgttgtcaat ataggtcact tagttaaatc agctggacaa ttgactcatg   3120
taactatagc tcatccttat gaaataatca ataaggaatg tgtagagact atatatctgc   3180
atcttgaaga ctgcacaaga caagattatg tcatatgtga tgtggtaaag atagtgcagc   3240
cttgtggcaa tagctcagac acgagtgatt gtcctgtctg ggctgaagct gtaaaagaac   3300
catttgtgca agtcaatcct ctgaaaaacg gaagttatct ggttttggca agttccacag   3360
actgtcagat cccaccatat gttcctagca tcgtgactgt taatgaaaca acgtcatgct   3420
ttggactgga ctttaaaagg ccactggttg cggaagaaag attgagcttt gagccacgac   3480
tgccaaatct acaactaaga ttaccacatt tggttggaat tattgcaaaa atcaaaggga   3540
taaaaataga agtcacatcc tctggagaaa gtataaaaga gcagattgaa agagcaaaag   3600
ctgagctcct tcgactggac attcacgagg gagatactcc tgcctggata caacagctag   3660
ctgcagcaac aaaggacgtc tggccagcag cagcttctgc tctacaagga attgggaact   3720
ttttatctgg gactgcccaa ggaatatttg gaactgcctt tagtctcttg ggatacttaa   3780
ggcctatcct aataggagta ggggtcattc tcttggttat tcttatattt agaattgtat   3840
cctggattcc tacgagaagg aggaatcagt agaattctgc agatatccag cacagtggcg   3900
gccgctcgag tctagagggc ccgtttaaac ccgctgatca gcctcgactg tgccttctag   3960
ttgccagcca tctgttgttt gcccctcccc cgtgccttcc ttgaccctgg aaggtgccac   4020
tcccactgtc ctttcctaat aaaatgagga aattgcatcg cattgtctga gtaggtgtca   4080
ttctattctg gggggtgggg tggggcagga cagcaagggg gaggattggg aagacaatag   4140
caggcatgct ggggatgcgg tgggctctat ggcttctgag gcggaaagaa ccagctgggg   4200
ctctaggggg tatccccacg cgccctgtag cggcgcatta agcgcggcgg gtgtggtggt   4260
tacgcgcagc gtgaccgcta cacttgccag cgccctagcg cccgctcctt tcgctttctt   4320
cccttccttt ctcgccacgt tcgccggctt tccccgtcaa gctctaaatc ggggcatccc   4380
tttagggttc cgatttagtg ctttacggca cctcgacccc aaaaaacttg attagggtga   4440
tggttcacgt agtgggccat cgccctgata gacggttttt cgccctttga cgttggagtc   4500
cacgttcttt aatagtggac tcttgttcca aactggaaca acactcaacc ctatctcggt   4560
ctattctttt gatttataag ggattttggg gatttcggcc tattggttaa aaaatgagct   4620
gatttaacaa aaatttaacg cgaattaatt ctgtggaatg tgtgtcagtt agggtgtgga   4680
```

```
aagtccccag gctccccagg caggcagaag tatgcaaagc atgcatctca attagtcagc   4740
aaccaggtgt ggaaagtccc caggctcccc agcaggcaga agtatgcaaa gcatgcatct   4800
caattagtca gcaaccatag tcccgcccct aactccgccc atcccgcccc taactccgcc   4860
cagttccgcc cattctccgc cccatggctg actaattttt tttatttatg cagaggccga   4920
ggccgcctct gcctctgagc tattccagaa gtagtgagga ggcttttttg gaggcctagg   4980
cttttgcaaa aagctcccgg gagcttgtat atccattttc ggatctgatc agcacgtgtt   5040
gacaattaat catcggcata gtatatcggc atagtataat acgacaaggt gaggaactaa   5100
accatggcca agttgaccag tgccgttccg gtgctcaccg cgcgcgacgt cgccggagcg   5160
gtcgagttct ggaccgaccg gctcgggttc tcccgggact tcgtggagga cgacttcgcc   5220
ggtgtggtcc gggacgacgt gaccctgttc atcagcgcgg tccaggacca ggtggtgccg   5280
gacaacaccc tggcctgggt gtgggtgcgc ggcctggacg agctgtacgc cgagtggtcg   5340
gaggtcgtgt ccacgaactt ccgggacgcc tccgggccgg ccatgaccga gatcggcgag   5400
cagccgtggg ggcgggagtt cgccctgcgc gacccggccg gcaactgcgt gcacttcgtg   5460
gccgaggagc aggactgaca cgtgctacga gatttcgatt ccaccgccgc cttctatgaa   5520
aggttgggct tcggaatcgt tttccgggac gccggctgga tgatcctcca gcgcggggat   5580
ctcatgctgg agttcttcgc ccaccccaac ttgtttattg cagcttataa tggttacaaa   5640
taaagcaata gcatcacaaa tttcacaaat aaagcatttt tttcactgca ttctagttgt   5700
ggtttgtcca aactcatcaa tgtatcttat catgtctgta taccgtcgac ctctagctag   5760
agcttggcgt aatcatggtc atagctgttt cctgtgtgaa attgttatcc gctcacaatt   5820
ccacacaaca tacgagccgg aagcataaag tgtaaagcct ggggtgccta atgagtgagc   5880
taactcacat taattgcgtt gcgctcactg cccgctttcc agtcgggaaa cctgtcgtgc   5940
cagctgcatt aatgaatcgg ccaacgcgcg gggagaggcg gtttgcgtat tgggcgctct   6000
tccgcttcct cgctcactga ctcgctgcgc tcggtcgttc ggctgcggcg agcggtatca   6060
gctcactcaa aggcggtaat acggttatcc acagaatcag gggataacgc aggaaagaac   6120
atgtgagcaa aaggccagca aaaggccagg aaccgtaaaa aggccgcgtt gctggcgttt   6180
ttccataggc tccgcccccc tgacgagcat cacaaaaatc gacgctcaag tcagaggtgg   6240
cgaaacccga caggactata aagataccag gcgtttcccc ctggaagctc cctcgtgcgc   6300
tctcctgttc cgaccctgcc gcttaccgga tacctgtccg cctttctccc ttcgggaagc   6360
gtggcgcttt ctcaatgctc acgctgtagg tatctcagtt cggtgtaggt cgttcgctcc   6420
aagctgggct gtgtgcacga accccccgtt cagcccgacc gctgcgcctt atccggtaac   6480
tatcgtcttg agtccaaccc ggtaagacac gacttatcgc cactggcagc agccactggt   6540
aacaggatta gcagagcgag gtatgtaggc ggtgctacag agttcttgaa gtggtggcct   6600
aactacggct acactagaag gacagtattt ggtatctgcg ctctgctgaa gccagttacc   6660
ttcggaaaaa gagttggtag ctcttgatcc ggcaaacaaa ccaccgctgg tagcggtggt   6720
ttttttgttt gcaagcagca gattacgcgc agaaaaaaag gatctcaaga agatcctttg   6780
atcttttcta cggggtctga cgctcagtgg aacgaaaact cacgttaagg gattttggtc   6840
atgagattat caaaaaggat cttcacctag atccttttaa attaaaaatg aagttttaaa   6900
tcaatctaaa gtatatatga gtaaacttgg tctgacagtt accaatgctt aatcagtgag   6960
gcacctatct cagcgatctg tctatttcgt tcatccatag ttgcctgact ccccgtcgtg   7020
tagataacta cgatacggga gggcttacca tctggcccca gtgctgcaat gataccgcga   7080
```

```
gacccacgct caccggctcc agatttatca gcaataaacc agccagccgg aagggccgag   7140

cgcagaagtg gtcctgcaac tttatccgcc tccatccagt ctattaattg ttgccgggaa   7200

gctagagtaa gtagttcgcc agttaatagt ttgcgcaacg ttgttgccat tgctacaggc   7260

atcgtggtgt cacgctcgtc gtttggtatg gcttcattca gctccggttc ccaacgatca   7320

aggcgagtta catgatcccc catgttgtgc aaaaaagcgg ttagctcctt cggtcctccg   7380

atcgttgtca gaagtaagtt ggccgcagtg ttatcactca tggttatggc agcactgcat   7440

aattctctta ctgtcatgcc atccgtaaga tgcttttctg tgactggtga gtactcaacc   7500

aagtcattct gagaatagtg tatgcggcga ccgagttgct cttgcccggc gtcaatacgg   7560

gataataccg cgccacatag cagaacttta aaagtgctca tcattggaaa acgttcttcg   7620

gggcgaaaac tctcaaggat cttaccgctg ttgagatcca gttcgatgta acccactcgt   7680

gcacccaact gatcttcagc atcttttact ttcaccagcg tttctgggtg agcaaaaaca   7740

ggaaggcaaa atgccgcaaa aaagggaata agggcgacac ggaaatgttg aatactcata   7800

ctcttccttt ttcaatatta ttgaagcatt tatcagggtt attgtctcat gagcggatac   7860

atatttgaat gtatttagaa aaataaacaa ataggggttc cgcgcacatt tccccgaaaa   7920

gtgccacctg acgtcatggc accaccaatg acactgcaac aatggatcat ttggaaaaaa   7980

atgaataaag cgcatgaggc acttcaaaat acaacaactg tgactgaaca gcagaaggaa   8040

caaattatac tggacattca aaatgaagaa gtacaaccaa ctaggagaga taaatttaga   8100

tatctgcttt atacttgttg tgctactagc tcaagagtat tggcctggat gtttttagtt   8160

tgtatattgt taatcattgt tttggtttca tgctttgtga ctatatccag aatacaatgg   8220

aataaggata ttcaggtatt aggacctgta atagactgga atgttactca aagagctgtt   8280

tatcaaccct tacagactag aaggattgca cgttccctta gaatgcagca tcctgttcca   8340

aaatatgtgg aggtaaatat gactagtatt ccacaaggtg tatactatga accccatccg   8400

gaacccatag tggtgaagga gagggtcctg ggtctttctc aaattctgat gattaattca   8460

gaaaacattg ctaataatgc taatttgaca caagaagtaa agaagttgtt aactgaaatg   8520

gttaatgaag aaatgcaaag tttgtcagat gtaatgattg actttgaaat tcctttagga   8580

gaccctcgtg atcaagaaca atatatacat agaaaatgct atcaagaatt tgcaaattgt   8640

tatttagtaa aatataaaga acccaaaccg tggcctaagg agggccttat agctgatcaa   8700

tgcccattac caggttacca tgctggatta acctataata gacagtctat ttgggattac   8760

tatattaaag tggagagtat tagacctgca aattggacaa caaagagtaa atatggacaa   8820

gctagactag gaagttttta tattcctagc agtctgagac aaatcaatgt tagtcatgta   8880

ctattctgta gtgatcaatt atattctaaa tggtataata tagaaaatac catagaacaa   8940

aacgagcggt ttctgcttaa taaactaaat aaccttacat ctggaacctc agtattgaag   9000

aaaagagctc ttccgaagga ttggagttct caaggtaaaa atgctctgtt tagagaaatc   9060

aatgtgttag atatctgcag taaacctgaa tctgtaatac tattgaatac ttcatactat   9120

tccttctctt tatgggaagg agattgtaat tttactaaag atatgatttc tcagttggtt   9180

ccagaatgtg atggatttta taacaattct aagtggatgc atatgcatcc atatgcttgt   9240

agattctgga gaagtaagaa tgaaaaagaa gaaactaaat gtagagatgg ggaaactaag   9300

agatgtctgt attatccttt atgggacagt cccgaatcta catatgattt tggttattta   9360

gcataccaaa agaattttcc ttcccctatc tgtatagaac aacagaaaat tagagatcaa   9420

gattatgaag tttattcttt gtatcaagaa tgcaaaatag cttctaaagc atatggaatt   9480
```

-continued

```
gatacagttt tattctctct aaagaatttt cttaattata caggaactcc tgtaaatgaa   9540

atgcctaatg caagagcttt tgtaggccta atagatccca agtttcctcc ttcctatccc   9600

aatgttacta gggaacatta tacttcctgt aataatagga aaagaagaag tgttgataat   9660

aactatgcta agttaaggtc tatggggtat gcacttacag gagcagtgca aaccttatct   9720

caaatatcag atattaatga tgaaaactta cagcaaggaa tatatttatt aagggatcat   9780

gtaataacct taatggaagc tacattgcat gatatatctg ttatggaagg aatgtttgct   9840

gtacaacatt tgcatacaca tttgaatcat ttgaagacaa tgcttctaga aagaagaata   9900

gactggacct atatgtctag tacttggcta caacaacaat tacagaaatc tgatgatgag   9960

atgaaagtaa taaagagaat tgctagaagt ttggtatatt atgttaaaca aacccatagt  10020

tctcccacag ctacagcctg ggagattgga ttatattatg aattggttat acctaaacat  10080

atttacttga ataattggaa tgttgtcaat ataggtcact tagttaaatc agctggacaa  10140

ttgactcatg taactatagc tcatccttat gaaataatca ataaggaatg tgtagagact  10200

atatatctgc atcttgaaga ctgcacaaga caagattatg tcatatgtga tgtggtaaag  10260

atagtgcagc cttgtggcaa tagctcagac acgagtgatt gtcctgtctg ggctgaagct  10320

gtaaaagaac catttgtgca agtcaatcct ctgaaaaacg gaagttatct ggttttggca  10380

agttccacag actgtcagat cccaccatat gttcctagca tcgtgactgt taatgaaaca  10440

acgtcatgct ttggactgga ctttaaaagg ccactggttg cggaagaaag attgagcttt  10500

gagccacgac tgccaaatct acaactaaga ttaccacatt tggttggaat tattgcaaaa  10560

atcaaaggga taaaaataga agtcacatcc tctggagaaa gtataaaaga gcagattgaa  10620

agagcaaaag ctgagctcct tcgactggac attcacgagg gagatactcc tgcctggata  10680

caacagctag ctgcagcaac aaaggacgtc tggccagcag cagcttctgc tctacaagga  10740

attgggaact ttttatctgg gactgcccaa ggaatatttg gaactgcctt tagtctcttg  10800

ggatacttaa ggcctatcct aataggagta ggggtcattc tcttggttat tcttatattt  10860

agaattgtat cctggattcc tacgagaagg aggaatcagt ag                     10902
```